United States Patent
Dockal et al.

(10) Patent No.: US 9,447,147 B2
(45) Date of Patent: Sep. 20, 2016

(54) PEPTIDES AND METHODS OF USE

(71) Applicants: BAXTER INTERNATIONAL INC., Deerfield, IL (US); BAXTER HEALTHCARE SA, Glattpark (Opfikon) (CH)

(72) Inventors: Michael Dockal, Vienna (AT); Thomas Polakowski, Berlin (DE); Frank Osterkamp, Berlin (DE); Rudolf Hartmann, Bisamberg (AT); Matthias Paschke, Berlin (DE); Bettina Hartlieb, Vienna (AT); Friedrich Scheiflinger, Vienna (AT)

(73) Assignees: BAXALTA GMBH, Glattpark (Opfikon) (CH); BAXALTA INCORPORATED, Bannockburn, IL (US)

( * ) Notice: Subject to any disclaimer, the term of this patent is extended or adjusted under 35 U.S.C. 154(b) by 0 days.

(21) Appl. No.: 14/634,028

(22) Filed: Feb. 27, 2015

(65) Prior Publication Data

US 2015/0246947 A1 Sep. 3, 2015

Related U.S. Application Data

(60) Provisional application No. 61/946,103, filed on Feb. 28, 2014.

(51) Int. Cl.
| | |
|---|---|
| C07K 7/08 | (2006.01) |
| A61K 38/10 | (2006.01) |
| A61K 47/48 | (2006.01) |
| C07K 14/745 | (2006.01) |
| A61K 38/00 | (2006.01) |

(52) U.S. Cl.
CPC ............... *C07K 7/08* (2013.01); *A61K 38/10* (2013.01); *A61K 47/48215* (2013.01); *C07K 14/745* (2013.01); *A61K 38/00* (2013.01)

(58) Field of Classification Search
None
See application file for complete search history.

(56) References Cited

U.S. PATENT DOCUMENTS

2013/0252896 A1 9/2013 Dockal et al.

FOREIGN PATENT DOCUMENTS

| WO | WO-2011/115712 A2 | 9/2011 |
| WO | WO-2011/125015 A2 | 10/2011 |

OTHER PUBLICATIONS

Linse et al., A region of vitamin K-dependent protein S that binds to C4b binding protein (C4BP) identified using bacteriophage peptide display libraries. *J. Biol. Chem.* 272(23): 14658-65 (1997).
International Search Report and Written Opinion of the International Searching Authority issued in connection with International Application No. PCT/US2015/018041, dated Jun. 1, 2015.
Dahlback, "Advances in understanding pathogenic mechanisms of thrombophilic disorders", *Blood*, 112: 19-27 (2008).
Franchini et al., "Factor V Leiden and hemophilia", *Thromb. Res.*, 125: 119-23 (2010).
Hackeng et al., "Human protein S inhibits prothrombinase complex activity on endothelial cells and platelets via direct interactions with factor Va and Xa", *J. Biol. Chem.*, 269(33): 21051-8 (1994).
Rezende et al., "Coagulation, inflammation, and apoptosis: Different roles for protein S and the protein S-C4b binding protein complex", *Blood*, 103: 1192-201 (2004).
Rosing et al., "Effects of protein S and factor Xa on peptide bond cleavages during inactivation of factor Va and factor VaR506Q by activated protein C", *J. Biol. Chem.*, 270(46): 27852-8 (1995).
Sere et al., "Inhibition of thrombin generation by protein S at low procoagulant stimuli: Implications for maintenance of the hemostatic balance", *Blood*, 104: 3624-30 (2004).
van't Veer et al., "Increased prothrombin activation in protein S-deficient plasma under flow conditions on endothelial cell matrix: An independent anticoagulant function of protein S in plasma", *Blood*, 85: 1815-21 (1995).
Walker et al., Regulation of activated protein C by protein S. The role of phospholipid in factor Va inactivation, *J. Biol. Chem.*, 256(21): 11128-31 (1981).

*Primary Examiner* — Christina Bradley
*Assistant Examiner* — Ronald Niebauer
(74) *Attorney, Agent, or Firm* — Marshall, Gerstein & Borun LLP

(57) ABSTRACT

The invention provides peptides, including peptides that bind and, optionally, inhibit Protein S, and compositions thereof. The peptides may be used to, e.g., inhibit Protein S activity, enhance thrombin formation in a subject, increase blood clot formation in a subject, treat a blood coagulation disorder in a subject, purify Protein S, and identify a Protein S binding compound.

9 Claims, 39 Drawing Sheets

| SEQ ID | Peptide | Mean IC50 [nM] | SEQ ID | Peptide | Mean IC50 [nM] | SEQ ID | Peptide | Mean IC50 [nM] |
|---|---|---|---|---|---|---|---|---|
| 2 | JBS2512 | 21.5 | 149 | JBS2659 | 16.4 | 195 | JBS2731 | 4337.0 |
| 6 | JBS2516 | 9.9 | 151 | JBS2661 | 7.8 | 196 | JBS2732 | 10265.9 |
| 18 | JBS2528 | 18.8 | 153 | JBS2663 | 28.4 | 197 | JBS2733 | 110.9 |
| 36 | JBS2546 | 31.0 | 165 | JBS2676 | 11.6 | 198 | JBS2734 | 792.0 |
| 42 | JBS2552 | 16.6 | 167 | JBS2678 | 1811.3 | 204 | JBS2740 | 16.4 |
| 60 | JBS2570 | 18.8 | 168 | JBS2679 | 30.0 | 214 | JBS2750 | 3.6 |
| 62 | JBS2572 | 10.0 | 169 | JBS2680 | 6.0 | 216 | JBS2752 | 6.8 |
| 72 | JBS2582 | 7.4 | 170 | JBS2681 | 18.7 | 234 | JBS2770 | 5.2 |
| 76 | JBS2586 | 11.0 | 171 | JBS2682 | 7.5 | 252 | JBS2788 | 2.2 |
| 80 | JBS2590 | 11.4 | 172 | JBS2683 | 5.6 | 254 | JBS2790 | 3.4 |
| 82 | JBS2592 | 20.0 | 173 | JBS2684 | 12.5 | 258 | JBS2794 | 5.6 |
| 92 | JBS2602 | 10.9 | 183 | JBS2713 | 20.1 | 258 | JBS2794 | 4.0 |
| 100 | JBS2610 | 15.5 | 185 | JBS2721 | 3.6 | 270 | JBS2806 | 5.7 |
| 101 | JBS2611 | 12.5 | 186 | JBS2722 | 24.4 | 274 | JBS2810 | 4.4 |
| 102 | JBS2612 | 17.0 | 187 | JBS2723 | 1493.3 | 274 | JBS2810 | 5.5 |
| 113 | JBS2623 | 15.1 | 188 | JBS2724 | 13.9 | 287 | JBS2823 | 13.5 |
| 115 | JBS2625 | 6.6 | 189 | JBS2725 | 5897.9 | 289 | JBS2825 | 4.4 |
| 118 | JBS2628 | 27.0 | 190 | JBS2726 | 15691.4 | 288 | JBS2845 | 8.4 |
| 135 | JBS2645 | 9.4 | 191 | JBS2727 | 7.6 | 311 | JBS2847 | 5.4 |
| 138 | JBS2648 | 18.6 | 192 | JBS2728 | 8.4 | 349 | JBS2885 | 4.4 |
| 139 | JBS2649 | 31.8 | 193 | JBS2729 | 6.2 | 351 | JBS2887 | 4.0 |
| 140 | JBS2650 | 25.1 | 194 | JBS2730 | 13751.7 | 367 | JBS2903 | 3.1 |
| 369 | JBS2905 | 5.9 | 442 | JBS3190 | 1.6 | 467 | JBS3221 | 0.6 |
| 388 | JBS2924 | 3.6 | 443 | JBS3191 | 1.6 | 468 | JBS3222 | 1.5 |

FIGURE 1A

| SEQ ID | Peptide | Mean IC50 [nM] | SEQ ID | Peptide | Mean IC50 [nM] | SEQ ID | Peptide | Mean IC50 [nM] |
|---|---|---|---|---|---|---|---|---|
| 392 | JBS2928 | 3.7 | 444 | JBS3192 | 2.8 | 469 | JBS3223 | 0.7 |
| 405 | JBS2941 | 1.4 | 445 | JBS3193 | 2.7 | 470 | JBS3224 | 1.3 |
| 409 | JBS3152 | 5.1 | 446 | JBS3194 | 2.0 | 477 | JBS3231 | 1.5 |
| 409 | JBS3152 | 4.4 | 447 | JBS3195 | 2.1 | 478 | JBS3232 | 0.9 |
| 412 | JBS3157 | 812.0 | 448 | JBS3196 | 2.5 | 479 | JBS3233 | 0.9 |
| 415 | JBS3160 | 981.4 | 449 | JBS3197 | 6.1 | 480 | JBS3234 | 2.7 |
| 417 | JBS3162 | 1508.3 | 450 | JBS3198 | 2.5 | 481 | JBS3235 | 1.4 |
| 423 | JBS3168 | 604.4 | 451 | JBS3199 | 2.4 | 482 | JBS3236 | 2.6 |
| 424 | JBS3169 | 543.9 | 452 | JBS3200 | 4.8 | 483 | JBS3237 | 1.5 |
| 425 | JBS3170 | 205.7 | 453 | JBS3201 | 1.8 | 484 | JBS3238 | 1.3 |
| 426 | JBS3171 | 335.6 | 454 | JBS3202 | 1.6 | 485 | JBS3239 | 2.0 |
| 427 | JBS3172 | 55.2 | 455 | JBS3203 | 1.8 | 486 | JBS3240 | 2.0 |
| 428 | JBS3173 | 207.5 | 457 | JBS3205 | 4.3 | 487 | JBS3241 | 1.2 |
| 433 | JBS3179 | 8.0 | 458 | JBS3206 | 0.8 | 488 | JBS3242 | 67.8 |
| 434 | JBS3180 | 9.0 | 460 | JBS3208 | 11.1 | 489 | JBS3243 | 1.3 |
| 435 | JBS3181 | 9.5 | 461 | JBS3215 | 0.8 | 490 | JBS3244 | 4.7 |
| 436 | JBS3182 | 20.9 | 462 | JBS3216 | 0.7 | 491 | JBS3245 | 2.0 |
| 437 | JBS3185 | 7.2 | 463 | JBS3217 | 1.3 | 492 | JBS3246 | 2.2 |
| 438 | JBS3186 | 2.6 | 464 | JBS3218 | 0.9 | 493 | JBS3247 | 1.9 |
| 440 | JBS3188 | 2.9 | 465 | JBS3219 | 1.1 | 494 | JBS3248 | 3.7 |
| 441 | JBS3189 | 5.0 | 466 | JBS3220 | 3.5 | 496 | JBS3250 | 22.7 |
| 497 | JBS3251 | 0.6 | 519 | JBS3273 | 2.3 | 541 | JBS3295 | 14.6 |
| 498 | JBS3252 | 12.8 | 520 | JBS3274 | 1.0 | 542 | JBS3296 | 2.2 |

FIGURE 1B

| SEQ ID | Peptide | Mean IC50 [nM] | SEQ ID | Peptide | Mean IC50 [nM] | SEQ ID | Peptide | Mean IC50 [nM] |
|---|---|---|---|---|---|---|---|---|
| 499 | JBS3253 | 2.8 | 521 | JBS3275 | 1.2 | 543 | JBS3297 | 1.0 |
| 500 | JBS3254 | 1.6 | 522 | JBS3276 | 3.0 | 544 | JBS3298 | 1.0 |
| 501 | JBS3255 | 9.5 | 523 | JBS3277 | 3.4 | 545 | JBS3299 | 2.0 |
| 502 | JBS3256 | 1.7 | 524 | JBS3278 | 1.1 | 546 | JBS3300 | 3.2 |
| 503 | JBS3257 | 14.8 | 525 | JBS3279 | 1.5 | 547 | JBS3301 | 1.3 |
| 504 | JBS3258 | 0.9 | 526 | JBS3280 | 5.3 | 548 | JBS3302 | 3.5 |
| 504 | JBS3258 | 0.8 | 527 | JBS3281 | 2.3 | 549 | JBS3303 | 1.7 |
| 505 | JBS3259 | 3.7 | 527 | JBS3281 | 1.7 | 550 | JBS3304 | 1.5 |
| 506 | JBS3260 | 1.6 | 528 | JBS3282 | 4.1 | 551 | JBS3305 | 3.7 |
| 507 | JBS3261 | 2.0 | 529 | JBS3283 | 0.9 | 552 | JBS3306 | 0.8 |
| 508 | JBS3262 | 1.0 | 530 | JBS3284 | 1.3 | 553 | JBS3307 | 1.4 |
| 509 | JBS3263 | 1.2 | 531 | JBS3285 | 1.2 | 554 | JBS3308 | 1.4 |
| 510 | JBS3264 | 2.0 | 532 | JBS3286 | 1.3 | 555 | JBS3309 | 1.1 |
| 511 | JBS3265 | 1.4 | 533 | JBS3287 | 1.2 | 560 | JBS3314 | 0.8 |
| 512 | JBS3266 | 1.6 | 534 | JBS3288 | 3.1 | 563 | JBS3317 | 0.6 |
| 513 | JBS3267 | 1.7 | 535 | JBS3289 | 2.5 | 564 | JBS3318 | 2.8 |
| 514 | JBS3268 | 1.5 | 536 | JBS3290 | 3.4 | 566 | JBS3320 | 0.5 |
| 515 | JBS3269 | 56.9 | 537 | JBS3291 | 8.0 | 567 | JBS3321 | 0.7 |
| 516 | JBS3270 | 1.2 | 538 | JBS3292 | 2.7 | 568 | JBS3322 | 4.5 |
| 517 | JBS3271 | 1.9 | 539 | JBS3293 | 2.1 | 571 | JBS3325 | 0.7 |
| 518 | JBS3272 | 1.4 | 540 | JBS3294 | 6.3 | 572 | JBS3326 | 1.0 |
| 999 | JBS3754 | 3.2 | 1000 | JBS3755 | 7.6 | 1001 | JBS3756 | 10.1 |
| 1002 | JBS3757 | 26.5 | 1003 | JBS3758 | 0.9 | 1005 | JBS3761 | 2.8 |

FIGURE 1C

| SEQ ID | Compound | Sequence | SEQ ID | Compound | Sequence |
| --- | --- | --- | --- | --- | --- |
| 1 | JBS-0684 | Bio-Ttds-TGHVSAGWYDYNFDHYREFT-NH₂ | 42 | JBS-2552 | Ac-GGHVSAGWYDYNFDHYREFT-NH2 |
| 2 | JBS-2512 | Ac-TGHVSAGWYDYNFDHYREFT-NH2 | 43 | JBS-2553 | Ac-TGGVSAGWYDYNFDHYREFT-NH2 |
| 3 | JBS-2513 | Ac-ATFYGTNHFVERDWHSDYYG-NH2 | 44 | JBS-2554 | Ac-TGHGSAGWYDYNFDHYREFT-NH2 |
| 4 | JBS-2514 | Ac-WYFYTGDHEHSFNVGYARDT-NH2 | 45 | JBS-2555 | Ac-TGHVGAGWYDYNFDHYREFT-NH2 |
| 5 | JBS-2515 | Ac-AGHVSAGWYDYNFDHYREFT-NH2 | 46 | JBS-2556 | Ac-TGHVSGGWYDYNFDHYREFT-NH2 |
| 6 | JBS-2516 | Ac-TAHVSAGWYDYNFDHYREFT-NH2 | 47 | JBS-2557 | Ac-TGHVSAGGYDYNFDHYREFT-NH2 |
| 7 | JBS-2517 | Ac-TGAVSAGWYDYNFDHYREFT-NH2 | 48 | JBS-2558 | Ac-TGHVSAGWGDYNFDHYREFT-NH2 |
| 8 | JBS-2518 | Ac-TGHASAGWYDYNFDHYREFT-NH2 | 49 | JBS-2559 | Ac-TGHVSAGWYGNFDHYREFT-NH2 |
| 9 | JBS-2519 | Ac-TGHVAAGWYDYNFDHYREFT-NH2 | 50 | JBS-2560 | Ac-TGHVSAGWYDGNFDHYREFT-NH2 |
| 10 | JBS-2520 | Ac-TGHVSAAWYDYNFDHYREFT-NH2 | 51 | JBS-2561 | Ac-TGHVSAGWYDYGFDHYREFT-NH2 |
| 11 | JBS-2521 | Ac-TGHVSAGAYDYNFDHYREFT-NH2 | 52 | JBS-2562 | Ac-TGHVSAGWYDYNGDHYREFT-NH2 |
| 12 | JBS-2522 | Ac-TGHVSAGWADYNFDHYREFT-NH2 | 53 | JBS-2563 | Ac-TGHVSAGWYDYNFDGYREFT-NH2 |
| 13 | JBS-2523 | Ac-TGHVSAGWYAYNFDHYREFT-NH2 | 54 | JBS-2564 | Ac-TGHVSAGWYDYNFDHGREFT-NH2 |
| 14 | JBS-2524 | Ac-TGHVSAGWYDANFDHYREFT-NH2 | 55 | JBS-2565 | Ac-TGHVSAGWYDYNFDHYGEFT-NH2 |
| 15 | JBS-2525 | Ac-TGHVSAGWYDYAFDHYREFT-NH2 | 56 | JBS-2566 | Ac-TGHVSAGWYDYNFDHYRGFT-NH2 |
| 16 | JBS-2526 | Ac-TGHVSAGWYDYNADHYREFT-NH2 | 57 | JBS-2567 | Ac-TGHVSAGWYDYNFDHYRGFT-NH2 |
| 17 | JBS-2527 | Ac-TGHVSAGWYDYNFAHYREFT-NH2 | 58 | JBS-2568 | Ac-TGHVSAGWYDYNFDHYREGT-NH2 |
| 18 | JBS-2528 | Ac-TGHVSAGWYDYNFDAYREFT-NH2 | 59 | JBS-2569 | Ac-TGHVSAGWYDYNFDHYREFG-NH2 |
| 19 | JBS-2529 | Ac-TGHVSAGWYDYNFDHAREFT-NH2 | 60 | JBS-2570 | Ac-LGHVSAGWYDYNFDHYREFT-NH2 |
| 20 | JBS-2530 | Ac-TGHVSAGWYDYNFDHYAEFT-NH2 | 61 | JBS-2571 | Ac-TLHVSAGWYDYNFDHYREFT-NH2 |
| 21 | JBS-2531 | Ac-TGHVSAGWYDYNFDHYRAFT-NH2 | 62 | JBS-2572 | Ac-TGHLSAGWYDYNFDHYREFT-NH2 |
| 22 | JBS-2532 | Ac-TGHVSAGWYDYNFDHYREAT-NH2 | 63 | JBS-2573 | Ac-TGHVLAGWYDYNFDHYREFT-NH2 |
| 23 | JBS-2533 | Ac-TGHVSAGWYDYNFDHYREFA-NH2 | 64 | JBS-2574 | Ac-TGHVSLGWYDYNFDHYREFT-NH2 |
| 24 | JBS-2534 | Ac-DGHVSAGWYDYNFDHYREFT-NH2 | 65 | JBS-2575 | Ac-TGHVSALWYDYNFDHYREFT-NH2 |
| 25 | JBS-2535 | Ac-TDHVSAGWYDYNFDHYREFT-NH2 | 66 | JBS-2576 | Ac-TGHVSAGLYDYNFDHYREFT-NH2 |
| 26 | JBS-2536 | Ac-TGDVSAGWYDYNFDHYREFT-NH2 | 67 | JBS-2577 | Ac-TGHVSAGWLDYNFDHYREFT-NH2 |
| 27 | JBS-2537 | Ac-TGHDSAGWYDYNFDHYREFT-NH2 | 68 | JBS-2578 | Ac-TGHVSAGWYLNFDHYREFT-NH2 |
| 28 | JBS-2538 | Ac-TGHVDAGWYDYNFDHYREFT-NH2 | 69 | JBS-2579 | Ac-TGHVSAGWYDLNFDHYREFT-NH2 |
| 29 | JBS-2539 | Ac-TGHVSDGWYDYNFDHYREFT-NH2 | 70 | JBS-2580 | Ac-TGHVSAGWYDYLFDHYREFT-NH2 |
| 30 | JBS-2540 | Ac-TGHVSADWYDYNFDHYREFT-NH2 | 71 | JBS-2581 | Ac-TGHVSAGWYDYNLDHYREFT-NH2 |
| 31 | JBS-2541 | Ac-TGHVSAGDYDYNFDHYREFT-NH2 | 72 | JBS-2582 | Ac-TGHVSAGWYDYNFLHYREFT-NH2 |
| 32 | JBS-2542 | Ac-TGHVSAGWDDYNFDHYREFT-NH2 | 73 | JBS-2583 | Ac-TGHVSAGWYDYNFDLYREFT-NH2 |
| 33 | JBS-2543 | Ac-TGHVSAGWYDDNFDHYREFT-NH2 | 74 | JBS-2584 | Ac-TGHVSAGWYDYNFDHLREFT-NH2 |
| 34 | JBS-2544 | Ac-TGHVSAGWYDDFDHYREFT-NH2 | 75 | JBS-2585 | Ac-TGHVSAGWYDYNFDHLREFT-NH2 |
| 35 | JBS-2545 | Ac-TGHVSAGWYDYNDDHYREFT-NH2 | | | |
| 36 | JBS-2546 | Ac-TGHVSAGWYDYNFDDYREFT-NH2 | | | |
| 37 | JBS-2547 | Ac-TGHVSAGWYDYNFDHDREFT-NH2 | | | |
| 38 | JBS-2548 | Ac-TGHVSAGWYDYNFDHDEFT-NH2 | | | |
| 39 | JBS-2549 | Ac-TGHVSAGWYDYNFDHYRDFT-NH2 | | | |
| 40 | JBS-2550 | Ac-TGHVSAGWYDYNFDHYREDT-NH2 | | | |
| 41 | JBS-2551 | Ac-TGHVSAGWYDYNFDHYREFD-NH2 | | | |

FIGURE 2A

| SEQ ID | Compound | Sequence | SEQ ID | Compound | Sequence |
|---|---|---|---|---|---|
| 76 | JBS-2586 | Ac-TGHVSAGWYDYNFDHYLEFT-NH2 | 117 | JBS-2627 | Ac-TGHVSAGWYDYNFDHYREFF-NH2 |
| 77 | JBS-2587 | Ac-TGHVSAGWYDYNFDHYRLFT-NH2 | 118 | JBS-2628 | Ac-PGHVSAGWYDYNFDHYREFT-NH2 |
| 78 | JBS-2588 | Ac-TGHVSAGWYDYNFDHYRELT-NH2 | 119 | JBS-2629 | Ac-TFHVSAGWYDYNFDHYREFT-NH2 |
| 79 | JBS-2589 | Ac-TGHVSAGWYDYNFDHYREFL-NH2 | 120 | JBS-2630 | Ac-TGPVSAGWYDYNFDHYREFT-NH2 |
| 80 | JBS-2590 | Ac-KGHVSAGWYDYNFDHYREFT-NH2 | 121 | JBS-2631 | Ac-TGHPSAGWYDYNFDHYREFT-NH2 |
| 81 | JBS-2591 | Ac-TKHVSAGWYDYNFDHYREFT-NH2 | 122 | JBS-2632 | Ac-TGHVPAGWYDYNFDHYREFT-NH2 |
| 82 | JBS-2592 | Ac-TGKVSAGWYDYNFDHYREFT-NH2 | 123 | JBS-2633 | Ac-TGHVSPGWYDYNFDHYREFT-NH2 |
| 83 | JBS-2593 | Ac-TGHKSAGWYDYNFDHYREFT-NH2 | 124 | JBS-2634 | Ac-TGHVSAPWYDYNFDHYREFT-NH2 |
| 84 | JBS-2594 | Ac-TGHVKAGWYDYNFDHYREFT-NH2 | 125 | JBS-2635 | Ac-TGHVSAGPYDYNFDHYREFT-NH2 |
| 85 | JBS-2595 | Ac-TGHVSKGWYDYNFDHYREFT-NH2 | 126 | JBS-2636 | Ac-TGHVSAGWPDYNFDHYREFT-NH2 |
| 86 | JBS-2596 | Ac-TGHVSAKWYDYNFDHYREFT-NH2 | 127 | JBS-2637 | Ac-TGHVSAGWYPYNFDHYREFT-NH2 |
| 87 | JBS-2597 | Ac-TGHVSAGKYDYNFDHYREFT-NH2 | 128 | JBS-2638 | Ac-TGHVSAGWYDPNFDHYREFT-NH2 |
| 88 | JBS-2598 | Ac-TGHVSAGWKDYNFDHYREFT-NH2 | 129 | JBS-2639 | Ac-TGHVSAGWYDYPFDHYREFT-NH2 |
| 89 | JBS-2599 | Ac-TGHVSAGWYKYNFDHYREFT-NH2 | 130 | JBS-2640 | Ac-TGHVSAGWYDYNPDHYREFT-NH2 |
| 90 | JBS-2600 | Ac-TGHVSAGWYDKNFDHYREFT-NH2 | 131 | JBS-2641 | Ac-TGHVSAGWYDYNFPHYREFT-NH2 |
| 91 | JBS-2601 | Ac-TGHVSAGWYDYKFDHYREFT-NH2 | 132 | JBS-2642 | Ac-TGHVSAGWYDYNFDPYREFT-NH2 |
| 92 | JBS-2602 | Ac-TGHVSAGWYDYNKDHYREFT-NH2 | 133 | JBS-2643 | Ac-TGHVSAGWYDYNFDHPREFT-NH2 |
| 93 | JBS-2603 | Ac-TGHVSAGWYDYNFKHYREFT-NH2 | 134 | JBS-2644 | Ac-TGHVSAGWYDYNFDHYPEFT-NH2 |
| 94 | JBS-2604 | Ac-FGHVSAGWYDYNFDKYREFT-NH2 | 135 | JBS-2645 | Ac-TGHVSAGWYDYNFDHYRPFT-NH2 |
| 95 | JBS-2605 | Ac-TFHVSAGWYDYNFDHKREFT-NH2 | 136 | JBS-2646 | Ac-TGHVSAGWYDYNFDHYREPT-NH2 |
| 96 | JBS-2606 | Ac-TGFVSAGWYDYNFDHYKEFT-NH2 | 137 | JBS-2647 | Ac-TGHVSAGWYDYNFDHYREFP-NH2 |
| 97 | JBS-2607 | Ac-TGHFSAGWYDYNFDHYRKFT-NH2 | 138 | JBS-2648 | Ac-SGHVSAGWYDYNFDHYREFT-NH2 |
| 98 | JBS-2608 | Ac-TGHVFAGWYDYNFDHYREKT-NH2 | 139 | JBS-2649 | Ac-TSHVSAGWYDYNFDHYREFT-NH2 |
| 99 | JBS-2609 | Ac-TGHVSFGWYDYNFDHYREFK-NH2 | 140 | JBS-2650 | Ac-TGSVSAGWYDYNFDHYREFT-NH2 |
| 100 | JBS-2610 | Ac-TGHVSAFWYDYNFDHYREKT-NH2 | 141 | JBS-2651 | Ac-TGHSSAGWYDYNFDHYREFT-NH2 |
| 101 | JBS-2611 | Ac-FGHVSAGWYDYNFDHYREFT-NH2 | 142 | JBS-2652 | Ac-TGHVSSGWYDYNFDHYREFT-NH2 |
| 102 | JBS-2612 | Ac-TGFVSAGWYDYFFDHYREFT-NH2 | 143 | JBS-2653 | Ac-TGHVSASWYDYNFDHYREFT-NH2 |
| 103 | JBS-2613 | Ac-TGHFSAGWYDYNFFHYREFT-NH2 | 144 | JBS-2654 | Ac-TGHVSAGSYDYNFDHYREFT-NH2 |
| 104 | JBS-2614 | Ac-TGHVFAGWYDYNFDFYREFT-NH2 | 145 | JBS-2655 | Ac-TGHVSAGWSDYNFDHYREFT-NH2 |
| 105 | JBS-2615 | Ac-TGHVSFGWYDYNFDHFREFT-NH2 | 146 | JBS-2656 | Ac-TGHVSAGWYSYNFDHYREFT-NH2 |
| 106 | JBS-2616 | Ac-TGHVSAFWYDYNFDHYFEFT-NH2 | 147 | JBS-2657 | Ac-TGHVSAGWYDSNFDHYREFT-NH2 |
| 107 | JBS-2617 | Ac-TGHVSAGFYDYNFDHYRFFT-NH2 | 148 | JBS-2658 | Ac-TGHVSAGWYDYSFDHYREFT-NH2 |
| 108 | JBS-2618 | Ac-TGHVSAGWFDYNFDHYREFT-NH2 | 149 | JBS-2659 | Ac-TGHVSAGWYDYNSDHYREFT-NH2 |
| 109 | JBS-2619 | Ac-TGHVSAGWYFYNFDHYREFT-NH2 | 150 | JBS-2660 | Ac-TGHVSAGWYDYNFSHYREFT-NH2 |
| 110 | JBS-2620 | Ac-TGHVSAGWYDFNFDHYREFT-NH2 | 151 | JBS-2661 | Ac-TGHVSAGWYDYNFDSYREFT-NH2 |
| 111 | JBS-2621 | Ac-TGHVSAGWYDYFFDHYREFT-NH2 | 152 | JBS-2662 | Ac-TGHVSAGWYDYNFDHSREFT-NH2 |
| 112 | JBS-2622 | Ac-TGHVSAGWYDYNFFHYREFT-NH2 | 153 | JBS-2663 | Ac-TGHVSAGWYDYNFDHYSEFT-NH2 |
| 113 | JBS-2623 | Ac-TGHVSAGWYDYNFDFYREFT-NH2 | 154 | JBS-2664 | Ac-TGHVSAGWYDYNFDHYRSFT-NH2 |
| 114 | JBS-2624 | Ac-TGHVSAGWYDYNFDHFREFT-NH2 | 155 | JBS-2665 | Ac-TGHVSAGWYDYNFDHYREST-NH2 |
| 115 | JBS-2625 | Ac-TGHVSAGWYDYNFDHYFEFT-NH2 | 156 | JBS-2666 | Ac-TGHVSAGWYDYNFDHYREFS-NH2 |
| 116 | JBS-2626 | Ac-TGHVSAGWYDYNFDHYRFFT-NH2 | 157 | JBS-2667 | Ac-TGHVSAGWYDYNFDHYR-NH2 |

FIGURE 2B

| SEQ ID | Compound | Sequence | SEQ ID | Compound | Sequence |
|---|---|---|---|---|---|
| 158 | JBS-2668 | Ac-TGHVSAGWYDYNFD-NH2 | 199 | JBS-2735 | Ac-TGHVSAGWYDYNFDHYREFT-Ttds-K(Bio)-NH2 |
| 159 | JBS-2669 | Ac-TGHVSAGWYDYNFDY-NH2 | 200 | JBS-2736 | Ac-BGLVSAGWYDYNFDHYREFT-NH2 |
| 160 | JBS-2670 | Ac-VSAGWYDYNFDHYREFT-NH2 | 201 | JBS-2737 | Ac-TELVSAGWYDYNFDHYREFT-NH2 |
| 161 | JBS-2671 | Ac-GWYDYNFDHYREFT-NH2 | 202 | JBS-2738 | Ac-TGEVSAGWYDYNFDHYREFT-NH2 |
| 162 | JBS-2672 | Ac-DYNFDHYREFT-NH2 | 203 | JBS-2739 | Ac-TGLESAGWYDYNFDHYREFT-NH2 |
| 163 | JBS-2673 | Ac-VSAGWYDYNFDHYR-NH2 | 204 | JBS-2740 | Ac-TGLVEAGWYDYNFDHYREFT-NH2 |
| 164 | JBS-2674 | Ac-GWYDYNFD-NH2 | 205 | JBS-2741 | Ac-TGLVSEGWYDYNFDHYREFT-NH2 |
| 165 | JBS-2676 | Ac-GGHVSAGWYDYNKDHYREFT-NH2 | 206 | JBS-2742 | Ac-TGLVSAEWYDYNFDHYREFT-NH2 |
| 166 | JBS-2677 | Ac-TGHVSAGWYDYNFDHYREF-NH2 | 207 | JBS-2743 | Ac-TGLVSAGEYDYNFDHYREFT-NH2 |
| 167 | JBS-2678 | Ac-TGHVSAGWYDYNFDHYRE-NH2 | 208 | JBS-2744 | Ac-TGLVSAGWEDYNFDHYREFT-NH2 |
| 168 | JBS-2679 | Ac-TAHVSAGWYDYNFDDYREFT-NH2 | 209 | JBS-2745 | Ac-TGLVSAGWEYNFDHYREFT-NH2 |
| 169 | JBS-2680 | Ac-TAHVSAGWYDYNFDLYREFT-NH2 | 210 | JBS-2746 | Ac-TGLVSAGWYDENFDHYREFT-NH2 |
| 170 | JBS-2681 | Ac-GAHVSAGWYDYNFDLYREFT-NH2 | 211 | JBS-2747 | Ac-TGLVSAGWYDYEFDHYREFT-NH2 |
| 171 | JBS-2682 | Ac-GGHVSAGWYDYNFDDYREFT-NH2 | 212 | JBS-2748 | Ac-TGLVSAGWYDYNEDHYREFT-NH2 |
| 172 | JBS-2683 | Ac-GGHVSAGWYDYNFDLYREFT-NH2 | 213 | JBS-2749 | Ac-TGLVSAGWYDYNFEHYREFT-NH2 |
| 173 | JBS-2684 | Ac-GGHVSAGWYDYNADHYREFT-NH2 | 214 | JBS-2750 | Ac-TGLVSAGWYDYNFDEYREFT-NH2 |
| 174 | JBS-2685 | Ac-TGHVsAGWYDYNFDHYREFT-NH2 | 215 | JBS-2751 | Ac-TGLVSAGWYDYNFDHEREFT-NH2 |
| 175 | JBS-2686 | Ac-TGHVSAGWYDYNFDHYREFT-NH2 | 216 | JBS-2752 | Ac-TGLVSAGWYDYNFDHYEEFT-NH2 |
| 176 | JBS-2687 | Ac-TGHVSAaWYDYNFDHYREFT-NH2 | 217 | JBS-2753 | Ac-TGLVSAGWYDYNFDHYREET-NH2 |
| 177 | JBS-2688 | Ac-TGHVSAGWyDYNFDHYREFT-NH2 | 218 | JBS-2754 | Ac-TGLVSAGWYDYNFDHYREFE-NH2 |
| 178 | JBS-2689 | Ac-TGHVEVGWYDYNFDHYREFT-NH2 | 219 | JBS-2755 | Ac-HGLVSAGWYDYNFDHYREFT-NH2 |
| 179 | JBS-2696 | Bio-Ttds-TGHVSAGWYDYNADHYREFT-NH2 | 220 | JBS-2756 | Ac-THLVSAGWYDYNFDHYREFT-NH2 |
| 180 | JBS-2697 | Bio-Ttds-TGLVSAGWYDYNFDHYREFT-NH2 | 221 | JBS-2757 | Ac-TGLHSAGWYDYNFDHYREFT-NH2 |
| 181 | JBS-2698 | Bio-Ttds-TPHVSAGWYDYNFDHYREFT-NH2 | 222 | JBS-2758 | Ac-TGLVHAGWYDYNFDHYREFT-NH2 |
| 182 | JBS-2699 | Bio-Ttds-TGHVSAGWYDYNFDHYREF-NH2 | 223 | JBS-2759 | Ac-TGLVSHGWYDYNFDHYREFT-NH2 |
| 183 | JBS-2713 | Ac-TGLVSAGWYDYNFDHYREFTC(ME-400MA)-NH2 | 224 | JBS-2760 | Ac-TGLVSAHWYDYNFDHYREFT-NH2 |
| 184 | JBS-2714 | Ac-C(ME-400MA)-TGLVSAGWYDYNFDHYREFT-NH2 | 225 | JBS-2761 | Ac-TGLVSAGHYDYNFDHYREFT-NH2 |
| 185 | JBS-2721 | Ac-TGL-Tle-SAGWYDYNFDHYREFT-NH2 | 226 | JBS-2762 | Ac-TGLVSAGWHDYNFDHYREFT-NH2 |
| 186 | JBS-2722 | Ac-TGLV-Dap-AGWYDYNFDHYREFT-NH2 | 227 | JBS-2763 | Ac-TGLVSAGWYHYNFDHYREFT-NH2 |
| 187 | JBS-2723 | Ac-TGLVSAG-Aib-YDYNFDHYREFT-NH2 | 228 | JBS-2764 | Ac-TGLVSAGWYDHNFDHYREFT-NH2 |
| 188 | JBS-2724 | Ac-TGLVS-Tle-GWYDYNFDHYREFT-NH2 | 229 | JBS-2765 | Ac-TGLVSAGWYDYHFDHYREFT-NH2 |
| 189 | JBS-2725 | Ac-TGLVSA-Aib-WYDYNFDHYREFT-NH2 | 230 | JBS-2766 | Ac-TGLVSAGWYDYNHDHYREFT-NH2 |
| 190 | JBS-2726 | Ac-TGLVSA-Nmg-WYDYNFDHYREFT-NH2 | 231 | JBS-2767 | Ac-TGLVSAGWYDYNFHHYREFT-NH2 |
| 191 | JBS-2727 | Ac-TGLVSAG-Bta-YDYNFDHYREFT-NH2 | 232 | JBS-2768 | Ac-TGLVSAGWYDYNFDHHREFT-NH2 |
| 192 | JBS-2728 | Ac-TGLVSAG-1Ni-YDYNFDHYREFT-NH2 | 233 | JBS-2769 | Ac-TGLVSAGWYDYNFDHYHEFT-NH2 |
| 193 | JBS-2729 | Ac-TGLVSAGWyDYNFDHYREFT-NH2 | 234 | JBS-2770 | Ac-TGLVSAGWYDYNFDHYRHFT-NH2 |
| 194 | JBS-2730 | Ac-TGLVSAGWYDYNaDHYREFT-NH2 | 235 | JBS-2771 | Ac-TGLVSAGWYDYNFDHYRHEFT-NH2 |
| 195 | JBS-2731 | Ac-TGLVSAGWYDYNFDHYREFT-NH2 | 236 | JBS-2772 | Ac-TGLVSAGWYDYNFDHYREHT-NH2 |
| 196 | JBS-2732 | Ac-TGLVSAGWYDYNFDHYREFT-NH2 | 237 | JBS-2773 | Ac-TGLVSAGWYDYNFDHYREFH-NH2 |
| 197 | JBS-2733 | Ac-TGLVSAGWYDYnFDHYREFT-NH2 | 238 | JBS-2774 | Ac-IGLVSAGWYDYNFDHYREFT-NH2 |
| 198 | JBS-2734 | Ac-TGLVSAGWYDYNaDHYREFT-NH2 | 239 | JBS-2775 | Ac-TILVSAGWYDYNFDHYREFT-NH2 |

FIGURE 2C

| SEQ ID | Compound | Sequence | SEQ ID | Compound | Sequence |
|---|---|---|---|---|---|
| 240 | JBS-2776 | Ac-TGLVSAGWYDYNFDHYREFT-NH2 | 281 | JBS-2817 | Ac-TGLNSAGWYDYNFDHYREFT-NH2 |
| 241 | JBS-2777 | Ac-TGLISAGWYDYNFDHYREFT-NH2 | 282 | JBS-2818 | Ac-TGLVNAGWYDYNFDHYREFT-NH2 |
| 242 | JBS-2778 | Ac-TGLVIAGWYDYNFDHYREFT-NH2 | 283 | JBS-2819 | Ac-TGLVSNGWYDYNFDHYREFT-NH2 |
| 243 | JBS-2779 | Ac-TGLVSIGWYDYNFDHYREFT-NH2 | 284 | JBS-2820 | Ac-TGLVSANWYDYNFDHYREFT-NH2 |
| 244 | JBS-2780 | Ac-TGLVSAIWYDYNFDHYREFT-NH2 | 285 | JBS-2821 | Ac-TGLVSAGNYDYNFDHYREFT-NH2 |
| 245 | JBS-2781 | Ac-TGLVSAGIYDYNFDHYREFT-NH2 | 286 | JBS-2822 | Ac-TGLVSAGWNDYNFDHYREFT-NH2 |
| 246 | JBS-2782 | Ac-TGLVSAGWIDYNFDHYREFT-NH2 | 287 | JBS-2823 | Ac-TGLVSAGWYNYNFDHYREFT-NH2 |
| 247 | JBS-2783 | Ac-TGLVSAGWYIDINFDHYREFT-NH2 | 288 | JBS-2824 | Ac-TGLVSAGWYDNNFDHYREFT-NH2 |
| 248 | JBS-2784 | Ac-TGLVSAGWYDINFDHYREFT-NH2 | 289 | JBS-2825 | Ac-TGLVSAGWYDYNNDHYREFT-NH2 |
| 249 | JBS-2785 | Ac-TGLVSAGWYDYIFDHYREFT-NH2 | 290 | JBS-2826 | Ac-TGLVSAGWYDYNFNHYREFT-NH2 |
| 250 | JBS-2786 | Ac-TGLVSAGWYDYNIDHYREFT-NH2 | 291 | JBS-2827 | Ac-TGLVSAGWYDYNFDNYREFT-NH2 |
| 251 | JBS-2787 | Ac-TGLVSAGWYDYNFIHYREFT-NH2 | 292 | JBS-2828 | Ac-TGLVSAGWYDYNFDHNREFT-NH2 |
| 252 | JBS-2788 | Ac-TGLVSAGWYDYNFDIYREFT-NH2 | 293 | JBS-2829 | Ac-TGLVSAGWYDYNFDHYNEFT-NH2 |
| 253 | JBS-2789 | Ac-TGLVSAGWYDYNFDHIREFT-NH2 | 294 | JBS-2830 | Ac-TGLVSAGWYDYNFDHYRNFT-NH2 |
| 254 | JBS-2790 | Ac-TGLVSAGWYDYNFDHYIEFT-NH2 | 295 | JBS-2831 | Ac-TGLVSAGWYDYNFDHYRENT-NH2 |
| 255 | JBS-2791 | Ac-TGLVSAGWYDYNFDHYRIFT-NH2 | 296 | JBS-2832 | Ac-TGLVSAGWYDYNFDHYREFN-NH2 |
| 256 | JBS-2792 | Ac-TGLVSAGWYDYNFDHYREIT-NH2 | 297 | JBS-2833 | Ac-QGLVSAGWYDYNFDHYREFT-NH2 |
| 257 | JBS-2793 | Ac-TGLVSMGWYDYNFDHYREFI-NH2 | 298 | JBS-2834 | Ac-TQLVSAGWYDYNFDHYREFT-NH2 |
| 258 | JBS-2794 | Ac-MGLVSAGWYDYNFDHYREFT-NH2 | 299 | JBS-2835 | Ac-TGQVSAGWYDYNFDHYREFT-NH2 |
| 259 | JBS-2795 | Ac-TMLVSAGWYDYNFDHYREFT-NH2 | 300 | JBS-2836 | Ac-TGLQSAGWYDYNFDHYREFT-NH2 |
| 260 | JBS-2796 | Ac-TGMVSAGWYDYNFDHYREFT-NH2 | 301 | JBS-2837 | Ac-TGLVQAGWYDYNFDHYREFT-NH2 |
| 261 | JBS-2797 | Ac-TGLMSAGWYDYNFDHYREFT-NH2 | 302 | JBS-2838 | Ac-TGLVSQGWYDYNFDHYREFT-NH2 |
| 262 | JBS-2798 | Ac-TGLVMAGWYDYNFDHYREFT-NH2 | 303 | JBS-2839 | Ac-TGLVSAQWYDYNFDHYREFT-NH2 |
| 263 | JBS-2799 | Ac-TGLVSMGWYDYNFDHYREFT-NH2 | 304 | JBS-2840 | Ac-TGLVSAGQYDYNFDHYREFT-NH2 |
| 264 | JBS-2800 | Ac-TGLVSAMWYDYNFDHYREFT-NH2 | 305 | JBS-2841 | Ac-TGLVSAGWQDYNFDHYREFT-NH2 |
| 265 | JBS-2801 | Ac-TGLVSAGMYDYNFDHYREFT-NH2 | 306 | JBS-2842 | Ac-TGLVSAGWYQYNFDHYREFT-NH2 |
| 266 | JBS-2802 | Ac-TGLVSAGWMDYNFDHYREFT-NH2 | 307 | JBS-2843 | Ac-TGLVSAGWYDQNFDHYREFT-NH2 |
| 267 | JBS-2803 | Ac-TGLVSAGWYMYNFDHYREFT-NH2 | 308 | JBS-2844 | Ac-TGLVSAGWYDYQFDHYREFT-NH2 |
| 268 | JBS-2804 | Ac-TGLVSAGWYDMNFDHYREFT-NH2 | 309 | JBS-2845 | Ac-TGLVSAGWYDYNQDHYREFT-NH2 |
| 269 | JBS-2805 | Ac-TGLVSAGWYDYMFDHYREFT-NH2 | 310 | JBS-2846 | Ac-TGLVSAGWYDYNFQHYREFT-NH2 |
| 270 | JBS-2806 | Ac-TGLVSAGWYDYNMDHYREFT-NH2 | 311 | JBS-2847 | Ac-TGLVSAGWYDYNFDQYREFT-NH2 |
| 271 | JBS-2807 | Ac-TGLVSAGWYDYNFMHYREFT-NH2 | 312 | JBS-2848 | Ac-TGLVSAGWYDYNFDHQREFT-NH2 |
| 272 | JBS-2808 | Ac-TGLVSAGWYDYNFDMYREFT-NH2 | 313 | JBS-2849 | Ac-TGLVSAGWYDYNFDHYQEFT-NH2 |
| 273 | JBS-2809 | Ac-TGLVSAGWYDYNFDHMREFT-NH2 | 314 | JBS-2850 | Ac-TGLVSAGWYDYNFDHYRQFT-NH2 |
| 274 | JBS-2810 | Ac-TGLVSAGWYDYNFDHYMFT-NH2 | 315 | JBS-2851 | Ac-TGLVSAGWYDYNFDHYREQT-NH2 |
| 275 | JBS-2811 | Ac-TGLVSAGWYDYNFDHYRMFT-NH2 | 316 | JBS-2852 | Ac-TGLVSAGWYDYNFDHYREFQ-NH2 |
| 276 | JBS-2812 | Ac-TGLVSAGWYDYNFDHYREMT-NH2 | 317 | JBS-2853 | Ac-TGLVSAGWYDYNFDHYREFT-NH2 |
| 277 | JBS-2813 | Ac-TGLVSAGWYDYNFDHYREFM-NH2 | 318 | JBS-2854 | Ac-RGLVSAGWYDYNFDHYREFT-NH2 |
| 278 | JBS-2814 | Ac-NGLVSAGWYDYNFDHYREFT-NH2 | 319 | JBS-2855 | Ac-TRLVSAGWYDYNFDHYREFT-NH2 |
| 279 | JBS-2815 | Ac-TNLVSAGWYDYNFDHYREFT-NH2 | 320 | JBS-2856 | Ac-TGRVSAGWYDYNFDHYREFT-NH2 |
| 280 | JBS-2816 | Ac-TGNVSAGWYDYNFDHYREFT-NH2 | 321 | JBS-2857 | Ac-TGLRSAGWYDYNFDHYREFT-NH2 |

FIGURE 2D

| SEQ ID | Compound | Sequence | SEQ ID | Compound | Sequence |
|---|---|---|---|---|---|
| 322 | JBS-2858 | Ac-TGLVSRGWYDYNFDHYREFT-NH2 | 363 | JBS-2899 | Ac-TGLVSAGWYDYNFDHYREFT-NH2 |
| 323 | JBS-2859 | Ac-TGLVSARWYDYNFDHYREFT-NH2 | 364 | JBS-2900 | Ac-TGLVSAGWYDYVFDHYREFT-NH2 |
| 324 | JBS-2860 | Ac-TGLVSAGRYDYNFDHYREFT-NH2 | 365 | JBS-2901 | Ac-TGLVSAGWYDYNVDHYREFT-NH2 |
| 325 | JBS-2861 | Ac-TGLVSAGWRDYNFDHYREFT-NH2 | 366 | JBS-2902 | Ac-TGLVSAGWYDYNFVHYREFT-NH2 |
| 326 | JBS-2862 | Ac-TGLVSAGWYRYNFDHYREFT-NH2 | 367 | JBS-2903 | Ac-TGLVSAGWYDYNFDVYREFT-NH2 |
| 327 | JBS-2863 | Ac-TGLVSAGWYDRNFDHYREFT-NH2 | 368 | JBS-2904 | Ac-TGLVSAGWYDYNFDHVREFT-NH2 |
| 328 | JBS-2864 | Ac-TGLVSAGWYDYRFDHYREFT-NH2 | 369 | JBS-2905 | Ac-TGLVSAGWYDYNFDHYVEFT-NH2 |
| 329 | JBS-2865 | Ac-TGLVSAGWYDYNRDHYREFT-NH2 | 370 | JBS-2906 | Ac-TGLVSAGWYDYNFDHYRVFT-NH2 |
| 330 | JBS-2866 | Ac-TGLVSAGWYDYNFRHYREFT-NH2 | 371 | JBS-2907 | Ac-TGLVSAGWYDYNFDHYREVT-NH2 |
| 331 | JBS-2867 | Ac-TGLVSAGWYDYNFDRYREFT-NH2 | 372 | JBS-2908 | Ac-TGLVSAGWYDYNFDHYREFV-NH2 |
| 332 | JBS-2868 | Ac-TGLVSAGWYDYNFDHRREFT-NH2 | 373 | JBS-2909 | Ac-WGLVSAGWYDYNFDHYREFT-NH2 |
| 333 | JBS-2869 | Ac-TGLVSAGWYDYNFDHYRRFT-NH2 | 374 | JBS-2910 | Ac-TWLVSAGWYDYNFDHYREFT-NH2 |
| 334 | JBS-2870 | Ac-TGLVSAGWYDYNFDHYRERT-NH2 | 375 | JBS-2911 | Ac-TGWVSAGWYDYNFDHYREFT-NH2 |
| 335 | JBS-2871 | Ac-TGLVSAGWYDYNFDHYREFR-NH2 | 376 | JBS-2912 | Ac-TGLWSAGWYDYNFDHYREFT-NH2 |
| 336 | JBS-2872 | Ac-TTLVSAGWYDYNFDHYREFT-NH2 | 377 | JBS-2913 | Ac-TGLVWAGWYDYNFDHYREFT-NH2 |
| 337 | JBS-2873 | Ac-TGTVSAGWYDYNFDHYREFT-NH2 | 378 | JBS-2914 | Ac-TGLVSWGWYDYNFDHYREFT-NH2 |
| 338 | JBS-2874 | Ac-TGLTSAGWYDYNFDHYREFT-NH2 | 379 | JBS-2915 | Ac-TGLVSAWWYDYNFDWYREFT-NH2 |
| 339 | JBS-2875 | Ac-TGLVTAGWYDYNFDHYREFT-NH2 | 380 | JBS-2916 | Ac-TGLVSAGWWDYNFDHYREFT-NH2 |
| 340 | JBS-2876 | Ac-TGLVSTGWYDYNFDHYREFT-NH2 | 381 | JBS-2917 | Ac-TGLVSAGWYWYNFDHYREFT-NH2 |
| 341 | JBS-2877 | Ac-TGLVSATWYDYNFDHYREFT-NH2 | 382 | JBS-2918 | Ac-TGLVSAGWYDWNFDHYREFT-NH2 |
| 342 | JBS-2878 | Ac-TGLVSAGTYDYNFDHYREFT-NH2 | 383 | JBS-2919 | Ac-TGLVSAGWYDYWFDHYREFT-NH2 |
| 343 | JBS-2879 | Ac-TGLVSAGWTDYNFDHYREFT-NH2 | 384 | JBS-2920 | Ac-TGLVSAGWYDYNWDHYREFT-NH2 |
| 344 | JBS-2880 | Ac-TGLVSAGWYTYNFDHYREFT-NH2 | 385 | JBS-2921 | Ac-TGLVSAGWYDYNFWHYREFT-NH2 |
| 345 | JBS-2881 | Ac-TGLVSAGWYDTNFDHYREFT-NH2 | 386 | JBS-2922 | Ac-TGLVSAGWYDYNFDWYREFT-NH2 |
| 346 | JBS-2882 | Ac-TGLVSAGWYDYTFDHYREFT-NH2 | 387 | JBS-2923 | Ac-TGLVSAGWYDYNFDHWREFT-NH2 |
| 347 | JBS-2883 | Ac-TGLVSAGWYDYNTDHYREFT-NH2 | 388 | JBS-2924 | Ac-TGLVSAGWYDYNFDHYWEFT-NH2 |
| 348 | JBS-2884 | Ac-TGLVSAGWYDYNFTHYREFT-NH2 | 389 | JBS-2925 | Ac-TGLVSAGWYDYNFDHYRWFT-NH2 |
| 349 | JBS-2885 | Ac-TGLVSAGWYDYNFDTYREFT-NH2 | 390 | JBS-2926 | Ac-TGLVSAGWYDYNFDHYREWT-NH2 |
| 350 | JBS-2886 | Ac-TGLVSAGWYDYNFDHTREFT-NH2 | 391 | JBS-2927 | Ac-TGLVSAGWYDYNFDHYREFW-NH2 |
| 351 | JBS-2887 | Ac-TGLVSAGWYDYNFDHYTEFT-NH2 | 392 | JBS-2928 | Ac-YGLVSAGWYDYNFDHYREFT-NH2 |
| 352 | JBS-2888 | Ac-TGLVSAGWYDYNFDHYRTFT-NH2 | 393 | JBS-2929 | Ac-TYLVSAGWYDYNFDHYREFT-NH2 |
| 353 | JBS-2889 | Ac-TGLVSAGWYDYNFDHYRETT-NH2 | 394 | JBS-2930 | Ac-TGYVSAGWYDYNFDHYREFT-NH2 |
| 354 | JBS-2890 | Ac-VGLVSAGWYDYNFDHYREFT-NH2 | 395 | JBS-2931 | Ac-TGLYSAGWYDYNFDHYREFT-NH2 |
| 355 | JBS-2891 | Ac-TVLVSAGWYDYNFDHYREFT-NH2 | 396 | JBS-2932 | Ac-TGLVYAGWYDYNFDHYREFT-NH2 |
| 356 | JBS-2892 | Ac-TGVVSAGWYDYNFDHYREFT-NH2 | 397 | JBS-2933 | Ac-TGLVSYGWYDYNFDHYREFT-NH2 |
| 357 | JBS-2893 | Ac-TGLVSAGYYDYNFDHYREFT-NH2 | 398 | JBS-2934 | Ac-TGLVSAYWYDYNFDHYREFT-NH2 |
| 358 | JBS-2894 | Ac-TGLVSAGWYYDYNFDHYREFT-NH2 | 399 | JBS-2935 | Ac-TGLVSAGYYDYNFDHYREFT-NH2 |
| 359 | JBS-2895 | Ac-TGLVSVGWYDYNFDHYREFT-NH2 | 400 | JBS-2936 | Ac-TGLVSAGWYYYNFDHYREFT-NH2 |
| 360 | JBS-2896 | Ac-TGLVSAVWYDYNFDHYREFT-NH2 | 401 | JBS-2937 | Ac-TGLVSAGWYDYYFDHYREFT-NH2 |
| 361 | JBS-2897 | Ac-TGLVSAGWVYDYNFDHYREFT-NH2 | 402 | JBS-2938 | Ac-TGLVSAGWYDYNYDHYREFT-NH2 |
| 362 | JBS-2898 | Ac-TGLVSAGWVYYNFDHYREFT-NH2 | 403 | JBS-2939 | Ac-TGLVSAGWYDYNFYHYREFT-NH2 |

FIGURE 2E

| SEQ ID | Compound | Sequence | SEQ ID | Compound | Sequence |
|---|---|---|---|---|---|
| 404 | JBS-2940 | Ac-TGLVSAGWYDYNFDYHYREFT-NH2 | 445 | JBS-3193 | Ac-TGLVEAGWYDYNFDVYREFT-NH2 |
| 405 | JBS-2941 | Ac-TGLVSAGWYDYNFDHYREFT-NH2 | 446 | JBS-3194 | Ac-TGLVSAGWYDYNNDTYREFT-NH2 |
| 406 | JBS-2942 | Ac-TGLVSAGWYDYNFDHYRFYT-NH2 | 447 | JBS-3195 | Ac-TGLVSAGWYDYNNDVYREFT-NH2 |
| 407 | JBS-2943 | Ac-TGLVSAGWYDYNFDHYREFY-NH2 | 448 | JBS-3196 | Ac-YGLVSAGWYDYNFDHYMEFT-NH2 |
| 408 | JBS-2944 | Ac-TGLVSAGWYDYNFDHYREFTC(NEM)-NH2 | 449 | JBS-3197 | Ac-TGLVEAGWYDYNFDHYMEFT-NH2 |
| 409 | JBS-3152 | Ac-TGLVSAGWYDYNFDHYREFTC(NEM)-NH2 | 450 | JBS-3198 | Ac-TGLVSAGWYDYNNDHYMEFT-NH2 |
| 410 | JBS-3153 | Ac-C(NEM)-TGLVSAGWYDYNFDHYREFT-NH2 | 451 | JBS-3199 | Ac-TGLVSAGWYDYNFD-Tle-YREFT-NH2 |
| 411 | JBS-3156 | Ac-[CGLVSAGWYC]DYNFDHYREFT-NH2 | 452 | JBS-3200 | Ac-TGLVSAGWYDYNFDHY-Nle-EFT-NH2 |
| 412 | JBS-3157 | Ac-[CGLVSAGWYDC]YNFDHYREFT-NH2 | 453 | JBS-3201 | Ac-YGLVSAGWYDYNNDTYMEFT-NH2 |
| 413 | JBS-3158 | Ac-[CGLVSAGWYDYC]NFDHYREFT-NH2 | 454 | JBS-3202 | Ac-TGL-Tle-SAGWYDYNFDTYREFT-NH2 |
| 414 | JBS-3159 | Ac-[CGLVSAGWYDYNC]FDHYREFT-NH2 | 455 | JBS-3203 | Ac-TGL-Tle-SAGWYDYNFDHYMEFT-NH2 |
| 415 | JBS-3160 | Ac-[CGLVSAGWYDYNFC]DHYREFT-NH2 | 456 | JBS-3204 | Ac-TGL-Tle-SAGWYDYNFDTYMEFT-NH2 |
| 416 | JBS-3161 | Ac-T[CLVSAGWYC]DYNFDHYREFT-NH2 | 457 | JBS-3205 | Ac-TGLVSAGWYDYNFDHYREFT-Bpa--NH2 |
| 417 | JBS-3162 | Ac-T[CLVSAGWYDC]YNFDHYREFT-NH2 | 458 | JBS-3206 | Ac-TGLVSAGWYDYNFDHYREFTC-NH2 |
| 418 | JBS-3163 | Ac-T[CLVSAGWYDYC]NFDHYREFT-NH2 | 459 | JBS-3207 | Ac-CTGLVSAGWYDYNFDHYREFT-NH2 |
| 419 | JBS-3164 | Ac-T[CLVSAGWYDYNC]FDHYREFT-NH2 | 460 | JBS-3208 | Ac-Bpa-TGLVSAGWYDYNFDHYREFT-NH2 |
| 420 | JBS-3165 | Ac-T[CLVSAGWYDYNFC]DHYREFT-NH2 | 461 | JBS-3215 | Ac-MEYVSAGWYDYNTDTYYEFE-NH2 |
| 421 | JBS-3166 | Ac-TGLV[CAGWYDYNC]DHYREFT-NH2 | 462 | JBS-3216 | Ac-EYYVSAGWYDYNTDTYYEFE-NH2 |
| 422 | JBS-3167 | Ac-TGLV[CSAGWYDYNC]FDHYREFT-NH2 | 463 | JBS-3217 | Ac-EYYVSAGWYDYNNDKYYEFE-NH2 |
| 423 | JBS-3168 | Ac-TGL[CSAGWYDYNC]DHYREFT-NH2 | 464 | JBS-3218 | Ac-EYYVSAGWYDYNNDIYYEFE-NH2 |
| 424 | JBS-3169 | Ac-TG[CLVSAGWYDYNC]DHYREFT-NH2 | 465 | JBS-3219 | Ac-EYYVSAGWYDYNKDTYEEEK-NH2 |
| 425 | JBS-3170 | Ac-[CGLVSAGWYDYNC]DHYREFT-NH2 | 466 | JBS-3220 | Ac-EYYVSAGWYDYNTDTYYEFY-NH2 |
| 426 | JBS-3171 | Ac-T[CLVSAGWYDYNC]DHYREFT-NH2 | 467 | JBS-3221 | Ac-YGLVSAGWYDYNTDTYYEFY-NH2 |
| 427 | JBS-3172 | Ac-T[CLVSAGWYDYNFDC]YREFT-NH2 | 468 | JBS-3222 | Ac-EGYVSAGWYDYNTDTYYEFE-NH2 |
| 428 | JBS-3173 | Ac-T[CLVSAGWYDYNFDC]YREFT-NH2 | 469 | JBS-3223 | Ac-ESYVSAGWYDYNTDTYYEFE-NH2 |
| 429 | JBS-3175 | Ac-CGLVSAGWYDYNFDCYREFT-NH2 | 470 | JBS-3224 | H-MEYVSAGWYDYNTDTYYEFE-NH2 |
| 430 | JBS-3176 | Ac-CCGLVSAGWYDYNFDCYREFT-NH2 | 471 | JBS-3225 | Ac-TGLVSAGWYDYNFDHYREFTC(Atf-Bio)-NH2 |
| 431 | JBS-3177 | Ac-TGLVSAGWYDYNCDHYREFT-NH2 | 472 | JBS-3226 | Ac-TGLVSAGWYDYNFDHYREFTC(Atf-LC-Bio)-NH2 |
| 432 | JBS-3178 | Ac-CGLVSAGWYDCYNFDHYREFT-NH2 | 473 | JBS-3227 | Ac-C(Atf-Bio)-TGLVSAGWYDYNFDHYREFT-NH2 |
| 433 | JBS-3179 | (Ac-TGLVSAGWYDYNFDHYREFTC-NH2)4-M4PEG4 | 474 | JBS-3228 | Ac-C(Atf-LC-Bio)-TGLVSAGWYDYNFDHYREFT-NH2 |
| 434 | JBS-3180 | Ac-GLVSAGWYDYNFDHYREF-NH2 | 475 | JBS-3229 | Ac-TGLVSAGWYDYNFDHYREFT-Bpa-K(Bio)-NH2 |
| 435 | JBS-3181 | Ac-GLVSAGWYDYNFDHYREF-NH2 | 476 | JBS-3230 | H-Bpa-TGLVSAGWYDYNFDHYREFT-NH2 |
| 436 | JBS-3182 | Ac-SGLVSAGWYDYNFDSYREFT-NH2 | 477 | JBS-3231 | Ac-EYYVSAGWYDYNTDTYYEFD-NH2 |
| 437 | JBS-3185 | Ac-YGLVSAGWYDYNFDVYTEFT-NH2 | 478 | JBS-3232 | Ac-EYYVTAGWYDYNTDTYYEFE-NH2 |
| 438 | JBS-3186 | Ac-YGLVSAGWYDYNFDTYREFT-NH2 | 479 | JBS-3233 | Ac-EYYVSAGWYDYNNDTYYEFE-NH2 |
| 439 | JBS-3187 | Ac-TGLVEAGWYDYNFDVIMEFT-NH2 | 480 | JBS-3234 | Ac-EYYVSAGWYDYNADTYYEFE-NH2 |
| 440 | JBS-3188 | Ac-TGLVSAGWYDYNFDVIYEFT-NH2 | 471 | JBS-3225 | Ac-TGLVSAGWYDYNFDHYREFTC(Atf-Bio)-NH2 |
| 441 | JBS-3189 | Ac-TGLVSAGWYDYNFDVYTEFT-NH2 | 472 | JBS-3226 | Ac-TGLVSAGWYDYNFDHYREFTC(Atf-LC-Bio)-NH2 |
| 442 | JBS-3190 | Ac-YGLVSAGWYDYNFDTYREFT-NH2 | 473 | JBS-3227 | Ac-C(Atf-Bio)-TGLVSAGWYDYNFDHYREFT-NH2 |
| 443 | JBS-3191 | Ac-YGLVSAGWYDYNFDTYREFT-NH2 | 474 | JBS-3228 | Ac-C(Atf-LC-Bio)-TGLVSAGWYDYNFDHYREFT-NH2 |
| 444 | JBS-3192 | Ac-TGLVEAGWYDYNFDTYREFT-NH2 | 475 | JBS-3229 | Ac-TGLVSAGWYDYNFDHYREFT-Bpa-K(Bio)-NH2 |

FIGURE 2F

| SEQ ID | Compound | Sequence |
|---|---|---|
| 476 | JBS-3230 | H--Bpa-TGLVSAGWYDYNFDHYREFT-NH2 |
| 477 | JBS-3231 | Ac-EYYVSAGWYDYNTDTYYEFD-NH2 |
| 478 | JBS-3232 | Ac-EYYVTAGWYDYNTDTYYEFE-NH2 |
| 479 | JBS-3233 | Ac-EYYVSAGWYDYNNDTYYEFE-NH2 |
| 480 | JBS-3234 | Ac-EYYVSAGWYDYNADTYYEFE-NH2 |
| 481 | JBS-3235 | Ac-EYYVSAGWYDYMTDTYEFE-NH2 |
| 482 | JBS-3236 | Ac-EYYVEAGWYEYNTDNYYPFE-NH2 |
| 483 | JBS-3237 | Ac-EYYVSAGWYDYNTDKYYEFI-NH2 |
| 484 | JBS-3238 | Ac-EYYVSAGWYDYNTDRYYEFY-NH2 |
| 485 | JBS-3239 | Ac-EYYVSAGWYDTNNDRYYEFI-NH2 |
| 486 | JBS-3240 | Ac-EYYVSAGWYDYNNDIYYEFY-NH2 |
| 487 | JBS-3241 | Ac-EYYVSAGWYDYNNDIYLEFE-NH2 |
| 488 | JBS-3242 | Ac-EYYVSAGWHDYNKDIYFEFF-NH2 |
| 489 | JBS-3243 | Ac-EYYVSAGWYDYNNDTYNEFW-NH2 |
| 490 | JBS-3244 | Ac-EYYVSAGWYDYNSDITYEFI-NH2 |
| 491 | JBS-3245 | Ac-EYYVSAGWYDYNSDTYFEFI-NH2 |
| 492 | JBS-3246 | Ac-EYYVSAGWYDYEHDTYLEFY-NH2 |
| 493 | JBS-3247 | Ac-EYYVSAGWYNYEEDSYYEFE-NH2 |
| 494 | JBS-3248 | Ac-EYYVSAGWYDYNDVYTEFE-NH2 |
| 495 | JBS-3249 | Ac-EQYVSAGWYEYNTDTYYEFD-NH2 |
| 496 | JBS-3250 | Ac-EYYVSAGWYEYNTDTYYEFD-NH2 |
| 497 | JBS-3251 | Ac-QYYVVAGWYGYNNDRYYEFW-NH2 |
| 498 | JBS-3252 | Ac-EYYVSAGWYDMNNDTSYYEFD-NH2 |
| 499 | JBS-3253 | Ac-EYYVSAGWYDMNRDTYTEFY-NH2 |
| 500 | JBS-3254 | Ac-EYTVSAGWYNYNADEYYEFE-NH2 |
| 501 | JBS-3255 | Ac-EYTISAGWYDYNTDMYYEFY-NH2 |
| 502 | JBS-3256 | Ac-EYTASAGWYDYNSDTYYEFE-NH2 |
| 503 | JBS-3257 | Ac-YGIVEAGWYEYNTDEYIEFW-NH2 |
| 504 | JBS-3258 | Ac-YGIVSAGWYEYNTDIYYEEFW-NH2 |
| 505 | JBS-3259 | Ac-YGIVSAGWYDMNNDYFEFY-NH2 |
| 506 | JBS-3260 | Ac-EGYVSAGWYDYNKDIYLEFY-NH2 |
| 507 | JBS-3261 | Ac-EGYVSAGWYDYNQDIYFEFA-NH2 |
| 508 | JBS-3262 | Ac-ESYVSAGWYDYNIDAYYEFY-NH2 |
| 509 | JBS-3263 | Ac-ESYVSAGWYDYNTDVYYEFE-NH2 |
| 510 | JBS-3264 | Ac-EYIVTAGWYDYNKDIYYEFK-NH2 |
| 511 | JBS-3265 | Ac-EYIVEAGWYDINEDKYLEFY-NH2 |
| 512 | JBS-3266 | Ac-EYSVSAGWYDYNTDVYYEFY-NH2 |
| 513 | JBS-3267 | Ac-EYSVSAGWYDYNTDEYYEFF-NH2 |
| 514 | JBS-3268 | Ac-ESIVSAGWYDYNTDTYYEFT-NH2 |
| 515 | JBS-3269 | Ac-FGIVSAGWYDYNEDAYSEFY-NH2 |
| 516 | JBS-3270 | Ac-FGIISAGWYDYNEDAYSEFY-NH2 |
| 517 | JBS-3271 | Ac-FEYVSAGWYDYNTDTYYEFY-NH2 |
| 518 | JBS-3272 | Ac-FEYVIAGWYDYNTDTYHEFN-NH2 |
| 519 | JBS-3273 | Ac-SAIVSAGWYDYNKDVYFEFE-NH2 |
| 520 | JBS-3274 | Ac-EVIVSAGWYDYNNDIYYEFW-NH2 |
| 521 | JBS-3275 | Ac-EVIVSAGWYDYNNDTYYEFG-NH2 |
| 522 | JBS-3276 | Ac-EAMVSAGWYDYNDDKYYEFG-NH2 |
| 523 | JBS-3277 | Ac-EYEVSAGWYDYNNDVYNEFY-NH2 |
| 524 | JBS-3278 | Ac-EYFVSAGWYDYNADIYYEFD-NH2 |
| 525 | JBS-3279 | Ac-YNIVSAGWYDYNKDIYYEFF-NH2 |
| 526 | JBS-3280 | Ac-YNEVSAGWYDMNEDTYYEFY-NH2 |
| 527 | JBS-3281 | Ac-YYEVSAGWYDYNTDTYSEFW-NH2 |
| 528 | JBS-3282 | Ac-EVEVSAGWYEYNTDTYYEFW-NH2 |
| 529 | JBS-3283 | Ac-AIYVTAGWYDYNNDTYYEFT-NH2 |
| 530 | JBS-3284 | Ac-HIYVTAGWYDYNTDTYHEFE-NH2 |
| 531 | JBS-3285 | Ac-RIYVSAGWYDIIQDTYFEFY-NH2 |
| 532 | JBS-3286 | Ac-NYIVSAGWYDYNNDEYIEFY-NH2 |
| 533 | JBS-3287 | Ac-EVVVSAGWYNYNEDAYYEFW-NH2 |
| 534 | JBS-3288 | Ac-DVYVSAGWYDYNEDTYYEFS-NH2 |
| 535 | JBS-3289 | Ac-NMVVSAGWYNYNEDTYEEFY-NH2 |
| 536 | JBS-3290 | Ac-NMEVSAGWYDYNSDTYHEFW-NH2 |
| 537 | JBS-3291 | Ac-EAIVSIGWYDYNKDEYYEFY-NH2 |
| 538 | JBS-3292 | Ac-EFIVSAGWYDYNKDTYIEFE-NH2 |
| 539 | JBS-3293 | Ac-EAMVSAGWYDYMNDTYYEFE-NH2 |
| 540 | JBS-3294 | Ac-EHIVSAGWYDYNMDEYYEFW-NH2 |
| 541 | JBS-3295 | Ac-DDEVSIGWYDYNTDEYYEFW-NH2 |
| 542 | JBS-3296 | Ac-DVHVSAGWYDYNKDIYYEFT-NH2 |
| 543 | JBS-3297 | Ac-DNIVSAGWYDYNTDTYEFY-NH2 |
| 544 | JBS-3298 | Ac-VIEVSAGWYDYNEDKYYEFW-NH2 |
| 545 | JBS-3299 | Ac-VFIVSAGWYDYNDDKYYEFW-NH2 |
| 546 | JBS-3300 | Ac-KVEVSAGWYDYNKDVYYEFE-NH2 |
| 547 | JBS-3301 | Ac-KDKVSAGWYDYNSDTYYEFT-NH2 |
| 548 | JBS-3302 | Ac-IIMVSAGWYDYNTDTYYEFE-NH2 |
| 549 | JBS-3303 | Ac-ITHVTAGWYDYNTDTYYEFI-NH2 |
| 550 | JBS-3304 | Ac-VIEVSAGWYDYNEDKYYEFW-NH2 |
| 551 | JBS-3305 | Ac-VF1VSAGWYDYNDDKYYEFW-NH2 |
| 552 | JBS-3306 | Ac-AYIVEAGWYDYNTDTYEFW-NH2 |
| 553 | JBS-3307 | Ac-HWVSAGWYDYNEDKYYEFE-NH2 |
| 554 | JBS-3308 | Ac-HYNVSAGWYDYNTDTYYEFY-NH2 |
| 555 | JBS-3309 | Ac-WYEVEIGWYDYNTDTYQEFY-NH2 |
| 556 | JBS-3310 | Ac-YVTVSAGWYDYNKDEYYEFY-NH2 |
| 557 | JBS-3311 | Ac-NFIVSAGWYDYNTDTYYEFQ-NH2 |

FIGURE 2G

| SEQ ID | Compound | Sequence | SEQ ID | Compound | Sequence |
|---|---|---|---|---|---|
| 558 | JBS-3312 | Ac-EYYVSAGWYDYNTDTYYEF-NH2 | 599 | JBS-3353 | Ac-EYYVSCGWYDYNTDTYYEFE-NH2 |
| 559 | JBS-3313 | Ac-EYYVSAGWYDYNTDTYYEFN-NH2 | 600 | JBS-3354 | Ac-EYYVSACWYDYNTDTYYEFE-NH2 |
| 560 | JBS-3314 | Ac-EYYVSAGWYDYNTDTYYEFT-NH2 | 601 | JBS-3355 | Ac-EYYVSAGCYDYNTDTYYEFE-NH2 |
| 561 | JBS-3315 | Ac-TGLvSAGWYDYNFDHYREFT-C(MalCy5)-NH2 | 602 | JBS-3356 | Ac-EYYVSAGWCDYNTDTYYEFE-NH2 |
| 562 | JBS-3316 | Bio-Ttds-EYYVSAGWYDYNTDTYYEFE-NH2 | 603 | JBS-3357 | Ac-EYYVSAGWYCYNTDTYYEFE-NH2 |
| 563 | JBS-3317 | Ac-EYY-Tle-GAGWYDYNTDTYYEFE-NH2 | 604 | JBS-3358 | Ac-EYYVSAGWYDCNTDTYYEFE-NH2 |
| 564 | JBS-3318 | Ac-EYYVSAGWYDYNTDTYYEFEC(ME-400MA)-NH2 | 605 | JBS-3359 | Ac-EYYVSAGWYDYCTDTYYEFE-NH2 |
| 565 | JBS-3319 | Ac-EYYVSAGWYDYNTDTYYEFEC-NH2 | 606 | JBS-3360 | Ac-EYYVSAGWYDYNCDTYYEFE-NH2 |
| 566 | JBS-3320 | Ac-EYYVSAGWYDYNTDTYYEFE-C(NEM)--NH2 | 607 | JBS-3361 | Ac-EYYVSAGWYDYNTCTYYEFE-NH2 |
| 567 | JBS-3321 | (Ac-EYYVSAGWYDYNTDTYYEFE-NH2)4-M4PEG1 | 608 | JBS-3362 | Ac-EYYVSAGWYDYNTDCYYEFE-NH2 |
| 568 | JBS-3322 | Ac-EYYVTAGWYDYNKDIYYEFC(ME-400MA)-NH2 | 609 | JBS-3363 | Ac-EYYVSAGWYDYNTDTCYEFE-NH2 |
| 569 | JBS-3323 | Ac-YAEYGYSVWDEEYNYTYFD-NH2 | 610 | JBS-3364 | Ac-EYYVSAGWYDYNTDTYCEFE-NH2 |
| 570 | JBS-3324 | Ac-YWYTDEDVYEFSYNYATYEG-NH2 | 611 | JBS-3365 | Ac-EYYVSAGWYDYNTDTYYCFE-NH2 |
| 571 | JBS-3325 | Ac-EYYVSAGWYDYNTDTYYEFE-K(Ac)--NH2 | 612 | JBS-3366 | Ac-EYYVSAGWYDYNTDTYYECE-NH2 |
| 572 | JBS-3326 | Ac--Ahx-EYYVSAGWYDYNTDTYYEFE-K(Ac)--NH2 | 613 | JBS-3367 | Ac-EYYVSAGWYDCNTDTYYEFC-NH2 |
| 573 | JBS-3327 | Ac-EYYVSAGWYDYNTDTYYEFE-C(FeBABE)--NH2 | 614 | JBS-3368 | Ac-DYYVSAGWYDYNTDTYYEFE-NH2 |
| 574 | JBS-3328 | Ac-YAEYGYSVWDEEYNYTYFD-C(FeBABE)--NH2 | 615 | JBS-3369 | Ac-EDYVSAGWYDYNTDTYYEFE-NH2 |
| 575 | JBS-3329 | Ac-EYYVSAGWYDYNTDTYYEFE-K(TtdsMal)--NH2 | 616 | JBS-3370 | Ac-EYDVSAGWYDYNTDTYYEFE-NH2 |
| 576 | JBS-3330 | Ac-AYYVSAGWYDYNTDTYYEFE-NH2 | 617 | JBS-3371 | Ac-EYYDSAGWYDYNTDTYYEFE-NH2 |
| 577 | JBS-3331 | Ac-EAVVSAGWYDYNTDTYYEFE-NH2 | 618 | JBS-3372 | Ac-EYYVDAGWYDYNTDTYYEFE-NH2 |
| 578 | JBS-3332 | Ac-EYAVSAGWYDYNTDTYYEFE-NH2 | 619 | JBS-3373 | Ac-EYYVSDGWYDYNTDTYYEFE-NH2 |
| 579 | JBS-3333 | Ac-EYYASAGWYDYNTDTYYEFE-NH2 | 620 | JBS-3374 | Ac-EYYVSAGDYDYNTDTYYEFE-NH2 |
| 580 | JBS-3334 | Ac-EYYVAAGWYDYNTDTYYEFE-NH2 | 621 | JBS-3375 | Ac-EYYVSAGWDDYNTDTYYEFE-NH2 |
| 581 | JBS-3335 | Ac-EYYVSAAWYDYNTDTYYEFE-NH2 | 622 | JBS-3376 | Ac-EYYVSAGWYDDNTDTYYEFE-NH2 |
| 582 | JBS-3336 | Ac-EYYVSAGAYDYNTDTYYEFE-NH2 | 623 | JBS-3377 | Ac-EYYVSAGWYDYDTDTYYEFE-NH2 |
| 583 | JBS-3337 | Ac-EYYVSAGWADYNTDTYYEFE-NH2 | 624 | JBS-3378 | Ac-EYYVSAGWYDYNDDTYYEFE-NH2 |
| 584 | JBS-3338 | Ac-EYYVSAGWYANTDTYYEFE-NH2 | 625 | JBS-3379 | Ac-EYYVSAGWYDYNTDDYYEFE-NH2 |
| 585 | JBS-3339 | Ac-EYYVSAGWYDANTDTYYEFE-NH2 | 626 | JBS-3380 | Ac-EYYVSAGWYDYNTDTDYEFE-NH2 |
| 586 | JBS-3340 | Ac-EYYVSAGWYDAIDTYYEFE-NH2 | 627 | JBS-3381 | Ac-EYYVSAGWYDYNTDTYDEFE-NH2 |
| 587 | JBS-3341 | Ac-EYYVSAGWYDYNTATYYEFE-NH2 | 628 | JBS-3382 | Ac-EYYVSAGWYDYNTDTYYDFE-NH2 |
| 588 | JBS-3342 | Ac-EYYVSAGWYDYNTDAYYEFE-NH2 | 629 | JBS-3383 | Ac-EYYVSAGWYDYNTDTYYEDE-NH2 |
| 589 | JBS-3343 | Ac-EYYVSAGWYDYNTDTAYEFE-NH2 | 630 | JBS-3384 | Ac-EYYVSAGWYDYNTDTYYEFD-NH2 |
| 590 | JBS-3344 | Ac-EYYVSAGWYDYNTDTYABFE-NH2 | 631 | JBS-3385 | Ac-EEYVSAGWYDYNTDTYYEFE-NH2 |
| 591 | JBS-3345 | Ac-EYYVSAGWYDYNTDTYYAFE-NH2 | 632 | JBS-3386 | Ac-EYEVSAGWYDYNTDTYYEFE-NH2 |
| 592 | JBS-3346 | Ac-EYYVSAGWYDYNTDTYYEAE-NH2 | 633 | JBS-3387 | Ac-EYYESAGWYDYNTDTYYEFE-NH2 |
| 593 | JBS-3347 | Ac-EYYVSAGWYDYNTDTYYEFA-NH2 | 634 | JBS-3388 | Ac-EYYVEAGWYDYNTDTYYEFE-NH2 |
| 594 | JBS-3348 | Ac-CYYVSAGWYDYNTDTYYEFE-NH2 | 635 | JBS-3389 | Ac-EYYVSEGWYDYNTDTYYEFE-NH2 |
| 595 | JBS-3349 | Ac-ECYVSAGWYDYNTDTYYEFE-NH2 | 636 | JBS-3390 | Ac-EYYVSAEWYDYNTDTYYEFE-NH2 |
| 596 | JBS-3350 | Ac-EYCVSAGWYDYNTDTYYEFE-NH2 | 637 | JBS-3391 | Ac-EYYVSAGEYDYNTDTYYEFE-NH2 |
| 597 | JBS-3351 | Ac-EYYCSAGWYDYNTDTYYEFE-NH2 | 638 | JBS-3392 | Ac-EYYVSAGWEDYNTDTYYEFE-NH2 |
| 598 | JBS-3352 | Ac-EYYVCAGWYDYNTDTYYEFE-NH2 | 639 | JBS-3393 | Ac-EYYVSAGWYENTDTYYEFE-NH2 |

FIGURE 2H

| SEQ ID | Compound | Sequence | SEQ ID | Compound | Sequence |
|---|---|---|---|---|---|
| 640 | JBS-3394 | Ac-EYYVSAGWYDENTDTYYEFE-NH2 | 681 | JBS-3435 | Ac-EYYVSAGWYDYNTDTYYEFE-NH2 |
| 641 | JBS-3395 | Ac-EYYVSAGWYDYETDTYYEFE-NH2 | 682 | JBS-3436 | Ac-EYYVSAGWYDYNTDTYYGFE-NH2 |
| 642 | JBS-3396 | Ac-EYYVSAGWYDYNEDTYYEFE-NH2 | 683 | JBS-3437 | Ac-EYYVSAGWYDYNTDTYYGE-NH2 |
| 643 | JBS-3397 | Ac-EYYVSAGWYDYNTETYYEFE-NH2 | 684 | JBS-3438 | Ac-EYYVSAGWYDYNTDTYYEFG-NH2 |
| 644 | JBS-3398 | Ac-EYYVSAGWYDYNTDEYYEFE-NH2 | 685 | JBS-3439 | Ac-HYYVSAGWYDYNTDTYYEFE-NH2 |
| 645 | JBS-3399 | Ac-EYYVSAGWYDYNTDTEYEFE-NH2 | 686 | JBS-3440 | Ac-EHYVSAGWYDYNTDTYYEFE-NH2 |
| 646 | JBS-3400 | Ac-EYYVSAGWYDYNTDTYEEFE-NH2 | 687 | JBS-3441 | Ac-EYHVSAGWYDYNTDTYYEFE-NH2 |
| 647 | JBS-3401 | Ac-EYYVSAGWYDYNTDTYYEEE-NH2 | 688 | JBS-3442 | Ac-EYYHSAGWYDYNTDTYYEFE-NH2 |
| 648 | JBS-3402 | Ac-EYYVSAGWYDYNTDTYYEFE-NH2 | 689 | JBS-3443 | Ac-EYVHAGWYDYNTDTYYEFE-NH2 |
| 649 | JBS-3403 | Ac-EYYVSAGWYDYNTDTYYEFE-NH2 | 690 | JBS-3444 | Ac-EYYVSHGWYDYNTDTYYEFE-NH2 |
| 650 | JBS-3404 | Ac-EYFVSAGWYDYNTDTYYEFE-NH2 | 691 | JBS-3445 | Ac-EYYVSAHWYDYNTDTYYEFE-NH2 |
| 651 | JBS-3405 | Ac-EYYFSAGWYDYNTDTYYEFE-NH2 | 692 | JBS-3446 | Ac-EYYVSAGHYDYNTDTYYEFE-NH2 |
| 652 | JBS-3406 | Ac-EYYVFAGWYDYNTDTYYEFE-NH2 | 693 | JBS-3447 | Ac-EYYVSAGWHDYNTDTYYEFE-NH2 |
| 653 | JBS-3407 | Ac-EYYVSFGWYDYNTDTYYEFE-NH2 | 694 | JBS-3448 | Ac-EYYVSAGWYHYNTDTYYEFE-NH2 |
| 654 | JBS-3408 | Ac-EYYVSAFWYDYNTDTYYEFE-NH2 | 695 | JBS-3449 | Ac-EYYVSAGWYDHNTDTYYEFE-NH2 |
| 655 | JBS-3409 | Ac-EYYVSAGFYDYNTDTYYEFE-NH2 | 696 | JBS-3450 | Ac-EYYVSAGWYDYHTDTYYEFE-NH2 |
| 656 | JBS-3410 | Ac-EYYVSAGWFDYNTDTYYEFE-NH2 | 697 | JBS-3451 | Ac-EYYVSAGWYDYNHDTYYEFE-NH2 |
| 657 | JBS-3411 | Ac-EYYVSAGWYFYNTDTYYEFE-NH2 | 698 | JBS-3452 | Ac-EYYVSAGWYDYNTHTYYEFE-NH2 |
| 658 | JBS-3412 | Ac-EYYVSAGWYDFNTDTYYEFE-NH2 | 699 | JBS-3453 | Ac-EYYVSAGWYDYNTDHYYEFE-NH2 |
| 659 | JBS-3413 | Ac-EYYVSAGWYDYFTDTYYEFE-NH2 | 700 | JBS-3454 | Ac-EYYVSAGWYDYNTDTHYEFE-NH2 |
| 660 | JBS-3414 | Ac-EYYVSAGWYDYNFDTYYEFE-NH2 | 701 | JBS03455 | Ac-EYYVSAGWYDYNTDTYHFE-NH2 |
| 661 | JBS-3415 | Ac-EYYVSAGWYDYNTFTYYEFE-NH2 | 702 | JBS-3456 | Ac-EYYVSAGWYDYNTDTYYHFE-NH2 |
| 662 | JBS-3416 | Ac-EYYVSAGWYDYNTDFYYEFE-NH2 | 703 | JBS-3457 | Ac-EYYVSAGWYDYNTDTYYEHE-NH2 |
| 663 | JBS-3417 | Ac-EYYVSAGWYDYNTDTFYEFE-NH2 | 704 | JBS-3458 | Ac-EYYVSAGWYDYNTDTYYEFH-NH2 |
| 664 | JBS-3418 | Ac-EYYVSAGWYDYNTDTYFEFE-NH2 | 705 | JBS-3459 | Ac-IYYVSAGWYDYNTDTYYEFE-NH2 |
| 665 | JBS-3419 | Ac-EYYVSAGWYDYNTDTYYFFE-NH2 | 706 | JBS-3460 | Ac-EIYVSAGWYDYNTDTYYEFE-NH2 |
| 666 | JBS-3420 | Ac-EYYVSAGWYDYNTDTYYEFF-NH2 | 707 | JBS-3461 | Ac-EYIVSAGWYDYNTDTYYEFE-NH2 |
| 667 | JBS-3421 | Ac-GYYVSAGWYDYNTDTYYEFE-NH2 | 708 | JBS-3462 | Ac-EYYISAGWYDYNTDTYYEFE-NH2 |
| 668 | JBS-3422 | Ac-EYGVSAGWYDYNTDTYYEFE-NH2 | 709 | JBS-3463 | Ac-EYYVIAGWYDYNTDTYYEFE-NH2 |
| 669 | JBS-3423 | Ac-EYYGSAGWYDYNTDTYYEFE-NH2 | 710 | JBS-3464 | Ac-EYYVSIGWYDYNTDTYYEFE-NH2 |
| 670 | JBS-3424 | Ac-EYYVGAGWYDYNTDTYYEFE-NH2 | 711 | JBS-3465 | Ac-EYYVSAIWYDYNTDTYYEFE-NH2 |
| 671 | JBS-3425 | Ac-EYYVSGGWYDYNTDTYYEFE-NH2 | 712 | JBS-3466 | Ac-EYYVSAGIYDYNTDTYYEFE-NH2 |
| 672 | JBS-3426 | Ac-EYYVSAGGYDYNTDTYYEFE-NH2 | 713 | JBS-3467 | Ac-EYYVSAGWIDYNTDTYYEFE-NH2 |
| 673 | JBS-3427 | Ac-EYYVSAGWGDYNTDTYYEFE-NH2 | 714 | JBS-3468 | Ac-EYYVSAGWYIYNTDTYYEFE-NH2 |
| 674 | JBS-3428 | Ac-EYYVSAGWYGYNTDTYYEFE-NH2 | 715 | JBS-3469 | Ac-EYYVSAGWYDINTDTYYEFE-NH2 |
| 675 | JBS-3429 | Ac-EYYVSAGWYDGNTDTYYEFE-NH2 | 716 | JBS-3470 | Ac-EYYVSAGWYDYITDTYYEFE-NH2 |
| 676 | JBS-3430 | Ac-EYYVSAGWYDYGTDTYYEFE-NH2 | 717 | JBS-3471 | Ac-EYYVSAGWYDYNIDTYYEFE-NH2 |
| 677 | JBS-3431 | Ac-EYYVSAGWYDYNGDTYYEFE-NH2 | 718 | JBS-3472 | Ac-EYYVSAGWYDYNTITYYEFE-NH2 |
| 678 | JBS-3432 | Ac-EYYVSAGWYDYNTGTYYEFE-NH2 | 719 | JBS-3473 | Ac-EYYVSAGWYDYNTDIYYEFE-NH2 |
| 679 | JBS-3433 | Ac-EYYVSAGWYDYNTDGYYEFE-NH2 | 720 | JBS-3474 | Ac-EYYVSAGWYDYNTDTIYEFE-NH2 |
| 680 | JBS-3434 | Ac-EYYVSAGWYDYNTDTGYEFE-NH2 | 721 | JBS-3475 | Ac-EYYVSAGWYDYNTDTYIEFE-NH2 |

FIGURE 21

| SEQ ID | Compound | Sequence | SEQ ID | Compound | Sequence |
|---|---|---|---|---|---|
| 722 | JBS-3476 | Ac-EYYVSAGWYDYNTDTYYIFE-NH2 | 763 | JBS-3517 | Ac-EYYVSAGWYDYNTDTYYELE-NH2 |
| 723 | JBS-3477 | Ac-EYYVSAGWYDYNTDTYYEIE-NH2 | 764 | JBS-3518 | Ac-EYYVSAGWYDYNTDTYYEFL-NH2 |
| 724 | JBS-3478 | Ac-EYYVSAGWYDYNTDTYYEFI-NH2 | 765 | JBS-3519 | Ac-MYYVSAGWYDYNTDTYYEFE-NH2 |
| 725 | JBS-3479 | Ac-KYYVSAGWYDYNTDTYYEFE-NH2 | 766 | JBS-3520 | Ac-EMYVSAGWYDYNTDTYYEFE-NH2 |
| 726 | JBS-3480 | Ac-EKYVSAGWYDYNTDTYYEFE-NH2 | 767 | JBS-3521 | Ac-EYMVSAGWYDYNTDTYYEFE-NH2 |
| 727 | JBS-3481 | Ac-EYKVSAGWYDYNTDTYYEFE-NH2 | 768 | JBS-3522 | Ac-EYYMSAGWYDYNTDTYYEFE-NH2 |
| 728 | JBS-3482 | Ac-EYYKSAGWYDYNTDTYYEFE-NH2 | 769 | JBS-3523 | Ac-EYYVMAGWYDYNTDTYYEFE-NH2 |
| 729 | JBS-3483 | Ac-EYYVKAGWYDYNTDTYYEFE-NH2 | 770 | JBS-3524 | Ac-EYYVSMGWYDYNTDTYYEFE-NH2 |
| 730 | JBS-3484 | Ac-EYYVSKGWYDYNTDTYYEFE-NH2 | 771 | JBS-3525 | Ac-EYYVSAMWYDYNTDTYYEFE-NH2 |
| 731 | JBS-3485 | Ac-EYYVSAKWYDYNTDTYYEFE-NH2 | 772 | JBS-3526 | Ac-EYYVSAGMYDYNTDTYYEFE-NH2 |
| 732 | JBS-3486 | Ac-EYYVSAGKYDYNTDTYYEFE-NH2 | 773 | JBS-3527 | Ac-EYYVSAGWMDYNTDTYYEFE-NH2 |
| 733 | JBS-3487 | Ac-EYYVSAGWKDYNTDTYYEFE-NH2 | 774 | JBS-3528 | Ac-EYYVSAGWYMYNTDTYYEFE-NH2 |
| 734 | JBS-3488 | Ac-EYYVSAGWYKYNTDTYYEFE-NH2 | 775 | JBS-3529 | Ac-EYYVSAGWYDMNTDTYYEFE-NH2 |
| 735 | JBS-3489 | Ac-EYYVSAGWYDKNTDTYYEFE-NH2 | 776 | JBS-3530 | Ac-EYYVSAGWYDYMTDTYYEFE-NH2 |
| 736 | JBS-3490 | Ac-EYYVSAGWYDYKTDTYYEFE-NH2 | 777 | JBS-3531 | Ac-EYYVSAGWYDYNMDTYYEFE-NH2 |
| 737 | JBS-3491 | Ac-EYYVSAGWYDYNKDTYYEFE-NH2 | 778 | JBS-3532 | Ac-EYYVSAGWYDYNTMTYYEFE-NH2 |
| 738 | JBS-3492 | Ac-EYYVSAGWYDYNTKTYYEFE-NH2 | 779 | JBS-3533 | Ac-EYYVSAGWYDYNTDMYYEFE-NH2 |
| 739 | JBS-3493 | Ac-EYYVSAGWYDYNTDKYYEFE-NH2 | 780 | JBS-3534 | Ac-EYYVSAGWYDYNTDTMYEFE-NH2 |
| 740 | JBS-3494 | Ac-EYYVSAGWYDYNTDTKYEFE-NH2 | 781 | JBS-3535 | Ac-EYYVSAGWYDYNTDTYMEFE-NH2 |
| 741 | JBS-3495 | Ac-EYYVSAGWYDYNTDTYKEFE-NH2 | 782 | JBS-3536 | Ac-EYYVSAGWYDYNTDTYYMFE-NH2 |
| 742 | JBS-3496 | Ac-EYYVSAGWYDYNTDTYYKFE-NH2 | 783 | JBS-3537 | Ac-EYYVSAGWYDYNTDTYYEME-NH2 |
| 743 | JBS-3497 | Ac-EYYVSAGWYDYNTDTYYEKE-NH2 | 784 | JBS-3538 | Ac-EYYVSAGWYDYNTDTYYEFM-NH2 |
| 744 | JBS-3498 | Ac-EYYVSAGWYDYNTDTYYEFK-NH2 | 785 | JBS-3539 | Ac-NYYVSAGWYDYNTDTYYEFE-NH2 |
| 745 | JBS-3499 | Ac-LYYVSAGWYDYNTDTYYEFE-NH2 | 786 | JBS-3540 | Ac-ENYVSAGWYDYNTDTYYEFE-NH2 |
| 746 | JBS-3500 | Ac-ELYVSAGWYDYNTDTYYEFE-NH2 | 787 | JBS-3541 | Ac-EYNVSAGWYDYNTDTYYEFE-NH2 |
| 747 | JBS-3501 | Ac-EYLVSAGWYDYNTDTYYEFE-NH2 | 788 | JBS-3542 | Ac-EYYNSAGWYDYNTDTYYEFE-NH2 |
| 748 | JBS-3502 | Ac-EYYLSAGWYDYNTDTYYEFE-NH2 | 789 | JBS-3543 | Ac-EYYVNAGWYDYNTDTYYEFE-NH2 |
| 749 | JBS-3503 | Ac-EYYVLAGWYDYNTDTYYEFE-NH2 | 790 | JBS-3544 | Ac-EYYVSNGWYDYNTDTYYEFE-NH2 |
| 750 | JBS-3504 | Ac-EYYVSLGWYDYNTDTYYEFE-NH2 | 791 | JBS-3545 | Ac-EYYVSANWYDYNTDTYYEFE-NH2 |
| 751 | JBS-3505 | Ac-EYYVSALWYDYNTDTYYEFE-NH2 | 792 | JBS-3546 | Ac-EYYVSAGNYDYNTDTYYEFE-NH2 |
| 752 | JBS-3506 | Ac-EYYVSAGLYDYNTDTYYEFE-NH2 | 793 | JBS-3547 | Ac-EYYVSAGWNDYNTDTYYEFE-NH2 |
| 753 | JBS-3507 | Ac-EYYVSAGWLDYNTDTYYEFE-NH2 | 794 | JBS-3548 | Ac-EYYVSAGWYNYNTDTYYEFE-NH2 |
| 754 | JBS-3508 | Ac-EYYVSAGWYLYNTDTYYEFE-NH2 | 795 | JBS-3549 | Ac-EYYVSAGWYDNNTDTYYEFE-NH2 |
| 755 | JBS-3509 | Ac-EYYVSAGWYLNTDTYYEFE-NH2 | 796 | JBS-3550 | Ac-EYYVSAGWYDYNNTDTYYEFE-NH2 |
| 756 | JBS-3510 | Ac-EYYVSAGWYDLTDTYYEFE-NH2 | 797 | JBS-3551 | Ac-EYYVSAGWYDYNTDNYYEFE-NH2 |
| 757 | JBS-3511 | Ac-EYYVSAGWYDYLDTYYEFE-NH2 | 798 | JBS-3552 | Ac-EYYVSAGWYDYNTDTNYEFE-NH2 |
| 758 | JBS-3512 | Ac-EYYVSAGWYDYNLTYYEFE-NH2 | 799 | JBS-3553 | Ac-EYYVSAGWYDYNTDTYNEFE-NH2 |
| 759 | JBS-3513 | Ac-EYYVSAGWYDYNTLYYEFE-NH2 | 800 | JBS-3554 | Ac-EYYVSAGWYDYNTDTYYNFE-NH2 |
| 760 | JBS-3514 | Ac-EYYVSAGWYDYNTDLYEFE-NH2 | 801 | JBS-3555 | Ac-EYYVSAGWYDYNTDTYYENE-NH2 |
| 761 | JBS-3515 | Ac-EYYVSAGWYDYNTDTLEFE-NH2 | 802 | JBS-3556 | Ac-PYYVSAGWYDYNTDTYYEFE-NH2 |
| 762 | JBS-3516 | Ac-EYYVSAGWYDYNTDTYLFE-NH2 | 803 | JBS-3557 | Ac-EPYVSAGWYDYNTDTYYEFE-NH2 |

FIGURE 2J

| SEQ ID | Compound | Sequence | SEQ ID | Compound | Sequence |
|---|---|---|---|---|---|
| 804 | JBS-3558 | Ac-EYYVSAGWYDYNTDTYYEFE-NH2 | 845 | JBS-3599 | Ac-EYRSAGWYDYNTDTYYEFE-NH2 |
| 805 | JBS-3559 | Ac-EYPSAGWYDYNTDTYYEFE-NH2 | 846 | JBS-3600 | Ac-EYYVRAGWYDYNTDTYYEFE-NH2 |
| 806 | JBS-3560 | Ac-EYYVPAGWYDYNTDTYYEFE-NH2 | 847 | JBS-3601 | Ac-EYYVSRGWYDYNTDTYYEFE-NH2 |
| 807 | JBS-3561 | Ac-EYYVSPGWYDYNTDTYYEFE-NH2 | 848 | JBS-3602 | Ac-EYYVSARWYDYNTDTYYEFE-NH2 |
| 808 | JBS-3562 | Ac-EYYVSAPWYDYNTDTYYEFE-NH2 | 849 | JBS-3603 | Ac-EYYVSAGRYDYNTDTYYEFE-NH2 |
| 809 | JBS-3563 | Ac-EYYVSAGPYDYNTDTYYEFE-NH2 | 850 | JBS-3604 | Ac-EYYVSAGWRDYNTDTYYEFE-NH2 |
| 810 | JBS-3564 | Ac-EYYVSAGWPDYNTDTYYEFE-NH2 | 851 | JBS-3605 | Ac-EYYVSAGWYRYNTDTYYEFE-NH2 |
| 811 | JBS-3565 | Ac-EYYVSAGWYPYNTDTYYEFE-NH2 | 852 | JBS-3606 | Ac-EYYVSAGWYDRNTDTYYEFE-NH2 |
| 812 | JBS-3566 | Ac-EYYVSAGWYDPNTDTYYEFE-NH2 | 853 | JBS-3607 | Ac-EYYVSAGWYDYRTDTYYEFE-NH2 |
| 813 | JBS-3567 | Ac-EYYVSAGWYDYPTDTYYEFE-NH2 | 854 | JBS-3608 | Ac-EYYVSAGWYDYNRDTYYEFE-NH2 |
| 814 | JBS-3568 | Ac-EYYVSAGWYDYNPDTYYEFE-NH2 | 855 | JBS-3609 | Ac-EYYVSAGWYDYNTRTYYEFE-NH2 |
| 815 | JBS-3569 | Ac-EYYVSAGWYDYNTPTYYEFE-NH2 | 856 | JBS-3610 | Ac-EYYVSAGWYDYNTDRYYEFE-NH2 |
| 816 | JBS-3570 | Ac-EYYVSAGWYDYNTDPYYEFE-NH2 | 857 | JBS-3611 | Ac-EYYVSAGWYDYNTDTRYEFE-NH2 |
| 817 | JBS-3571 | Ac-EYYVSAGWYDYNTDTPYEFE-NH2 | 858 | JBS-3612 | Ac-EYYVSAGWYDYNTDTYREFE-NH2 |
| 818 | JBS-3572 | Ac-EYYVSAGWYDYNTDTYPEFE-NH2 | 859 | JBS-3613 | Ac-EYYVSAGWYDYNTDTYYRFE-NH2 |
| 819 | JBS-3573 | Ac-EYYVSAGWYDYNTDTYYPFE-NH2 | 860 | JBS-3614 | Ac-EYYVSAGWYDYNTDTYYERE-NH2 |
| 820 | JBS-3574 | Ac-EYYVSAGWYDYNTDTYYEPE-NH2 | 861 | JBS-3615 | Ac-EYYVSAGWYDYNTDTYYEFR-NH2 |
| 821 | JBS-3575 | Ac-EYYVSAGWYDYNTDTYYEFP-NH2 | 862 | JBS-3616 | Ac-SYYVSAGWYDYNTDTYYEFE-NH2 |
| 822 | JBS-3576 | Ac-QYYVSAGWYDYNTDTYYEFE-NH2 | 863 | JBS-3617 | Ac-ESYVSAGWYDYNSDTYYEFE-NH2 |
| 823 | JBS-3577 | Ac-EQYVSAGWYDYNTDTYYEFE-NH2 | 864 | JBS-3618 | Ac-EYSVSAGWYDYNTDTYYEFE-NH2 |
| 824 | JBS-3578 | Ac-EYQVSAGWQDYNTDTYYEFE-NH2 | 865 | JBS-3619 | Ac-EYYSSAGWYDYNTDTYYEFE-NH2 |
| 825 | JBS-3579 | Ac-EYYQSAGWYDYNTDTYYEFE-NH2 | 866 | JBS-3620 | Ac-EYYVSSGWYDYNTDTYYEFE-NH2 |
| 826 | JBS-3580 | Ac-EYYVQAGWYDQTDTYYEFE-NH2 | 867 | JBS-3621 | Ac-EYYVSAGSYDYNTDTYYEFE-NH2 |
| 827 | JBS-3581 | Ac-EYYVSAGWYQGWYDYNTDTYYEFE-NH2 | 868 | JBS-3622 | Ac-EYYVSAGWSDYNTDTYYEFE-NH2 |
| 828 | JBS-3582 | Ac-EYYVSAQWYDYNTDTYYEFE-NH2 | 869 | JBS-3623 | Ac-EYYVSAGWYSYNTDTYYEFE-NH2 |
| 829 | JBS-3583 | Ac-EYYVSAGQYDYNTDTYYEFE-NH2 | 870 | JBS-3624 | Ac-EYYVSAGWYSNTDTYYEFE-NH2 |
| 830 | JBS-3584 | Ac-EYYVSAGWQDYNTDTYYEFE-NH2 | 871 | JBS-3625 | Ac-EYYVSAGWYDYNSTDTYYEFE-NH2 |
| 831 | JBS-3585 | Ac-EYYVSAGWYDNTDTYYEFE-NH2 | 872 | JBS-3626 | Ac-EYYVSAGWYDYSTDTYYEFE-NH2 |
| 832 | JBS-3586 | Ac-EYYVSAGWYDQTDTYYEFE-NH2 | 873 | JBS-3627 | Ac-EYYVSAGWYDYNSDTYYEFE-NH2 |
| 833 | JBS-3587 | Ac-EYYVSAGWYDQTDTYYEFE-NH2 | 874 | JBS-3628 | Ac-EYYVSAGWYDYNTSYYEFE-NH2 |
| 834 | JBS-3588 | Ac-EYYVSAGWYDYNQDTYYEFE-NH2 | 875 | JBS-3629 | Ac-EYYVSAGWYDYNTDSYYEFE-NH2 |
| 835 | JBS-3589 | Ac-EYYVSAGWYDYNTDQYYEFE-NH2 | 876 | JBS-3630 | Ac-EYYVSAGWYDYNTDTSYEFE-NH2 |
| 836 | JBS-3590 | Ac-EYYVSAGWYDYNTDTQYEFE-NH2 | 877 | JBS-3631 | Ac-EYYVSAGWYDYNTDTYSFE-NH2 |
| 837 | JBS-3591 | Ac-EYYVSAGWYDYNTDTQEFE-NH2 | 878 | JBS-3632 | Ac-EYYVSAGWYDYNTDTYYSFE-NH2 |
| 838 | JBS-3592 | Ac-EYYVSAGWYDYNTDTYQEFE-NH2 | 879 | JBS-3633 | Ac-EYYVSAGWYDYNTDTYYESE-NH2 |
| 839 | JBS-3593 | Ac-EYYVSAGWYDYNTDTYYQFE-NH2 | 880 | JBS-3634 | Ac-EYYVSAGWYDYNTDTYYEFS-NH2 |
| 840 | JBS-3594 | Ac-EYYVSAGWYDYNTDTYYEQE-NH2 | 881 | JBS-3635 | Ac-TYYVSAGWYDYNTDTYYEFE-NH2 |
| 841 | JBS-3595 | Ac-EYYVSAGWYDYNTDTYYEFQ-NH2 | 882 | JBS-3636 | Ac-ETYVSAGWYDYNTDTYYEFE-NH2 |
| 842 | JBS-3596 | Ac-RYYVSAGWYDYNTDTYYEFE-NH2 | 883 | JBS-3637 | Ac-EYTVSAGWYDYNTDTYYEFE-NH2 |
| 843 | JBS-3597 | Ac-ERYVSAGWYDYNTDTYYEFE-NH2 | 884 | JBS-3638 | Ac-EYYTSAGWYDYNTDTYYEFE-NH2 |
| 844 | JBS-3598 | Ac-EYRVSAGWYDYNTDTYYEFE-NH2 | 885 | JBS-3639 | Ac-EYYVSTGWYDYNTDTYYEFE-NH2 |

FIGURE 2K

| SEQ ID | Compound | Sequence | SEQ ID | Compound | Sequence |
|---|---|---|---|---|---|
| 886 | JBS-3640 | Ac-EYYVSATWDYNTDTYYEFE-NH2 | 927 | JBS-3681 | Ac-EYYVSAGWYDYNWDTYYEFE-NH2 |
| 887 | JBS-3641 | Ac-EYYVSAGTYDYNTDTYYEFE-NH2 | 928 | JBS-3682 | Ac-EYYVSAGWYDYNTWTYYEFE-NH2 |
| 888 | JBS-3642 | Ac-EYYVSAGWTDYNTDTYYEFE-NH2 | 929 | JBS-3683 | Ac-EYYVSAGWYDYNTDWYYEFE-NH2 |
| 889 | JBS-3643 | Ac-EYYVSAGWYTYNTDTYYEFE-NH2 | 930 | JBS-3684 | Ac-EYYVSAGWYDYNTDTWEFE-NH2 |
| 890 | JBS-3644 | Ac-EYYVSAGWYDTNTDTYYEFE-NH2 | 931 | JBS-3685 | Ac-EYYVSAGWYDYNTDTYWEFE-NH2 |
| 891 | JBS-3645 | Ac-EYYVSAGWYDYTTDTYYEFE-NH2 | 932 | JBS-3686 | Ac-EYYVSAGWYDYNTDTYYWFE-NH2 |
| 892 | JBS-3646 | Ac-EYYVSAGWYDYNTTTYYEFE-NH2 | 933 | JBS-3687 | Ac-EYYVSAGWYDYNTDTYYEWE-NH2 |
| 893 | JBS-3647 | Ac-EYYVSAGWYDYNTDTYEFE-NH2 | 934 | JBS-3688 | Ac-EYYVSAGWYDYNTDTYYEFW-NH2 |
| 894 | JBS-3648 | Ac-EYYVSAGWYDYNTDTYYFFE-NH2 | 935 | JBS-3689 | Ac-YYYVSAGWYDYNTDTYYEFE-NH2 |
| 895 | JBS-3649 | Ac-EYYVSAGWYDYNTDTYYTFE-NH2 | 936 | JBS-3690 | Ac-EYYVSAGWYDYNTDTYYEFE-NH2 |
| 896 | JBS-3650 | Ac-EYYVSAGWYDYNTDTYYETE-NH2 | 937 | JBS-3691 | Ac-EYYVYAGWYDYNTDTYYEFE-NH2 |
| 897 | JBS-3651 | Ac-VYYVSAGWYDYNTDTYYEFE-NH2 | 938 | JBS-3692 | Ac-EYYVSYGWYDYNTDTYYEFE-NH2 |
| 898 | JBS-3652 | Ac-EYYVSAGWYDYNTDTYYEFE-NH2 | 939 | JBS-3693 | Ac-EYYVSAYWYDYNTDTYYEFE-NH2 |
| 899 | JBS-3653 | Ac-EYYVAGWYDYNTDTYYEFE-NH2 | 940 | JBS-3694 | Ac-EYYVSAGWYYDYNTDTYYEFE-NH2 |
| 900 | JBS-3654 | Ac-EYYVSAGWYDYNTDTYYEFE-NH2 | 941 | JBS-3695 | Ac-EYYVSAGWNYDYNTDTYYEFE-NH2 |
| 901 | JBS-3655 | Ac-EYYVSVGWYDYNTDTYYEFE-NH2 | 942 | JBS-3696 | Ac-EYYVSAGWYDYTDTYYEFE-NH2 |
| 902 | JBS-3656 | Ac-EYYVSAVWYDYNTDTYYEFE-NH2 | 943 | JBS-3697 | Ac-EYYVSAGWYDYNYDTYYEFE-NH2 |
| 903 | JBS-3657 | Ac-EYYVSAGVYDYNTDTYYEFE-NH2 | 944 | JBS-3698 | Ac-EYYVSAGWYDYNTYTYYEFE-NH2 |
| 904 | JBS-3658 | Ac-EYYVSAGWVDYNTDTYYEFE-NH2 | 945 | JBS-3699 | Ac-EYYVSAGWYDYNTDYYYEFE-NH2 |
| 905 | JBS-3659 | Ac-EYYVSAGWYVYNTDTYYEFE-NH2 | 946 | JBS-3700 | Ac-EYYVSAGWYDYNTDTYYFE-NH2 |
| 906 | JBS-3660 | Ac-EYYVSAGWYDVNTDTYYEFE-NH2 | 947 | JBS-3701 | Ac-EYYVSAGWYDYNTDTYYEYE-NH2 |
| 907 | JBS-3661 | Ac-EYYVSAGWYDYVTDTYYEFE-NH2 | 948 | JBS-3702 | Ac-EYYVSAGWYDYNTDTYYEFY-NH2 |
| 908 | JBS-3662 | Ac-EYYVSAGWYDYNVDTYYEFE-NH2 | 949 | JBS-3703 | Ac-eYYVSAGwYDYNTDTYYEFE-NH2 |
| 909 | JBS-3663 | Ac-EYYVSAGWYDYNTVTYYEFE-NH2 | 950 | JBS-3704 | Ac-EYYVSAGWyDYNTDTYYEFE-NH2 |
| 910 | JBS-3664 | Ac-EYYVSAGWYDYNTDVYYEFE-NH2 | 951 | JBS-3705 | Ac-EYYVSAGWYDYNTDTYYEFE-NH2 |
| 911 | JBS-3665 | Ac-EYYWSAGWYDYNTDTYYEFE-NH2 | 952 | JBS-3706 | Ac-EYYvSAGWYDYNTDTYYEFE-NH2 |
| 912 | JBS-3666 | Ac-EYYVWAGWYDYNTDTYYEFE-NH2 | 953 | JBS-3707 | Ac-EYYVSAGWYDYNtDTYYEFE-NH2 |
| 913 | JBS-3667 | Ac-EYYVSWGWYDYNTDTYYVFE-NH2 | 954 | JBS-3708 | Ac-EYYVSaGWYDYNTDtYYEFE-NH2 |
| 914 | JBS-3668 | Ac-EYYVSAWWYDYNTDTYYEVE-NH2 | 955 | JBS-3709 | Ac-EYYVSAGWYDYNTDtYYEFE-NH2 |
| 915 | JBS-3669 | Ac-EYYVSAGWWYDYNTDTYYEFV-NH2 | 956 | JBS-3710 | Ac-EYYVSAGwyDYNTDTYYEFE-NH2 |
| 916 | JBS-3670 | Ac-WYYVSAGWYDYNTDTYYEFE-NH2 | 957 | JBS-3711 | Ac-EYYVSAGwyDYNTDTYYEFE-NH2 |
| 917 | JBS-3671 | Ac-EWYVSAGWYDYNTDTYYEFE-NH2 | 958 | JBS-3712 | Ac-EYYVSAGWyDYNTDTYYEFE-NH2 |
| 918 | JBS-3672 | Ac-EYWVSAGWYDYNTDTYYEFE-NH2 | 959 | JBS-3713 | Ac-EYYVSAGWYdYNTDTYYEFE-NH2 |
| 919 | JBS-3673 | Ac-EYYWSAGWYDYNTDTYYEFE-NH2 | 960 | JBS-3714 | Ac-EYYVSAGWYDyNTDTYYEFE-NH2 |
| 920 | JBS-3674 | Ac-EYYVWAGWYDYNTDTYYEFE-NH2 | 961 | JBS-3715 | Ac-EYYVSAGWYDYntDTYYEFE-NH2 |
| 921 | JBS-3675 | Ac-EYYVSWGWYDYNTDTYYEFE-NH2 | 962 | JBS-3716 | Ac-EYYVSAGWYDYNTdTYYEFE-NH2 |
| 922 | JBS-3676 | Ac-EYYVSAWWYDYNTDTYYEFE-NH2 | 963 | JBS-3717 | Ac-EYYVSAGWYDYNTDtYYEFE-NH2 |
| 923 | JBS-3677 | Ac-EYYVSAGWWYDYNTDTYYEFE-NH2 | 964 | JBS-3718 | Ac-EYYVSAGWYDYNTDTyYEFE-NH2 |
| 924 | JBS-3678 | Ac-EYYVSAGWWYNTDTYYEFE-NH2 | 965 | JBS-3719 | Ac-EYYVSAGWYDYNTDTYyEFE-NH2 |
| 925 | JBS-3679 | Ac-EYYVSAGWYDMNTDTYYEFE-NH2 | 966 | JBS-3720 | Ac-EYYVSAGWYDYNTDTYYeFE-NH2 |
| 926 | JBS-3680 | Ac-EYYVSAGWYDWTDTYYEFE-NH2 | 967 | JBS-3721 | Ac-EYYVSAGWYDYNTDTYYEfE-NH2 |

FIGURE 2L

| SEQ ID | Compound | Sequence | SEQ ID | Compound | Sequence |
|---|---|---|---|---|---|
| 968 | JBS-3722 | Ac-EYYVSAGWYDYNTDTYYEFe-NH2 | 1007 | JBS-0448 | Bio-Ttds-RGLEEQET[CVRVSSRVEIC]W-NH2 |
| 969 | JBS-3723 | Ac-pYYVSAGWYDYNTDTYYEFE-NH2 | 1008 | JBS-0449 | Bio-Ttds-NW[CIAISPTMDLC]LYLRKEN-NH2 |
| 970 | JBS-3724 | Ac-EpYVSAGWYDYNTDTYYEFE-NH2 | 1009 | JBS-0450 | Bio-Ttds-LDDM[CYALTEHVSIC]YGAAS-NH2 |
| 971 | JBS-3725 | Ac-EYpVSAGWYDYNTDTYYEFE-NH2 | 1010 | JBS-0451 | Bio-Ttds-RREM[CHALGGMVTVC]VGWEW-NH2 |
| 972 | JBS-3726 | Ac-EYYpSAGWYDYNTDTYYEFE-NH2 | 1011 | JBS-0452 | Bio-Ttds-VFQKEE[CVLATSVWVC]WGN-NH2 |
| 973 | JBS-3727 | Ac-EYYVpAGWYDYNTDTYYEFE-NH2 | 1012 | JBS-0453 | Bio-Ttds-WEV[CVPLSAGGMIC]VGRTDR-NH2 |
| 974 | JBS-3728 | Ac-EYYVSpGWYDYNTDTYYEFE-NH2 | 1013 | JBS-0454 | Bio-Ttds-VWL[CLEETGLC]VQVLGAARF-NH2 |
| 975 | JBS-3729 | Ac-EYYVSApWYDYNTDTYYEFE-NH2 | 1014 | JBS-0455 | Bio-Ttds-ANKMLGSSGPWYWIEVGWSS-NH2 |
| 976 | JBS-3730 | Ac-EYYVSAgpYDYNTDTYYEFE-NH2 | 1015 | JBS-0456 | Bio-Ttds-GGSLSIHIDWGWAPSSRWTH-NH2 |
| 977 | JBS-3731 | Ac-EYYVSAGWpDYNTDTYYEFE-NH2 | 1016 | JBS-0457 | Bio-Ttds-WRHGAIQWGWSESSRYRHSL-NH2 |
| 978 | JBS-3732 | Ac-EYYVSAGWYpNTDTYYEFE-NH2 | 1017 | JBS-0458 | Bio-Ttds-WFGWTWGLTRSSEYQHSGNK-NH2 |
| 979 | JBS-3733 | Ac-EYYVSAGWYDpNTDTYYEFE-NH2 | 1018 | JBS-0459 | Bio-Ttds-GRNVKRSYWGVVDWGWEESS-NH2 |
| 980 | JBS-3734 | Ac-EYYVSAGWYDpTDTYYEFE-NH2 | 1019 | JBS-0460 | Bio-Ttds-GLGWEVGWHVLESSHDLTIH-NH2 |
| 981 | JBS-3735 | Ac-EYYVSAGWYDYNpDTYYEFE-NH2 | 1020 | JBS-0461 | Bio-Ttds-YYVAVGWYRITTGESMWMMV-NH2 |
| 982 | JBS-3736 | Ac-EYYVSAGWYDYNTpTYYEFE-NH2 | 1021 | JBS-0462 | Bio-Ttds-YSVQVGWYMDASHYQHAMRH-NH2 |
| 983 | JBS-3737 | Ac-EYYVSAGWYDYNTDpYYEFE-NH2 | 1022 | JBS-0463 | Bio-Ttds-VIRVGWYNNRVSGQIMWVGLI-NH2 |
| 984 | JBS-3738 | Ac-EYYVSAGWYDYNTDTpYEFE-NH2 | 1023 | JBS-0464 | Bio-Ttds-WVLGWYDKALETEYDYMYGG-NH2 |
| 985 | JBS-3739 | Ac-EYYVSAGWYDYNTDTYpEFE-NH2 | 1024 | JBS-0465 | Bio-Ttds-VEVGWYLVDRDVWMLWSDHE-NH2 |
| 986 | JBS-3740 | Ac-EYYVSAGWYDYNTDTYYpFE-NH2 | 1025 | JBS-0466 | Bio-Ttds-GWFMEVATVLGVIEVGWVV-NH2 |
| 987 | JBS-3741 | Ac-EYYVSAGWYDYNTDTYYEpE-NH2 | 1026 | JBS-0467 | Bio-Ttds-MWIGWHTVSEESDHWFAWVT-NH2 |
| 988 | JBS-3742 | Ac-EYYVSAGWYDYNTDTYYEFp-NH2 | 1027 | JBS-0468 | Bio-Ttds-WENETLLRLPSGAMVWVGFT-NH2 |
| 989 | JBS-3743 | Ac-YYVSAGWYDYNTDTYYEFE-NH2 | 1028 | JBS-0469 | Bio-Ttds-RLGIQLWGATLSQEWLVWEL-NH2 |
| 990 | JBS-3744 | Ac-YVSAGWYDYNTDTYYEFE-NH2 | 1029 | JBS-0470 | Bio-Ttds-NYVRTEVLWENEVVGVWLEW-NH2 |
| 991 | JBS-3745 | Ac-VSAGWYDYNTDTYYEFE-NH2 | 1030 | JBS-0471 | Bio-Ttds-GLSWHLYLGNGGTVTIGYET-NH2 |
| 992 | JBS-3746 | Ac-SAGWYDYNTDTYYEFE-NH2 | 1031 | JBS-0472 | Bio-Ttds-SLGHVHMGRRYTVELRWERA-NH2 |
| 993 | JBS-3747 | Ac-EYYVSAGWYDYNTDTYYF-NH2 | 1032 | JBS-0473 | Bio-Ttds-ELPLALQGMESHGIVSWGWA-NH2 |
| 994 | JBS-3748 | Ac-EYYVSAGWYDYNTDTYY-NH2 | 1033 | JBS-0474 | Bio-Ttds-FGSEWQIMILLDSGDEYMLG-NH2 |
| 995 | JBS-3750 | Ac-YVSAGWYDYNTDTYYEF-NH2 | 1034 | JBS-0475 | Bio-Ttds-IFGVIETFAGTVSFGWENYD-NH2 |
| 996 | JBS-3751 | Ac-VSAGWYDYNTDTYYE-NH2 | 1035 | JBS-0476 | Bio-Ttds-KDNEELVLMRGRLEIWLGME-NH2 |
| 997 | JBS-3752 | Ac-SAGWYDYNTDTYY-NH2 | 1036 | JBS-0477 | Bio-Ttds-RPTTLRLGANSWIEIGWEI-NH2 |
| 998 | JBS-3753 | Ac-AGWYDYNTDTY-NH2 | 1037 | JBS-0478 | Bio-Ttds-YILWSYVGPGIEVGWTESA-NH2 |
| 999 | JBS-3754 | Ac-EYYVSAGWYDYN_DTYYEFE-K([Ttds-Mal-MSA]-NH2 | 1038 | JBS-0479 | Bio-Ttds-WKVWRLGGVELWYKEFGSER-NH2 |
| 1000 | JBS-3755 | Me-200HS-Ahx-EYYVSAGWYDYNTDTYYEFEK(Me-2COHS)-NE2 | 1039 | JBS-0480 | Bio-Ttds-REREFRINFYVSWGWEPSGI-NH2 |
| 1001 | JBS-3756 | Me-200GS-Ahx-EYYVSAGWYDYNTDTYYEFEK(Me-2COGS)-NE2 | 1040 | JBS-0481 | Bio-Ttds-LRKRLTNLDSIFVVELWWEY-NH2 |
| 1002 | JBS-3757 | Ac EYYVSAGWYDYNTDTYYEFE K(Oddc cGlu Ttds) NH2 | 1041 | JBS-0482 | Bio-Ttds-WWVINNVMVGWEFVQPGEFT-NH2 |
| 1003 | JBS-3758 | GL2-200GS2-Ahx-EYYVSAGWYDYNTDTYYEFE-K(Oddc cGlu Ttds)NH2 | 1042 | JBS-0483 | Bio-Ttds-HEQIVTLMYHHRETGVDYRS-NH2 |
| 1004 | JBS-3760 | Glutar-Atx-EYYVSAGWYDYNTDTYYEFE-K(Glutar)-NH2 | 1043 | JBS-0484 | Bio-Ttds-GRWKSGESTWTVELFWVWNG-NH2 |
| 1005 | JBS-3761 | Ac-EYYVSAGWYDYNTDTYYEFE-K(Ttds-Mal-HSA)-NH2 | 1044 | JBS-0485 | Bio-Ttds-VEWELWEVVEGQEVRVKL-NH2 |
| 1006 | JBS-0447 | Bio-Ttds-VLSWSV[CYLQQEAYRSTIIC]-NH2 | 1045 | JBS-0486 | Bio-Ttds-WMVKFSVVRGITEVGWEVLD-NH2 |

FIGURE 2M

| SEQ ID | Compound | Sequence | SEQ ID | Compound | Sequence |
|---|---|---|---|---|---|
| 1046 | JBS-0487 | Bio-Ttds-GFAIWIGLIKGHHSYEWELR-NH2 | 1087 | JBS-0547 | Bio-Ttds-FATLHEWRSGFMRHRHLRAS-NH2 |
| 1047 | JBS-0488 | Bio-Ttds-ESTIEFWIEGKLVPEFIFTY-NH2 | 1088 | JBS-0548 | Bio-Ttds-HGDSMWKWTVMRAPATGRGM-NH2 |
| 1048 | JBS-0489 | Bio-Ttds-HLYLMWQRWPSPWVEVGWEFV-NH2 | 1089 | JBS-0549 | Bio-Ttds-GHGMRWHRRLEAIMDIKRL-NH2 |
| 1049 | JBS-0507 | Bio-Ttds-GSTVQV[CWYWEEVEVEIC]VS-NH2 | 1090 | JBS-0550 | Bio-Ttds-RRYERATASSRRESQLVDSI-NH2 |
| 1050 | JBS-0508 | Bio-Ttds-GNAKVWL[CVEDKHMTVC]TLI-NH2 | 1091 | JBS-0551 | Bio-Ttds-GGHCTHTPWTYGYLAWVSRT-NH2 |
| 1051 | JBS-0510 | Bio-Ttds-DLDPRIVLVGNGEIEIGWSI-NH2 | 1092 | JBS-0552 | Bio-Ttds-FWSMGYQSLDGEWTSEWARI-NH2 |
| 1052 | JBS-0511 | Bio-Ttds-DQVWWWGFKARMGLIEYGWE-NH2 | 1093 | JBS-0553 | Bio-Ttds-TRSGERGRKRVLSSYWLHSW-NH2 |
| 1053 | JBS-0512 | Bio-Ttds-NQGYTHNTKLRFYVELGWEH-NH2 | 1094 | JBS-0554 | Bio-Ttds-WHWWMGTYQSSPWSTETEWW-NH2 |
| 1054 | JBS-0513 | Bio-Ttds-WIEVGWFEANTGRHRTWTIV-NH2 | 1095 | JBS-0555 | Bio-Ttds-SSGHPRVRSKYSWGLIPLRR-NH2 |
| 1055 | JBS-0515 | Bio-Ttds-IMVGWEDVRRGRILEEITWK-NH2 | 1096 | JBS-0556 | Bio-Ttds-TGIYAWGWEIRSEWQNDSWF-NH2 |
| 1056 | JBS-0516 | Bio-Ttds-KYLLLDFTFWLTKEVGVGW-NH2 | 1097 | JBS-0557 | Bio-Ttds-GWNVFYIFRVFEGKPKAWVM-NH2 |
| 1057 | JBS-0517 | Bio-Ttds-VWVGWTERRGSKEQVLWEVK-NH2 | 1098 | JBS-0558 | Bio-Ttds-GGTLWQFEHGEHYLIMLGWE-NH2 |
| 1058 | JBS-0518 | Bio-Ttds-EVRYRFEGIPFFHVIFGWEF-NH2 | 1099 | JBS-0559 | Bio-Ttds-LEGNHWRDRYHHSVKASVPM-NH2 |
| 1059 | JBS-0519 | Bio-Ttds-YSVLVWRAGGGQVELMMSRV-NH2 | 1100 | JBS-0560 | Bio-Ttds-IWGAQRWDHRKGLVSMSMS-NH2 |
| 1060 | JBS-0520 | Bio-Ttds-PIWERDSVPRMMYSIELYWE-NH2 | 1101 | JBS-0561 | Bio-Ttds-RGVRRMPKSYPRQHTAIRVL-NH2 |
| 1061 | JBS-0521 | Bio-Ttds-WRWSIVVGYQWKGTDHDLWA-NH2 | 1102 | JBS-0562 | Bio-Ttds-LMAVHVPSTNNTKWVIDICK-NH2 |
| 1062 | JBS-0522 | Bio-Ttds-VYEVGWDHGNWYEIIWRYPS-NH2 | 1103 | JBS-0563 | Bio-Ttds-GIWIGQSKYIWRSQRGEQTI-NH2 |
| 1063 | JBS-0523 | Bio-Ttds-WFQREYEIKKGQIWLVIRVG-NH2 | 1104 | JBS-0564 | Bio-Ttds-YEGIKPWTGSRVMMLMDMLT-NH2 |
| 1064 | JBS-0524 | Bio-Ttds-QVWVGYYNTIEDTELVMWTV-NH2 | 1105 | JBS-0565 | Bio-Ttds-KES[CFWVSKWVAVC]GHY-NH2 |
| 1065 | JBS-0525 | Bio-Ttds-RIWIGMYLGGTLIWEWEVIP-NH2 | 1106 | JBS-0566 | Bio-Ttds-VISQGHH[CWHVNEKIAVC]WL-NH2 |
| 1066 | JBS-0526 | Bio-Ttds-YSEITIGVYMEQYSYDFYNF-NH2 | 1107 | JBS-0567 | Bio-Ttds-EREDITY[CVVVASGVELC]WQ-NH2 |
| 1067 | JBS-0527 | Bio-Ttds-VVRHWHYVGMEFGFEKVREV-NH2 | 1108 | JBS-0568 | Bio-Ttds-EH[CRQIAPDVMLC]WEWRAKS-NH2 |
| 1068 | JBS-0528 | Bio-Ttds-GES[CVRINHKVWVC]WDMGSE-NH2 | 1109 | JBS-0569 | Bio-Ttds-SAGSVS[CFWVSQSVSVC]WQL-NH2 |
| 1069 | JBS-0529 | Bio-Ttds-YERGTFHT[CSRYDERIDVC]W-NH2 | 1110 | JBS-0570 | Bio-Ttds-QLELGF-NH2 |
| 1070 | JBS-0530 | Bio-Ttds-GVIV[CYTHTCSWHGHNDWC]Y-NH2 | 1111 | JBS-0571 | Bio-Ttds-RGWTRYWIEVGWWHIDEELI-NH2 |
| 1071 | JBS-0531 | Bio-Ttds-SHRKSQLHQQYRSR[CERC]SN-NH2 | 1112 | JBS-0572 | Bio-Ttds-FVHVGMVEYGWVLRSDYRHS-NH2 |
| 1072 | JBS-0532 | Bio-Ttds-LVRVRLITQFAQYSRRSGVAF-NH2 | 1113 | JBS-0573 | Bio-Ttds-HSEVSWLRSNDYYIEFGWEW-NH2 |
| 1073 | JBS-0533 | Bio-Ttds-SSWNGQRAWMLVGMRGVAVN-NH2 | 1114 | JBS-0574 | Bio-Ttds-RDIWDLWTYRIEFGWEMSDD-NH2 |
| 1074 | JBS-0534 | Bio-Ttds-GVPGLKSRYSEGLSLDTSWL-NH2 | 1115 | JBS-0575 | Bio-Ttds-YQHGEDGWYWIEFGWEFVDL-NH2 |
| 1075 | JBS-0535 | Bio-Ttds-SVFASDLNFYFVMSAWSKIT-NH2 | 1116 | JBS-0576 | Bio-Ttds-AEKVDKRESHVSYTVELMWEY-NH2 |
| 1076 | JBS-0536 | Bio-Ttds-TLEGRRVILVMMVWRWTYHV-NH2 | 1117 | JBS-0577 | Bio-Ttds-RWQRLGKGETWEFWAYIPVV-NH2 |
| 1077 | JBS-0537 | Bio-Ttds-KWFTITRFATILHTSYIFQN-NH2 | 1118 | JBS-0578 | Bio-Ttds-WTIGLMWENEHEEVMIWQVQ-NH2 |
| 1078 | JBS-0538 | Bio-Ttds-NRIHLSWGTKNQGFTKLKRI-NH2 | 1119 | JBS-0579 | Bio-Ttds-WIKIGWHHRDHEWDEDIGFM-NH2 |
| 1079 | JBS-0539 | Bio-Ttds-QAIKGRIHGDIESDRYSVYY-NH2 | 1120 | JBS-0580 | Bio-Ttds-WELWSMDSLGKHTILGFGKW-NH2 |
| 1080 | JBS-0540 | Bio-Ttds-AGIQLVLEWYGHRVIVIQLG-NH2 | 1121 | JBS-0581 | Bio-Ttds-FRIELWYREGKSGNEKLVWS-NH2 |
| 1081 | JBS-0541 | Bio-Ttds-VYADINMLASITWFARPYMD-NH2 | 1122 | JBS-0587 | Bio-Ttds-SLGHVHMGRRYTVELRWERA-NH2 |
| 1082 | JBS-0542 | Bio-Ttds-FINVLMPRRGTPKREWAYY-NH2 | 1123 | JBS-0588 | Bio-Ttds-SVEFGFYDVENSMDWTVGWV-NH2 |
| 1083 | JBS-0543 | Bio-Ttds-WSRLLARVVWKSGTIEVGWA-NH2 | 1124 | JBS-0589 | Bio-Ttds-DK[CMQASQVVWVC]VHQEWDP-NH2 |
| 1084 | JBS-0544 | Bio-Ttds-GYWTVEFWVQWSGGDDVLIR-NH2 | 1125 | JBS-0590 | Bio-Ttds-DLDPRIVLVGNGEIEIGWSI-NH2 |
| 1085 | JBS-0545 | Bio-Ttds-EDVGKFKWYIEVWWQNMDEA-NH2 | 1126 | JBS-0591 | Bio-Ttds-EAWN[CIVVSKNISVC]WSKSY-NH2 |
| 1086 | JBS-0546 | Bio-Ttds-EDWGIRWGWRYTLRWEAVLW-NH2 | 1127 | JBS-0592 | Bio-Ttds-EGEQ[CVVLRSGGSVC]VGFER-NH2 |

FIGURE 2N

| SEQ ID | Compound | Sequence | SEQ ID | Compound | Sequence |
|---|---|---|---|---|---|
| 1128 | JBS-0593 | Bio-Ttds-ELPLALQGMESHGIVSWGWA-NH2 | 1169 | JBS-0634 | Bio-Ttds-GKYLLLDFTFWLTKEVGVGW-NH2 |
| 1129 | JBS-0594 | Bio-Ttds-EY[CIWLIDDSIAVC]WEESGN-NH2 | 1170 | JBS-0635 | Bio-Ttds-GLGWEVGWHVLESSHDLTIH-NH2 |
| 1130 | JBS-0595 | Bio-Ttds-GEY[CWEVNENVHVC]YHVPDS-NH2 | 1171 | JBS-0636 | Bio-Ttds-GLIEWGWYSRQEDQHWLMGT-NH2 |
| 1131 | JBS-0596 | Bio-Ttds-IWM[CWEDLKGSYC]WEFVRQG-NH2 | 1172 | JBS-0637 | Bio-Ttds-GRWLIGLAPQAEVWFLWQPM-NH2 |
| 1132 | JBS-0597 | Bio-Ttds-LDGGHW[CWEISDSVMLC]VAV-NH2 | 1173 | JBS-0638 | Bio-Ttds-GTEIGWLDLLTDHVIWSVTI-NH2 |
| 1133 | JBS-0598 | Bio-Ttds-LSIWL[CWEGEDHTFTVC]RVL-NH2 | 1174 | JBS-0639 | Bio-Ttds-GTQERGSKRMFTVELWWEP-NH2 |
| 1134 | JBS-0599 | Bio-Ttds-PGVEL[CWEANGWTTC]ISWPY-NH2 | 1175 | JBS-0640 | Bio-Ttds-GWFMEVATVLGVIEVGWVV-NH2 |
| 1135 | JBS-0600 | Bio-Ttds-RDEWQITV[CWLGSIYEAC]WD-NH2 | 1176 | JBS-0641 | Bio-Ttds-GWFIGLHSYHTGMESEWPG-NH2 |
| 1136 | JBS-0601 | Bio-Ttds-RGQQGDH[CTVITSFVTLC]KE-NH2 | 1177 | JBS-0642 | Bio-Ttds-HLHYNGGTIVWGSEPFNASW-NH2 |
| 1137 | JBS-0602 | Bio-Ttds-RS[CIRINERLELC]WEKTDLE-NH2 | 1178 | JBS-0643 | Bio-Ttds-HMRGTATSERRYWIEVGWFD-NH2 |
| 1138 | JBS-0603 | Bio-Ttds-SGGLYQ[CWGDDRIMLC]WAYD-NH2 | 1179 | JBS-0644 | Bio-Ttds-HMTVEFGYYWVEMDTNTVIW-NH2 |
| 1139 | JBS-0604 | Bio-Ttds-SVGIWL[CWMDSRGSVC]HQLK-NH2 | 1180 | JBS-0645 | Bio-Ttds-IEVGWYNVVTQKHSKLGMLI-NH2 |
| 1140 | JBS-0605 | Bio-Ttds-TRAMGAI[CHRITEHVSVC]YM-NH2 | 1181 | JBS-0646 | Bio-Ttds-ISVGMYFWAIDNYKEFGNTL-NH2 |
| 1141 | JBS-0606 | Bio-Ttds-TRTMGAI[CHRITEHVSVC]YM-NH2 | 1182 | JBS-0647 | Bio-Ttds-KFKRMEIGFMLESGEEYVLA-NH2 |
| 1142 | JBS-0607 | Bio-Ttds-VDH[CTPLSRERAQVWVC]WEV-NH2 | 1183 | JBS-0648 | Bio-Ttds-KVWSRVQIIRGGWIEVGYEF-NH2 |
| 1143 | JBS-0608 | Bio-Ttds-VRNITVWV[CWYERSSTREWC]H-NH2 | 1184 | JBS-0649 | Bio-Ttds-LGVEMGYHVYQTGEDYIVLT-NH2 |
| 1144 | JBS-0609 | Bio-Ttds-VSVWI[CWETLEGVPLEC]KLM-NH2 | 1185 | JBS-0650 | Bio-Ttds-LGVEMGYHVYQTGGDYIVLT-NH2 |
| 1145 | JBS-0610 | Bio-Ttds-VWI[CAVAARGPDIC]YYLVMA-NH2 | 1186 | JBS-0651 | Bio-Ttds-LIEAGYHDIASQSDRILVRY-NH2 |
| 1146 | JBS-0611 | Bio-Ttds-WQWEVLM[CNDHNTVC]VGLLIQ-NH2 | 1187 | JBS-0652 | Bio-Ttds-LIVFGYSYIETEEEFIISLH-NH2 |
| 1147 | JBS-0612 | Bio-Ttds-WYGHDY[CFKFSREIWIC]QMD-NH2 | 1188 | JBS-0653 | Bio-Ttds-LLMHTGDHSVSLFYEVLDYP-NH2 |
| 1148 | JBS-0613 | Bio-Ttds-AEIEWGWYVSDAEEFIVLGH-NH2 | 1189 | JBS-0654 | Bio-Ttds-LMMVRILRIDGAEVVGWEL-NH2 |
| 1149 | JBS-0614 | Bio-Ttds-AFWEAGWYDSVGNSWNVFFK-NH2 | 1190 | JBS-0655 | Bio-Ttds-MGLWYGWEYVNGLGGHEIEI-NH2 |
| 1150 | JBS-0615 | Bio-Ttds-AGVASEVTWGWINMVDDTH-NH2 | 1191 | JBS-0656 | Bio-Ttds-NHVWEVQLDKSVWIGWEWID-NH2 |
| 1151 | JBS-0616 | Bio-Ttds-AIELGYYSQSTDSSIILWQE-NH2 | 1192 | JBS-0657 | Bio-Ttds-NSSNSNGQKFRYFIEVGWYH-NH2 |
| 1152 | JBS-0617 | Bio-Ttds-AIEVGWYYLESTHEVFTNA-NH2 | 1193 | JBS-0658 | Bio-Ttds-NTTGRIELWIQLPDRDWLLW-NH2 |
| 1153 | JBS-0618 | Bio-Ttds-AWTWEFGTYNFMTDSYTLQW-NH2 | 1194 | JBS-0659 | Bio-Ttds-PYFVELGYEQGVFYKIELL-NH2 |
| 1154 | JBS-0619 | Bio-Ttds-DSTIVGWYSYDHDYDIWGY-NH2 | 1195 | JBS-0660 | Bio-Ttds-PYGVWYSWDNTSWLQISTHV-NH2 |
| 1155 | JBS-0620 | Bio-Ttds-EHRHTRSKDPYYSVELMWEF-NH2 | 1196 | JBS-0661 | Bio-Ttds-QFFGLISGDGRLQIWIGWYE-NH2 |
| 1156 | JBS-0621 | Bio-Ttds-EIEVGYETFESGEAVWWVAF-NH2 | 1197 | JBS-0662 | Bio-Ttds-QGKYGIVAWGWVPSGGHRYQ-NH2 |
| 1157 | JBS-0622 | Bio-Ttds-ELVLVWESTDGRVQLWAQWD-NH2 | 1198 | JBS-0663 | Bio-Ttds-QIQWGYEYASGWQNWWERSN-NH2 |
| 1158 | JBS-0623 | Bio-Ttds-EVRWELGIESRFSGWYMVLG-NH2 | 1199 | JBS-0664 | Bio-Ttds-QVELMFEDRSTGQQYRLATI-NH2 |
| 1159 | JBS-0624 | Bio-Ttds-EWQVTSTVWIGWELQMDLAT-NH2 | 1200 | JBS-0665 | Bio-Ttds-QVSSIELWAEYGDVPRLIWS-NH2 |
| 1160 | JBS-0625 | Bio-Ttds-EYAVWELGYYSMWEDDHVII-NH2 | 1133 | JBS-0598 | Bio-Ttds-LSIWL[CWEGEDHTFTVC]RVL-NH2 |
| 1161 | JBS-0626 | Bio-Ttds-FDVPLWAWSSGEMYIEIGLH-NH2 | 1134 | JBS-0599 | Bio-Ttds-PGVEL[CWEANGWTTC]ISWPY-NH2 |
| 1162 | JBS-0627 | Bio-Ttds-FGVVAVGYDREYDKWTLIA-NH2 | 1135 | JBS-0600 | Bio-Ttds-RDEWQITV[CWLGSIYEAC]WD-NH2 |
| 1163 | JBS-0628 | Bio-Ttds-FIVVGAYSKLTGLHIQWGYE-NH2 | 1136 | JBS-0601 | Bio-Ttds-RGQQGDH[CTVITSFVTLC]KE-NH2 |
| 1164 | JBS-0629 | Bio-Ttds-FSGSGPWFVYLIGGSIEMGY-NH2 | 1137 | JBS-0602 | Bio-Ttds-RS[CIRINERLELC]WEKTDLE-NH2 |
| 1165 | JBS-0630 | Bio-Ttds-FVSLMWETSNGRGEIARWII-NH2 | 1138 | JBS-0603 | Bio-Ttds-SGGLYQ[CWGDDRIMLC]WAYD-NH2 |
| 1166 | JBS-0631 | Bio-Ttds-GAAWFITLDGGTVEIGWEQI-NH2 | 1139 | JBS-0604 | Bio-Ttds-SVGIWL[CWMDSRGSVC]HQLK-NH2 |
| 1167 | JBS-0632 | Bio-Ttds-GFYWEVGFYDYGSDSINVHA-NH2 | 1140 | JBS-0605 | Bio-Ttds-TRAMGAI[CHRITEHVSVC]YM-NH2 |
| 1168 | JBS-0633 | Bio-Ttds-GHSVEIGWYNVAKDQPDMYY-NH2 | 1141 | JBS-0606 | Bio-Ttds-TRTMGAI[CHRITEHVSVC]YM-NH2 |

FIGURE 20

| SEQ ID | Compound | Sequence | SEQ ID | Compound | Sequence |
|---|---|---|---|---|---|
| 1142 | JBS-0607 | Bio-Ttds-VDH[CTPLSRERAQWWC]WEV-NH2 | 1183 | JBS-0648 | Bio-Ttds-KVWSRVQIIRGGWIEVGYEF-NH2 |
| 1143 | JBS-0608 | Bio-Ttds-VRNTVWV[CWYERSSTREWC]H-NH2 | 1184 | JBS-0649 | Bio-Ttds-LGVEMGYHVYQTGEDYIVLT-NH2 |
| 1144 | JBS-0609 | Bio-Ttds-VSVWI[CWETLEGVPLEC]KLW-NH2 | 1185 | JBS-0650 | Bio-Ttds-LGVEMGYHVYQTGDYIVLI-NH2 |
| 1145 | JBS-0610 | Bio-Ttds-VWI[CAVAARGPDIC]YYLVNA-NH2 | 1186 | JBS-0651 | Bio-Ttds-LIEAGYHDIASQSDRILVRY-NH2 |
| 1146 | JBS-0611 | Bio-Ttds-WQWEVLW[CNDHNTVC]VGLIQ-NH2 | 1187 | JBS-0652 | Bio-Ttds-LIVFGYSYIETEEFIISLH-NH2 |
| 1147 | JBS-0612 | Bio-Ttds-WYGHDY[CFKFSREIWTC]QMD-NH2 | 1188 | JBS-0653 | Bio-Ttds-LLWHTGDHSVSLFYEVLDYP-NH2 |
| 1148 | JBS-0613 | Bio-Ttds-AEIEWGWYSDAEEFIVLGH-NH2 | 1189 | JBS-0654 | Bio-Ttds-LWMVRILRTDGAEVVVGWEL-NH2 |
| 1149 | JBS-0614 | Bio-Ttds-AFWEAGWYDSVGNSWNVFFK-NH2 | 1190 | JBS-0655 | Bio-Ttds-MGLWYGWEYVNGLGGHEIEI-NH2 |
| 1150 | JBS-0615 | Bio-Ttds-AGVAVSEVTWGWYNMVDDTH-NH2 | 1185 | JBS-0650 | Bio-Ttds-LGVEMGYHVYQTGDYIVLI-NH2 |
| 1151 | JBS-0616 | Bio-Ttds-AIELGYYSQCIDSSIILWQE-NH2 | 1186 | JBS-0651 | Bio-Ttds-LIEAGYHDIASQSDRILVRY-NH2 |
| 1152 | JBS-0617 | Bio-Ttds-AIEVGWYYLESTRHEVFTNA-NH2 | 1187 | JBS-0652 | Bio-Ttds-LIVFGYSYIETEEFIISLH-NH2 |
| 1153 | JBS-0618 | Bio-Ttds-AWTWEFGTYNFMTDSYTLQW-NH2 | 1188 | JBS-0653 | Bio-Ttds-LLWHTGDHSVSLFYEVLDYP-NH2 |
| 1154 | JBS-0619 | Bio-Ttds-DSTIYVGWYSYDHDYDIWGY-NH2 | 1189 | JBS-0654 | Bio-Ttds-LWMVRILRTDGAEVVVGWEL-NH2 |
| 1155 | JBS-0620 | Bio-Ttds-EHRHTRSKDPYYSVELMWEF-NH2 | 1190 | JBS-0655 | Bio-Ttds-MGLWYGWEYVNGLGGHEIEI-NH2 |
| 1156 | JBS-0621 | Bio-Ttds-EIEVGYETFESGEAVMWVAF-NH2 | 1191 | JBS-0656 | Bio-Ttds-NHVWEVQLDKSWIGWEWID-NH2 |
| 1157 | JBS-0622 | Bio-Ttds-ELVLVWESTDGRVQLWAQWD-NH2 | 1192 | JBS-0657 | Bio-Ttds-NSSNSNGQKFRYFIEVGWYH-NH2 |
| 1158 | JBS-0623 | Bio-Ttds-EVRWELGIESRFSGWYMVLG-NH2 | 1193 | JBS-0658 | Bio-Ttds-NTTGRIELWIQLPDRDWLLW-NH2 |
| 1159 | JBS-0624 | Bio-Ttds-EWQVTSTVWIGWELQMDLAT-NH2 | 1194 | JBS-0659 | Bio-Ttds-PYFVELGYEGYGVFYKIELL-NH2 |
| 1160 | JBS-0625 | Bio-Ttds-EYAWELGYWSMWDNTSWLQISTHV-NH2 | 1195 | JBS-0660 | Bio-Ttds-PYGVWYSWDNTSWLQISTHV-NH2 |
| 1161 | JBS-0626 | Bio-Ttds-FDVPLMAWSGEMYIEIGLH-NH2 | 1196 | JBS-0661 | Bio-Ttds-QFFGLISGDGRLQIWGWYE-NH2 |
| 1162 | JBS-0627 | Bio-Ttds-FGVVAVGYYDREYDKWTLIA-NH2 | 1197 | JBS-0662 | Bio-Ttds-QGKYGIVAWGWVPSGGHRYQ-NH2 |
| 1163 | JBS-0628 | Bio-Ttds-FIVVGAYSKLTGLHIQWGYE-NH2 | 1198 | JBS-0663 | Bio-Ttds-QIQWGYEYASGWQMWWERSN-NH2 |
| 1164 | JBS-0629 | Bio-Ttds-FSGSGPWFVYLIGGSIEMGY-NH2 | 1199 | JBS-0664 | Bio-Ttds-QVELMFEDRSTGQYRLATI-NH2 |
| 1165 | JBS-0630 | Bio-Ttds-FVSLMWETSNGRGEIARWII-NH2 | 1200 | JBS-0665 | Bio-Ttds-QVSSIELWAEYGDVPRLIWS-NH2 |
| 1166 | JBS-0631 | Bio-Ttds-GAAWFITLDGGIVEIGWEQI-NH2 | 1201 | JBS-0666 | Bio-Ttds-QWDWVEYEWGNTIGLVGWYE-NH2 |
| 1167 | JBS-0632 | Bio-Ttds-GFYWEVGFYDYGSDSINVHA-NH2 | 1202 | JBS-0667 | Bio-Ttds-QWRILGLHEMGTGYDLVLW-NH2 |
| 1168 | JBS-0633 | Bio-Ttds-GHSVEIGWYNNVAKDQPDMY-NH2 | 1203 | JBS-0668 | Bio-Ttds-RLIELGFWYEIAREHVVVWS-NH2 |
| 1169 | JBS-0634 | Bio-Ttds-GKYLLLDFFTWLTKEVGVGM-NH2 | 1204 | JBS-0669 | Bio-Ttds-RLIELGFWYEIAREHVVVWS-NH2 |
| 1170 | JBS-0635 | Bio-Ttds-GLGWEVGWHVLESSHDLTIH-NH2 | 1205 | JBS-0670 | Bio-Ttds-RRITILGWYVYSNNTYMIWTT-NH2 |
| 1171 | JBS-0636 | Bio-Ttds-GLIEWGWYSRQEDQHWLMGT-NH2 | 1206 | JBS-0671 | Bio-Ttds-RWIVYSHEVEISKGVWLGYE-NH2 |
| 1172 | JBS-0637 | Bio-Ttds-GRMLIGLAPQAEVWFLMQPM-NH2 | 1207 | JBS-0672 | Bio-Ttds-RYGYIVVGWYDFNKDLYTRF-NH2 |
| 1173 | JBS-0638 | Bio-Ttds-GTEIGWLDLLITDHVIWSVTI-NH2 | 1208 | JBS-0673 | Bio-Ttds-SGIILGMYSVYRNEWFEWGT-NH2 |
| 1174 | JBS-0639 | Bio-Ttds-GTQERGSKRMMFTVELMWEP-NH2 | 1209 | JBS-0674 | Bio-Ttds-SGRGTPAGDHKYSIEAFYYT-NH2 |
| 1175 | JBS-0640 | Bio-Ttds-GWFMEVATVLGVIEVGWVY-NH2 | 1210 | JBS-0675 | Bio-Ttds-SIRQRDQYTIELYWEWVDSP-NH2 |
| 1176 | JBS-0641 | Bio-Ttds-GWIFIGLHSYHIGMESEWPG-NH2 | 1211 | JBS-0676 | Bio-Ttds-SLIWSSNTSGRYVELWAER-NH2 |
| 1177 | JBS-0642 | Bio-Ttds-HLEYNGGTIYWGSEPFNASM-NH2 | 1212 | JBS-0677 | Bio-Ttds-SLSRSDEAKLLWRIEFGWEY-NH2 |
| 1178 | JBS-0643 | Bio-Ttds-HMRGTATSERRYWIEVGWFD-NH2 | 1213 | JBS-0678 | Bio-Ttds-SNKYRLVSDLQYTVEFGWEW-NH2 |
| 1179 | JBS-0644 | Bio-Ttds-HMTVEFGYYWEMDTNTVIW-NH2 | 1214 | JBS-0679 | Bio-Ttds-SQKPDETRMSRYSIELFWEL-NH2 |
| 1180 | JBS-0645 | Bio-Ttds-IEVGWYNVVTQKHSKLGMLI-NH2 | 1215 | JBS-0680 | Bio-Ttds-STIWLMTNGIVEVGWEFTDY-NH2 |
| 1181 | JBS-0646 | Bio-Ttds-ISVGWYFWATDNYKEFGNTL-NH2 | 1216 | JBS-0681 | Bio-Ttds-SVSVGWYYTVEERHYMLWLG-NH2 |
| 1182 | JBS-0647 | Bio-Ttds-KFKRWEIGFMLESGEEYVLA-NH2 | 1217 | JBS-0682 | Bio-Ttds-SVTVGWYSWIEDMEWTVYSQ-NH2 |

FIGURE 2P

| SEQ ID | Compound | Sequence | SEQ ID | Compound | Sequence |
| --- | --- | --- | --- | --- | --- |
| 1218 | JBS-0683 | Bio-Ttds-SWRVEIGWHWLISGIDEPTI-NH2 | 1259 | JBS-1069 | Ac-HLALWQRWPSPWVEVGWEFV-NH2 |
| 1219 | JBS-0685 | Bio-Ttds-TIVIGHLDRVSGVETDFYSV-NH2 | 1260 | JBS-1070 | Ac-HLYAWQRWPSPWVEVGWEFV-NH2 |
| 1220 | JBS-0686 | Bio-Ttds-TRRIGFSVQFGWEVSSQYTH-NH2 | 1261 | JBS-1071 | Ac-HLYLAQRWPSPWVEVGWEFV-NH2 |
| 1221 | JBS-0687 | Bio-Ttds-TVELWIWNIFTDHSHMIASI-NH2 | 1262 | JBS-1072 | Ac-HLYLWARWPSPWVEVGWEFV-NH2 |
| 1222 | JBS-0688 | Bio-Ttds-TYVYWEVGLESANGAKEIWQ-NH2 | 1263 | JBS-1073 | Ac-HLYLWQAWPSPWVEVGWEFV-NH2 |
| 1223 | JBS-0689 | Bio-Ttds-VEFGWYRRESDTWHSWGKVN-NH2 | 1264 | JBS-1074 | Ac-HLYLWQRAPSPWVEVGWEFV-NH2 |
| 1224 | JBS-0690 | Bio-Ttds-VEIGWHFLKYEKELVWYMHQ-NH2 | 1265 | JBS-1075 | Ac-HLYLWQRWASPWVEVGWEFV-NH2 |
| 1225 | JBS-0691 | Bio-Ttds-VEIGWHFLNYEKELVWYMHQ-NH2 | 1266 | JBS-1076 | Ac-HLYLWQRWPAPWVEVGWEFV-NH2 |
| 1226 | JBS-0692 | Bio-Ttds-VEVGWEQDGVTVTVTWHT-NH2 | 1267 | JBS-1077 | Ac-HLYLWQRWPSAWVEVGWEFV-NH2 |
| 1227 | JBS-0693 | Bio-Ttds-VEVGWVSLFKDLTVFKEWIP-NH2 | 1268 | JBS-1078 | Ac-HLYLWQRWPSPAEVGWEFV-NH2 |
| 1228 | JBS-0694 | Bio-Ttds-VFEVGWVTSDGRVLWRTIRN-NH2 | 1269 | JBS-1079 | Ac-HLYLWQRWPSPWAEVGWEFV-NH2 |
| 1229 | JBS-0695 | Bio-Ttds-VIWRDGRSLERWSIEFGWEA-NH2 | 1270 | JBS-1080 | Ac-HLYLWQRWPSPWVAVGWEFV-NH2 |
| 1230 | JBS-0696 | Bio-Ttds-VRPKEIRKRPLFYVELFWEH-NH2 | 1271 | JBS-1081 | Ac-HLYLWQRWPSPWVEAGWEFV-NH2 |
| 1231 | JBS-0697 | Bio-Ttds-VVEIGWVLVSSLGNERKVVLW-NH2 | 1272 | JBS-1082 | Ac-HLYLWQRWPSPWVEVAWEFV-NH2 |
| 1232 | JBS-0698 | Bio-Ttds-VYSVESGWYSFNDDEWMSFY-NH2 | 1273 | JBS-1083 | Ac-HLYLWQRWPSPWVEVGAEFV-NH2 |
| 1233 | JBS-0699 | Bio-Ttds-WEIELGLVMNGQEYMIVTLY-NH2 | 1274 | JBS-1084 | Ac-HLYLWQRWPSPWVEVGWAFV-NH2 |
| 1234 | JBS-0700 | Bio-Ttds-WEYWEVYTIGPVTVGWELIA-NH2 | 1275 | JBS-1085 | Ac-HLYLWQRWPSPWVEVGWEAV-NH2 |
| 1235 | JBS-0701 | Bio-Ttds-WGIMELGMYWYEDGRHKAIW-NH2 | 1276 | JBS-1086 | Ac-HLYLWQRWPSPWVEVGWEFA-NH2 |
| 1236 | JBS-0702 | Bio-Ttds-WGITLGWEDGHGNEHDFYVL-NH2 | 1277 | JBS-1087 | Ac-DLYLWQRWPSPWVEVGWEFV-NH2 |
| 1237 | JBS-0703 | Bio-Ttds-WGVVEVGYHFVATGSNEALM-NH2 | 1278 | JBS-1088 | Ac-HDYLWQRWPSPWVEVGWEFV-NH2 |
| 1238 | JBS-0704 | Bio-Ttds-WGMWIVSAGWHYSAMAEDHPW-NH2 | 1279 | JBS-1089 | Ac-HLDLWQRWPSPWVEVGWEFV-NH2 |
| 1239 | JBS-0705 | Bio-Ttds-WIFTWSSGDHIGVIEMGYES-NH2 | 1280 | JBS-1090 | Ac-HLYDWQRWPSPWVEVGWEFV-NH2 |
| 1240 | JBS-0706 | Bio-Ttds-WIVIGWEDAYGRSVIWYKVG-NH2 | 1281 | JBS-1091 | Ac-HLYLDQRWPSPWVEVGWEFV-NH2 |
| 1241 | JBS-0707 | Bio-Ttds-WKIIVGWELFDTGETTWWKV-NH2 | 1282 | JBS-1092 | Ac-HLYLWDRWPSPWVEVGWEFV-NH2 |
| 1242 | JBS-0708 | Bio-Ttds-WKWRTFDGSIEIGFVAVQWS-NH2 | 1283 | JBS-1093 | Ac-HLYLWQDWPSPWVEVGWEFV-NH2 |
| 1243 | JBS-0709 | Bio-Ttds-WLIEFGYMWNGENRTLAVWE-NH2 | 1284 | JBS-1094 | Ac-HLYLWQRDPSPWVEVGWEFV-NH2 |
| 1244 | JBS-0710 | Bio-Ttds-WRETIFYYTDQISVVILEKV-NH2 | 1285 | JBS-1095 | Ac-HLYLWQRMDSPWVEVGWEFV-NH2 |
| 1245 | JBS-0711 | Bio-Ttds-WSPGMKEIELGSTGIYWGWS-NH2 | 1286 | JBS-1096 | Ac-HLYLWQRWPDPWVEVGWEFV-NH2 |
| 1246 | JBS-0712 | Bio-Ttds-WWEFGYYDPETDESTILTEM-NH2 | 1287 | JBS-1097 | Ac-HLYLWQRWPSDWVEVGWEFV-NH2 |
| 1247 | JBS-0713 | Bio-Ttds-YSIVYGHYQKQTNTWTELVY-NH2 | 1288 | JBS-1098 | Ac-HLYLWQRWPSPDVEVGWEFV-NH2 |
| 1248 | JBS-0714 | Bio-Ttds-YTVEVGWHTVHTGRDNYMWM-NH2 | 1289 | JBS-1099 | Ac-HLYLWQRWPSPWDEVGWEFV-NH2 |
| 1249 | JBS-0715 | Bio-Ttds-YVEVGYYFHTTDNEVIYAN-NH2 | 1290 | JBS-1100 | Ac-HLYLWQRWPSPWVDVGWEFV-NH2 |
| 1250 | JBS-0716 | Bio-Ttds-YVEVGYYFYTTDNEVIYAN-NH2 | 1291 | JBS-1101 | Ac-HLYLWQRWPSPWVEDGWEFV-NH2 |
| 1251 | JBS-1027 | Ac-AFWEAGWYDSVGNSWNVFFK-NH2 | 1292 | JBS-1102 | Ac-HLYLWQRWPSPWVEVDWEFV-NH2 |
| 1252 | JBS-1028 | Ac-HLYLWQRWPSPWVEVGWEFV-NH2 | 1293 | JBS-1103 | Ac-HLYLWQRWPSPWVEVGDEFV-NH2 |
| 1253 | JBS-1047 | Ac-RPTTLIRLGANSWIEIGWEI-NH2 | 1294 | JBS-1104 | Ac-HLYLWQRWPSPWVEVGWDFV-NH2 |
| 1254 | JBS-1048 | Ac-YILWSVYVPGIEVGWTESA-NH2 | 1295 | JBS-1105 | Ac-HLYLWQRWPSPWVEVGWEDV-NH2 |
| 1255 | JBS-1049 | Ac-DLDPRIVLVGNGEIEIGWSI-NH2 | 1296 | JBS-1106 | Ac-HLYLWQRWPSPWVEVGWEFD-NH2 |
| 1256 | JBS-1050 | Ac-WKIIVGWELFDTGETTWWKV-NH2 | 1297 | JBS-1107 | Ac-FLYLWQRWPSPWVEVGWEFV-NH2 |
| 1257 | JBS-1067 | Ac-ALYLWQRWPSPWVEVGWEFV-NH2 | 1298 | JBS-1108 | Ac-HFYLWQRWPSPWVEVGWEFV-NH2 |
| 1258 | JBS-1068 | Ac-HAYLWQRWPSPWVEVGWEFV-NH2 | 1299 | JBS-1109 | Ac-HLFLWQRWPSPWVEVGWEFV-NH2 |

FIGURE 2Q

| SEQ ID | Compound | Sequence | SEQ ID | Compound | Sequence |
|---|---|---|---|---|---|
| 1300 | JBS-1110 | Ac-HLYLYFWQRWPSPWVEVGWEFV-NH2 | 1341 | JBS-1152 | Ac-HLYLMQKWPSPWVEVGWEFV-NH2 |
| 1301 | JBS-1111 | Ac-HLYLFQRWPSPWVEVGWEFV-NH2 | 1342 | JBS-1153 | Ac-HLYLMQRKPSPWVEVGWEFV-NH2 |
| 1302 | JBS-1112 | Ac-HLYLMFRWPSPWVEVGWEFV-NH2 | 1343 | JBS-1154 | Ac-HLYLMQRWKSPWVEVGWEFV-NH2 |
| 1303 | JBS-1113 | Ac-HLYLMQFWPSPWVEVGWEFV-NH2 | 1344 | JBS-1155 | Ac-HLYLMQRWPKPWVEVGWEFV-NH2 |
| 1304 | JBS-1114 | Ac-HLYLMQRFPSPWVEVGWEFV-NH2 | 1345 | JBS-1156 | Ac-HLYLMQRWPSKWVEVGWEFV-NH2 |
| 1305 | JBS-1115 | Ac-HLYLMQRWFPSPWVEVGWEFV-NH2 | 1346 | JBS-1157 | Ac-HLYLMQRWPSPKVEVGWEFV-NH2 |
| 1306 | JBS-1116 | Ac-HLYLMQRWPFPWVEVGWEFV-NH2 | 1347 | JBS-1158 | Ac-HLYLMQRWPSPWKEVGWEFV-NH2 |
| 1307 | JBS-1117 | Ac-HLYLMQRWPSFWVEVGWEFV-NH2 | 1348 | JBS-1159 | Ac-HLYLMQRWPSPWVKVGWEFV-NH2 |
| 1308 | JBS-1118 | Ac-HLYLMQRWPSPFVEVGWEFV-NH2 | 1349 | JBS-1160 | Ac-HLYLMQRWPSPWVEKGWEFV-NH2 |
| 1309 | JBS-1119 | Ac-HLYLMQRWPSPWFEVGWEFV-NH2 | 1350 | JBS-1161 | Ac-HLYLMQRWPSPWVEVKWEFV-NH2 |
| 1310 | JBS-1120 | Ac-HLYLMQRWPSPWVFVGWEFV-NH2 | 1351 | JBS-1162 | Ac-HLYLMQRWPSPWVEVGKEFV-NH2 |
| 1311 | JBS-1121 | Ac-HLYLMQRWPSPWVEFGWEFV-NH2 | 1352 | JBS-1163 | Ac-HLYLMQRWPSPWVEVGWKFV-NH2 |
| 1312 | JBS-1122 | Ac-HLYLMQRWPSPWVEVFWEFV-NH2 | 1353 | JBS-1164 | Ac-HLYLMQRWPSPWVEVGWEKV-NH2 |
| 1313 | JBS-1123 | Ac-HLYLMQRWPSPWVEVGFEFV-NH2 | 1354 | JBS-1165 | Ac-HLYLMQRWPSPWVEVGWEFK-NH2 |
| 1314 | JBS-1124 | Ac-HLYLMQRWPSPWVEVGWFFV-NH2 | 1355 | JBS-1166 | Ac-LLYLMQRWPSPWVEVGWEFV-NH2 |
| 1315 | JBS-1126 | Ac-HLYLMQRWPSPWVEVGWEFF-NH2 | 1356 | JBS-1167 | Ac-HLLLMQRWPSPWVEVGWEFV-NH2 |
| 1316 | JBS-1127 | Ac-GLYLMQRWPSPWVEVGWEFV-NH2 | 1357 | JBS-1168 | Ac-HLYLLQRWPSPWVEVGWEFV-NH2 |
| 1317 | JBS-1128 | Ac-HGYLMQRWPSPWVEVGWEFV-NH2 | 1358 | JBS-1169 | Ac-HLYLMLRWPSPWVEVGWEFV-NH2 |
| 1318 | JBS-1129 | Ac-HLGLMQRWPSPWVEVGWEFV-NH2 | 1359 | JBS-1170 | Ac-HLYLMQLWPSPWVEVGWEFV-NH2 |
| 1319 | JBS-1130 | Ac-HLYGMQRWPSPWVEVGWEFV-NH2 | 1360 | JBS-1171 | Ac-HLYLMQRLPSPWVEVGWEFV-NH2 |
| 1320 | JBS-1131 | Ac-HLYLGQRWPSPWVEVGWEFV-NH2 | 1361 | JBS-1172 | Ac-HLYLMQRWLSPWVEVGWEFV-NH2 |
| 1321 | JBS-1132 | Ac-HLYLMGRWPSPWVEVGWEFV-NH2 | 1362 | JBS-1173 | Ac-HLYLMQRWPLPWVEVGWEFV-NH2 |
| 1322 | JBS-1133 | Ac-HLYLMQGWPSPWVEVGWEFV-NH2 | 1363 | JBS-1174 | Ac-HLYLMQRWPSLWVEVGWEFV-NH2 |
| 1323 | JBS-1134 | Ac-HLYLMQRGPSPWVEVGWEFV-NH2 | 1364 | JBS-1175 | Ac-HLYLMQRWPSPLVEVGWEFV-NH2 |
| 1324 | JBS-1135 | Ac-HLYLMQRWGSPWVEVGWEFV-NH2 | 1365 | JBS-1176 | Ac-HLYLMQRWPSPWLEVGWEFV-NH2 |
| 1325 | JBS-1136 | Ac-HLYLGQRWPSPWVEVGWEFG-NH2 | 1366 | JBS-1177 | Ac-HLYLMQRWPSPWVLGWEFV-NH2 |
| 1326 | JBS-1137 | Ac-HLYLMQRWPSGWVEVGWEFV-NH2 | 1367 | JBS-1178 | Ac-HLYLMQRWPSPWVELGWEFV-NH2 |
| 1327 | JBS-1138 | Ac-HLYLMQRWPSPGVEVGWEFV-NH2 | 1368 | JBS-1179 | Ac-HLYLMQRWPSPWVEVLWEFV-NH2 |
| 1328 | JBS-1139 | Ac-HLYLMQRWPSPWGEVGWEFV-NH2 | 1369 | JBS-1180 | Ac-HLYLMQRWPSPWVEVGLEFV-NH2 |
| 1329 | JBS-1140 | Ac-HLYLMQRWPSPWVGVGWEFV-NH2 | 1370 | JBS-1181 | Ac-HLYLMQRWPSPWVEVGWLFV-NH2 |
| 1330 | JBS-1141 | Ac-HLYLMQRWPSPWVEGGWEFV-NH2 | 1371 | JBS-1182 | Ac-HLYLMQRWPSPWVEVGWELV-NH2 |
| 1331 | JBS-1142 | Ac-HLYLMQRWPSPWVEVGGEFV-NH2 | 1372 | JBS-1183 | Ac-HLYLMQRWPSPWVEVGWEFL-NH2 |
| 1332 | JBS-1143 | Ac-HLYLMQRWPSPWVEVGWGFV-NH2 | 1373 | JBS-1184 | Ac-SLYLMQRWPSPWVEVGWEFV-NH2 |
| 1333 | JBS-1144 | Ac-HLYLMQRWPSPWVEVGWEGV-NH2 | 1374 | JBS-1185 | Ac-HSYLMQRWPSPWVEVGWEFV-NH2 |
| 1334 | JBS-1145 | Ac-HLYLMQRWPSPWVEVGWEFG-NH2 | 1375 | JBS-1186 | Ac-HLSLMQRWPSPWVEVGWEFV-NH2 |
| 1335 | JBS-1146 | Ac-KLYLMQRWPSPWVEVGWEFV-NH2 | 1376 | JBS-1187 | Ac-HLYSMQRWPSPWVEVGWEFV-NH2 |
| 1336 | JBS-1147 | Ac-HKYLMQRWPSPWVEVGWEFV-NH2 | 1377 | JBS-1188 | Ac-HLYLSQRWPSPWVEVGWEFV-NH2 |
| 1337 | JBS-1148 | Ac-HLKLMQRWPSPWVEVGWEFV-NH2 | 1378 | JBS-1189 | Ac-HLYLMSRWPSPWVEVGWEFV-NH2 |
| 1338 | JBS-1149 | Ac-HLYKMQRWPSPWVEVGWEFV-NH2 | 1379 | JBS-1190 | Ac-HLYLMQSWPSPWVEVGWEFV-NH2 |
| 1339 | JBS-1150 | Ac-HLYLKQRWPSPWVEVGWEFV-NH2 | 1380 | JBS-1191 | Ac-HLYLMQRSPSPWVEVGWEFV-NH2 |
| 1340 | JBS-1151 | Ac-HLYLMKRWPSPWVEVGWEFV-NH2 | 1381 | JBS-1192 | Ac-HLYLMQRWKSSPWVEVGWEFV-NH2 |

FIGURE 2R

| SEQ ID | Compound | Sequence | SEQ ID | Compound | Sequence |
|---|---|---|---|---|---|
| 1382 | JBS-1193 | Ac-HLYLMQRWPSSWVEVGWEFV-NH2 | 1423 | JBS-1234 | Ac-RPTALLIRLGANSWIEIGWEI-NH2 |
| 1383 | JBS-1194 | Ac-HLYLMQRWPSPSVEVGWEFV-NH2 | 1424 | JBS-1235 | Ac-RPTTAIRLGANSWIEIGWEI-NH2 |
| 1384 | JBS-1195 | Ac-HLYLMQRWPSPWSEVGWEFV-NH2 | 1425 | JBS-1236 | Ac-RPTTLARLGANSWIEIGWEI-NH2 |
| 1385 | JBS-1196 | Ac-HLYLMQRWPSPWVSVGWEFV-NH2 | 1426 | JBS-1237 | Ac-RPTTLIALGANSWIEIGWEI-NH2 |
| 1386 | JBS-1197 | Ac-HLYLMQRWPSPWVESGWEFV-NH2 | 1427 | JBS-1238 | Ac-RPTTLIRAGANSWIEIGWEI-NH2 |
| 1387 | JBS-1198 | Ac-HLYLMQRWPSPWVEVSWEFV-NH2 | 1428 | JBS-1239 | Ac-RPTTLIRLAANSWIEIGWEI-NH2 |
| 1388 | JBS-1199 | Ac-HLYLMQRWPSPWVEVGSEFV-NH2 | 1429 | JBS-1241 | Ac-RPTTLIRLGAASWIEIGWEI-NH2 |
| 1389 | JBS-1200 | Ac-HLYLMQRWPSPWVEVGWSFV-NH2 | 1430 | JBS-1242 | Ac-RPTTLIRLGANAWIEIGWEI-NH2 |
| 1390 | JBS-1201 | Ac-HLYLMQRWPSPWVEVGWESV-NH2 | 1431 | JBS-1243 | Ac-RPTTLIRLGANSAIEIGWEI-NH2 |
| 1391 | JBS-1202 | Ac-HLYLMQRWPSPWVEVGWEFS-NH2 | 1432 | JBS-1244 | Ac-RPTTLIRLGANSWAEIGWEI-NH2 |
| 1392 | JBS-1203 | Ac-PLYLMQRWPSPWVEVGWEFV-NH2 | 1433 | JBS-1245 | Ac-RPTTLIRLGANSWIAIGWEI-NH2 |
| 1393 | JBS-1204 | Ac-HPYLMQRWPSPWVEVGWEFV-NH2 | 1434 | JBS-1246 | Ac-RPTTLIRLGANSWIEAGWEI-NH2 |
| 1394 | JBS-1205 | Ac-HLPLMQRWPSPWVEVGWEFV-NH2 | 1435 | JBS-1247 | Ac-RPTTLIRLGANSWIEIAWEI-NH2 |
| 1395 | JBS-1206 | Ac-HLYPMQRWPSPWVEVGWEFV-NH2 | 1436 | JBS-1248 | Ac-RPTTLIRLGANSWIEIGAEI-NH2 |
| 1396 | JBS-1207 | Ac-HLYLPQRWPSPWVEVGWEFV-NH2 | 1437 | JBS-1249 | Ac-RPTTLIRLGANSWIEIGWAI-NH2 |
| 1397 | JBS-1208 | Ac-HLYLMPRWPSPWVEVGWEFV-NH2 | 1438 | JBS-1250 | Ac-RPTTLIRLGANSWIEIGWEA-NH2 |
| 1398 | JBS-1209 | Ac-HLYLMQPWPSPWVEVGWEFV-NH2 | 1439 | JBS-1251 | Ac-DPTTLIRLGANSWIEIGWEI-NH2 |
| 1399 | JBS-1210 | Ac-HLYLMQRPPSPWVEVPWEFV-NH2 | 1440 | JBS-1252 | Ac-RDTTLIRLGANSWIEIGWEI-NH2 |
| 1400 | JBS-1211 | Ac-HLYLMQRWPPPWVEVGWEFV-NH2 | 1441 | JBS-1253 | Ac-RPDTLIRLGANSWIEIGWEI-NH2 |
| 1401 | JBS-1212 | Ac-HLYLMQRWPSPPVEVGWEFV-NH2 | 1442 | JBS-1254 | Ac-RPTDLIRLGANSWIEIGWEI-NH2 |
| 1402 | JBS-1213 | Ac-HLYLMQRWPSPWPEVGWEFV-NH2 | 1443 | JBS-1255 | Ac-RPTTDIRLGANSWIEIGWEI-NH2 |
| 1403 | JBS-1214 | Ac-HLYLMQRWPSPWVPVGWEFV-NH2 | 1444 | JBS-1256 | Ac-RPTTLDRLGANSWIEIGWEI-NH2 |
| 1404 | JBS-1215 | Ac-HLYLMQRWPSPWVEPGWEFV-NH2 | 1445 | JBS-1257 | Ac-RPTTLIDLGANSWIEIGWEI-NH2 |
| 1405 | JBS-1216 | Ac-HLYLMQRWPSPWVEVPWEFV-NH2 | 1446 | JBS-1258 | Ac-RPTTLIRDGANSWIEIGWEI-NH2 |
| 1406 | JBS-1217 | Ac-HLYLMQRWPSPWVEVGPEFV-NH2 | 1447 | JBS-1259 | Ac-RPTTLIRLDANSWIEIGWEI-NH2 |
| 1407 | JBS-1218 | Ac-HLYLMQRWPSPWVEVGWPFV-NH2 | 1448 | JBS-1260 | Ac-RPTTLIRLGDNSWIEIGWEI-NH2 |
| 1408 | JBS-1219 | Ac-HLYLMQRWPSPWVEVGWEPV-NH2 | 1449 | JBS-1261 | Ac-RPTTLIRLGADSWIEIGWEI-NH2 |
| 1409 | JBS-1220 | Ac-HLYLMQRWPSPWVEVGWEFP-NH2 | 1450 | JBS-1262 | Ac-RPTTLIRLGANDWIEIGWEI-NH2 |
| 1410 | JBS-1221 | Ac-HLYLMQRWPSPWVEVGW-NH2 | 1451 | JBS-1263 | Ac-RPTTLIRLGANSDIEIGWEI-NH2 |
| 1411 | JBS-1222 | Ac-HLYLMQRWPSPWVE-NH2 | 1452 | JBS-1264 | Ac-RPTTLIRLGANSWDEIGWEI-NH2 |
| 1412 | JBS-1223 | Ac-HLYLMQRWPSF-NH2 | 1453 | JBS-1265 | Ac-RPTTLIRLGANSWIDIGWEI-NH2 |
| 1413 | JBS-1224 | Ac-HLYLMQRW-NH2 | 1454 | JBS-1266 | Ac-RPTTLIRLGANSWIEDGWEI-NH2 |
| 1414 | JBS-1225 | Ac-LMQRWPSPWVEVGWEFV-NH2 | 1455 | JBS-1267 | Ac-RPTTLIRLGANSWIEIDWEI-NH2 |
| 1415 | JBS-1226 | Ac-RWPSPWVEVGWEFV-NH2 | 1456 | JBS-1268 | Ac-RPTTLIRLGANSWIEIGDEI-NH2 |
| 1416 | JBS-1227 | Ac-SPWVEVGWEFV-NH2 | 1457 | JBS-1269 | Ac-RPTTLIRLGANSWIEIGWDI-NH2 |
| 1417 | JBS-1228 | Ac-VEVGWEFV-NH2 | 1458 | JBS-1270 | Ac-RPTTLIRLGANSWIEIGWED-NH2 |
| 1418 | JBS-1229 | Ac-LMQRWPSPWVEVGW-NH2 | 1459 | JBS-1271 | Ac-FPTTLIRLGANSWIEIGWEI-NH2 |
| 1419 | JBS-1230 | Ac-RWPSPWVE-NH2 | 1460 | JBS-1272 | Ac-RFTTLIRLGANSWIEIGWEI-NH2 |
| 1420 | JBS-1231 | Ac-APTTLIRLGANSWIEIGWEI-NH2 | 1461 | JBS-1273 | Ac-RPFTLIRLGANSWIEIGWEI-NH2 |
| 1421 | JBS-1232 | Ac-RATTLIRLGANSWIEIGWEI-NH2 | 1462 | JBS-1274 | Ac-RPTFLIRLGANSWIEIGWEI-NH2 |
| 1422 | JBS-1233 | Ac-RPATLIRLGANSWIEIGWEI-NH2 | 1463 | JBS-1275 | Ac-RPTTFIRLGANSWIEIGWEI-NH2 |

FIGURE 2S

| SEQ ID | Compound | Sequence | SEQ ID | Compound | Sequence |
|---|---|---|---|---|---|
| 1464 | JBS-1276 | Ac-RPTTLFRLGANSWIEIGWEI-NH2 | 1505 | JBS-1317 | Ac-RPTTLIRLKANSWIEIGWEI-NH2 |
| 1465 | JBS-1277 | Ac-RPTTLIFLGANSWIEIGWEI-NH2 | 1506 | JBS-1318 | Ac-RPTTLIRLGKNSWIEIGWEI-NH2 |
| 1466 | JBS-1278 | Ac-RPTTLIRFGANSWIEIGWEI-NH2 | 1507 | JBS-1319 | Ac-RPTTLIRLGAKSWIEIGWEI-NH2 |
| 1467 | JBS-1279 | Ac-RPTTLIRLFANSWIEIGWEI-NH2 | 1508 | JBS-1320 | Ac-RPTTLIRLGANKWIEIGWEI-NH2 |
| 1468 | JBS-1280 | Ac-RPTTLIRLGFNSWIEIGWEI-NH2 | 1509 | JBS-1321 | Ac-RPTTLIRLGANSKIEIGWEI-NH2 |
| 1469 | JBS-1281 | Ac-RPTTLIRLGAFSWIEIGWEI-NH2 | 1510 | JBS-1322 | Ac-RPTTLIRLGANSWKEIGWEI-NH2 |
| 1470 | JBS-1282 | Ac-RPTTLIRLGANFWIEIGWEI-NH2 | 1511 | JBS-1323 | Ac-RPTTLIRLGANSWIKIGWEI-NH2 |
| 1471 | JBS-1283 | Ac-RPTTLIRLGANSFIEIGWEI-NH2 | 1512 | JBS-1324 | Ac-RPTTLIRLGANSWIEKGWEI-NH2 |
| 1472 | JBS-1284 | Ac-RPTTLIRLGANSWFEIGWEI-NH2 | 1513 | JBS-1325 | Ac-RPTTLIRLGANSWIEIKWEI-NH2 |
| 1473 | JBS-1285 | Ac-RPTTLIRLGANSWIFIGWEI-NH2 | 1514 | JBS-1326 | Ac-RPTTLIRLGANSWIEIGKEI-NH2 |
| 1474 | JBS-1286 | Ac-RPTTLIRLGANSWIEFGWEI-NH2 | 1515 | JBS-1327 | Ac-RPTTLIRLGANSWIEIGWKI-NH2 |
| 1475 | JBS-1287 | Ac-RPTTLIRLGANSWIEIFWEI-NH2 | 1516 | JBS-1328 | Ac-RPTTLIRLGANSWIEIGWEK-NH2 |
| 1476 | JBS-1288 | Ac-RPTTLIRLGANSWIEIGFEI-NH2 | 1517 | JBS-1329 | Ac-LPTTLIRLGANSWIEIGWEI-NH2 |
| 1477 | JBS-1289 | Ac-RPTTLIRLGANSWIEIGWFI-NH2 | 1518 | JBS-1330 | Ac-RLTTLIRLGANSWIEIGWEI-NH2 |
| 1478 | JBS-1290 | Ac-RPTTLIRLGANSWIEIGWEF-NH2 | 1519 | JBS-1331 | Ac-RPLTLIRLGANSWIEIGWEI-NH2 |
| 1479 | JBS-1291 | Ac-GPTTLIRLGANSWIEIGWEI-NH2 | 1520 | JBS-1332 | Ac-RPTLLIRLGANSWIEIGWEI-NH2 |
| 1480 | JBS-1292 | Ac-RGTTLIRLGANSWIEIGWEI-NH2 | 1521 | JBS-1333 | Ac-RPTTLLRLGANSWIEIGWEI-NH2 |
| 1481 | JBS-1293 | Ac-RPGTLIRLGANSWIEIGWEI-NH2 | 1522 | JBS-1334 | Ac-RPTTLIRLLANSWIEIGWEI-NH2 |
| 1482 | JBS-1294 | Ac-RPTGLIRLGANSWIEIGWEI-NH2 | 1523 | JBS-1335 | Ac-RPTTLIRLLANSWIEIGWEI-NH2 |
| 1483 | JBS-1295 | Ac-RPTTGIRLGANSWIEIGWEI-NH2 | 1524 | JBS-1336 | Ac-RPTTLIRLGLNSWIEIGWEI-NH2 |
| 1484 | JBS-1296 | Ac-RPTTLGRLGANSWIEIGWEI-NH2 | 1525 | JBS-1337 | Ac-RPTTLIRLGALSWIEIGWEI-NH2 |
| 1485 | JBS-1297 | Ac-RPTTLIGLGANSWIEIGWEI-NH2 | 1526 | JBS-1338 | Ac-RPTTLIRLGANLWIEIGWEI-NH2 |
| 1486 | JBS-1298 | Ac-RPTTLIRGGANSWIEIGWEI-NH2 | 1527 | JBS-1339 | Ac-RPTTLIRLGANSLIEIGWEI-NH2 |
| 1487 | JBS-1299 | Ac-RPTTLIRLGGNSWIEIGWEI-NH2 | 1528 | JBS-1340 | Ac-RPTTLIRLGANSWLEIGWEI-NH2 |
| 1488 | JBS-1300 | Ac-RPTTLIRLGAGSWIEIGWEI-NH2 | 1529 | JBS-1341 | Ac-RPTTLIRLGANSWILIGWEI-NH2 |
| 1489 | JBS-1301 | Ac-RPTTLIRLGANGWIEIGWEI-NH2 | 1530 | JBS-1342 | Ac-RPTTLIRLGANSWIELGWEI-NH2 |
| 1490 | JBS-1302 | Ac-RPTTLIRLGANSGIEIGWEI-NH2 | 1531 | JBS-1343 | Ac-RPTTLIRLGANSWIEILWEI-NH2 |
| 1491 | JBS-1303 | Ac-RPTTLIRLGANSWGEIGWEI-NH2 | 1532 | JBS-1344 | Ac-RPTTLIRLGANSWIEIGLEI-NH2 |
| 1492 | JBS-1304 | Ac-RPTTLIRLGANSWIGIGWEI-NH2 | 1533 | JBS-1345 | Ac-RPTTLIRLGANSWIEIGWLI-NH2 |
| 1493 | JBS-1305 | Ac-RPTTLIRLGANSWIEGGWEI-NH2 | 1534 | JBS-1346 | Ac-RPTTLIRLGANSWIEIGWEL-NH2 |
| 1494 | JBS-1306 | Ac-RPTTLIRLGANSWIEIGGEI-NH2 | 1535 | JBS-1347 | Ac-SPTTLIRLGANSWIEIGWEI-NH2 |
| 1495 | JBS-1307 | Ac-RPTTLIRLGANSWIEIGWGI-NH2 | 1536 | JBS-1348 | Ac-RSTTLIRLGANSWIEIGWEI-NH2 |
| 1496 | JBS-1308 | Ac-RPTTLIRLGANSWIEIGWEG-NH2 | 1537 | JBS-1349 | Ac-RPSTLIRLGANSWIEIGWEI-NH2 |
| 1497 | JBS-1309 | Ac-KPTTLIRLGANSWIEIGWEI-NH2 | 1538 | JBS-1350 | Ac-RPTSLIRLGANSWIEIGWEI-NH2 |
| 1498 | JBS-1310 | Ac-RKTTLIRLGANSWIEIGWEI-NH2 | 1539 | JBS-1351 | Ac-RPTTSIRLGANSWIEIGWEI-NH2 |
| 1499 | JBS-1311 | Ac-RPKTLIRLGANSWIEIGWEI-NH2 | 1540 | JBS-1352 | Ac-RPTTLSRLGANSWIEIGWEI-NH2 |
| 1500 | JBS-1312 | Ac-RPTKLIRLGANSWIEIGWEI-NH2 | 1541 | JBS-1353 | Ac-RPTTLISLGANSWIEIGWEI-NH2 |
| 1501 | JBS-1313 | Ac-RPTTLKRLGANSWIEIGWEI-NH2 | 1542 | JBS-1354 | Ac-RPTTLIRSGANSWIEIGWEI-NH2 |
| 1502 | JBS-1314 | Ac-RPTTLIKLGANSWIEIGWEI-NH2 | 1543 | JBS-1355 | Ac-RPTTLIRLSANSWIEIGWEI-NH2 |
| 1503 | JBS-1315 | Ac-RPTTLIRKGANSWIEIGWEI-NH2 | 1544 | JBS-1356 | Ac-RPTTLIRLGSNSWIEIGWEI-NH2 |
| 1504 | JBS-1316 | Ac-RPTTLIRLKANSWIEIGWEI-NH2 | 1545 | JBS-1357 | Ac-RPTTLIRLGASSWIEIGWEI-NH2 |

FIGURE 2T

| SEQ ID | Compound | Sequence | SEQ ID | Compound | Sequence |
| --- | --- | --- | --- | --- | --- |
| 1546 | JBS-1358 | Ac-RPTTLIRLGANSSIEIGWEI-NH2 | 1587 | JBS-1399 | Ac-WKIIAGWELFDTGETTWWKV-NH2 |
| 1547 | JBS-1359 | Ac-RPTTLIRLGANSWSEIGWEI-NH2 | 1588 | JBS-1400 | Ac-WKIIVAWELFDTGETTWWKV-NH2 |
| 1548 | JBS-1360 | Ac-RPTTLIRLGANSWISIGWEI-NH2 | 1589 | JBS-1401 | Ac-WKIIVGAELFDTGETTWWKV-NH2 |
| 1549 | JBS-1361 | Ac-RPTTLIRLGANSWIESGWEI-NH2 | 1590 | JBS-1402 | Ac-WKIIVGWALFDTGETTWWKV-NH2 |
| 1550 | JBS-1362 | Ac-RPTTLIRLGANSWIEISWEI-NH2 | 1591 | JBS-1403 | Ac-WKIIVGWEAFDTGETTWWKV-NH2 |
| 1551 | JBS-1363 | Ac-RPTTLIRLGANSWIEIGSEI-NH2 | 1592 | JBS-1404 | Ac-WKIIVGWELADTGETTWWKV-NH2 |
| 1552 | JBS-1364 | Ac-RPTTLIRLGANSWIEIGWSI-NH2 | 1593 | JBS-1405 | Ac-WKIIVGWELFATGETTWWKV-NH2 |
| 1553 | JBS-1365 | Ac-RPTTLIRLGANSWIEIGWES-NH2 | 1594 | JBS-1406 | Ac-WKIIVGWELFDAGETTWWKV-NH2 |
| 1554 | JBS-1366 | Ac-PPTTLIRLGANSWIEIGWEI-NH2 | 1595 | JBS-1407 | Ac-WKIIVGWELFDTAETTWWKV-NH2 |
| 1555 | JBS-1367 | Ac-RPPTLIRLGANSWIEIGWEI-NH2 | 1596 | JBS-1408 | Ac-WKIIVGWELFDTGATTWWKV-NH2 |
| 1556 | JBS-1368 | Ac-RPTPLIRLGANSWIEIGWEI-NH2 | 1597 | JBS-1409 | Ac-WKIIVGWELFDTGEATWWKV-NH2 |
| 1557 | JBS-1369 | Ac-RPTTPIRLGANSWIEIGWEI-NH2 | 1598 | JBS-1410 | Ac-WKIIVGWELFDTGETAWWKV-NH2 |
| 1558 | JBS-1370 | Ac-RPTTLPRLGANSWIEIGWEI-NH2 | 1599 | JBS-1411 | Ac-WKIIVGWELFDTGETTAWKV-NH2 |
| 1559 | JBS-1371 | Ac-RPTTLIPLGANSWIEIGWEI-NH2 | 1600 | JBS-1412 | Ac-WKIIVGWELFDTGETTWAKV-NH2 |
| 1560 | JBS-1372 | Ac-RPTTLIRPGANSWIEIGWEI-NH2 | 1601 | JBS-1413 | Ac-WKIIVGWELFDTGETTWWAV-NH2 |
| 1561 | JBS-1373 | Ac-RPTTLIRLPANSWIEIGWEI-NH2 | 1602 | JBS-1414 | Ac-WKIIVGWELFDTGETTWWKA-NH2 |
| 1562 | JBS-1374 | Ac-RPTTLIRLGPNSWIEIGWEI-NH2 | 1603 | JBS-1415 | Ac-DKIIVGWELFDTGETTWWKV-NH2 |
| 1563 | JBS-1375 | Ac-RPTTLIRLGAPSWIEIGWEI-NH2 | 1604 | JBS-1416 | Ac-WDIIVGWELFDTGETTWWKV-NH2 |
| 1564 | JBS-1376 | Ac-RPTTLIRLGANPWIEIGWEI-NH2 | 1605 | JBS-1417 | Ac-WKDIVGWELFDTGETTWWKV-NH2 |
| 1565 | JBS-1377 | Ac-RPTTLIRLGANSPIEIGWEI-NH2 | 1606 | JBS-1418 | Ac-WKIDVGWELFDTGETTWWKV-NH2 |
| 1566 | JBS-1378 | Ac-RPTTLIRLGANSWPEIGWEI-NH2 | 1607 | JBS-1419 | Ac-WKIIDGWELFDTGETTWWKV-NH2 |
| 1567 | JBS-1379 | Ac-RPTTLIRLGANSWIPIGWEI-NH2 | 1608 | JBS-1420 | Ac-WKIIVDWELFDTGETTWWKV-NH2 |
| 1568 | JBS-1380 | Ac-RPTTLIRLGANSWIEPGWEI-NH2 | 1609 | JBS-1421 | Ac-WKIIVGDELFDTGETTWWKV-NH2 |
| 1569 | JBS-1381 | Ac-RPTTLIRLGANSWIEIPWEI-NH2 | 1610 | JBS-1422 | Ac-WKIIVGWDLFDTGETTWWKV-NH2 |
| 1570 | JBS-1382 | Ac-RPTTLIRLGANSWIEIGPEI-NH2 | 1611 | JBS-1423 | Ac-WKIIVGWEDFDTGETTWWKV-NH2 |
| 1571 | JBS-1383 | Ac-RPTTLIRLGANSWIEIGWPI-NH2 | 1612 | JBS-1424 | Ac-WKIIVGWELDDTGETTWWKV-NH2 |
| 1572 | JBS-1384 | Ac-RPTTLIRLGANSWIEIGWEP-NH2 | 1613 | JBS-1426 | Ac-WKIIVGWELFDDGETTWWKV-NH2 |
| 1573 | JBS-1385 | Ac-RPTTLIRLGANSWIEIG-NH2 | 1614 | JBS-1427 | Ac-WKIIVGWELFDTDETTWWKV-NH2 |
| 1574 | JBS-1386 | Ac-RPTTLIRLGANSWI-NH2 | 1615 | JBS-1428 | Ac-WKIIVGWELFDTGDTTWWKV-NH2 |
| 1575 | JBS-1387 | Ac-RPTTLIRLGAN-NH2 | 1616 | JBS-1429 | Ac-WKIIVGWELFDTGEDTWWKV-NH2 |
| 1576 | JBS-1388 | Ac-RPTTLIRL-NH2 | 1617 | JBS-1430 | Ac-WKIIVGWELFDTGETDWWKV-NH2 |
| 1577 | JBS-1389 | Ac-TLIRLGANSWIEIGWEI-NH2 | 1618 | JBS-1431 | Ac-WKIIVGWELFDTGETTDWKV-NH2 |
| 1578 | JBS-1390 | Ac-RLGANSWIEIGWEI-NH2 | 1619 | JBS-1432 | Ac-WKIIVGWELFDTGETTWDKV-NH2 |
| 1579 | JBS-1391 | Ac-ANSWIEIGWEI-NH2 | 1620 | JBS-1433 | Ac-WKIIVGWELFDTGETTWWDV-NH2 |
| 1580 | JBS-1392 | Ac-WIEIGWEI-NH2 | 1621 | JBS-1434 | Ac-WKIIVGWELFDTGETTWWKD-NH2 |
| 1581 | JBS-1393 | Ac-TLIRLGANSWIEIG-NH2 | 1622 | JBS-1435 | Ac-FKIIVGWELFDTGETTWWKV-NH2 |
| 1582 | JBS-1394 | Ac-RLGANSWI-NH2 | 1623 | JBS-1436 | Ac-WFIIVGWELFDTGETTWWKV-NH2 |
| 1583 | JBS-1395 | Ac-AKIIVGWELFDTGETTWWKV-NH2 | 1624 | JBS-1437 | Ac-WKFIVGWELFDTGETTWWKV-NH2 |
| 1584 | JBS-1396 | Ac-WAIIVGWELFDTGETTWWKV-NH2 | 1625 | JBS-1438 | Ac-WKIFVGWELFDTGETTWDKV-NH2 |
| 1585 | JBS-1397 | Ac-WKAIVGWELFDTGETTWWKV-NH2 | 1626 | JBS-1439 | Ac-WKIIFGWELFDTGETTWWKV-NH2 |
| 1586 | JBS-1398 | Ac-WKIAVGWELFDTGETTWWKV-NH2 | 1627 | JBS-1440 | Ac-WKIIVFWELFDTGETTWWKV-NH2 |

FIGURE 2U

| SEQ ID | Compound | Sequence | SEQ ID | Compound | Sequence |
|---|---|---|---|---|---|
| 1628 | JBS-1441 | Ac-WKIIVGFELFDTGETTWWKV-NH2 | 1669 | JBS-1482 | Ac-WKIIVGWELFDKGETTWWKV-NH2 |
| 1629 | JBS-1442 | Ac-WKIIVGWELFDTGETTWWKV-NH2 | 1670 | JBS-1483 | Ac-WKIIVGWELFDTKETTWWKV-NH2 |
| 1630 | JBS-1443 | Ac-WKIIVGWEFFDTGETTWWKV-NH2 | 1671 | JBS-1484 | Ac-WKIIVGWELFDTGKTTWWKV-NH2 |
| 1631 | JBS-1444 | Ac-WKIIVGWELFFTGETTWWKV-NH2 | 1672 | JBS-1485 | Ac-WKIIVGWELFDTGEKTTWWKV-NH2 |
| 1632 | JBS-1445 | Ac-WKIIVGWELFDFGETTWWKV-NH2 | 1673 | JBS-1486 | Ac-WKIIVGWELFDTGETKWWKV-NH2 |
| 1633 | JBS-1446 | Ac-WKIIVGWELFDTFETTWWKV-NH2 | 1674 | JBS-1487 | Ac-WKIIVGWELFDTGETTKWKV-NH2 |
| 1634 | JBS-1447 | Ac-WKIIVGWELFDTGFTTWWKV-NH2 | 1675 | JBS-1488 | Ac-WKIIVGWELFDTGETTWKKV-NH2 |
| 1635 | JBS-1448 | Ac-WKIIVGWELFDTGEIFWWKV-NH2 | 1676 | JBS-1489 | Ac-WKIIVGWELFDTGETTWWKK-NH2 |
| 1636 | JBS-1449 | Ac-WKIIVGWELFDTGETFWWKV-NH2 | 1677 | JBS-1490 | Ac-LKIIVGWELFDTGETTWWKV-NH2 |
| 1637 | JBS-1450 | Ac-WKIIVGWELFDTGETTFWKV-NH2 | 1678 | JBS-1491 | Ac-WLIIVGWELFDTGETTWWKV-NH2 |
| 1638 | JBS-1451 | Ac-WKIIVGWELFDTGETTWFKV-NH2 | 1679 | JBS-1492 | Ac-WKLIVGWELFDTGETTWWKV-NH2 |
| 1639 | JBS-1452 | Ac-WKIIVGWELFDTGETTWWFV-NH2 | 1680 | JBS-1493 | Ac-WKILVGWELFDTGETTWWKV-NH2 |
| 1640 | JBS-1453 | Ac-WKIIVGWELFDTGETTWWKF-NH2 | 1681 | JBS-1494 | Ac-WKIILGWELFDTGETTWWKV-NH2 |
| 1641 | JBS-1454 | Ac-GKIIVGWELFDTGETTWWKV-NH2 | 1682 | JBS-1495 | Ac-WKIIVLWELFDTGETTWWKV-NH2 |
| 1642 | JBS-1455 | Ac-WGIIVGWELGDTGETTWWKV-NH2 | 1683 | JBS-1496 | Ac-WKIIVGLELFDTGETTWWKV-NH2 |
| 1643 | JBS-1456 | Ac-WKGIVGWELFDTGETTWWKV-NH2 | 1684 | JBS-1497 | Ac-WKIIVGWLLDTGETTWWKV-NH2 |
| 1644 | JBS-1457 | Ac-WKGVGWELFDTGETTWWKV-NH2 | 1685 | JBS-1498 | Ac-WKIIVGWELLDTGETTWWKV-NH2 |
| 1645 | JBS-1458 | Ac-WKIIGGWELFDTGETTWWKV-NH2 | 1686 | JBS-1499 | Ac-WKIIVGWELFLTGETTWWKV-NH2 |
| 1646 | JBS-1459 | Ac-WKIIVGGELFDTGETTWWKV-NH2 | 1687 | JBS-1500 | Ac-WKIIVGWELFDLGETTWWKV-NH2 |
| 1647 | JBS-1460 | Ac-WKIIVGWLFDTGETTWWKV-NH2 | 1688 | JBS-1501 | Ac-WKIIVGWELFDTLETTWWKV-NH2 |
| 1648 | JBS-1461 | Ac-WKIIVGWEGFDTGETTWWKV-NH2 | 1689 | JBS-1502 | Ac-WKIIVGWELFDTGLTTWWKV-NH2 |
| 1649 | JBS-1462 | Ac-WKIIVGWELGDTGETTWWKV-NH2 | 1690 | JBS-1503 | Ac-WKIIVGWELFDTGELTWWKV-NH2 |
| 1650 | JBS-1463 | Ac-WKIIVGWELFGTGETTWWKV-NH2 | 1691 | JBS-1504 | Ac-WKIIVGWELFDTGETLWWKV-NH2 |
| 1651 | JBS-1464 | Ac-WKIIVGWELFDGGETTWWKV-NH2 | 1692 | JBS-1505 | Ac-WKIIVGWELFDTGETTLWKV-NH2 |
| 1652 | JBS-1465 | Ac-WKIIVGWELFDTGGTTWWKV-NH2 | 1693 | JBS-1506 | Ac-WKIIVGWELFDTGETTWLKV-NH2 |
| 1653 | JBS-1466 | Ac-WKIIVGWELFDTGEGTWWKV-NH2 | 1694 | JBS-1507 | Ac-WKIIVGWELFDTGETTWWLV-NH2 |
| 1654 | JBS-1467 | Ac-WKIIVGWELFDTGETGWWKV-NH2 | 1695 | JBS-1508 | Ac-WKIIVSWELFDTGETTWWKL-NH2 |
| 1655 | JBS-1468 | Ac-WKIIVGWELFDTGETTGWKV-NH2 | 1696 | JBS-1509 | Ac-WKIIVGWELFDTGETTWWKV-NH2 |
| 1656 | JBS-1469 | Ac-WKIIVGWELFDTGETTWGKV-NH2 | 1697 | JBS-1510 | Ac-SKIIVGWELFDTGETTWWKV-NH2 |
| 1657 | JBS-1470 | Ac-WKIIVGWELFDTGETTWWGV-NH2 | 1698 | JBS-1511 | Ac-WSIIVGWELFDTGETTWWKV-NH2 |
| 1658 | JBS-1471 | Ac-WKIIVGWELFDTGETTWWKG-NH2 | 1699 | JBS-1512 | Ac-WKSIVGWELFDTGETTWWKV-NH2 |
| 1659 | JBS-1472 | Ac-RKIIVGWELFDTGETTWWKV-NH2 | 1700 | JBS-1513 | Ac-WKISVGWELFDTGETTWWKV-NH2 |
| 1660 | JBS-1473 | Ac-WKIIVGWEKFDTGETTWWKV-NH2 | 1701 | JBS-1514 | Ac-WKIISGWELFDTGETTWWKV-NH2 |
| 1661 | JBS-1474 | Ac-WKIIVSWELFDTGETTWWKV-NH2 | 1702 | JBS-1515 | Ac-WKIIVSWELFDTGETTWWKV-NH2 |
| 1662 | JBS-1475 | Ac-WKIIKGWELFDTGETTWWKV-NH2 | 1703 | JBS-1516 | Ac-WKIIVGSELFDTGETTWWKV-NH2 |
| 1663 | JBS-1476 | Ac-WKIIVKWELFDTGETTWWKV-NH2 | 1704 | JBS-1517 | Ac-WKIIVGWESFDTGETTWWKV-NH2 |
| 1664 | JBS-1477 | Ac-WKGKELFDTGETTWWKG-NH2 | 1705 | JBS-1518 | Ac-WKIIVGWELSDTGETTWWKV-NH2 |
| 1665 | JBS-1478 | Ac-WKIIVGWELKDTGETTWWKV-NH2 | 1706 | JBS-1519 | Ac-WKIIVGWELFSTGETTWWKV-NH2 |
| 1666 | JBS-1479 | Ac-WKIIVGWELFKTGETTWWKV-NH2 | 1707 | JBS-1520 | Ac-WKIIVGWELFDSGETTWWKV-NH2 |
| 1667 | JBS-1480 | Ac-WKIIVGWELKDTGETTWWKV-NH2 | 1708 | JBS-1521 | Ac-WKIIVGWELFDTSETTWWKV-NH2 |
| 1668 | JBS-1481 | Ac-WKIIVGWELFKTGETTWWKV-NH2 | 1709 | JBS-1522 | Ac-WKIIVGWELFDTGSTTWWKV-NH2 |

FIGURE 2V

| SEQ ID | Compound | Sequence | SEQ ID | Compound | Sequence |
| --- | --- | --- | --- | --- | --- |
| 1710 | JBS-1523 | Ac-WKIIVGWELFDTGESTWWKV-NH2 | 1751 | JBS-1565 | Ac-PATGLIINSETRGIRLIWNE-NH2 |
| 1711 | JBS-1524 | Ac-WKIIVGWELFDTGETSWWKV-NH2 | 1752 | JBS-1567 | Ac-TSGSAWGWEIPVVEYGIVYL-NH2 |
| 1712 | JBS-1525 | Ac-WKIIVGWELFDTGETTCWKV-NH2 | 1753 | JBS-1568 | Ac-VAYVWTLYVGISEEPGIGW-NH2 |
| 1713 | JBS-1526 | Ac-WKIIVGWELFDTGETTWSKV-NH2 | 1754 | JBS-1569 | Ac-TGIVLGWTDIKTEFVWWK-NH2 |
| 1714 | JBS-1527 | Ac-WKIIVGWELFDTGETTWWSV-NH2 | 1755 | JBS-1570 | Ac-KWLWTKGWVDIFVIIIGWE-NH2 |
| 1715 | JBS-1528 | Ac-WKIIVGWELFDTGETTWWKS-NH2 | 1756 | JBS-1572 | Ac-LDGISLGGPVIWVNIEDIER-NH2 |
| 1716 | JBS-1529 | Ac-PKIIVGWELFDTGETTWWKV-NH2 | 1757 | JBS-1573 | Ac-CLVIIEPDLIVDSGGWENRI-NH2 |
| 1717 | JBS-1530 | Ac-WPIIVGWELFDTGETTWWKV-NH2 | 1758 | JBS-1587 | Bio-Ttds-GQIEWGFYDHTTNQYWSMDV-NH2 |
| 1718 | JBS-1531 | Ac-WKPIVGWELFDTGETTWWKV-NH2 | 1759 | JBS-1588 | Bio-Ttds-LHELGRIQTEQYSIEIYYVH-NH2 |
| 1719 | JBS-1532 | Ac-WKIPVGWELFDTGETTWWKV-NH2 | 1760 | JBS-1589 | Bio-Ttds-HRIEIWWYNSGTNKHGLVHT-NH2 |
| 1720 | JBS-1533 | Ac-WKIIPGWELFDTGETTWWKV-NH2 | 1761 | JBS-1590 | Bio-Ttds-GRHTNDINKMRRAVQALFEN-NH2 |
| 1721 | JBS-1534 | Ac-WKIIVPWELFDTGETTWWKV-NH2 | 1762 | JBS-1591 | Bio-Ttds-WGLGFYDVITWRHTPIAFKT-NH2 |
| 1722 | JBS-1535 | Ac-WKIIVGPELFDTGETTWWKV-NH2 | 1763 | JBS-1592 | Bio-Ttds-VWISLGWYDMVNDRHSSLIM-NH2 |
| 1723 | JBS-1536 | Ac-WKIIVGWPLFDTGETTWWKV-NH2 | 1764 | JBS-1593 | Bio-Ttds-RKEYEWAEREGWKTTLSMFL-NH2 |
| 1724 | JBS-1537 | Ac-WKIIVGWEPFDTGETTWWKV-NH2 | 1765 | JBS-1594 | Bio-Ttds-AYMMMIGMYTELDTHKVVA-NH2 |
| 1725 | JBS-1538 | Ac-WKIIVGWELPDTGETTWWKV-NH2 | 1766 | JBS-1595 | Bio-Ttds-IVNSSVDWGYEMYASQWRHN-NH2 |
| 1726 | JBS-1539 | Ac-WKIIVGWELFPTGETTWWKV-NH2 | 1767 | JBS-1596 | Bio-Ttds-HVHLTYQIEVGWEYVKEIYK-NH2 |
| 1727 | JBS-1540 | Ac-WKIIVGWELFDPGETTWWKV-NH2 | 1768 | JBS-1597 | Bio-Ttds-RLRIELGVIVDGQVLIWKVL-NH2 |
| 1728 | JBS-1541 | Ac-WKIIVGWELFDTPETTWWKV-NH2 | 1769 | JBS-1598 | Bio-Ttds-HGVEVGFWDTVMDKVYIVHM-NH2 |
| 1729 | JBS-1542 | Ac-WKIIVGWELFDTGPTTWWKV-NH2 | 1770 | JBS-1599 | Bio-Ttds-IWVGYFNYEDIYWSQIGSMT-NH2 |
| 1730 | JBS-1543 | Ac-WKIIVGWELFDTGEPTWWKV-NH2 | 1771 | JBS-1600 | Bio-Ttds-SHRWRRLRELKWYVEFGWEV-NH2 |
| 1731 | JBS-1544 | Ac-WKIIVGWELFDTGETPWWKV-NH2 | 1772 | JBS-1601 | Bio-Ttds-YEWVDRAGMALFTLRDFYA-NH2 |
| 1732 | JBS-1545 | Ac-WKIIVGWELFDTGETTPWKV-NH2 | 1773 | JBS-1602 | Bio-Ttds-IFTVELWDSTQGEGMIWSI-NH2 |
| 1733 | JBS-1546 | Ac-WKIIVGWELFDTGETTWPKV-NH2 | 1774 | JBS-1603 | Bio-Ttds-WVSLGWYDSRSVNEQWYSVW-NH2 |
| 1734 | JBS-1547 | Ac-WKIIVGWELFDTGETTWWPV-NH2 | 1775 | JBS-1604 | Bio-Ttds-LMVFRRHSDKNGIYEVGYEV-NH2 |
| 1735 | JBS-1548 | Ac-WKIIVGWELFDTGETTWWKP-NH2 | 1776 | JBS-1605 | Bio-Ttds-GVTAGHYYIDINTYKPFESG-NH2 |
| 1736 | JBS-1549 | Ac-WKIIVGWELFDTGETTW-NH2 | 1777 | JBS-1606 | Bio-Ttds-WLVVRVNQISVWWDVGFTT-NH2 |
| 1737 | JBS-1550 | Ac-WKIIVGWELFDTGE-NH2 | 1778 | JBS-1607 | Bio-Ttds-EDPWEWQVWISVNGTEIRLH-NH2 |
| 1738 | JBS-1551 | Ac-WKIIVGWELFDTGE-NH2 | 1779 | JBS-1608 | Bio-Ttds-WRFWHAHENSGFLVEIGYER-NH2 |
| 1739 | JBS-1552 | Ac-WKIIVGWE-NH2 | 1780 | JBS-1609 | Bio-Ttds-EKTIEVGLYFKKEDVYKPMG-NH2 |
| 1740 | JBS-1553 | Ac-IVGWELFDTGETTWWKV-NH2 | 1781 | JBS-1610 | Bio-Ttds-KLIRVGFYNLNTNTHTYWED-NH2 |
| 1741 | JBS-1554 | Ac-WELFDTGETTWWKV-NH2 | 1782 | JBS-1611 | Bio-Ttds-SIVIMGFYNYNSDTYKLWSM-NH2 |
| 1742 | JBS-1555 | Ac-FDTGETTWWKV-NH2 | 1864 | JBS-1693 | Ac-VYEVGWDHGNWYEIIARYPS-NH2 |
| 1743 | JBS-1556 | Ac-GETTWWKV-NH2 | 1865 | JBS-1694 | Ac-VYEVGWDHGNWYEIIWAYPS-NH2 |
| 1744 | JBS-1557 | Ac-IVGWELFDIGETTW-NH2 | 1866 | JBS-1695 | Ac-VYEVGWDHGNWYEIIWRAPS-NH2 |
| 1745 | JBS-1558 | Ac-WELFDTGE-NH2 | 1867 | JBS-1696 | Ac-VYEVGWDHGNWYEIIWRYAS-NH2 |
| 1746 | JBS-1560 | Ac-DFGNENKWGSVWAVSFAFWY-NH2 | 1868 | JBS-1697 | Ac-VYEVGWDHGNWYEIIWRYPA-NH2 |
| 1747 | JBS-1561 | Ac-VFANGKSGWWFYNFEWDVAS-NH2 | 1869 | JBS-1698 | Ac-DYEVGWDHGNWYEIIWRYPS-NH2 |
| 1748 | JBS-1562 | Ac-WLELYSVVFRPPEQGWHVWW-NH2 | 1870 | JBS-1699 | Ac-VDEVGWDHGNWYEIIWRYPS-NH2 |
| 1749 | JBS-1563 | Ac-WHQSEYPVVFGLWPREWWLV-NH2 | 1871 | JBS-1700 | Ac-VYDVGWDHGNWYEIIWRYPS-NH2 |
| 1750 | JBS-1564 | Ac-GGLITTWNIEWELRRIIAPS-NH2 | 1872 | JBS-1701 | Ac-VYEDGWDHGNWYEIIWRYPS-NH2 |

| SEQ ID | Compound | Sequence | SEQ ID | Compound | Sequence |
|---|---|---|---|---|---|
| 1873 | JBS-1702 | Ac-VYEVDWDHGNWYEIIWRYPS-NH2 | 1914 | JBS-1743 | Ac-VYEVGWDHLNWYEIIWRYPS-NH2 |
| 1874 | JBS-1703 | Ac-VYEVGWDDGNWYEIIWRYPS-NH2 | 1915 | JBS-1744 | Ac-VYEVGWDHGLWYEIIWRYPS-NH2 |
| 1875 | JBS-1704 | Ac-VYEVGWDDGNWYEIIWRYPS-NH2 | 1916 | JBS-1745 | Ac-VYEVGWDHGNLYEIIWRYPS-NH2 |
| 1876 | JBS-1705 | Ac-VYEVGWDHDNWYEIIWRYPS-NH2 | 1917 | JBS-1746 | Ac-VYEVGWDHGNWLEIIWRYPS-NH2 |
| 1877 | JBS-1706 | Ac-VYEVGWDHGDWYEIIWRYPS-NH2 | 1918 | JBS-1747 | Ac-VYEVGWDHGNWYLIIWRYPS-NH2 |
| 1878 | JBS-1707 | Ac-VYEVGWDHGNDYEIIWRYPS-NH2 | 1919 | JBS-1748 | Ac-VYEVGWDHGNWYELIWRYPS-NH2 |
| 1879 | JBS-1708 | Ac-VYEVGWDHGNWDEIIWRYPS-NH2 | 1920 | JBS-1749 | Ac-VYEVGWDHGNWYEILRYPS-NH2 |
| 1880 | JBS-1709 | Ac-VYEVGWDHGNWYDIIWRYPS-NH2 | 1921 | JBS-1750 | Ac-VYEVGWDHGNWYEIILRYPS-NH2 |
| 1881 | JBS-1710 | Ac-VYEVGWDHGNWYEDIWRYPS-NH2 | 1922 | JBS-1751 | Ac-VYEVGWDHGNWYEIIWLYPS-NH2 |
| 1882 | JBS-1711 | Ac-VYEVGWDHGNWYEIDWRYPS-NH2 | 1923 | JBS-1752 | Ac-VYEVGWDHGNWYEIIWRLPS-NH2 |
| 1883 | JBS-1712 | Ac-VYEVGWDHGNWYEIIDRYPS-NH2 | 1924 | JBS-1753 | Ac-VYEVGWDHGNWYEIIWRYLS-NH2 |
| 1884 | JBS-1713 | Ac-VYEVGWDHGNWYEIIWDYPS-NH2 | 1925 | JBS-1754 | Ac-VYEVGWDHGNWYEIIWRYPL-NH2 |
| 1885 | JBS-1714 | Ac-VYEVGWDHGNWYEIIWRDPS-NH2 | 1926 | JBS-1755 | Ac-KYEVGWDHGNWYEIIWRYPS-NH2 |
| 1886 | JBS-1715 | Ac-VYEVGWDHGNWYEIIWRYDS-NH2 | 1927 | JBS-1756 | Ac-VKEVGWDHGNWYEIIWRYPS-NH2 |
| 1887 | JBS-1716 | Ac-VYEVGWDHGNWYEIIWRYPD-NH2 | 1928 | JBS-1757 | Ac-VYKVGWDHGNWYEIIWRYPS-NH2 |
| 1888 | JBS-1717 | Ac-GYEVGWDHGNWYEIIWRYPS-NH2 | 1929 | JBS-1758 | Ac-VYEKGWDHGNWYEIIWRYPL-NH2 |
| 1889 | JBS-1718 | Ac-VGEVGWDHGNWYEIIWRYPS-NH2 | 1930 | JBS-1759 | Ac-VYEVKWDHGNWYEIIWRYPS-NH2 |
| 1890 | JBS-1719 | Ac-VYGVGWDHGNWYEIIWRYPS-NH2 | 1931 | JBS-1760 | Ac-VYEVGKDHGNWYEIIWRYPS-NH2 |
| 1891 | JBS-1720 | Ac-VYEGGWDHGNWYEIIWRYPS-NH2 | 1932 | JBS-1761 | Ac-VYEVGWKHGNWYEIIWRYPS-NH2 |
| 1892 | JBS-1721 | Ac-VYEVGGDHGNWYEIIWRYPS-NH2 | 1933 | JBS-1762 | Ac-VYEVGWDKGNWYEIIWRYPS-NH2 |
| 1893 | JBS-1722 | Ac-VYEVGWGHGNWYEIIWRYPS-NH2 | 1934 | JBS-1763 | Ac-VYEVGWDHKNWYEIIKRYPS-NH2 |
| 1894 | JBS-1723 | Ac-VYEVGWDGGNWYEIIWRYPS-NH2 | 1935 | JBS-1764 | Ac-VYEVGWDHGKWYEIIWKYPS-NH2 |
| 1895 | JBS-1724 | Ac-VYEVGWDHGGWYEIIWGYPS-NH2 | 1936 | JBS-1765 | Ac-VYEVGWDHGNKYEIIWRKPS-NH2 |
| 1896 | JBS-1725 | Ac-VYEVGWDHGNGYEIIWRYPS-NH2 | 1937 | JBS-1766 | Ac-VYEVGWDHGNWKEIIWRYKS-NH2 |
| 1897 | JBS-1726 | Ac-VYEVGWDHGNWGEIIWRYPS-NH2 | 1938 | JBS-1767 | Ac-VYEVGWDHGNWYKIIWRYPK-NH2 |
| 1898 | JBS-1727 | Ac-VYEVGWDHGNWYGIIWRYPS-NH2 | 1939 | JBS-1768 | Ac-VYEVGWDHGNWYEKIWRYPS-NH2 |
| 1899 | JBS-1728 | Ac-VYEVGWDHGNWYEGIWRYPS-NH2 | 1940 | JBS-1769 | Ac-VYEFGWDHGNWYEIKRYPS-NH2 |
| 1900 | JBS-1729 | Ac-VYEVGWDHGNWYEIGWRYPS-NH2 | 1941 | JBS-1770 | Ac-VYEVGWDHGNWYEIIKRYPS-NH2 |
| 1901 | JBS-1730 | Ac-VYEVGWDHGNWYEIIGRYPS-NH2 | 1942 | JBS-1771 | Ac-VYEVGWDHGNWYEIIWKPS-NH2 |
| 1902 | JBS-1731 | Ac-VYEVGWDHGNWYEIIWGYPS-NH2 | 1943 | JBS-1772 | Ac-VYEVGWDHGNWYEIIWRKPS-NH2 |
| 1903 | JBS-1732 | Ac-VYEVGWDHGNWYEIIWRGPS-NH2 | 1944 | JBS-1773 | Ac-VYEVGWDHGNWYEIIWRYKS-NH2 |
| 1904 | JBS-1733 | Ac-VYEVGWDHGNWYEIIWRYGS-NH2 | 1945 | JBS-1774 | Ac-VYEVGWDHGNWYEIIWRYPK-NH2 |
| 1905 | JBS-1734 | Ac-VYEVGWDHGNWYEIIWRYPG-NH2 | 1946 | JBS-1775 | Ac-VYEVGWDHGNWYEIIWRYPS-NH2 |
| 1906 | JBS-1735 | Ac-LYEVGWDHGNWYEIIWRYPS-NH2 | 1947 | JBS-1776 | Ac-FYEVGWDHGNWYEIIWRYPS-NH2 |
| 1907 | JBS-1736 | Ac-VLEVGWDHGNWYEIIWRYPS-NH2 | 1948 | JBS-1777 | Ac-VFEVGWDHGNWYEIKWRYPS-NH2 |
| 1908 | JBS-1737 | Ac-VYLVGWDHGNWYEIIWRYPS-NH2 | 1949 | JBS-1778 | Ac-VYFVGWDHGNWYEIIWRYPS-NH2 |
| 1909 | JBS-1738 | Ac-VYELGWDHGNWYEIIWRYPS-NH2 | 1950 | JBS-1779 | Ac-VYEFGWDHGNWYEIIWRYPS-NH2 |
| 1910 | JBS-1739 | Ac-VYEVLWDHGNWYEIIWGYPS-NH2 | 1951 | JBS-1780 | Ac-VYEVGWDHGNWYEIIWRKPS-NH2 |
| 1911 | JBS-1740 | Ac-VYEVGLDHGNWYEIIWRYPS-NH2 | 1952 | JBS-1781 | Ac-VYEVGFDHGNWYEIIWRYPS-NH2 |
| 1912 | JBS-1741 | Ac-VYEVGWLHGNWYEIIWRYPS-NH2 | 1953 | JBS-1782 | Ac-VYEVGWDFGNWYEIIWRYPS-NH2 |
| 1913 | JBS-1742 | Ac-VYEVGWDLGNWYEIIWRYPS-NH2 | 1954 | JBS-1783 | Ac-VYEVGWDHFNWYEIIWRYPS-NH2 |

| SEQ ID | Compound | Sequence | SEQ ID | Compound | Sequence |
|---|---|---|---|---|---|
| 1955 | JBS-1784 | Ac-VYEVGWDHGFWYEIIWRYPS-NH2 | 1996 | JBS-1825 | Ac-VYEVGWDHGNWSEIIWRYPS-NH2 |
| 1956 | JBS-1785 | Ac-VYEVGWDHGNFYEIIWRYPS-NH2 | 1997 | JBS-1826 | Ac-VYEVGWDHGNWYSIIWRYPS-NH2 |
| 1957 | JBS-1786 | Ac-VYEVGWDHGNWFEIIWRYPS-NH2 | 1998 | JBS-1827 | Ac-VYEAGWDHGNWYESIWRYPS-NH2 |
| 1958 | JBS-1787 | Ac-VYEVGWDHGNWYFIIWRYPS-NH2 | 1999 | JBS-1828 | Ac-VYEVGWDHGNWYEISWRYPS-NH2 |
| 1959 | JBS-1788 | Ac-VYEVGWDHGNWYEIFWRYPS-NH2 | 2000 | JBS-1829 | Ac-VYEVGWDHGNWYEIISRYPS-NH2 |
| 1960 | JBS-1789 | Ac-VYEVGWDHGNWYEIFWRYPS-NH2 | 2001 | JBS-1830 | Ac-VYEVGWDHGNWYEIIWSYPS-NH2 |
| 1961 | JBS-1790 | Ac-VYEVGWDHGNWYEIIFRYPS-NH2 | 2002 | JBS-1831 | Ac-VYEVGWDHGNWYEIIWRSPS-NH2 |
| 1962 | JBS-1791 | Ac-VYEVGWDHGNWYEIIWFYPS-NH2 | 2003 | JBS-1832 | Ac-VYEVGWDHGNWYEIIWRYSS-NH2 |
| 1963 | JBS-1792 | Ac-VYEVGWDHGNWYEIIWRFPS-NH2 | 2004 | JBS-1833 | Ac-VYEVGWDHGNWYEIIWR-NH2 |
| 1964 | JBS-1793 | Ac-VYEVGWDHGNWYEIIWRYFS-NH2 | 2005 | JBS-1834 | Ac-VYEVGWDHGNWYEI-NH2 |
| 1965 | JBS-1794 | Ac-VYEVGWDHGNWYEIIWRYPF-NH2 | 2006 | JBS-1835 | Ac-VYEVGWDHGNW-NH2 |
| 1966 | JBS-1795 | Ac-PYEVGWDHGNWYEIIWRYPS-NH2 | 2007 | JBS-1836 | Ac-VGDHGNWYEIIWRYPS-NH2 |
| 1967 | JBS-1796 | Ac-VPEVGWDHGNWYEIIWRYPS-NH2 | 2008 | JBS-1837 | Ac-DHGNWYEIIWRYPS-NH2 |
| 1968 | JBS-1797 | Ac-VYPVGWDHGNWYEIIWRYPS-NH2 | 2009 | JBS-1838 | Ac-NWYEIIWRYPS-NH2 |
| 1969 | JBS-1798 | Ac-VYEPGWDHGNWYEIIWRYPS-NH2 | 2010 | JBS-1839 | Ac-VGWDHGNWYEIIWR-NH2 |
| 1970 | JBS-1799 | Ac-VYEVPWDHGNWYEIIWRYPS-NH2 | 2011 | JBS-1840 | Ac-ATVEVGWHTVHTGRDNYMWM-NH2 |
| 1971 | JBS-1800 | Ac-VYEVGPDHGNWYEIIWRYPS-NH2 | 2012 | JBS-1841 | Ac-YAVEVGWHTVHTGRDNYMWM-NH2 |
| 1972 | JBS-1801 | Ac-VYEVGWPHGNWYEIIWRYPS-NH2 | 2013 | JBS-1842 | Ac-YTAEVGWHTVHTGRDNYMWM-NH2 |
| 1973 | JBS-1802 | Ac-VYEVGWDPHGNWYEIIWRYPS-NH2 | 2014 | JBS-1843 | Ac-YTVAVGWHTVHTGRDNYMWM-NH2 |
| 1974 | JBS-1803 | Ac-VYEVGWDHPNWYEIIWRYPS-NH2 | 2015 | JBS-1844 | Ac-YTVEAGWHTVHTGRDNYMWM-NH2 |
| 1975 | JBS-1804 | Ac-VYEVGWDHGPWYEIIWRYPS-NH2 | 2016 | JBS-1845 | Ac-YTVEVAWHTVHTGRDNYMWM-NH2 |
| 1976 | JBS-1805 | Ac-VYEVGWDHGNPYEIIWRYPS-NH2 | 2017 | JBS-1846 | Ac-YTVEGAHTVHTGRDNYMWM-NH2 |
| 1977 | JBS-1806 | Ac-VYEVGWDHGNWPEIIWRYPS-NH2 | 2018 | JBS-1847 | Ac-YTVEVGMATVHTGRDNYMWM-NH2 |
| 1978 | JBS-1807 | Ac-VYEVGWDHGNWYPIIWRYPS-NH2 | 2019 | JBS-1848 | Ac-YTVEVGWHAVHTGRDNYMWM-NH2 |
| 1979 | JBS-1808 | Ac-VYEVGWDHGNWYEPIWRYPS-NH2 | 2020 | JBS-1849 | Ac-YTVEVGWHTAHTGRDNYMWM-NH2 |
| 1980 | JBS-1809 | Ac-VYEVGWDHGNWYEIPWRYPS-NH2 | 2021 | JBS-1850 | Ac-YTVEVGWHTVATGRDNYMWM-NH2 |
| 1981 | JBS-1810 | Ac-VYEVGWDHGNWYEIIPRYPS-NH2 | 2022 | JBS-1851 | Ac-YTVEVGWHTVHAGRDNYMWM-NH2 |
| 1982 | JBS-1811 | Ac-VYEVGWDHGNWYEIIWNPYPS-NH2 | 2023 | JBS-1852 | Ac-YTVEVGWHTVHTNPDNYMWM-NH2 |
| 1983 | JBS-1812 | Ac-VYEVGWDHGNWYEIIWRPPS-NH2 | 2024 | JBS-1853 | Ac-YTVEVGWHTVHTGADNYMWM-NH2 |
| 1984 | JBS-1813 | Ac-VYEVGWDHGNWYEIIWRYPP-NH2 | 2025 | JBS-1854 | Ac-YTVEVGWHTVHTGRANYMWM-NH2 |
| 1985 | JBS-1814 | Ac-SYEVGWDHGNWYEIIWRYPS-NH2 | 2026 | JBS-1855 | Ac-YTVEVGWHTVHTGRDAYMWM-NH2 |
| 1986 | JBS-1815 | Ac-VSEVGWDHGNWYEIIWRYPS-NH2 | 2027 | JBS-1856 | Ac-YTVEVGWHTVHTGRDNAMWM-NH2 |
| 1987 | JBS-1816 | Ac-VYSVGWDHGNWYEIIWRYPS-NH2 | 2028 | JBS-1857 | Ac-YTVEVGWHTVHTGRDNYAWM-NH2 |
| 1988 | JBS-1817 | Ac-VYESGWDHGNWYEIIWRYPS-NH2 | 2029 | JBS-1858 | Ac-YTVEVGWHTVHTGRDNYMAM-NH2 |
| 1989 | JBS-1818 | Ac-VYEVSWDHGNWYEIIWRYPS-NH2 | 2030 | JBS-1859 | Ac-YTVEVGWHTVHTGRDNYMWA-NH2 |
| 1990 | JBS-1819 | Ac-VYEVGSDHGNWYEIIWRYPS-NH2 | 2031 | JBS-1860 | Ac-DTVEVGWHTVHTGRDNYMWM-NH2 |
| 1991 | JBS-1820 | Ac-VYEVGSHGNWYEIIWRYPS-NH2 | 2032 | JBS-1861 | Ac-YDVEVGWHTVHTGRDNYMWM-NH2 |
| 1992 | JBS-1821 | Ac-VYEVGWDSGNWYEIIWRYPS-NH2 | 2033 | JBS-1862 | Ac-YTDEVGWHTVHTGRDNYMWM-NH2 |
| 1993 | JBS-1822 | Ac-VYEVGWDHSNWYEIIWRYPS-NH2 | 2034 | JBS-1863 | Ac-YTVDVGWHTVHTGRDNYMWM-NH2 |
| 1994 | JBS-1823 | Ac-VYEVGWDHGSWYEIIWRYPS-NH2 | 2035 | JBS-1864 | Ac-YTVEDGWHTVHTGRDNYMWM-NH2 |
| 1995 | JBS-1824 | Ac-VYEVGWDHGNSYEIIWRYPS-NH2 | 2036 | JBS-1865 | Ac-YTVEVDWHTVHTGRDNYMWM-NH2 |

FIGURE 2Y

| SEQ ID | Compound | Sequence | SEQ ID | Compound | Sequence |
|---|---|---|---|---|---|
| 2037 | JBS-1866 | Ac-YTVEVGDHTVHTGRDNYMWM-NH2 | 2078 | JBS-1907 | Ac-YTVEVGWHTVLTGRDNYMWM-NH2 |
| 2038 | JBS-1867 | Ac-YTVEVGWDTVHTGRDNYMWM-NH2 | 2079 | JBS-1908 | Ac-YTVEVGWHTVHLGRDNYMWM-NH2 |
| 2039 | JBS-1868 | Ac-YTVEVGWHDVHTGRDNYMWM-NH2 | 2080 | JBS-1909 | Ac-YTVEVGWHTVHTLRDNYMWM-NH2 |
| 2040 | JBS-1869 | Ac-YTVEVGWHTDHTGRDNYMWM-NH2 | 2081 | JBS-1910 | Ac-YTVEVGWHTVHTGLDNYMWM-NH2 |
| 2041 | JBS-1870 | Ac-YTVEVGWHTVDTGRDNYMWM-NH2 | 2082 | JBS-1911 | Ac-YTVEVGWHTVHTGRLNYMWM-NH2 |
| 2042 | JBS-1871 | Ac-YTVEVGWHTVHDGRDNYMWM-NH2 | 2083 | JBS-1912 | Ac-YTVEVGWHTVHTGRDLYMWM-NH2 |
| 2043 | JBS-1872 | Ac-YTVEVGWHTVHTDRDNYMWM-NH2 | 2084 | JBS-1913 | Ac-YTVEVGWHTVHTGRDNLMWM-NH2 |
| 2044 | JBS-1873 | Ac-YTVEVGWHTVHTGDDNYMWM-NH2 | 2085 | JBS-1914 | Ac-YTVEVGWHTVHTGRDNYLWM-NH2 |
| 2045 | JBS-1874 | Ac-YTVEVGWHTVHTGRDDYMWM-NH2 | 2086 | JBS-1915 | Ac-YTVEVGWHTVHTGRDNYMLM-NH2 |
| 2046 | JBS-1875 | Ac-YTVEVGWHTVHTGRDNDMWM-NH2 | 2087 | JBS-1916 | Ac-YTVEVGWHTVHTGRDNYMWL-NH2 |
| 2047 | JBS-1876 | Ac-YTVEVGWHTVHTGRDNYDWM-NH2 | 2088 | JBS-1917 | Ac-KTVEVGWHTVHTGRDNYMWM-NH2 |
| 2048 | JBS-1877 | Ac-YTVEVGWHTVHTGRDNYMDM-NH2 | 2089 | JBS-1918 | Ac-YKVEVGWHTVHTGRDNYMWM-NH2 |
| 2049 | JBS-1878 | Ac-YTVEVGWHTVHTGRDNYMWD-NH2 | 2090 | JBS-1919 | Ac-YTKEVGWHTVHTGRDNYMWM-NH2 |
| 2050 | JBS-1879 | Ac-GTVEVGWHTVHTGRDNYMWM-NH2 | 2091 | JBS-1920 | Ac-YTVKVGWHTVHTGRDNYMWM-NH2 |
| 2051 | JBS-1880 | Ac-YGVEVGWHTVHTGRDNYMWM-NH2 | 2092 | JBS-1921 | Ac-YTVEKGWHTVHTGRDNYMWM-NH2 |
| 2052 | JBS-1881 | Ac-YTGEVGWHTVHTGRDNYMWM-NH2 | 2093 | JBS-1922 | Ac-YTVEVKWHTVHTGRDNYMWM-NH2 |
| 2053 | JBS-1882 | Ac-YTVGVGWHTVHTGRDNYMWM-NH2 | 2094 | JBS-1923 | Ac-YTVEVGKHTVHTGRDNYMWM-NH2 |
| 2054 | JBS-1883 | Ac-YTVEGGWHTVHTGRDNYMWM-NH2 | 2095 | JBS-1924 | Ac-YTVEVGWKTVHTGRDNYMWM-NH2 |
| 2055 | JBS-1884 | Ac-YTVEVGGHTVHTGRDNYMWM-NH2 | 2096 | JBS-1925 | Ac-YTVEVGWHKVHTGRDNYMWM-NH2 |
| 2056 | JBS-1885 | Ac-YTVEVGWHTVHTGRDNYMWM-NH2 | 2097 | JBS-1926 | Ac-YTVEVGWHTKHTGRDNYMWM-NH2 |
| 2057 | JBS-1886 | Ac-YTVEVGWHTVHTGRDNYMWM-NH2 | 2098 | JBS-1927 | Ac-YTVEVGWHTVKTGRDNYMWM-NH2 |
| 2058 | JBS-1887 | Ac-YTVEVGWHTGHTGRDNYMWM-NH2 | 2099 | JBS-1928 | Ac-YTVEVGWHTVHKGRDNYMWM-NH2 |
| 2059 | JBS-1888 | Ac-YTVEVGWHTVGTGRDNYMWM-NH2 | 2100 | JBS-1929 | Ac-YTVEVGWHTVHTKRDNYMWM-NH2 |
| 2060 | JBS-1889 | Ac-YTVEVGWHTVHGGRDNYMWM-NH2 | 2101 | JBS-1930 | Ac-YTVEVGWHTVHTGKDNYMWM-NH2 |
| 2061 | JBS-1890 | Ac-YTVEVGWHTVHTGGDNYMWG-NH2 | 2102 | JBS-1931 | Ac-YTVEVGWHTVHTGRKNYMWM-NH2 |
| 2062 | JBS-1891 | Ac-LTVEVGWHTVHTGRGNYMWM-NH2 | 2103 | JBS-1932 | Ac-FTVEVGWHTVHTGRDKYMWM-NH2 |
| 2063 | JBS-1892 | Ac-YTVEVGWHTVHTGRDGYMWM-NH2 | 2104 | JBS-1933 | Ac-YTVEVGWHTVHTGRDNKMWM-NH2 |
| 2064 | JBS-1893 | Ac-YTVEVGWHTVHTGRDNGMWM-NH2 | 2105 | JBS-1934 | Ac-YTVEVGWHTVHTGRDNYKWM-NH2 |
| 2065 | JBS-1894 | Ac-YTVEVGWHTVHTGRDNYGWM-NH2 | 2106 | JBS-1935 | Ac-YTVEVGWHTVHTGRDNYMKM-NH2 |
| 2066 | JBS-1895 | Ac-YTVEVGWHTVHTGRDNYMGM-NH2 | 2107 | JBS-1936 | Ac-YTVEVGWHTVHTGRDNYMWK-NH2 |
| 2067 | JBS-1896 | Ac-YTVEVGWHTVHTGRDNYMWG-NH2 | 2108 | JBS-1937 | Ac-FTVEVGWHTVHTGRKNYMWM-NH2 |
| 2068 | JBS-1897 | Ac-YTVEVGWHTVHTGRGNYMWM-NH2 | 2109 | JBS-1938 | Ac-YTVEVGFHTVHTGRDKYMWM-NH2 |
| 2069 | JBS-1898 | Ac-YTVEVGWHTVHTGRDGYMWM-NH2 | 2110 | JBS-1939 | Ac-YTFEVGWHTVHTGRDNYMWM-NH2 |
| 2070 | JBS-1899 | Ac-YTLEVGWHTVHTGRDNYMWM-NH2 | 2111 | JBS-1940 | Ac-YTVFVGWHTVHTGRDNYMWM-NH2 |
| 2071 | JBS-1900 | Ac-YTVLVGWHTVHTGRDNYMWM-NH2 | 2112 | JBS-1941 | Ac-YTVEFGWHTVHTGRDNYMWM-NH2 |
| 2072 | JBS-1901 | Ac-YTVELGWHTVHTGRDNYMWM-NH2 | 2113 | JBS-1942 | Ac-YTVEVFWHTVHTGRDNYMWM-NH2 |
| 2073 | JBS-1902 | Ac-YTVEVLWHTVHTGRDNYMWM-NH2 | 2114 | JBS-1943 | Ac-YTVEVGFHTVHTGRDNYMWM-NH2 |
| 2074 | JBS-1903 | Ac-YTVEVGLHTVHTGRDNYMWM-NH2 | 2115 | JBS-1944 | Ac-YTVEVGWFTVHTGRDNYMWM-NH2 |
| 2075 | JBS-1904 | Ac-YTVEVGWLTVHTGRDNYMWM-NH2 | 2116 | JBS-1945 | Ac-YTVEVGWHFVHTGRDNYMWM-NH2 |
| 2076 | JBS-1905 | Ac-YTVEVGWHLVHTGRDNYMWM-NH2 | 2117 | JBS-1946 | Ac-YTVEVGWHTFHTGRDNYMWM-NH2 |
| 2077 | JBS-1906 | Ac-YTVEVGWHTLHTGRDNYMWM-NH2 | 2118 | JBS-1947 | Ac-YTVEVGWHTVFTGRDNYMWM-NH2 |

FIGURE 2Z

| SEQ ID | Compound | Sequence | SEQ ID | Compound | Sequence |
|---|---|---|---|---|---|
| 2119 | JBS-1948 | Ac-YTVEVGWHTVHFGRDNYMWM-NH2 | 2160 | JBS-1989 | Ac-YTVEVGWHTVHTSRDNYMWM-NH2 |
| 2120 | JBS-1949 | Ac-YTVEVGWHTVHFRDNYMWM-NH2 | 2161 | JBS-1990 | Ac-YTVEVGWHTVHTGSDNYMWM-NH2 |
| 2121 | JBS-1950 | Ac-YTVEVGWHTVHTGFDNYMWM-NH2 | 2162 | JBS-1991 | Ac-YTVEVGWHTVHTGRSNYMWM-NH2 |
| 2122 | JBS-1951 | Ac-YTVEVGWHTVHTGRFNYMWM-NH2 | 2163 | JBS-1992 | Ac-YTVEVGWHTVHTGRDSYMWM-NH2 |
| 2123 | JBS-1952 | Ac-YTVEVGWHTVHTGRDFYMWM-NH2 | 2164 | JBS-1993 | Ac-YTVEVGWHTVHTGRDNSMWM-NH2 |
| 2124 | JBS-1953 | Ac-YTVEVGWHTVHTGRDNFMWM-NH2 | 2165 | JBS-1994 | Ac-YTVEVGWHTVHTGRDNYSWM-NH2 |
| 2125 | JBS-1954 | Ac-YTVEVGWHTVHTGRDNYFWM-NH2 | 2166 | JBS-1995 | Ac-YTVEVGWHTVHTGRDNYMSM-NH2 |
| 2126 | JBS-1955 | Ac-YTVEVGWHTVHTGRDNYMFM-NH2 | 2167 | JBS-1996 | Ac-YTVEVGWHTVHTGRDNYMWS-NH2 |
| 2127 | JBS-1956 | Ac-YTVEVGWHTVHTGRDNYMWF-NH2 | 2168 | JBS-1997 | Ac-YTVEVGWHTVHTGRDNY-NH2 |
| 2128 | JBS-1957 | Ac-PTVEVGWHTVHTGRDNYMWM-NH2 | 2169 | JBS-1998 | Ac-YTVEVGWHTVHTGR-NH2 |
| 2129 | JBS-1958 | Ac-YPVEVGWHTVHTGRDNYMwM-NH2 | 2170 | JBS-1999 | Ac-YTVEVGWHTVH-NH2 |
| 2130 | JBS-1959 | Ac-YTPEVGWHTVHTGRDNYMWM-NH2 | 2171 | JBS-2000 | Ac-EVGWHTVHTGRDNYMWM-NH2 |
| 2131 | JBS-1960 | Ac-YTVPVGWHTVHTGRDNYMWM-NH2 | 2172 | JBS-2001 | Ac-WHTVHTGRDNYMWM-NH2 |
| 2132 | JBS-1961 | Ac-YTVEPGWHTVHTGRDNYMWM-NH2 | 2173 | JBS-2002 | Ac-VHTGRDNYMWM-NH2 |
| 2133 | JBS-1962 | Ac-YTVEVPWHTVHTGRDNYMwM-NH2 | 2174 | JBS-2003 | Ac-EVGWHTVHTGRDNY-NH2 |
| 2134 | JBS-1963 | Ac-YTVEVGPHTVHTGRDNYMWM-NH2 | 2175 | JBS-2004 | Ac-AVQIGWYSDSDRHYAYSSY-NH2 |
| 2135 | JBS-1964 | Ac-YTVEVGWPTVHTGRDNYMWM-NH2 | 2176 | JBS-2005 | Ac-HAQIGWYSVDSDRHYAYSSY-NH2 |
| 2136 | JBS-1965 | Ac-YTVEVGWHPVHTGRDNYMWM-NH2 | 2177 | JBS-2006 | Ac-HVAIGWYSVDSDRHYAYSSY-NH2 |
| 2137 | JBS-1966 | Ac-YTVEVGWHTPHTGRDNYMWM-NH2 | 2178 | JBS-2007 | Ac-HVQAGWYSVDSDRHYAYSSY-NH2 |
| 2138 | JBS-1967 | Ac-YTVEVGWHTVPTGRDNYMWM-NH2 | 2179 | JBS-2008 | Ac-HVQIAWYSVDSDRHYAYSSY-NH2 |
| 2139 | JBS-1968 | Ac-YTVEVGWHTVHPGRDNYMWM-NH2 | 2180 | JBS-2009 | Ac-HVQIGAYSVDSDRHYAYSSY-NH2 |
| 2140 | JBS-1969 | Ac-YTVEVGWHTVHTPRDNYMWM-NH2 | 2181 | JBS-2010 | Ac-HVQIGWASVDSDRHYAYSSY-NH2 |
| 2141 | JBS-1970 | Ac-YTVEVGWHTVHTGPDNYMWM-NH2 | 2182 | JBS-2011 | Ac-HVQIGWYAVDSDRHYAYSSY-NH2 |
| 2142 | JBS-1971 | Ac-YTVEVGWHTVHTGRPNYMWM-NH2 | 2183 | JBS-2012 | Ac-HVQIGWYSADSDRHYAYSSY-NH2 |
| 2143 | JBS-1972 | Ac-YTVEVGWHTVHTGRDPYMWM-NH2 | 2184 | JBS-2013 | Ac-HVQIGWYSVASDRHYAYSSY-NH2 |
| 2144 | JBS-1973 | Ac-YTVEVGWHTVHTGRDNPMWM-NH2 | 2185 | JBS-2014 | Ac-HVQIGWYSVDADRHYAYSSY-NH2 |
| 2145 | JBS-1974 | Ac-YTVEVGWHTVHTGRDNYPWM-NH2 | 2186 | JBS-2015 | Ac-HVQIGWYSVDSARHYAYSSY-NH2 |
| 2146 | JBS-1975 | Ac-YTVEVGWHTVHTGRDNYMPM-NH2 | 2187 | JBS-2016 | Ac-HVQIGWYSVDSDAHYAYSSY-NH2 |
| 2147 | JBS-1976 | Ac-YTVEVGWHTVHTGRDNYMwP-NH2 | 2188 | JBS-2017 | Ac-HVQIGWYSVDSDRAYAYSSY-NH2 |
| 2148 | JBS-1977 | Ac-STVEVGWHTVHTGRDNYMWM-NH2 | 2189 | JBS-2018 | Ac-HVQIGWYSVDSDRHAAYSSY-NH2 |
| 2149 | JBS-1978 | Ac-YSVEVGWHTVHTGRDNYMWM-NH2 | 2190 | JBS-2019 | Ac-HVQIGWYSVDSDRHYAASSY-NH2 |
| 2150 | JBS-1979 | Ac-YTSEVGWHTVHTGRDNYMWM-NH2 | 2191 | JBS-2020 | Ac-HVQIGWYSVDSDRHYAYASY-NH2 |
| 2151 | JBS-1980 | Ac-YTVSVGWHTVHTGRDNYMWM-NH2 | 2192 | JBS-2021 | Ac-HVQIGWYSVDSDRHYAYSAY-NH2 |
| 2152 | JBS-1981 | Ac-YTVESGWHTVHTGRDNYMWM-NH2 | 2193 | JBS-2022 | Ac-HVQIGWYSVDSDRHYAYSSA-NH2 |
| 2153 | JBS-1982 | Ac-YTVEVSWHTVHTGRDNYMWM-NH2 | 2194 | JBS-2023 | Ac-DVQIGWYSVDSDRHYAYSSY-NH2 |
| 2154 | JBS-1983 | Ac-YTVEVGSHTVHTGRDNYMWM-NH2 | 2195 | JBS-2024 | Ac-HDQIGWYSVDSDRHYAYSSY-NH2 |
| 2155 | JBS-1984 | Ac-YTVEVGWSTVHTGRDNYMWM-NH2 | 2196 | JBS-2025 | Ac-HVDIGWYSVDSDRHYAYSSY-NH2 |
| 2156 | JBS-1985 | Ac-YTVEVGWHSVHTGRDNYMWM-NH2 | 2197 | JBS-2026 | Ac-HVQDGWYSVDSDRHYAYSSY-NH2 |
| 2157 | JBS-1986 | Ac-YTVEVGWHTSHTGRDNYMWM-NH2 | 2198 | JBS-2027 | Ac-HVQIDWYSVDSDRHYAYSSY-NH2 |
| 2158 | JBS-1987 | Ac-YTVEVGWHTVSTGRDNYMWM-NH2 | 2199 | JBS-2028 | Ac-HVQIGDYSVDSDRHYAYSSY-NH2 |
| 2159 | JBS-1988 | Ac-YTVEVGWHTVHSGRDNYMWM-NH2 | 2200 | JBS-2029 | Ac-HVQIGWDSVDSDRHYAYSSY-NH2 |

FIGURE 2AA

| SEQ ID | Compound | Sequence | SEQ ID | Compound | Sequence |
| --- | --- | --- | --- | --- | --- |
| 2201 | JBS-2030 | Ac-HVQIGWYDVDSDRHYAYSSY-NH2 | 2242 | JBS-2071 | Ac-HVQIGWYSVDSLRHYAYSSY-NH2 |
| 2202 | JBS-2031 | Ac-HVQIGWYSDDSDRHYAYSSY-NH2 | 2243 | JBS-2072 | Ac-HVQIGWYSVDSDLHYAYSSY-NH2 |
| 2203 | JBS-2032 | Ac-HVQIGWYSVDDDRHYAYSSY-NH2 | 2244 | JBS-2073 | Ac-HVQIGWYSVDSDRLYAYSSY-NH2 |
| 2204 | JBS-2033 | Ac-HVQIGWYSVDSDDHYAYSSY-NH2 | 2245 | JBS-2074 | Ac-HVQIGWYSVDSDRHLAYSSY-NH2 |
| 2205 | JBS-2034 | Ac-HVQIGWYSVDSDRDYAYSSY-NH2 | 2246 | JBS-2075 | Ac-HVQIGWYSVDSDRHYLYSSY-NH2 |
| 2206 | JBS-2035 | Ac-HVQIGWYSVDSDRHDAYSSY-NH2 | 2247 | JBS-2076 | Ac-HVQIGWYSVDSDRHYALSSY-NH2 |
| 2207 | JBS-2036 | Ac-HVQIGWYSVDSDRHYDYSSY-NH2 | 2248 | JBS-2077 | Ac-HVQIGWYSVDSDRHYAYLSY-NH2 |
| 2208 | JBS-2037 | Ac-HVQIGWYSVDSDRHYADSSY-NH2 | 2249 | JBS-2078 | Ac-HVQIGWYSVDSDRHYAYSLY-NH2 |
| 2209 | JBS-2038 | Ac-HVQIGWYSVDSDRHYAYDSY-NH2 | 2250 | JBS-2079 | Ac-HVQIGWYSVDSDRHYAYSSL-NH2 |
| 2210 | JBS-2039 | Ac-HVQIGWYSVDSDRHYAYSDY-NH2 | 2251 | JBS-2080 | Ac-KVQIGWYSVDSDRHYAYSSY-NH2 |
| 2211 | JBS-2040 | Ac-HVQIGWYSVDSDRHYAYSSD-NH2 | 2252 | JBS-2081 | Ac-HKQIGWYSVDSDRHYAYSSY-NH2 |
| 2212 | JBS-2041 | Ac-GVQIGWYSVDSDRHYAYSSY-NH2 | 2253 | JBS-2082 | Ac-HVKIGWYSVDSDRHYAYSSY-NH2 |
| 2213 | JBS-2042 | Ac-HGQIGWYSVDSDRHYAYSSY-NH2 | 2254 | JBS-2083 | Ac-HVQKGWYSVDSDRHYAYSSY-NH2 |
| 2214 | JBS-2043 | Ac-HVGIGWYSVDSDRHYAYSSY-NH2 | 2255 | JBS-2084 | Ac-HVQIKWYSVDSDRHYAYSSY-NH2 |
| 2215 | JBS-2044 | Ac-HVQGGWYSVDSDRHYAYSSY-NH2 | 2256 | JBS-2085 | Ac-HVQIGKYSVDSDRHYAYSSY-NH2 |
| 2216 | JBS-2045 | Ac-HVQIGGYSVDSDRHYAYSSY-NH2 | 2257 | JBS-2086 | Ac-HVQIGWKSVDSDRHYAYSSY-NH2 |
| 2217 | JBS-2046 | Ac-HVQIGWGSVDSDRHYAYSSY-NH2 | 2258 | JBS-2087 | Ac-HVQIGWYKVDSDRHYAYSSY-NH2 |
| 2218 | JBS-2047 | Ac-HVQIGWYGVDSDRHYAYSSY-NH2 | 2259 | JBS-2088 | Ac-HVQIGWYSKDSDRHYAYSSY-NH2 |
| 2219 | JBS-2048 | Ac-HVQIGWYSGDSDRHYAYSSY-NH2 | 2260 | JBS-2089 | Ac-HVQIGWYSVKSDRHYAYSSY-NH2 |
| 2220 | JBS-2049 | Ac-HVQIGWYSVGDRHYAYSSY-NH2 | 2261 | JBS-2090 | Ac-HVQIGWYSVDKDRHYAYSSY-NH2 |
| 2221 | JBS-2050 | Ac-HVQIGWYSVDGRHYAYSSY-NH2 | 2262 | JBS-2091 | Ac-HVQIGWYSVDSKRHYAYSSY-NH2 |
| 2222 | JBS-2051 | Ac-HVQIGWYSVDSGHYAYSSY-NH2 | 2263 | JBS-2092 | Ac-HVQIGWYSVDSDKHYAYSSY-NH2 |
| 2223 | JBS-2052 | Ac-HVQIGWYSVDSDGHYAYSSY-NH2 | 2264 | JBS-2093 | Ac-HVQIGWYSVDSDRKYAYSSY-NH2 |
| 2224 | JBS-2053 | Ac-HVQIGWYSVDSDRGYAYSSY-NH2 | 2265 | JBS-2094 | Ac-HVQIGWYSVDSDRHKAYSSY-NH2 |
| 2225 | JBS-2054 | Ac-HVQIGWYSVDSDRHGAYSSY-NH2 | 2266 | JBS-2095 | Ac-HVQIGWYSVDSDRHYKYSSY-NH2 |
| 2226 | JBS-2055 | Ac-HVQIGWYSVDSDRHYGYSSY-NH2 | 2267 | JBS-2096 | Ac-HVQIGWYSVDSDRHYAKSSY-NH2 |
| 2227 | JBS-2056 | Ac-HVQIGWYSVDSDRHYAGSSY-NH2 | 2268 | JBS-2097 | Ac-HVQIGWYSVDSDRHYAYKSY-NH2 |
| 2228 | JBS-2057 | Ac-HVQIGWYSVDSDRHYAYGSY-NH2 | 2269 | JBS-2098 | Ac-HVQIGWYSVDSDRHYAYSKY-NH2 |
| 2229 | JBS-2058 | Ac-HVQIGWYSVDSDRHYAYSGY-NH2 | 2270 | JBS-2099 | Ac-HVQIGWYSVDSDRHYAYSSK-NH2 |
| 2230 | JBS-2059 | Ac-HVQIGWYSVDSDRHYAYSSG-NH2 | 2271 | JBS-2100 | Ac-FVQIGWYSVDSDRHYAYSSY-NH2 |
| 2231 | JBS-2060 | Ac-LVQIGWYSVDSDRHYAYSSY-NH2 | 2272 | JBS-2101 | Ac-HFQIGWYSVDSDRHYAYSSY-NH2 |
| 2232 | JBS-2061 | Ac-HLQIGWYSVDSDRHYAYSSY-NH2 | 2273 | JBS-2102 | Ac-HVFIGWYSVDSDRHYAYSSY-NH2 |
| 2233 | JBS-2062 | Ac-HVLIGWYSVDSDRHYAYSSY-NH2 | 2274 | JBS-2103 | Ac-HVQFGWYSVDSDRHYAYSSY-NH2 |
| 2234 | JBS-2063 | Ac-HVQLGWYSVDSDRHYAYSSY-NH2 | 2275 | JBS-2104 | Ac-HVQIFWYSVDSDRHYAYSSY-NH2 |
| 2235 | JBS-2064 | Ac-HVQILWYSVDSDRHYAYSSY-NH2 | 2276 | JBS-2105 | Ac-HVQIGFYSVDSDRHYAYSSY-NH2 |
| 2236 | JBS-2065 | Ac-HVQIGLYSVDSDRHYAYSSY-NH2 | 2277 | JBS-2106 | Ac-HVQIGWFSVDSDRHYAYSSY-NH2 |
| 2237 | JBS-2066 | Ac-HVQIGWLSVDSDRHYAYSSY-NH2 | 2278 | JBS-2107 | Ac-HVQIGWYFVDSDRHYAYSSY-NH2 |
| 2238 | JBS-2067 | Ac-HVQIGWYLVDSDRHYAYSSY-NH2 | 2279 | JBS-2108 | Ac-HVQIGWYSFDSDRHYAYSSY-NH2 |
| 2239 | JBS-2068 | Ac-HVQIGWYSLDSDRHYAYSSY-NH2 | 2280 | JBS-2109 | Ac-HVQIGWYSVFSDRHYAYSSY-NH2 |
| 2240 | JBS-2069 | Ac-HVQIGWYSVLSDRHYAYSSY-NH2 | 2281 | JBS-2110 | Ac-HVQIGWYSVDFDRHYAYSSY-NH2 |
| 2241 | JBS-2070 | Ac-HVQIGWYSVDLDRHYAYSSY-NH2 | 2282 | JBS-2111 | Ac-HVQIGWYSVDSFRHYAYSSY-NH2 |

| SEQ ID | Compound | Sequence | SEQ ID | Compound | Sequence |
|---|---|---|---|---|---|
| 2283 | JBS-2112 | Ac-HVQIGWYSVDSDFHYAYSSY-NH2 | 2324 | JBS-2153 | Ac-HVQIGWYSVDSDRHYSYSSY-NH2 |
| 2284 | JBS-2113 | Ac-HVQIGWYSVDSDRFYAYSSY-NH2 | 2325 | JBS-2154 | Ac-HVQIGWYSVDSDRHYASSSY-NH2 |
| 2285 | JBS-2114 | Ac-HVQIGWYSVDSDRHFAYSSY-NH2 | 2326 | JBS-2155 | Ac-HVQIGWYSVDSDRHYAYSSS-NH2 |
| 2286 | JBS-2115 | Ac-HVQIGWYSVDSDRHYFYSSY-NH2 | 2327 | JBS-2156 | Ac-HVQIGWYSVDSDRHYAY-NH2 |
| 2287 | JBS-2116 | Ac-HVQIGWYSVDSDRHYAFSSY-NH2 | 2328 | JBS-2157 | Ac-HVQIGWYSVDSDRH-NH2 |
| 2288 | JBS-2117 | Ac-HVQIGWYSVDSDRHYAYFSY-NH2 | 2329 | JBS-2158 | Ac-HVQIGWYSVDS-NH2 |
| 2289 | JBS-2118 | Ac-HVQIGWYSVDSDRHYAYSFY-NH2 | 2330 | JBS-2159 | Ac-IGWYSVDSDRHYAYSSY-NH2 |
| 2290 | JBS-2119 | Ac-HVQIGWYSVDSDRHYAYSSF-NH2 | 2331 | JBS-2160 | Ac-YSVDSDRHYAYSSY-NH2 |
| 2291 | JBS-2120 | Ac-PVQIGWYSVDSDRHYAYSSY-NH2 | 2332 | JBS-2161 | Ac-DSDRHYAYSSY-NH2 |
| 2292 | JBS-2121 | Ac-HPQIGWYSVDSDRHYAYSSY-NH2 | 2333 | JBS-2162 | Ac-IGWYSVDSDRHYAY-NH2 |
| 2293 | JBS-2122 | Ac-HVPIGWYSVDSDRHYAYSSY-NH2 | 2334 | JBS-2163 | Ac-AQVWWGPKARMGLIEYGWE-NH2 |
| 2294 | JBS-2123 | Ac-HVQPGWYSVDSDRHYAYSSY-NH2 | 2335 | JBS-2164 | Ac-DAVWWGPKARMGLIEYGWE-NH2 |
| 2295 | JBS-2124 | Ac-HVQIPWYSVDSDRHYAYSSY-NH2 | 2336 | JBS-2165 | Ac-DQAWWGPKARMGLIEYGWE-NH2 |
| 2296 | JBS-2125 | Ac-HVQIGPYSVDSDRHYAYSSY-NH2 | 2337 | JBS-2166 | Ac-DQVAWWGPKARMGLIEYGWE-NH2 |
| 2297 | JBS-2126 | Ac-HVQIGWPSVDSDRHYAYSSY-NH2 | 2338 | JBS-2167 | Ac-DQVWAWGPKARMGLIEYGWE-NH2 |
| 2298 | JBS-2127 | Ac-HVQIGWYPVDSDRHYAYSSY-NH2 | 2339 | JBS-2168 | Ac-DQVWWAGPKARMGLIEYGWE-NH2 |
| 2299 | JBS-2128 | Ac-HVQIGWYSPDSDRHYAYSSY-NH2 | 2340 | JBS-2169 | Ac-DQVWWAPKARMGLIEYGWE-NH2 |
| 2300 | JBS-2129 | Ac-HVQIGWYSVPSDRHYAYSSY-NH2 | 2341 | JBS-2170 | Ac-DQVWWGAKARMGLIEYGWE-NH2 |
| 2301 | JBS-2130 | Ac-HVQIGWYSVDPDRHYAYSSY-NH2 | 2342 | JBS-2171 | Ac-DQVWWGPAARMGLIEYGWE-NH2 |
| 2302 | JBS-2131 | Ac-HVQIGWYSVDSPRHYAYSSY-NH2 | 2343 | JBS-2172 | Ac-DQVWWGPKAAMGLIEYGWE-NH2 |
| 2303 | JBS-2132 | Ac-HVQIGWYSVDSDPHYAYSSY-NH2 | 2344 | JBS-2173 | Ac-DQVWWGPKARAGLIEYGWE-NH2 |
| 2304 | JBS-2133 | Ac-HVQIGWYSVDSDRPYAYSSY-NH2 | 2345 | JBS-2174 | Ac-DQVWWGPKARMALIEYGWE-NH2 |
| 2305 | JBS-2134 | Ac-HVQIGWYSVDSDRHPAYSSY-NH2 | 2346 | JBS-2175 | Ac-DQVWWGPKARMGAIEYGWE-NH2 |
| 2306 | JBS-2135 | Ac-HVQIGWYSVDSDRHYPYSSY-NH2 | 2347 | JBS-2176 | Ac-DQVWWGPKARMGLAEYGWE-NH2 |
| 2307 | JBS-2136 | Ac-HVQIGWYSVDSDRHYAPSSY-NH2 | 2348 | JBS-2177 | Ac-DQVWWGPKARMGLIAYGWE-NH2 |
| 2308 | JBS-2137 | Ac-HVQIGWYSVDSDRHYAYPSY-NH2 | 2349 | JBS-2178 | Ac-DQVWWGPKARMGLIEAGWE-NH2 |
| 2309 | JBS-2138 | Ac-HVQIGWYSVDSDRHYAYSPY-NH2 | 2350 | JBS-2179 | Ac-DQVWWGPKARMGLIEYAWE-NH2 |
| 2310 | JBS-2139 | Ac-HVQIGWYSVDSDRHYAYSSP-NH2 | 2351 | JBS-2180 | Ac-DQVWWGPKARMGLIEYGAE-NH2 |
| 2311 | JBS-2140 | Ac-SVQIGWYSVDSDRHYAYSSY-NH2 | 2352 | JBS-2181 | Ac-DQVWWGPKARMGLIEYGWA-NH2 |
| 2312 | JBS-2141 | Ac-HSQIGWYSVDSDRHYAYSSY-NH2 | 2353 | JBS-2182 | Ac-DDVWWGPKARMGLIEYGWE-NH2 |
| 2313 | JBS-2142 | Ac-HVSIGWYSVDSDRHYAYSSY-NH2 | 2354 | JBS-2183 | Ac-DQDWWGPKARMGLIEYGWE-NH2 |
| 2314 | JBS-2143 | Ac-HVQSGWYSVDSDRHYAYSSY-NH2 | 2355 | JBS-2184 | Ac-DQVDWWGPKARMGLIEYGWE-NH2 |
| 2315 | JBS-2144 | Ac-HVQISWYSVDSDRHYAYSSY-NH2 | 2356 | JBS-2185 | Ac-DQVWDWGPKARMGLIEYGWE-NH2 |
| 2316 | JBS-2145 | Ac-HVQIGSYSVDSDRHYAYSSY-NH2 | 2357 | JBS-2186 | Ac-DQVWWDGPKARMGLIEYGWE-NH2 |
| 2317 | JBS-2146 | Ac-HVQIGWSSVDSDRHYAYSSY-NH2 | 2358 | JBS-2187 | Ac-DQVWWGDKARMGLIEYGWE-NH2 |
| 2318 | JBS-2147 | Ac-HVQIGWYSSDSDRHYAYSSY-NH2 | 2359 | JBS-2188 | Ac-DQVWWGDPARMGLIEYGWE-NH2 |
| 2319 | JBS-2148 | Ac-HVQIGWYSVSSDRHYAYSSY-NH2 | 2360 | JBS-2189 | Ac-DQVWWGPDARMGLIEYGWE-NH2 |
| 2320 | JBS-2149 | Ac-HVQIGWYSVDSSRHYAYSSY-NH2 | 2361 | JBS-2190 | Ac-DQVWWGPKDRMGLIEYGWE-NH2 |
| 2321 | JBS-2150 | Ac-HVQIGWYSVDSDSHYAYSSY-NH2 | 2362 | JBS-2191 | Ac-DQVWWGPKADMGLIEYGWE-NH2 |
| 2322 | JBS-2151 | Ac-HVQIGWYSVDSDRSYAYSSY-NH2 | 2363 | JBS-2192 | Ac-DQVWWGPKARDGLIEYGWE-NH2 |
| 2323 | JBS-2152 | Ac-HVQIGWYSVDSDRHSAYSSY-NH2 | 2364 | JBS-2193 | Ac-DQVWWGPKARMDLIEYGWE-NH2 |

| SEQ ID | Compound | Sequence | SEQ ID | Compound | Sequence |
|---|---|---|---|---|---|
| 2365 | JBS-2194 | Ac-DQVWWWGPKARMGDLIEYGWE-NH2 | 2406 | JBS-2235 | Ac-DQVWWWGPKARMGLIEYGLE-NH2 |
| 2366 | JBS-2195 | Ac-DQVWWWGPKARMGLLDEYGWE-NH2 | 2407 | JBS-2236 | Ac-DQVWWWGPKARMGLIEYGWL-NH2 |
| 2367 | JBS-2196 | Ac-DQVWWWGPKARMGLIDYGWE-NH2 | 2408 | JBS-2237 | Ac-KQVWWWGPKARMGLIEYGWE-NH2 |
| 2368 | JBS-2197 | Ac-DQVWWWGPKARMGLIEDGWE-NH2 | 2409 | JBS-2238 | Ac-DKVWWWGPKARMGLIEYGWE-NH2 |
| 2369 | JBS-2198 | Ac-DQVWWWGPKARMGLIEYDWE-NH2 | 2410 | JBS-2239 | Ac-DQKWWWGPKARMGLIEYGWE-NH2 |
| 2370 | JBS-2199 | Ac-DQVWWWGPKARMGLIEYGDE-NH2 | 2411 | JBS-2240 | Ac-DQVKWWGPKARMGLIEYGWE-NH2 |
| 2371 | JBS-2200 | Ac-DQVWWWGPKARMGLIEYGWD-NH2 | 2412 | JBS-2241 | Ac-DQVWKWGPKARMGLIEYGWE-NH2 |
| 2372 | JBS-2201 | Ac-GQVWWWGPKARMGLLEYGWE-NH2 | 2413 | JBS-2242 | Ac-DQVWWKGPKARMGLIEYGWE-NH2 |
| 2373 | JBS-2202 | Ac-DGVWWWGPKARMGLIEYGWE-NH2 | 2414 | JBS-2243 | Ac-DQVWWWKPKARMGLIEYGWE-NH2 |
| 2374 | JBS-2203 | Ac-DQGWWWGPKARMGLIEYGWE-NH2 | 2415 | JBS-2244 | Ac-DQVWWWGKKARMGLIEYGWE-NH2 |
| 2375 | JBS-2204 | Ac-DQVGWWGPKARMGLIEYGWE-NH2 | 2416 | JBS-2245 | Ac-DQVWWWGPKKRMGLIEYGWE-NH2 |
| 2376 | JBS-2205 | Ac-DQVWGWGPKARMGLLEYGWE-NH2 | 2417 | JBS-2246 | Ac-DQVWWWGPKAKMGLIEYGWE-NH2 |
| 2377 | JBS-2206 | Ac-DQVWWGGPKARMGLIEYGWE-NH2 | 2418 | JBS-2247 | Ac-DQVWWWGPKARKGLIEYGWE-NH2 |
| 2378 | JBS-2207 | Ac-DQVWWWGPKARMGLIEYGWE-NH2 | 2419 | JBS-2248 | Ac-DQVWWWGPKARMKLIEYGWE-NH2 |
| 2379 | JBS-2208 | Ac-DQVWWWGPGARMGLLEYGWE-NH2 | 2420 | JBS-2249 | Ac-DQVWWWGPKARMGKIEYGWE-NH2 |
| 2380 | JBS-2209 | Ac-DQVWWWGPKGRMGLLEYGWE-NH2 | 2421 | JBS-2250 | Ac-DQVWWWGPKARMGLKEYGWE-NH2 |
| 2381 | JBS-2210 | Ac-DQVWWWGPKAGMGLIEYGWE-NH2 | 2422 | JBS-2251 | Ac-DQVWWWGPKARMGLIKYGWE-NH2 |
| 2382 | JBS-2211 | Ac-DQVWWWGPKARGGLIEYGWE-NH2 | 2423 | JBS-2252 | Ac-DQVWWWGPKARMGLIEKGWE-NH2 |
| 2383 | JBS-2212 | Ac-DQVWWWGPKARMGGIEYGWE-NH2 | 2424 | JBS-2253 | Ac-DQVWWWGPKARMGLIEYKWE-NH2 |
| 2384 | JBS-2213 | Ac-DQVWWWGPKARMGLGEYGWE-NH2 | 2425 | JBS-2254 | Ac-DQVWWWGPKARMGLIEYGKE-NH2 |
| 2385 | JBS-2214 | Ac-DQVWWWGPKARMGLIGYGWE-NH2 | 2426 | JBS-2255 | Ac-DQVWWWGPKARMGLIEYGWK-NH2 |
| 2386 | JBS-2215 | Ac-DQVWWWGPKARMGLIEGGWE-NH2 | 2427 | JBS-2256 | Ac-FQVWWWGPKARMGLIEYGWE-NH2 |
| 2387 | JBS-2216 | Ac-DQVWWWGPKARMGLIEYGGE-NH2 | 2428 | JBS-2257 | Ac-DFVWWWGPKARMGLIEYGWE-NH2 |
| 2388 | JBS-2217 | Ac-DQVWWWGPKARMGLIEYGWG-NH2 | 2429 | JBS-2258 | Ac-DQFWWWGPKARMGLIEYGWE-NH2 |
| 2389 | JBS-2218 | Ac-LQVWWWGPKARMGLIEYGWE-NH2 | 2430 | JBS-2259 | Ac-DQVFWWGPKARMGLIEYGWE-NH2 |
| 2390 | JBS-2219 | Ac-DLVWWWGPKARMGLIEYGWE-NH2 | 2431 | JBS-2260 | Ac-DQVWFWGPKARMGLIEYGWE-NH2 |
| 2391 | JBS-2220 | Ac-DQLWWWGPKARMGLIEYGWE-NH2 | 2432 | JBS-2261 | Ac-DQVWWFGPKARMGLIEYGWE-NH2 |
| 2392 | JBS-2221 | Ac-DQVLWWGPKARMGLIEYGWE-NH2 | 2433 | JBS-2262 | Ac-DQVWWWFPKARMGLIEYGWE-NH2 |
| 2393 | JBS-2222 | Ac-DQVWLWGPKARMGLIEYGWE-NH2 | 2434 | JBS-2263 | Ac-DQVWWWGFKARMGLIEYGWE-NH2 |
| 2394 | JBS-2223 | Ac-DQVWWLGPKARMGLIEYGWE-NH2 | 2435 | JBS-2264 | Ac-DQVWWWGPFARMGLIEYGWE-NH2 |
| 2395 | JBS-2224 | Ac-DQVWWWLPKARMGLIEYGWE-NH2 | 2436 | JBS-2265 | Ac-DQVWWWGPKFRMGLIEYGWE-NH2 |
| 2396 | JBS-2225 | Ac-DQVWWWGLKARMGLIEYGWE-NH2 | 2437 | JBS-2266 | Ac-DQVWWWGPKAFMGLIEYGWE-NH2 |
| 2397 | JBS-2226 | Ac-DQVWWWGPLARMGLIEYGWE-NH2 | 2438 | JBS-2267 | Ac-DQVWWWGPKARFGLIEYGWE-NH2 |
| 2398 | JBS-2227 | Ac-DQVWWWGPKLRMGLIEYGWE-NH2 | 2439 | JBS-2268 | Ac-DQVWWWGPKARMFLIEYGWE-NH2 |
| 2399 | JBS-2228 | Ac-DQVWWWGPKALMGLIEYGWE-NH2 | 2440 | JBS-2269 | Ac-DQVWWWGPKARMGFIEYGWE-NH2 |
| 2400 | JBS-2229 | Ac-DQVWWWGPKARLGLIEYGWE-NH2 | 2441 | JBS-2270 | Ac-DQVWWWGPKARMGLFEYGWE-NH2 |
| 2401 | JBS-2230 | Ac-DQVWWWGPKARMLLIEYGWE-NH2 | 2442 | JBS-2271 | Ac-DQVWWWGPKARMGLIFYGWE-NH2 |
| 2402 | JBS-2231 | Ac-DQVWWWGPKARMGLLIEYGWE-NH2 | 2443 | JBS-2272 | Ac-DQVWWWGPKARMGLIEFGWE-NH2 |
| 2403 | JBS-2232 | Ac-DQVWWWGPKARMGLILYGWE-NH2 | 2444 | JBS-2273 | Ac-DQVWWWGPKARMGLIEYFWE-NH2 |
| 2404 | JBS-2233 | Ac-DQVWWWGPKARMGLIELGWE-NH2 | 2445 | JBS-2274 | Ac-DQVWWWGPKARMGLIEYGFE-NH2 |
| 2405 | JBS-2234 | Ac-DQVWWWGPKARMGLIEYLWE-NH2 | 2446 | JBS-2275 | Ac-DQVWWWGPKARMGLIEYGWF-NH2 |

FIGURE 2DD

| SEQ ID | Compound | Sequence | SEQ ID | Compound | Sequence |
| --- | --- | --- | --- | --- | --- |
| 2447 | JBS-2276 | Ac-PQVWWWGPKARMGLIEYGWE-NH2 | 2488 | JBS-2317 | Ac-DQVWWGPKAR-NH2 |
| 2448 | JBS-2277 | Ac-DPVWWWGPKARMGLIEYGWE-NH2 | 2489 | JBS-2318 | Ac-WWWGPKARMGLIEYGWE-NH2 |
| 2449 | JBS-2278 | Ac-DQPWWWGPKARMGLIEYGWE-NH2 | 2490 | JBS-2319 | Ac-GPKARMGLIEYGWE-NH2 |
| 2450 | JBS-2279 | Ac-DQVPWWWGPKARMGLIEYGWE-NH2 | 2491 | JBS-2320 | Ac-ARMGLIEYGWE-NH2 |
| 2451 | JBS-2280 | Ac-DQVWPWWGPKARMGLIEYGWE-NH2 | 2492 | JBS-2321 | Ac-WWWGPKARMGLIEY-NH2 |
| 2452 | JBS-2281 | Ac-DQVWWPGPKARMGLIEYGWE-NH2 | 2493 | JBS-2322 | Ac-AEVGWYNVVTQKHSKLGMLI-NH2 |
| 2453 | JBS-2282 | Ac-DQVWWWPPKARMGLIEYGWE-NH2 | 2494 | JBS-2323 | Ac-IAVGWYNVVTQKHSKLGMLI-NH2 |
| 2454 | JBS-2283 | Ac-DQVWWWGPPARMGLIEYGWE-NH2 | 2495 | JBS-2324 | Ac-IEAGWYNVVTQKHSKLGMLI-NH2 |
| 2455 | JBS-2284 | Ac-DQVWWWGPKPRMGLIEYGWE-NH2 | 2496 | JBS-2325 | Ac-IEVAWYNVVTQKHSKLGMLI-NH2 |
| 2456 | JBS-2285 | Ac-DQVWWWGPKAPMGLIEYGWE-NH2 | 2497 | JBS-2326 | Ac-IEVGAYNVVTQKHSKLGMLI-NH2 |
| 2457 | JBS-2286 | Ac-DQVWWWGPKARPGLIEYGWE-NH2 | 2498 | JBS-2327 | Ac-IEVGWANVVTQKHSKLGMLI-NH2 |
| 2458 | JBS-2287 | Ac-DQVWWWGPKARMPLIEYGWE-NH2 | 2499 | JBS-2328 | Ac-IEVGWYAVVTQKHSKLGMLI-NH2 |
| 2459 | JBS-2288 | Ac-DQVWWWGPKARMGPIEYGWE-NH2 | 2500 | JBS-2329 | Ac-IEVGWYNAVTQKHSKLGMLI-NH2 |
| 2460 | JBS-2289 | Ac-DQVWWWGPKARMGLPEYGWE-NH2 | 2501 | JBS-2330 | Ac-IEVGWYNVATQKHSKLGMLI-NH2 |
| 2461 | JBS-2290 | Ac-DQVWWWGPKARMGLIPYGWE-NH2 | 2502 | JBS-2331 | Ac-IEVGWYNVVAQKHSKLGMLI-NH2 |
| 2462 | JBS-2291 | Ac-DQVWWWGPKARMGLIEPGWE-NH2 | 2503 | JBS-2332 | Ac-IEVGWYNVVTAKHSKLGMLI-NH2 |
| 2463 | JBS-2292 | Ac-DQVWWWGPKARMGLIEYPWE-NH2 | 2504 | JBS-2333 | Ac-IEVGWYNVVTQAHSKLGMLI-NH2 |
| 2464 | JBS-2293 | Ac-DQVWWWGPKARMGLIEYGPE-NH2 | 2505 | JBS-2334 | Ac-IEVGWYNVVTQKASKLGMLI-NH2 |
| 2465 | JBS-2294 | Ac-DQVWWWGPKARMGLIEYGWP-NH2 | 2506 | JBS-2335 | Ac-IEVGWYNVVTQKHAKLGMLI-NH2 |
| 2466 | JBS-2295 | Ac-SQVWWWGPKARMGLIEYGWE-NH2 | 2507 | JBS-2336 | Ac-IEVGWYNVVTQKHSALGMLI-NH2 |
| 2467 | JBS-2296 | Ac-DSVWWWGPKARMGLIEYGWE-NH2 | 2508 | JBS-2337 | Ac-IEVGWYNVVTQKHSKAGMLI-NH2 |
| 2468 | JBS-2297 | Ac-DQVWWWGPSARMGLIEYGWE-NH2 | 2509 | JBS-2338 | Ac-IEVGWYNVVTQKHSKLAMLI-NH2 |
| 2469 | JBS-2298 | Ac-DQVSWWWGPKARMGLIEYGWE-NH2 | 2510 | JBS-2339 | Ac-IEVGWYNVVTQKHSKLGALI-NH2 |
| 2470 | JBS-2299 | Ac-DQVWSWGPKARMGLIEYGWE-NH2 | 2511 | JBS-2340 | Ac-IEVGWYNVVTQKHSKLGMAI-NH2 |
| 2471 | JBS-2300 | Ac-DQVWWSGPKARMGLIEYGWE-NH2 | 2512 | JBS-2341 | Ac-IEVGWYNVVTQKHSKLGMLA-NH2 |
| 2472 | JBS-2301 | Ac-DQVWWWSPKARMGLIEYGWE-NH2 | 2513 | JBS-2342 | Ac-DEVGWYNVVTQKHSKLGMLI-NH2 |
| 2473 | JBS-2302 | Ac-DQVWWWGSKARMGLIEYGWE-NH2 | 2514 | JBS-2343 | Ac-IDVGWYNVVTQKHSALGMLI-NH2 |
| 2474 | JBS-2303 | Ac-DQVWWWGPSARMGLIEYGWE-NH2 | 2515 | JBS-2344 | Ac-IEDGWYNVVTQKHSKAGMLI-NH2 |
| 2475 | JBS-2304 | Ac-DQVWWWGPKSRMGLIEYGWE-NH2 | 2516 | JBS-2345 | Ac-IEVDWYNVVTQKHSKLGALI-NH2 |
| 2476 | JBS-2305 | Ac-DQVWWWGPKASMGLIEYGWE-NH2 | 2517 | JBS-2346 | Ac-IEVGDYNVVTQKHSKLGMLI-NH2 |
| 2477 | JBS-2306 | Ac-DQVWWWGPKARSGLIEYGWE-NH2 | 2518 | JBS-2347 | Ac-IEVGWDNVVTQKHSKLGMLI-NH2 |
| 2478 | JBS-2307 | Ac-DQVWWWGPKARMSLIEYGWE-NH2 | 2519 | JBS-2348 | Ac-IEVGWYDVVTQKDSKLGMLI-NH2 |
| 2479 | JBS-2308 | Ac-DQVWWWGPKARMGSIEYGWE-NH2 | 2520 | JBS-2349 | Ac-IEVGWYNDVTQKHSKLGMLI-NH2 |
| 2480 | JBS-2309 | Ac-DQVWWWGPKARMGLSEYGWE-NH2 | 2521 | JBS-2350 | Ac-IEVGWYNVDTQKHSKLGMLI-NH2 |
| 2481 | JBS-2310 | Ac-DQVWWWGPKARMGLISYGWE-NH2 | 2522 | JBS-2351 | Ac-IEVGWYNVVDQKHSKLGMLI-NH2 |
| 2482 | JBS-2311 | Ac-DQVWWWGPKARMGLIESGWE-NH2 | 2523 | JBS-2352 | Ac-IEVGWYNVVTDKHSKLGMLI-NH2 |
| 2483 | JBS-2312 | Ac-DQVWWWGPKARMGLIEYSWE-NH2 | 2524 | JBS-2353 | Ac-IEVGWYNVVTQDHSKLGMLI-NH2 |
| 2484 | JBS-2313 | Ac-DQVWWWGPKARMGLIEYGSE-NH2 | 2525 | JBS-2354 | Ac-IEVGWYNVVTQKDSKLGMLI-NH2 |
| 2485 | JBS-2314 | Ac-DQVWWWGPKARMGLIEYGWS-NH2 | 2526 | JBS-2355 | Ac-IEVGWYNVVTQKHDKLGMLI-NH2 |
| 2486 | JBS-2315 | Ac-DQVWWWGPKARMGLIEY-NH2 | 2527 | JBS-2356 | Ac-IEVGWYNVVTQKHSDLGMLI-NH2 |
| 2487 | JBS-2316 | Ac-DQVWWWGPKARMGL-NH2 | 2528 | JBS-2357 | Ac-IEVGWYNVVTQKHSKDGMLI-NH2 |

| SEQ ID | Compound | Sequence | SEQ ID | Compound | Sequence |
|---|---|---|---|---|---|
| 2529 | JBS-2358 | Ac-IEVGWYNVVTQKHSKLDML I-NH2 | 2570 | JBS-2399 | Ac-IEVGWYNVVTQKHSKLGMLI-NH2 |
| 2530 | JBS-2359 | Ac-IEVGWYNVVTQKHSKLGDLI-NH2 | 2571 | JBS-2400 | Ac-IEKGWYNVVTQKHSKLGMLI-NH2 |
| 2531 | JBS-2360 | Ac-IEVGWYNVVTQKHSKLGMDI-NH2 | 2572 | JBS-2401 | Ac-IEVKWYNVVTQKHSKLGMLI-NH2 |
| 2532 | JBS-2361 | Ac-IEVGWYNVVTQKHSKLGMLD-NH2 | 2573 | JBS-2402 | Ac-IEVGKYNVVTQKHSKLGMLI-NH2 |
| 2533 | JBS-2362 | Ac-GEVGWYNVVTQKHSKLGMLI-NH2 | 2574 | JBS-2403 | Ac-IEVGWKNVVTQKHSKLGMLI-NH2 |
| 2534 | JBS-2363 | Ac-IGVGWYNVVTQKHSKLGMLI-NH2 | 2575 | JBS-2404 | Ac-IEVGWYKVVTQKHSKLGMLI-NH2 |
| 2535 | JBS-2364 | Ac-IEEGWYNVVTQKHSKLGMLI-NH2 | 2576 | JBS-2405 | Ac-IEVGWYNKVTQKHSKLGMLI-NH2 |
| 2536 | JBS-2365 | Ac-IEVGGYNVVTQKHSKLGMLI-NH2 | 2577 | JBS-2406 | Ac-IEVGWYNVKTQKHSKLGMLI-NH2 |
| 2537 | JBS-2366 | Ac-IEVGWGNVVTQKHSKLGMLI-NH2 | 2578 | JBS-2407 | Ac-IEVGWYNVVKQKHSKLGMLI-NH2 |
| 2538 | JBS-2367 | Ac-IEVGWYGVVTQKHSKLGMLI-NH2 | 2579 | JBS-2408 | Ac-IEVGWYNVVTKKHSKLGMLI-NH2 |
| 2539 | JBS-2368 | Ac-IEVGWYNGVTQKHSKLGMLI-NH2 | 2580 | JBS-2409 | Ac-IEVGWYNVVTQKKSKLGMLI-NH2 |
| 2540 | JBS-2369 | Ac-IEVGWYNVGTQKHSKLGMLI-NH2 | 2581 | JBS-2410 | Ac-IEVGWYNVVTQKHKKLGMLI-NH2 |
| 2541 | JBS-2370 | Ac-IEVGWYNVVGQKHSKLGMLI-NH2 | 2582 | JBS-2411 | Ac-IEVGWYNVVTQKHSKKGMLI-NH2 |
| 2542 | JBS-2371 | Ac-IEVGWYNVVTGKHSKLGMLI-NH2 | 2583 | JBS-2412 | Ac-IEVGWYNVVTQKHSKLKMLI-NH2 |
| 2543 | JBS-2372 | Ac-IEVGWYNVVTQGHSKLGMLI-NH2 | 2584 | JBS-2413 | Ac-IEVGWYNVVTQKHSKLGKLI-NH2 |
| 2544 | JBS-2373 | Ac-IEVGWYNVVTQKGSKLGMLI-NH2 | 2585 | JBS-2414 | Ac-IEVGWYNVVTQKHSKLGMKI-NH2 |
| 2545 | JBS-2374 | Ac-IEVGWYNVVTQKHGKLGMLI-NH2 | 2586 | JBS-2415 | Ac-IEVGWYNVVTQKHSKLGMLK-NH2 |
| 2546 | JBS-2375 | Ac-IEVGWYNVVTQKHSGLGMLI-NH2 | 2587 | JBS-2416 | Ac-FEVGWYNVVTQKHSKLGMLI-NH2 |
| 2547 | JBS-2376 | Ac-IEVGWYNVVTQKHSKGGMLI-NH2 | 2588 | JBS-2417 | Ac-IFVGWYNVVTQKHSKLGMLI-NH2 |
| 2548 | JBS-2377 | Ac-IEVGWYNVVTQKHSKLGGLI-NH2 | 2589 | JBS-2418 | Ac-IEFGWYNVVTQKHSKLGMLI-NH2 |
| 2549 | JBS-2378 | Ac-IEVGWYNVVTQKHSKLGMGI-NH2 | 2590 | JBS-2419 | Ac-IEVFWYNVVTQKHSKLGMLI-NH2 |
| 2550 | JBS-2379 | Ac-IEVGWYNVVTQKHSKLGMLG-NH2 | 2591 | JBS-2420 | Ac-IEVGFYNVVTQKHSKLGMLI-NH2 |
| 2551 | JBS-2380 | Ac-LEVGWYNVVTQKHSKLGMLI-NH2 | 2592 | JBS-2421 | Ac-IEVGWFNVVTQKHSKLGMLI-NH2 |
| 2552 | JBS-2381 | Ac-ILVGWYNVVTQKHSKLGMLI-NH2 | 2593 | JBS-2422 | Ac-IEVGWYFVVTQKHSKLGMLI-NH2 |
| 2553 | JBS-2382 | Ac-IELGWYNVVLQKHSKLGMLI-NH2 | 2594 | JBS-2423 | Ac-IEVGWYNFVTQKHFKLGMLI-NH2 |
| 2554 | JBS-2383 | Ac-IEVLWYNVVTLKHSKLGMLI-NH2 | 2595 | JBS-2424 | Ac-IEVGWYNVFTQKHSKLGMLI-NH2 |
| 2555 | JBS-2384 | Ac-IEVGLYNVVTQLHSKLGMLI-NH2 | 2596 | JBS-2425 | Ac-IEVGWYNVVFQKHSKLGMLI-NH2 |
| 2556 | JBS-2385 | Ac-IEVGWLNVVTQKLSKLGMLI-NH2 | 2597 | JBS-2426 | Ac-IEVGWYNVVTFKHSKLGMLI-NH2 |
| 2557 | JBS-2386 | Ac-IEVGWYLVVTQKHLKLGMLI-NH2 | 2598 | JBS-2427 | Ac-IEVGWYNVVTQFHSKLGMLI-NH2 |
| 2558 | JBS-2387 | Ac-IEVGWYNLVTQKHSLLGMLI-NH2 | 2599 | JBS-2428 | Ac-IEVGWYNVVTQKFSKLGMLI-NH2 |
| 2559 | JBS-2388 | Ac-IEVGWYNVLTQKHSKLLMLI-NH2 | 2600 | JBS-2429 | Ac-IEVGWYNVVTQKHFKLGMLI-NH2 |
| 2560 | JBS-2389 | Ac-IEVGWYNVVLQKHSKLGLLI-NH2 | 2601 | JBS-2430 | Ac-IEVGWYNVVTQKHSFLGMLI-NH2 |
| 2561 | JBS-2390 | Ac-IEVGWYNVVTLKHSKLGMLL-NH2 | 2602 | JBS-2431 | Ac-IEVGWYNVVTQKHSKFGMLI-NH2 |
| 2562 | JBS-2391 | Ac-IEVGWYNVVTQLHSKLGMLI-NH2 | 2603 | JBS-2432 | Ac-IEVGWYNVVTQKHSKLFMLI-NH2 |
| 2563 | JBS-2392 | Ac-IEVGWYNVVTQKLSKLGMLI-NH2 | 2604 | JBS-2433 | Ac-IEVGWYNVVTQKHSKLGFLI-NH2 |
| 2564 | JBS-2393 | Ac-IEVGWYNVVTQKHLKLGMLI-NH2 | 2605 | JBS-2434 | Ac-IEVGWYNVVTQKHSKLGMFI-NH2 |
| 2565 | JBS-2394 | Ac-IEVGWYNVVTQKHSLLGMLI-NH2 | 2606 | JBS-2435 | Ac-IEVGWYNVVTQKHSKLGMLF-NH2 |
| 2566 | JBS-2395 | Ac-IEVGWYNVVTQKHSKLLMLI-NH2 | 2607 | JBS-2436 | Ac-PEVGWYNVVTQKHSKLGMLI-NH2 |
| 2567 | JBS-2396 | Ac-IEVGWYNVVTQKHSKLGLLI-NH2 | 2608 | JBS-2437 | Ac-IPVGWYNVVTQKHSFLGMLI-NH2 |
| 2568 | JBS-2397 | Ac-IEVGWYNVVTQKHSKLGLLI-NH2 | 2609 | JBS-2438 | Ac-IEPGWYNVVTQKHSKLGMLI-NH2 |
| 2569 | JBS-2398 | Ac-KEVGWYNVVTQKHSKLGMLI-NH2 | 2610 | JBS-2439 | Ac-IEVPWYNVVTQKHSKLGMLI-NH2 |

FIGURE 2GG

| SEQ ID | Compound | Sequence |
|---|---|---|
| 2611 | JBS-2440 | Ac-IEVGPYNVVTQKHSKLGMLI-NH2 |
| 2612 | JBS-2441 | Ac-IEVGWPNVVTQKHSKLGMLI-NH2 |
| 2613 | JBS-2442 | Ac-IEVGWYPVVTQKHSKLGMLI-NH2 |
| 2614 | JBS-2443 | Ac-IEVGWYNPVTQKHSKLGMLI-NH2 |
| 2615 | JBS-2444 | Ac-IEVGWYNVPTQKHSKLGMLI-NH2 |
| 2616 | JBS-2445 | Ac-IEVGWYNVVPQKHSKLGMLI-NH2 |
| 2617 | JBS-2446 | Ac-IEVGWYNVVTPKHSKLGMLI-NH2 |
| 2618 | JBS-2447 | Ac-IEVGWYNVVTQPHSKLGMLI-NH2 |
| 2619 | JBS-2448 | Ac-IEVGWYNVVTQKPSKLGMLI-NH2 |
| 2620 | JBS-2449 | Ac-IEVGWYNVVTQKHPKLGMLI-NH2 |
| 2621 | JBS-2450 | Ac-IEVGWYNVVTQKHSPLGMLI-NH2 |
| 2622 | JBS-2451 | Ac-IEVGWYNVVTQKHSKPGMLI-NH2 |
| 2623 | JBS-2452 | Ac-IEVGWYNVVTQKHSKLPMLI-NH2 |
| 2624 | JBS-2453 | Ac-IEVGWYNVVTQKHSKLGPLI-NH2 |
| 2625 | JBS-2454 | Ac-IEVGWYNVVTQKHSKLGMPI-NH2 |
| 2626 | JBS-2455 | Ac-IEVGWYNVVTQKHSKLGMLP-NH2 |
| 2627 | JBS-2456 | Ac-SEVGWYNVVTQKHSKLGMLI-NH2 |
| 2628 | JBS-2457 | Ac-ISVGWYNVVTQKHSKLGMLI-NH2 |
| 2629 | JBS-2458 | Ac-IEESGWYNVVTQKHSKLGMLI-NH2 |
| 2630 | JBS-2459 | Ac-IEVSWYNVVTQKHSKLGMLI-NH2 |
| 2631 | JBS-2460 | Ac-IEVGSYNVVTQKHSKLGMLI-NH2 |
| 2632 | JBS-2461 | Ac-IEVGWSNVVTQKHSKLGMLI-NH2 |
| 2633 | JBS-2462 | Ac-IEVGWYSVVTQKHSKLGMLI-NH2 |
| 2634 | JBS-2463 | Ac-IEVGWYNSVTQKHSKLGMLI-NH2 |
| 2635 | JBS-2464 | Ac-IEVGWYNVSTQKHSKLGMLI-NH2 |
| 2636 | JBS-2465 | Ac-IEVGWYNVVSQKHSKLGMLI-NH2 |
| 2637 | JBS-2466 | Ac-IEVGWYNVVTSKHSKLGMLI-NH2 |
| 2638 | JBS-2467 | Ac-IEVGWYNVVTQSHSKLGMLI-NH2 |
| 2639 | JBS-2468 | Ac-IEVGWYNVVTQKSSKLGMLI-NH2 |
| 2640 | JBS-2469 | Ac-IEVGWYNVVTQKHSSKLGMLI-NH2 |
| 2641 | JBS-2471 | Ac-IEVGWYNVVTQKHSKSGMLI-NH2 |
| 2642 | JBS-2472 | Ac-IEVGWYNVVTQKHSKLSMLI-NH2 |
| 2643 | JBS-2473 | Ac-IEVGWYNVVTQKHSKLGSLI-NH2 |
| 2644 | JBS-2474 | Ac-IEVGWYNVVTQKHSKLGMSI-NH2 |
| 2645 | JBS-2475 | Ac-IEVGWYNVVTQKHSKLGMLS-NH2 |
| 2646 | JBS-2476 | Ac-IEVGWYNVVTQKHSKLG-NH2 |
| 2647 | JBS-2477 | Ac-IEVGWYNVVTQKHS-NH2 |
| 2648 | JBS-2478 | Ac-IEVGWYNVVTQ-NH2 |
| 2649 | JBS-2479 | Ac-GWYNVVTQKHSKLGMLI-NH2 |
| 2650 | JBS-2480 | Ac-NVVTQKHSKLGMLI-NH2 |
| 2651 | JBS-2480 | Ac-TQKHSKLGMLI-NH2 |
| 2652 | JBS-2481 | Ac-GWYNVVTQKHSKLG-NH2 |
| 2653 | JBS-2483 | Bio-Ttds-KLYLWQRWPSPWVEVGWEFV-NH2 |
| 2654 | JBS-2485 | Bio-Ttds-HKYLWQRWPSPWVEVGWEFV-NH2 |
| 2655 | JBS-2487 | Bio-Ttds-HAYLWQAWPSPWVEVGWEFV-NH2 |
| 2656 | JBS-2489 | Bio-Ttds-HLYLWQSMPSPWVEVGWEFV-NH2 |
| 2657 | JBS-2491 | Bio-Ttds-HLYLWQRAPSPWVEVGWEFV-NH2 |
| 2658 | JBS-2493 | Bio-Ttds-HLYLWQRFPSPWVEVGWEFV-NH2 |
| 2659 | JBS-2495 | Bio-Ttds-HLYLWQRMPSPFVEVGWEFV-NH2 |
| 2660 | JBS-2497 | Bio-Ttds-HLYLWQRMPSPGVEVGWEFV-NH2 |
| 2661 | JBS-2499 | Ac-KKYLWQAAPSPGVEVGWEFV-NH2 |
| 2662 | JBS-2500 | Bio-Ttds-KKYLWQAAPSPGVEVGWEFV-NH2 |
| 2663 | JBS-2501 | Ac-IPDQCCSPLPCNEDGYMSCKDGKASFTCT-NH2 |
| 2664 | JBS-2502 | Ac-VYEVGWDHGNWDEIIWR-NH2 |
| 2665 | JBS-2503 | Ac-VYEVGWDHGNWSEIIWR-NH2 |
| 2666 | JBS-2504 | Ac-VYEVGWDHGDWYEIIWR-NH2 |
| 2667 | JBS-2505 | Ac-VGWDHGNWDEIIWR-NH2 |
| 2668 | JBS-2506 | Ac-VGWDHGNWSEIIWR-NH2 |
| 2669 | JBS-2507 | Ac-VGWDHGDWYEIIWR-NH2 |
| 2670 | JBS-2508 | Ac-WWWGPKAPMGLIEYGWE-NH2 |
| 2671 | JBS-2509 | Ac-WWWGPKARMGLIEYGWL-NH2 |
| 2672 | JBS-2510 | Ac-WWWGPKARMGLLSYGWE-NH2 |
| 2673 | JBS-2511 | Ac-GFVWEDLWGTVEIWIWTKKT-NH2 |
| 2674 | JBS-2675 | Bio-Ttds-MKIIVGWELFDTGETLWWKV-NH2 |
| 2675 | JBS-2690 | Bio-Ttds-VYEVGWDHGNWDEIIWRYPS-NH2 |
| 2676 | JBS-2691 | Bio-Ttds-VYEVGWDHGNWYEIIWRDPS-NH2 |
| 2677 | JBS-2692 | Bio-Ttds-YTVEVGWHTVHTGRDNYFWM-NH2 |
| 2678 | JBS-2693 | Bio-Ttds-YTVEVGWHTVHTGRDNPMWM-NH2 |
| 2679 | JBS-2694 | Bio-Ttds-VYEVGWDHGDWYEIIWR-NH2 |
| 2680 | JBS-2695 | Bio-Ttds-HKYLWQRWPSPWVEVGWEFV-NH2 |
| 2681 | JBS-2700 | Bio-Ttds-HKYLWQRWPSPWVEVGWDHGNWYEIIWRDPS-NH2 |
| 2682 | JBS-2702 | Ac-HKYLWQRWPSPWVEVGWDHGNWYEIIWRDPS-NH2 |
| 2683 | JBS-2703 | Bio-Ttds-HKYLWQRWPSPWVEVGWDHGNWYFIIWRDPS-NH2 |
| 2684 | JBS-2704 | Ac-HKYLWQRWPSPLVSAGWYDYNFDHYREFT-NH2 |
| 2685 | JBS-2705 | Bio-Ttds-HKYLWQRWPSPLVSAGWYDYNFDHYREFT-NH2 |
| 2686 | JBS-2706 | Ac-HKYLWQRWPSPLVEVGWYDYNFDHYREFT-NH2 |
| 2687 | JBS-2707 | Bio-Ttds-HKYLWQRWPSPLVEVGWYDYNFDHYREFT-NH2 |
| 2688 | JBS-2708 | Ac-HLYLWQAWPSPWVEVGWDHGNWYEIIWRDPS-NH2 |
| 2689 | JBS-2709 | Bio-Ttds-HLYLWQAWPSPWVEVGWDHGNWYEIIWRDPS-NH2 |
| 2690 | JBS-2710 | Ac-HLYLWQAWPSPLVSAGWYDYNFDHYREFT-NH2 |
| 2691 | JBS-2711 | Bio-Ttds-HLYLWQAWPSPLVSAGWYDYNFDHYREFT-NH2 |
| 2692 | JBS-2711 | Ac-HLYLWQAWPSPLVEVGWYDYNFDHYREFT-NH2 |

| SEQ ID | Compound | Sequence | SEQ ID | Compound | Sequence |
|---|---|---|---|---|---|
| 2693 | JBS-2712 | Bio-Ttds-HLYLMQAWPSPLVEVGWYDYNFDHYREFT-NH2 | 2734 | JBS-2979 | Ac-HLYLMQAWPSPWVEVGWHFV-NH2 |
| 2694 | JBS-2715 | Ac-VYEVGWDHGNWYEIIWRDPSC(ME-400MA)-NH2 | 2735 | JBS-2980 | Ac-HLYLMQAWPSPWVEVGWEEV-NH2 |
| 2695 | JBS-2716 | Ac-C(ME-400MA)-VYEVGWDHGNWYEIIWRDPS-NH2 | 2736 | JBS-2981 | Ac-HLYLMQAWPSPWVEVGWEFH-NH2 |
| 2696 | JBS-2717 | Ac-NCSLDNGGCTHYCLEEVGWRRCS-NH2 | 2737 | JBS-2982 | Ac-ILYLMQAWPSPWVEVGWEFV-NH2 |
| 2697 | JBS-2718 | Bio-Ttds-NCSLDNGGCTHYCLEEVGWRRCS-NH2 | 2738 | JBS-2983 | Ac-HIYLMQAWPSPWVEVGWEFV-NH2 |
| 2698 | JBS-2719 | Ac-GCTHYSLEEVGWRRCS-NH2 | 2739 | JBS-2984 | Ac-HLILMQAWPSPWVEVGWEFV-NH2 |
| 2699 | JBS-2720 | Bio-Ttds-GCTHYSLEEVGWRRCS-NH2 | 2740 | JBS-2985 | Ac-HLYIMQAWPSPWVEVGWEFV-NH2 |
| 2700 | JBS-2945 | Ac-HLYLMQAWPSPWVEVGWEFV-NH2 | 2741 | JBS-2986 | Ac-HLYLIQAWPSPWVEVGWEFV-NH2 |
| 2701 | JBS-2946 | Ac-HEYLMQAWPSPWVEVGWEFV-NH2 | 2742 | JBS-2987 | Ac-HLYLMIAWPSPWVEVGWEFV-NH2 |
| 2702 | JBS-2947 | Ac-HLELMQAWPSPWVEVGWEFV-NH2 | 2743 | JBS-2988 | Ac-HLYLMQIWPSPWVEVGWEFV-NH2 |
| 2703 | JBS-2948 | Ac-HLYEWQAWPSPWVEVGWEFV-NH2 | 2744 | JBS-2989 | Ac-HLYLMQAIPSPWVEVGWEFV-NH2 |
| 2704 | JBS-2949 | Ac-HLYLEQAWPSPWVEVGWEFV-NH2 | 2745 | JBS-2990 | Ac-HLYLMQAWISPWVEVGWEFV-NH2 |
| 2705 | JBS-2950 | Ac-HLYLWEAWPSPWVEVGWEFV-NH2 | 2746 | JBS-2991 | Ac-HLYLMQAWPIPWVEVGWEFV-NH2 |
| 2706 | JBS-2951 | Ac-HLYLMQEWPSPWVEVGWEFV-NH2 | 2747 | JBS-2992 | Ac-HLYLMQAWPSIWVEVGWEFV-NH2 |
| 2707 | JBS-2952 | Ac-HLYLMQAEPSPWVEVGWEFV-NH2 | 2748 | JBS-2993 | Ac-HLYLMQAWPSPTVEVGWEFV-NH2 |
| 2708 | JBS-2953 | Ac-HLYLMQAWESPWVEVGWEFV-NH2 | 2749 | JBS-2994 | Ac-HLYLMQAWPSPWIEVGWEFV-NH2 |
| 2709 | JBS-2954 | Ac-HLYLMQAWPEPWVEVGWEEV-NH2 | 2750 | JBS-2995 | Ac-HLYLMQAWPSPWVIVGWEFV-NH2 |
| 2710 | JBS-2955 | Ac-HLYLMQAWPSEWVEVGWEFE-NH2 | 2751 | JBS-2996 | Ac-HLYLMQAWPSPWVEIGWEFV-NH2 |
| 2711 | JBS-2956 | Ac-HLYLMQAWPSPEVEVGWEFV-NH2 | 2752 | JBS-2997 | Ac-HLYLMQAWPSPWVEVIWEFV-NH2 |
| 2712 | JBS-2957 | Ac-HLYLMQAWPSPWEEVGWEFV-NH2 | 2753 | JBS-2998 | Ac-HLYLMQAWPSPWVEVGIEFV-NH2 |
| 2713 | JBS-2958 | Ac-HLYLMQAWPSPWVEEGWEFV-NH2 | 2754 | JBS-2999 | Ac-HLYLMQAWPSPWVEVGWIFV-NH2 |
| 2714 | JBS-2959 | Ac-HLYLMQAWPSPWVEVEWEFV-NH2 | 2755 | JBS-3000 | Ac-HLYLMQAWPSPWVEVGWETV-NH2 |
| 2715 | JBS-2960 | Ac-HLYLMQAWPSPWVEVGEEFV-NH2 | 2756 | JBS-3001 | Ac-HLYLMQAWPSPWVEVGWEFI-NH2 |
| 2716 | JBS-2961 | Ac-HLYLMQAWPSPWVEVGWEEV-NH2 | 2757 | JBS-3002 | Ac-MLYLMQAWPSPWVEVGWEFV-NH2 |
| 2717 | JBS-2962 | Ac-HLYLMQAWPSPWVEVGWEFE-NH2 | 2758 | JBS-3003 | Ac-HMYLMQAWPSPWVEIGWEFV-NH2 |
| 2718 | JBS-2963 | Ac-HHYLMQAWPSPWVEVGWEFV-NH2 | 2759 | JBS-3004 | Ac-HLMLMQAWPSPWVMSPWVEVGWEFV-NH2 |
| 2719 | JBS-2964 | Ac-HLHLMQAWPSPWVEVGWEFV-NH2 | 2760 | JBS-3005 | Ac-HLYMMQAWPMPWVEVGWEFV-NH2 |
| 2720 | JBS-2965 | Ac-HLYHMQAWPSPWVEVGWEFV-NH2 | 2761 | JBS-3006 | Ac-HLYLMMAWPSMWVEVGWEFV-NH2 |
| 2721 | JBS-2966 | Ac-HLYLHQAWPSPWVEVGWEFV-NH2 | 2762 | JBS-3007 | Ac-HLYLMMAWPSPWVEVGWEFV-NH2 |
| 2722 | JBS-2967 | Ac-HLYLWHAWPSPWVEVGWEFV-NH2 | 2763 | JBS-3008 | Ac-HLYLMQMWPSPWVEVGWEFV-NH2 |
| 2723 | JBS-2968 | Ac-HLYLWQHWPSPWVEVGWEFV-NH2 | 2764 | JBS-3009 | Ac-HLYLMQAMPSPWVEVGWEFV-NH2 |
| 2724 | JBS-2969 | Ac-HLYLWQAHPSPWVEVGWEFV-NH2 | 2765 | JBS-3010 | Ac-HLYLMQAWMSPWVEVGWEFV-NH2 |
| 2725 | JBS-2970 | Ac-HLYLWQAWHSPWVEVGWEFV-NH2 | 2766 | JBS-3011 | Ac-HLYLMQAWPMPWVEVGWEFV-NH2 |
| 2726 | JBS-2971 | Ac-HLYLWQAWPHPWVEVGWEFV-NH2 | 2767 | JBS-3012 | Ac-HLYLMQAWPSMWVEVGWEFV-NH2 |
| 2727 | JBS-2972 | Ac-HLYLWQAWPSHWVEVGWEFV-NH2 | 2768 | JBS-3013 | Ac-HLYLMQAWPSPMVEVGWEFV-NH2 |
| 2728 | JBS-2973 | Ac-HLYLWQAWPSPHVEVGWEFV-NH2 | 2769 | JBS-3014 | Ac-HLYLMQAWPSPWMEVGWEFV-NH2 |
| 2729 | JBS-2974 | Ac-HLYLWQAWPSPWHEVGWEFV-NH2 | 2770 | JBS-3015 | Ac-HLYLMQAWPSPWVMVGWEFV-NH2 |
| 2730 | JBS-2975 | Ac-HLYLWQAWPSPWVHVGWEFV-NH2 | 2771 | JBS-3016 | Ac-HLYLMQAWPSPWVEMGWEFV-NH2 |
| 2731 | JBS-2976 | Ac-HLYLWQAWPSPWVEHGWEFV-NH2 | 2772 | JBS-3017 | Ac-HLYLMQAWPSPWVEVMWEFV-NH2 |
| 2732 | JBS-2977 | Ac-HLYLWQAWPSPWVEVHWEFV-NH2 | 2773 | JBS-3018 | Ac-HLYLMQAWPSPWVEVGMEFV-NH2 |
| 2733 | JBS-2978 | Ac-HLYLMQAWPSPWVEVGHEFV-NH2 | 2774 | JBS-3019 | Ac-HLYLMQAWPSPWVEVGWMFV-NH2 |

FIGURE 2HH

| SEQ ID | Compound | Sequence | SEQ ID | Compound | Sequence |
|---|---|---|---|---|---|
| 2775 | JBS-3020 | Ac-HLYLMQAWPSPWVEVGWEMV-NH2 | 2816 | JBS-3061 | Ac-RLYLMQAWPSPWVEVGWEFV-NH2 |
| 2776 | JBS-3021 | Ac-HLYLMQAWPSPWVEVGWEFM-NH2 | 2817 | JBS-3062 | Ac-HRYLMQAWPSPWVEVGWEFV-NH2 |
| 2777 | JBS-3022 | Ac-NLYLMQAWPSPWVEVGWEFV-NH2 | 2818 | JBS-3063 | Ac-HLRLMQAWPSPWVEVGWEFV-NH2 |
| 2778 | JBS-3023 | Ac-HNYLMQAWPSPWVEVGWEFV-NH2 | 2819 | JBS-3064 | Ac-HLYRMQAWPSPWVEVGWEFV-NH2 |
| 2779 | JBS-3024 | Ac-HLNLMQAWPSPWVEVGWEFV-NH2 | 2820 | JBS-3065 | Ac-HLYLRQAWPSPWVEVGWEFV-NH2 |
| 2780 | JBS-3025 | Ac-HLYNMQAWPSPWVEVGWEFV-NH2 | 2821 | JBS-3066 | Ac-HLYLWRAWPSPWVEVGWEFV-NH2 |
| 2781 | JBS-3026 | Ac-HLYLNQAWPSPWVEVGWEFV-NH2 | 2822 | JBS-3067 | Ac-HLYLMQARPSPWVEVGWEFV-NH2 |
| 2782 | JBS-3027 | Ac-HLYLMNAWPSPWVEVGWEFV-NH2 | 2823 | JBS-3068 | Ac-HLYLMQAVRSPWVEVGWEFV-NH2 |
| 2783 | JBS-3028 | Ac-HLYLMQNWPSPWVEVGWEFV-NH2 | 2824 | JBS-3069 | Ac-HLYLMQAWPRPWVEVGWEFV-NH2 |
| 2784 | JBS-3029 | Ac-HLYLMQAWPSPWVEVGWEFV-NH2 | 2825 | JBS-3070 | Ac-HLYLMQAWPSRWVEVGWEFV-NH2 |
| 2785 | JBS-3030 | Ac-HLYLMQAWNSPWVEVGWEFV-NH2 | 2826 | JBS-3071 | Ac-HLYLMQAWPSPRVEVGWEFV-NH2 |
| 2786 | JBS-3031 | Ac-HLYLMQAWPNPWVEVGWEFV-NH2 | 2827 | JBS-3072 | Ac-HLYLMQAWPSPWREVGWEFV-NH2 |
| 2787 | JBS-3032 | Ac-HLYLMQAWPSNWVEVGWEFV-NH2 | 2828 | JBS-3073 | Ac-HLYLMQAWPSPWVRVGWEFV-NH2 |
| 2788 | JBS-3033 | Ac-HLYLMQAWPSPNVEVGWEFV-NH2 | 2829 | JBS-3074 | Ac-HLYLMQAWPSPWVERGWEFV-NH2 |
| 2789 | JBS-3034 | Ac-HLYLMQAWPSNWNEVGWEFV-NH2 | 2830 | JBS-3075 | Ac-HLYLMQAWPSPWVEVRWEFV-NH2 |
| 2790 | JBS-3035 | Ac-HLYLMQAWPSPWVNVGWEFV-NH2 | 2831 | JBS-3076 | Ac-HLYLMQAWPSPWVEVGREFV-NH2 |
| 2791 | JBS-3036 | Ac-HLYLMQAWPSPWVENGWEFV-NH2 | 2832 | JBS-3077 | Ac-HLYLMQAWPSPWVEVGWRFV-NH2 |
| 2792 | JBS-3037 | Ac-HLYLMQAWPSPWVEVNWEFV-NH2 | 2833 | JBS-3078 | Ac-HLYLMQAWPSPWVEVGWERV-NH2 |
| 2793 | JBS-3038 | Ac-HLYLMQAWPSPWVEVGNEFV-NH2 | 2834 | JBS-3079 | Ac-HLYLMQAWPSPWVEVGWEFR-NH2 |
| 2794 | JBS-3039 | Ac-HLYLMQAWPSPWVEVGWNFV-NH2 | 2835 | JBS-3080 | Ac-TLYLMQAWPSPWVEVGWEFV-NH2 |
| 2795 | JBS-3040 | Ac-HLYLMQAWPSPWVEVGWENV-NH2 | 2836 | JBS-3081 | Ac-HTYLMQAWPSPWVEVGWEFV-NH2 |
| 2796 | JBS-3041 | Ac-HLYLMQAWPSPWVEVGWEFN-NH2 | 2837 | JBS-3082 | Ac-HLTLMQAWPSPWVEVGWEFV-NH2 |
| 2797 | JBS-3042 | Ac-QLYLMQAWPSPWVEVGWEFV-NH2 | 2838 | JBS-3083 | Ac-HLYTMQAWPSPWVEVGWEFV-NH2 |
| 2798 | JBS-3043 | Ac-HQYLMQAWPSPWVEVGWEFV-NH2 | 2839 | JBS-3084 | Ac-HLYLTQAWPSPWVEVGWEFV-NH2 |
| 2799 | JBS-3044 | Ac-HLQLMQAWPSPWVEVGWEFV-NH2 | 2840 | JBS-3085 | Ac-HLYLMQAWPTPWVEVGWEFV-NH2 |
| 2800 | JBS-3045 | Ac-HLYQMQAWPSPWVEVGWEFV-NH2 | 2841 | JBS-3086 | Ac-HLYLWTAWPSPWVEVGWEFV-NH2 |
| 2801 | JBS-3046 | Ac-HLYLQQAWPSPWVEVGWEFV-NH2 | 2842 | JBS-3087 | Ac-HLYLMQTWPSPWVEVGWEFV-NH2 |
| 2802 | JBS-3047 | Ac-HLYLMQQWPSPWVEVGWEFV-NH2 | 2843 | JBS-3088 | Ac-HLYLMQATPSPWVEVGWEFV-NH2 |
| 2803 | JBS-3048 | Ac-HLYLMQAQPSPWVEVGWEFV-NH2 | 2844 | JBS-3089 | Ac-HLYLMQAWTPWVEVGWEFV-NH2 |
| 2804 | JBS-3049 | Ac-HLYLMQAWQSPWVEVGWEFV-NH2 | 2845 | JBS-3090 | Ac-HLYLMQAWPTPWVEVGWEFV-NH2 |
| 2805 | JBS-3050 | Ac-HLYLMQAWPQPWVEVGWEFV-NH2 | 2846 | JBS-3091 | Ac-HLYLMQAWPSTWVEVGWEFV-NH2 |
| 2806 | JBS-3051 | Ac-HLYLMQAWPSQWVEVGWEFV-NH2 | 2847 | JBS-3092 | Ac-HLYLMQAWPSPTVEVGWEFV-NH2 |
| 2807 | JBS-3052 | Ac-HLYLMQAWPSPQVEVGWEFV-NH2 | 2848 | JBS-3093 | Ac-HLYLMQAWPSPWTEVGWEFV-NH2 |
| 2808 | JBS-3053 | Ac-HLYLMQAWPSPWQEVGWEFV-NH2 | 2849 | JBS-3094 | Ac-HLYLMQAWPSPWVTVGWEFV-NH2 |
| 2809 | JBS-3054 | Ac-HLYLMQAWPSPWVQVGWEFV-NH2 | 2850 | JBS-3095 | Ac-HLYLMQAWPSPWVETGWEFV-NH2 |
| 2810 | JBS-3055 | Ac-HLYLMQAWPSPWVEQGWEFV-NH2 | 2851 | JBS-3096 | Ac-HLYLMQAWPSPWVEVTWEFV-NH2 |
| 2811 | JBS-3056 | Ac-HLYLMQAWPSPWVEVQWEFV-NH2 | 2852 | JBS-3097 | Ac-HLYLMQAWPSPWVEVGTEFV-NH2 |
| 2812 | JBS-3057 | Ac-HLYLMQAWPSPWVEVGQFV-NH2 | 2853 | JBS-3098 | Ac-HLYLMQAWPSPWVEVGWTFV-NH2 |
| 2813 | JBS-3058 | Ac-HLYLMQAWPSPWVEVGWQFV-NH2 | 2854 | JBS-3099 | Ac-HLYLMQAWPSPWVEVGWEFT-NH2 |
| 2814 | JBS-3059 | Ac-HLYLMQAWPSPWVEVGWEQV-NH2 | 2855 | JBS-3100 | Ac-VLYLMQAWPSPWVEVGWEFV-NH2 |
| 2815 | JBS-3060 | Ac-HLYLMQAWPSPWVEVGWEFQ-NH2 | 2856 | JBS-3101 | Ac-HVYLMQAWPSPWVEVGWEFV-NH2 |

| SEQ ID | Compound | Sequence |
|---|---|---|
| 2857 | JBS-3102 | Ac-HLYLMQAWPSPWVEVGWEFV-NH2 |
| 2858 | JBS-3103 | Ac-HLYLVQAWPSPWVEVGWEFV-NH2 |
| 2859 | JBS-3104 | Ac-HLYLLVQAWPSPWVEVGWEFV-NH2 |
| 2860 | JBS-3105 | Ac-HLYLWAWPSPWVEVGWEFV-NH2 |
| 2861 | JBS-3106 | Ac-HLYLMQVWPSPWVEVGWEFV-NH2 |
| 2862 | JBS-3107 | Ac-HLYLMQAVPSPWVEVGWEFV-NH2 |
| 2863 | JBS-3108 | Ac-HLYLMQAWVSPWVEVGWEFV-NH2 |
| 2864 | JBS-3109 | Ac-HLYLMQAWPVPWVEVGWEFV-NH2 |
| 2865 | JBS-3110 | Ac-HLYLMQAWPSVWVEVGWEFV-NH2 |
| 2866 | JBS-3111 | Ac-HLYLMQAWPSPVVEVGWEFV-NH2 |
| 2867 | JBS-3112 | Ac-HLYLMQAWPSPWVEVGWEFV-NH2 |
| 2868 | JBS-3113 | Ac-HLYLMQAWPSPWVEVVWEFV-NH2 |
| 2869 | JBS-3114 | Ac-HLYLMQAWPSPWVEVGVEFV-NH2 |
| 2870 | JBS-3115 | Ac-HLYLMQAWPSPWVEVGWVFV-NH2 |
| 2871 | JBS-3116 | Ac-HLYLMQAWPSPWVEVGWEVV-NH2 |
| 2872 | JBS-3117 | Ac-MLYLMQAWPSPWVEVGWEFV-NH2 |
| 2873 | JBS-3118 | Ac-HWYLMQAWPSPWVEVGWEFV-NH2 |
| 2874 | JBS-3119 | Ac-HLWLMQAWPSPWVEVGWEFV-NH2 |
| 2875 | JBS-3120 | Ac-HLYWMQAWPSPWVEVGWEFV-NH2 |
| 2876 | JBS-3121 | Ac-HLYLWAWPSPWVEVGWEFV-NH2 |
| 2877 | JBS-3122 | Ac-HLYLMQWWPSPWVEVGWEFV-NH2 |
| 2878 | JBS-3123 | Ac-HLYLMQAWWSPWVEVGWEFV-NH2 |
| 2879 | JBS-3124 | Ac-HLYLMQAWPWPWVEVGWEFV-NH2 |
| 2880 | JBS-3125 | Ac-HLYLMQAWPSWWVEVGWEFV-NH2 |
| 2881 | JBS-3126 | Ac-HLYLMQAWPSPWMVEVGWEFV-NH2 |
| 2882 | JBS-3127 | Ac-HLYLMQAWPSPWWVEVGWEFV-NH2 |
| 2883 | JBS-3128 | Ac-YLYLMQAWPSPWVEVGWEFV-NH2 |
| 2884 | JBS-3129 | Ac-HYYLMQAWPSPWVEVGWEFV-NH2 |
| 2885 | JBS-3130 | Ac-HLYLYQAWPSPWVEVGWEFV-NH2 |
| 2886 | JBS-3131 | Ac-HLYLMQAYPSPWVEVGWEFV-NH2 |
| 2887 | JBS-3132 | Ac-HLYLMQYWPSPWVEVGWEFV-NH2 |
| 2888 | JBS-3133 | Ac-HLYLMQAWYPSPWVEVGWEFV-NH2 |
| 2889 | JBS-3134 | Ac-HLYLMQAWPYPWVEVGWEFV-NH2 |
| 2890 | JBS-3135 | Ac-HLYLMQAWPSYWVEVGWEFV-NH2 |
| 2891 | JBS-3136 | Ac-HLYLYQAWPSPWVEVGWEFV-NH2 |
| 2892 | JBS-3137 | Ac-HLYLMQAWPSPYVEVGWEFV-NH2 |
| 2893 | JBS-3138 | Ac-HLYLMQYWPSPWVEVGWEFV-NH2 |
| 2894 | JBS-3139 | Ac-HLYLMQAYPSPWVEVGWEFV-NH2 |
| 2895 | JBS-3140 | Ac-HLYLMQAWYPSPWVEVGWEFV-NH2 |
| 2896 | JBS-3141 | Ac-HLYLMQAWPYPWVEVGWEFV-NH2 |
| 2897 | JBS-3142 | Ac-HLYLMQAWPSYWVEVGWEFV-NH2 |
| 2898 | JBS-3143 | Ac-HLYLMQAWPSPYVEVGWEFV-NH2 |
| 2899 | JBS-3144 | Ac-HLYLMQAWPSPWYEVGWEFV-NH2 |
| 2900 | JBS-3145 | Ac-HLYLMQAWPSPWVYVGWEFV-NH2 |
| 2901 | JBS-3146 | Ac-HLYLMQAWPSPWVEYGWEFV-NH2 |
| 2902 | JBS-3147 | Ac-HLYLMQAWPSPWVEVYWEFV-NH2 |
| 2903 | JBS-3148 | Ac-HLYLMQAWPSPWVEVGYEFV-NH2 |
| 2904 | JBS-3149 | Ac-HLYLMQAWPSPWVEVGWYFV-NH2 |
| 2905 | JBS-3150 | Ac-HLYLMQAWPSPWVEVGWEYV-NH2 |
| 2906 | JBS-3151 | Ac-HLYLMQAWPSPWVEVGWEFY-NH2 |
| 2907 | JBS-3154 | Ac-VYEVGWDHGNWYEIIWRDPSC(NEM)-NH2 |
| 2908 | JBS-3155 | Ac-C(NEM)-VYEVGWDHGNWYEIIWRDPS-NH2 |
| 2909 | JBS-3183 | Ac-HKYLMQAWPSPWVEVGWEFV-NH2 |
| 2910 | JBS-3184 | Ac-HPYLMQAWPSPWVEVGWEFV-NH2 |
| 2911 | JBS-3209 | Ac-HTYLMQAHPSPNVEVGWEFV-NH2 |
| 2912 | JBS-3210 | Ac-HTYLMQAHPSPEVEVGWEFV-NH2 |
| 2913 | JBS-3211 | Ac-HTYLMQAYPSPNVEVGWEFV-NH2 |
| 2914 | JBS-3212 | Ac-HTYLMQAYPSPEVEVGWEFV-NH2 |
| 2915 | JBS-3213 | Ac-HTYLMQAHPSPEVEVGYEFV-NH2 |
| 2916 | JBS-3214 | Ac-QTYLMQAHPSPEVEVGYEFV-NH2 |

PEPTIDES AND METHODS OF USE

CROSS-REFERENCE TO RELATED APPLICATION

This application claims priority to U.S. Provisional Patent Application No. 61/946,103, filed Feb. 28, 2014, which is incorporated by reference herein in its entirety.

TECHNICAL FIELD OF THE INVENTION

The invention generally relates to peptides that bind Protein S and uses thereof.

INCORPORATION BY REFERENCE

Incorporated by reference in its entirety is a computer-readable nucleotide/amino acid sequence listing submitted concurrently herewith and identified as follows: ASCII text file named "46380A_SeqListing.txt," 1,390,466 bytes, created Feb. 27, 2015.

BACKGROUND OF THE INVENTION

Hemostasis relies on the complex coagulation cascade, wherein a series of events mediated by blood clotting factors leads to conversion of prothrombin to thrombin. Factor X (FX) activation is the central event of both the intrinsic and extrinsic pathways of the coagulation cascade. The extrinsic pathway has been proposed as the primary activator of the coagulation cascade (Mackman et al., *Arterioscler. Thromb. Casc. Biol.*, 27, 1687-1693 (2007)). Circulating Tissue Factor (TF) and activated Factor VII (FVIIa) interact to form the "extrinsic complex," which mediates activation of FX. The coagulation cascade is amplified by the intrinsic pathway, during which successive activation of factors XII, XI, IX, and VIII results in formation of the "intrinsic" FIXa-FVIIIa complex that also mediates FX activation. Activated FX promotes thrombin formation, which is required for the body to create fibrin and effectively curb bleeding. Coagulation is down-regulated by the Protein C-mediated anticoagulant pathway. Thrombin in complex with thrombomodulin activates Protein C. Activated Protein C with its co-factor, Protein S, degrades and inactivates activated blood factors V (FVa) and VIII (FVIIIa).

Severe bleeding disorders, such as hemophilia, result from disruption of the blood coagulation cascade. Factor replacement therapy is the most common treatment for blood coagulation disorders. However, blood clotting factors typically are cleared from the bloodstream shortly after administration. To be effective, a patient must receive frequent intravenous infusions of plasma-derived or recombinant factor concentrates, which is uncomfortable, is expensive, and is time consuming. In addition, therapeutic efficacy of factor replacement therapy can diminish drastically upon formation of inhibitory antibodies. Few therapeutic options exist for patients with anti-Factor antibodies.

SUMMARY OF THE INVENTION

The invention includes, for example, a peptide comprising an amino acid sequence at least 50% identical to the amino acid sequence VSAGWYDYNTDTYYEF (SEQ ID NO: 2920) and comprising the structure of Formula I: X1004-X1005-X1006-X1007-X1008-X1009-X1010-X1011-X1012-X1013-X1014-X1015-X1016-X1017-X1018-X1019, wherein X1004 is A, C, D, E, F, G, H, I, K, L, M, N, P, p, Q, R, S, T, Tle, V, v, W, or Y; wherein X1005 is A, C, D, Dap, E, F, G, H, I, K, L, M, N, P, p, Q, R, S, s, T, V, W, or Y; wherein X1006 is A, a, Aib, C, D, E, F, G, H, I, K, L, M, N, P, p, Q, R, S, s, T, Tle, V, W, or Y; wherein X1007 is A, a, Aib, C, D, E, F, G, H, I, K, L, M, N, Nmg, P, p, Q, R, S, s, T, Tle, V, W, or Y; wherein X1008 is 1Ni, 2Ni, A, Bta, C, D, E, F, G, H, I, K, L, M, N, P, p, Q, R, S, T, V, W, w, or Y; wherein X1009 is A, C, D, E, F, G, H, I, K, L, M, N, P, p, Q, R, S, T, V, W, Y, or w; wherein X1010 is A, C, D, d, E, F, G, H, I, K, L, M, N, P, p, Q, R, S, T, V, W, w, or Y; wherein X1011 is A, C, D, E, F, G, H, I, K, L, M, N, P, p, Q, R, S, T, V, W, Y, or w; wherein X1012 is A, C, D, E, F, G, H, I, K, L, M, N, n, P, p, Q, R, S, T, V, W, or Y; wherein X1013 is A, a, C, D, E, F, G, H, I, K, L, M, N, P, p, Q, R, S, T, t, V, W, or Y; wherein X1014 is A, C, D, d, E, F, G, H, I, K, L, M, N, P, p, Q, R, S, T, V, W, or Y; wherein X1015 is A, C, D, E, F, G, H, I, K, L, M, N, P, p, Q, R, S, T, t, Tle, V, W, or Y; wherein X1016 is A, C, D, E, F, G, H, I, K, L, M, N, P, p, Q, R, S, T, V, W, or Y; wherein X1017 is A, C, D, E, F, G, H, I, K, L, M, N, Nle, P, p, Q, R, S, T, V, W, Y, or y; wherein X1018 is A, C, D, E, e, F, G, H, I, K, L, M, N, P, p, Q, R, S, T, V, W, or Y; and wherein X1019 is A, C, D, E, F, f, G, H, I, K, L, M, N, P, p, Q, R, S, T, V, W, or Y (SEQ ID NO: 2921). In various embodiments, the peptide further comprises one or more N-terminal amino acid(s) directly linked to X1004, wherein the N-terminal amino acid(s) comprise the amino acid sequence selected from the group consisting of X1003, X1002-X1003, and X1001-X1002-X1003. In this regard, X1003 is A, C, D, E, F, G, H, I, K, L, M, N, P, p, Q, R, S, T, Tle, V, W, Y, or y; X1002 is A, C, D, E, F, G, H, I, K, L, M, N, P, p, Q, R, S, T, V, W, Y, or y; and X1001 is A, Bpa, C, D, E, e, F, G, H, I, K, L, M, N, P, p, Q, R, S, T, V, W, or Y (SEQ ID NO: 2922). Alternatively or in addition, the peptide may comprise a C-terminal amino acid directly linked to X1019 and selected from the group consisting of A, C, D, E, e, F, G, H, I, K, L, M, N, P, p, Q, R, S, T, V, W, and Y (SEQ ID NO: 2923). For example, in various embodiments, the peptide comprises an amino acid sequence at least about 80% identical to EYYVSAGWYDYNTDTYYEFE (SEQ ID NO: 2924). The invention includes a peptide comprising (or consisting of) an amino acid sequence selected from the group consisting of SEQ ID NOs: 1-2916, 2920, and 2924.

In addition, the invention provides methods of using the peptide(s) of the invention. For example, the invention provides a method for inhibiting Protein S activity in a subject. A method of treating a subject suffering from a disease or being at risk of suffering from a disease also is provided. The invention also provides a method of enhancing thrombin formation, a method for increasing blood clot formation in a subject, and a method for treating a disease or disorder, such as a blood coagulation disorder. The methods are, in their entirety, also referred to herein as, e.g., "the method of the invention." The methods comprise administering to a subject a peptide described herein in an amount effective to achieve a desired effect, e.g., an amount effective to inhibit Protein S activity, enhance thrombin formation, enhance blood clot formation, or treat the blood coagulation disorder in the subject. Further aspects of the invention include use of the peptide of the invention in medicine or for the manufacture of a medicament.

DESCRIPTION OF THE FIGURES

FIG. 1A-C is a chart providing the binding affinity (Mean IC50 [nM]) of various peptides described herein measured by LANCE IC50 assay using JBS0684 as a tracer peptide.

FIG. 2A-JJ is a chart providing the amino acid sequences of various peptides described herein.

DETAILED DESCRIPTION OF THE INVENTION

The invention provides peptides that bind Protein S and, in some instances, block the inhibitory (i.e., anticoagulant) activity of Protein S within the blood coagulation cascade. Protein S functions as a co-factor to activated Protein C (APC) to degrade Factors Va (FVa) and VIIIa (FVIIIa). Inhibition of Protein S reduces Protein C-mediated FVa and FVIIIa degradation, allowing the blood factors to function in the blood coagulation cascade to produce thrombin, and ultimately fibrin. Protein S is a 70 kD vitamin K-dependent glycoprotein, 635 amino acids in length, comprising a γ-carboxy-glutamic acid domain (Gla domain), a thrombin-sensitive module, epidermal growth factor like domains (EGF domains), and a region having similarity to the sex hormone binding globulin. The protein is found free in plasma and also complexed to complement protein C4b-binding protein (C4BP). Free Protein S serves as APC co-factor; the complexed form does not have co-factor activity. Protein S increases the affinity of APC for phospholipid-containing membranes, enhances APC-mediated cleavage at R306 in FVa, and enhances APC-mediated inactivation of FVIIIa. Walker, *J. Biol. Chem.,* 256(21), 11128-11131 (1981); Rosing et al., *J. Biol. Chem.,* 270(46), 27852-27858 (1995). Protein S also interferes with coagulation independent of APC by, for example, binding to FXa and FVa. Hackeng, *J. Biol. Chem.,* 269(33), 21051-21058 (1994). The sequence of human Protein S is provided as SEQ ID NO: 2917 (nucleic acid sequence provided as SEQ ID NO: 2918). The invention provides, in one aspect, Protein S-binding peptides that optionally block one or more of Protein S's activities, thereby optionally enhancing thrombin formation. In the context of the disclosure, any peptide encompassed by Formula I described herein and any Protein S-binding peptide described herein is also referred to as "the peptide of the invention" and as "a peptide as described herein." "Peptide" is meant to include traditional peptides (i.e., having a traditional peptide backbone) as well as peptidomimetics (i.e., protein-like polymers having modified backbones and, optionally, side-chains found in amino acids).

The amino acid sequences of several peptides are provided herein. Conventional amino acids are identified according to their standard, one-letter or three-letter codes. Examples of non-conventional amino acids and additional peptide building blocks with their, e.g., three- or four-letter/number code (with the exception of Ttds and Dopa, which are common four-letter abbreviations) are described in Table 1 and elsewhere herein. The chemical structures of the non-conventional amino acids and building blocks are known in the art and described in, e.g., U.S. Patent Application Publication No. 2013/0252896, incorporated by reference herein in its entirety, including Tables 1-3.

The amino acid sequences of the peptides provided herein are depicted in typical peptide sequence format. For example, the three-letter code or one-letter code of an amino acid indicates the presence of the amino acid in a specified position within the peptide sequence. The code for each non-conventional amino acid or building block is connected to the code for the next and/or previous amino acid or building block in the sequence by a hyphen in many instances. Adjacent amino acids are connected by a chemical bond (typically an amide bond). The formation of the chemical bond removes a hydroxyl group from the 1-carboxyl group of the amino acid when it is located to the left of the adjacent amino acid (e.g., Hle-adjacent amino acid), and removes a hydrogen from the amino group of the amino acid when it is located on the right of the adjacent amino acid (e.g., adjacent amino acid-Hle). It is understood that both modifications can apply to the same amino acid and apply to adjacent conventional amino acids present in amino acid sequences without hyphens explicitly illustrated. Where an amino acid contains more than one amino and/or carboxy group in the amino acid side chain, the 2- or 3-amino group and/or the 1-carboxy group generally are used for the formation of peptide bonds. For some non-conventional amino acids, a three-letter code is used where the first letter indicates the stereochemistry of the C-α-atom. For example, a capital first letter indicates that the L-form of the amino acid is present in the peptide sequence, while a lower case first letter indicating that the D-form of the corresponding amino acid is present in the peptide sequence. When one-letter code is used, a lower case letter represents a D-amino acid, while an upper case letter represents an L-amino acid. Unless indicated to the contrary, the amino acid sequences are presented herein in N- to C-terminus direction.

The C-termini of several peptide sequences described herein are often explicitly illustrated by inclusion of an OH, $NH_2$, or an abbreviation for a specific terminating amine linked to the C-terminal amino acid code via a hyphen. The N-termini of several peptides described herein are explicitly illustrated by inclusion of a hydrogen (for a free N-terminus), or an abbreviation for a specific terminating carboxylic acid or other chemical group linked to the N-terminal amino acid code via a hyphen.

The invention provides a peptide comprising the structure of Formula (I): X1004-X1005-X1006-X1007-X1008-X1009-X1010-X1011-X1012-X1013-X1014-X1015-X1016-X1017-X1018-X1019, wherein X1004 is A, C, D, E, F, G, H, I, K, L, M, N, P, p, Q, R, S, T, Tle, V, v, W, or Y; wherein X1005 is A, C, D, Dap, E, F, G, H, I, K, L, M, N, P, p, Q, R, S, s, T, V, W, or Y; wherein X1006 is A, a, Aib, C, D, E, F, G, H, I, K, L, M, N, P, p, Q, R, S, s, T, Tle, V, W, or Y; wherein X1007 is A, a, Aib, C, D, E, F, G, H, I, K, L, M, N, Nmg, P, p, Q, R, S, s, T, Tle, V, W, or Y; wherein X1008 is 1Ni, 2Ni, A, Bta, C, D, E, F, G, H, I, K, L, M, N, P, p, Q, R, S, T, V, W, w, or Y; wherein X1009 is A, C, D, E, F, G, H, I, K, L, M, N, P, p, Q, R, S, T, V, W, Y, or w; wherein X1010 is A, C, D, d, E, F, G, H, I, K, L, M, N, P, p, Q, R, S, T, V, W, w, or Y; wherein X1011 is A, C, D, E, F, G, H, I, K, L, M, N, P, p, Q, R, S, T, V, W, Y, or w; wherein X1012 is A, C, D, E, F, G, H, I, K, L, M, N, n, P, p, Q, R, S, T, V, W, or Y; wherein X1013 is A, a, C, D, E, F, G, H, I, K, L, M, N, P, p, Q, R, S, T, t, V, W, or Y; wherein X1014 is A, C, D, d, E, F, G, H, I, K, L, M, N, P, p, Q, R, S, T, V, W, or Y; wherein X1015 is A, C, D, E, F, G, H, I, K, L, M, N, P, p, Q, R, S, T, t, Tle, V, W, or Y; wherein X1016 is A, C, D, E, F, G, H, I, K, L, M, N, P, p, Q, R, S, T, V, W, or Y; wherein X1017 is A, C, D, E, F, G, H, I, K, L, M, N, Nle, P, p, Q, R, S, T, V, W, Y, or y; wherein X1018 is A, C, D, E, e, F, G, H, I, K, L, M, N, P, p, Q, R, S, T, V, W, or Y; and wherein X1019 is A, C, D, E, F, f, G, H, I, K, L, M, N, P, p, Q, R, S, T, V, W, or Y (SEQ ID NO: 2921).

In various embodiments, the invention provides a peptide comprising (or consisting of) an amino acid sequence at least 50% identical (e.g., at least 55% identical, at least 60% identical, at least 65% identical, at least 70% identical, at least 75% identical, at least 80% identical, at least 85% identical, or at least 90% identical) to the amino acid sequence VSAGWYDYNTDTYYEF (SEQ ID NO: 2920)

and having the structure of Formula I, wherein X1004 is A, C, D, E, F, G, H, I, K, L, M, N, P, p, Q, R, S, T, Tle, V, v, W, or Y; wherein X1005 is A, C, D, Dap, E, F, G, H, I, K, L, M, N, P, p, Q, R, S, s, T, V, W, or Y; wherein X1006 is A, a, Aib, C, D, E, F, G, H, I, K, L, M, N, P, p, Q, R, S, s, T, Tle, V, W, or Y; wherein X1007 is A, a, Aib, C, D, E, F, G, H, I, K, L, M, N, Nmg, P, p, Q, R, S, s, T, Tle, V, W, or Y; wherein X1008 is 1Ni, 2Ni, A, Bta, C, D, E, F, G, H, I, K, L, M, N, P, p, Q, R, S, T, V, W, w, or Y; wherein X1009 is A, C, D, E, F, G, H, I, K, L, M, N, P, p, Q, R, S, T, V, W, Y, or w; wherein X1010 is A, C, D, d, E, F, G, H, I, K, L, M, N, P, p, Q, R, S, T, V, W, w, or Y; wherein X1011 is A, C, D, E, F, G, H, I, K, L, M, N, P, p, Q, R, S, T, V, W, Y, or w; wherein X1012 is A, C, D, E, F, G, H, I, K, L, M, N, n, P, p, Q, R, S, T, V, W, or Y; wherein X1013 is A, a, C, D, E, F, G, H, I, K, L, M, N, P, p, Q, R, S, T, t, V, W, or Y; wherein X1014 is A, C, D, d, E, F, G, H, I, K, L, M, N, P, p, Q, R, S, T, V, W, or Y; wherein X1015 is A, C, D, E, F, G, H, I, K, L, M, N, P, p, Q, R, S, T, t, Tle, V, W, or Y; wherein X1016 is A, C, D, E, F, G, H, I, K, L, M, N, P, p, Q, R, S, T, V, W, or Y; wherein X1017 is A, C, D, E, F, G, H, I, K, L, M, N, Nle, P, p, Q, R, S, T, V, W, Y, or y; wherein X1018 is A, C, D, E, e, F, G, H, I, K, L, M, N, P, p, Q, R, S, T, V, W, or Y; and wherein X1019 is A, C, D, E, F, f, G, H, I, K, L, M, N, P, p, Q, R, S, T, V, W, or Y (SEQ ID NO: 2921).

In various embodiments of the invention, X1004 is A, E, F, G, H, I, K, L, M, N, P, Q, R, T, V, W, or Y; X1005 is A, D, E, F, G, H, I, K, L, M, N, R, S, T, V, W, or Y; X1006 is A, a, F, G, H, I, L, M, P, S, T, V, W, or Y; X1007 is G or a; X1008 is F, H, L, W, or Y; X1009 is F or Y; X1010 is A, D, E, F, G, H, I, K, L, M, N, Q, R, S, T, V, W, or Y; X1011 is A, E, F, G, H, I, K, L, M, N, P, Q, R, S, T, V, W, or Y; X1012 is A, D, E, F, G, H, I, K, L, M, N, n, P, Q, R, S, T, V, W, or Y; X1013 is A, D, E, F, G, H, I, K, L, M, N, Q, R, S, T, V, W, or Y; X1014 is A, D, d, E, G, H, N, Q, or S; X1015 is A, D, E, F, G, H, I, K, L, M, N, Q, R, S, T, V, W, or Y; X1016 is A, D, E, F, H, I, L, M, N, S, T, W, or Y; X1017 is A, D, E, F, G, H, I, K, L, M, N, Q, R, S, T, V, W, or Y; X1018 is A, D, E, F, G, H, I, K, L, M, N, P, Q, R, S, T, V, W, or Y; and X1019 is E, F, f, H, I, L, M, V, W, or Y.

In one aspect, the peptide of the invention comprises the structure of Formula (I) wherein X1004 is A, F, H, I, K, L, T, V, W, or Y (e.g., X1004 is selected from the group consisting of A, F, I, L, T, V, and W); X1005 is A, E, F, G, H, I, K, L, M, N, Q, R, S, T, V, W, or Y (e.g., X1005 is selected from the group consisting of A, E, F, G, H, I, K, L, M, R, S, T, V, W, and Y); X1006 is A, F, G, I, L, M, V, W, or Y (e.g., X1006 is selected from the group consisting of A, F, G, I, L, V, W, and Y); X1007 is G; X1008 is F, L, W, or Y (e.g., F or Y); X1010 is A, D, E, F, H, I, K, L, M, N, Q, R, S, T, V, W, or Y (e.g., X1010 is selected from the group consisting of D, E, F, H, I, K, L, N, Q, V, W, and Y); X1011 is A, F, G, H, I, K, L, M, N, R, S, T, V, W, or Y (e.g., X1011 is selected from the group consisting of F, G, I, K, L, M, R, T, V, W, and Y); X1012 is A, D, E, F, G, H, I, K, L, M, N, n, P, Q, R, S, T, V, W, or Y (e.g., X1012 is selected from the group consisting of D, E, F, G, H, I, K, L, N, Q, R, S, T, V, and Y); X1013 is D, E, F, G, H, I, K, L, Q, R, S, T, V, or W; X1014 is D, d, E, G, H, or N (e.g., X1014 is selected from the group consisting of D, E, and H); X1015 is D, E, H, I, K, M, Q, R, S, T, V, or W; X1016 is D, E, F, H, S, W, or Y (e.g., X1016 is selected from the group consisting of F, H, W, and Y); X1017 is D, E, G, H, I, T, W, or Y; X1018 is A, D, E, G, H, I, K, L, M, P, Q, R, S, T, V, or W; and X1019 is F, I, M, W, or Y (e.g., X1019 is selected from the group consisting of F, I, M, and W). In one or more aspects, X1004 is V, X1005 is S, X1006 is A, X1007 is G, X1008 is W, and X1009 is Y. The peptide optionally comprises an amino acid sequence at least 50% identical to VSAGWYDYNTD-TYYEF (SEQ ID NO: 2920).

In some embodiments, the peptide of the invention comprises one or more additional amino acid residues attached to the N- or C-terminus of the amino acid sequence. For example, the peptide comprising the structure of Formula I, in some embodiments, further comprises one or more N-terminal amino acid(s) directly linked to X1004, wherein the N-terminal amino acid(s) comprise the amino acid sequence selected from the group consisting of X1003, X1002-X1003, and X1001-X1002-X1003. X1003 and X1002 are independently selected from A, C, D, E, F, G, H, I, K, L, M, N, P, p, Q, R, S, T, Tle, V, W, Y, or y (e.g., X1003 and X1002 are independently selected from A, D, E, F, G, H, I, K, L, M, N, P, p, Q, R, S, T, V, W, y, or Y). For example, in some aspects, X1003 is A, E, F, G, H, I, K, L, N, P, R, T, V, W, y, or Y; and X1002 is A, D, E, F, G, H, I, K, L, N, P, R, T, V, W, y, or Y. X1001 is A, Bpa, C, D, E, e, F, G, H, I, K, L, M, N, P, p, Q, R, S, T, V, W, or Y (e.g., X1001 is selected from the group consisting of A, D, E, e, F, G, H, I, K, L, M, N, P, p, Q, R, S, T, V, W, and Y).

In addition to the core structure set forth in Formula I, other structures that are specifically contemplated are those in which one or more additional amino acids are attached to the C-terminus of the core structure directly linked to X1019. For example, the C-terminal addition optionally comprises an amino acid sequence selected from the group consisting of A, C, D, E, e, F, G, H, I, K, L, M, N, P, p, Q, R, S, T, V, W, and Y, such as the group consisting of A, D, E, e, F, G, H, I, K, L, M, N, P, p, Q, R, S, T, V, W, and Y. The invention further provides a peptide comprising at least 50% identity to the amino acid sequence EYYVSAGWY-DYNTDTYYEFE (SEQ ID NO: 2924) and comprising the formula X1001-X1002-X1003-X1004-X1005-X1006-X1007-X1008-X1009-X1010-X1011-X1012-X1013-X1014-X1015-X1016-X1017-X1018-X1019-X1020, as each amino acid position is defined above (SEQ ID NO: 2923).

The invention includes a peptide comprising or consisting of an amino acid sequence having at least 60% identity, at least 65%, at least 70%, at least 75%, at least 80%, at least 85%, at least 90%, at least 95% or 100% identity to (i) the amino acid sequence VSAGWYDYNTDTYYEF (SEQ ID NO: 2920), (ii) the amino acid sequence EYYVSAGWY-DYNTDTYYEFE (SEQ ID NO: 2924), or (iii) the amino acid sequence of any one of SEQ ID NO: 1-2916. As used herein, "at least 60% identity" and similar terms encompass any integer from, e.g., 60% to 100%, such as 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% and the like. Also, the term "at least [percentage] identity" encompasses any percentage that is greater than or equal to the number of identical amino acids (or peptide building blocks) divided by the total number of amino acids (or building blocks) of the peptide of the invention ([at least percentage identity]≥[number of identical amino acids or building blocks]/[total number of amino acids or building blocks of the peptide of the invention]). The calculation of percent identity of aligned amino acids (or nucleotides) of two or more sequences is well understood in the art and is determined conventionally using known computer programs. For example, alignment of two or more sequences to determine percent sequence identity is optionally performed using the algorithm described by Altschul et al. (Nucleic Acids Res., 25:3389-402 (1997)) as incorporated into BLAST (basic local alignment search tool) programs, available on the National Center for Biotechnology Information website. The peptide preferably binds Protein S and, optionally, inhibits Protein S activity.

The invention includes peptides that comprise a cyclic structure. In this regard, the invention includes peptides comprising cyclic structures within the peptide (e.g., one or more loops formed by linkage between amino acids), peptides comprising a cyclic structure formed by the interaction of a terminal amino acid with an amino acid within the peptide sequence, and peptides cyclized head to tail. The peptides of the invention, in some instances, comprise intramolecular disulfide bonds. In some embodiments, the intramolecular disulfide bonds are formed by cysteine residues. Peptides comprising cyclic structures formed by non-cysteine residues, or a non-cysteine residue and a cysteine residue, also are provided. Suitable non-conventional amino acids or chemical moieties for cyclization include, but are not limited to, 3-[2-(2-{2-[2-(2-Amino-ethoxy)-ethoxy]-ethoxy}-ethoxy)-ethoxy]-propionic acid (FA19205), 3-(2-{2-[2-(2-Amino-ethoxy)-ethoxy]-ethoxy}-ethoxy)-propionic acid (FA19204), 3-{2-[2-(2-Amino-ethoxy)-ethoxy]-ethoxy}-propionic acid (FA19203), [2-(2-Amino-ethoxy)-ethoxy]-acetic acid (FA03202), (S)-Homo-cysteine (Hcy), D-Homo-cysteine (hcy), Aminoethylthiol (Cea), and c.

The peptides described herein are, in some embodiments, conjugated or attached to one or more moieties at the N- and/or C-terminus or at residues internal to the peptide. Exemplary moieties include, but are not limited to, carboxyfluorescein-Ttds (FAM-Ttds), a proline-glutamate tag ("PE"), Palmitoyl (Palm), 2-phenyl acetyl, 3-phenyl propionyl, 2-(naphth-2-yl)acetyl, hexanoyl, 2-methyl propionyl, 3-methyl butanoyl, 2-naphthylsulfonyl, acetyl, Aminooxy-acetic acid (AOA), levulinic acid (Lev), pentynoic acid (Pyn), 1-naphthylsulfonyl, C, c, N-ethylmaleiimido Ethylmaleiimido cysteine (C(NEM)), 3-[2-(2-{2-[2-(2-Amino-ethoxy)-ethoxy]-ethoxy}-ethoxy)-ethoxy]-propionic acid (FA19205), 3-(2-{2-[2-(2-Amino-ethoxy)-ethoxy]-ethoxy}-ethoxy)-propionic acid (FA19204), 3-{2-[2-(2-Amino-ethoxy)-ethoxy]-ethoxy}-propionic acid (FA19203), [2-(2-Amino-ethoxy)-ethoxy]-acetic acid (FA03202), K(Tdts-maleimid), 2-Amino-6-ε-(2-aminooxyAminooxy-acetylamino)-hexanoic acidL-lysine (K(AOA)), Aminoethylthiol (Cea), Eag, (S)-Homo-lysine (Hly), K, (S)-Ornithine (Orn), (S)-2,4-Diaminobutyric acid (Dab), (S)-Diaminopropionic acid (Dap), (S)-Diaminopropionic acid (Hcy), penicillamine (Pen), ε-(Myristyl)-L-lysine (K(Myr)), ε-(Myristyl-Ttds)-L-lysine (K(Ttds-Myr)), ε-(Palmityl-Ttds)-L-lysine (K(Ttds-Palm)), ε-(Myristyl-γ-glutamyl-Ttds)-L-lysine (K(Ttds-γGlu-Myr)), ε-(4-(p-Iodophenyl)butyryl))-L-lysine (K(AlbuTag)), ε-(4-(Pentyl)-benzolsulfonamidyl)-L-lysine (K(4PBSA)), (S)-4-Benzoylphenylalanine (Bpa), Bpa-K(Bio)-C, C(Atf-Bio), C(Atf-LC-Bio), C(FeBABE), C(MalCy5), C(PEG), ε-(Acetyl)-L-lysine (K(Ac)), K(Ttds), K(Ttds-γGlu), K(Glutar), K(Ttds-Mal), T, Ttds, or Ttds-K(Bio). K(Bio) is ε-(Biotinyl)-L-lysine. C(Atf-Bio) is 2-Amino-3-[2-(2-(4-azido-2,3,5,6-tetrafluoro-benzoylamino)-6-{6-[5-(2-oxo-hexahydro-thieno[3,4-d]imidazol-6-yl)-pentanoylamino]-hexanoylamino}-ethyldisulfanyl]-propionic acid. C(Atf-LC-Bio) is 2-Amino-3-[2-(2-[6-(4-azido-2,3,5,6-tetrafluoro-benzoylamino)-hexanoylamino]-6-{6-[5-(2-oxo-hexahydro-thieno[3,4-d]imidazol-6-yl)-pentanoylamino]-hexanoylamino)-ethyldisulfanyl]-propionic acid. C(FeBABE) is an Fe(III)-complex of 2-Amino-3-({4-[2,3-bis-(bis-carboxymethyl-amino)-propyl]-phenylcarbamoyl}-methylsulfanyl)-propionic acid. This is an ethylenediamine tetra acetic acid (EDTA)-complex of Fe(III) linked to the sulfur of the cysteine side chain via a thioether bond and an aromatic spacer. C(MalCy5) is 2-{5-[1-(5-{2-[3-(2-Amino-2-carboxy-ethylsulfanyl)-2,5-dioxo-pyrrolidin-1-yl]-ethylcarbamoyl}-pentyl)-3,3-dimethyl-1,3-dihydro-indol-2-ylidene]-penta-1,3-dienyl}-1,3,3-trimethyl-3H-indolium.

This is the dye Cy5 conjugated to the sulfur of the cysteine via a maleimide based thioether linkage.

In one aspect, the amino acid sequence of a peptide comprises a conservative substitution, wherein an amino acid residue is replaced with an amino acid residue having a similar side chain. Families of amino acid residues having similar side chains have been defined within the art, and include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), beta-branched side chains (e.g., threonine, valine, and isoleucine), and aromatic side chains (e.g., tyrosine, phenylalanine, tryptophan, and histidine). It will be appreciated, however, that a practitioner is not limited to conservative substitutions; preferably, the resulting peptide retains the ability to bind Protein S and, optionally, downregulates, in whole or in part, Protein S activity. For instance, FIG. 1 describes peptides that are substitutional mutants of the amino acid sequence of JBS2512 (SEQ ID NO: 2) and which retain Protein S binding characteristics.

In one aspect, the peptide of the invention consists of 60 amino acids or less, 55 amino acids or less, 40 amino acids or less, 35 amino acids or less, or 30 amino acids or less. Optionally, the peptide consists of 25 amino acids or less, 20 amino acids or less, 15 amino acids or less, or 10 amino acids or less. In various embodiments, the peptide comprises 15-35 amino acid residues (e.g., 15, 16, 17, 18, 19, 20, 21, 22, 23, 24, 25, 26, 27, 28, 29, 30, 31, 32, 33, 34, or 35 amino acid residues). In some aspects, amino acids are removed from the peptide described herein from within the amino acid sequence, at the N-terminus, and/or at the C-terminus. Such peptide fragments can comprise 3-14 amino acid residues (e.g., 3, 4, 5, 6, 7, 8, 9, 10, 11, 12, 13, or 14 amino acid residues). The peptide of the invention is, in various embodiments, fused or complexed to a second peptide domain that, for example, binds another target (such as a different region of Protein S or a different protein) or increases the half-life or stability of the inventive peptide. In such fusions or complexes, the size of the peptide of the invention is exclusive of the second peptide or heterologous peptide domain.

In one aspect, the peptide further comprises one or more amino acids that facilitate synthesis, handling, or use of the peptide, including, but not limited to, one or two lysines at the N-terminus and/or C-terminus to increase solubility of the peptide. Suitable fusion proteins include, but are not limited to, proteins comprising a peptide of the invention (e.g., Protein S-binding peptide) linked to one or more polypeptides, polypeptide fragments, or amino acids not generally recognized to be part of the protein sequence. In one aspect, a fusion peptide comprises the entire amino acid sequences of two or more peptides or, alternatively, comprises portions (fragments) of two or more peptides. In some aspects, a peptide (e.g., Protein S-binding peptide) is operably linked to, for instance, one or more of the following: a marker protein, a peptide that facilitates purification, a peptide sequence that promotes formation of multimeric proteins, or a fragment of any of the foregoing. Suitable fusion partners include, but are not limited to, a His tag, a FLAG tag, a strep tag, and a myc tag.

Optionally, the peptide of the invention is fused to one or more entities that enhance the half life of the peptide. Half life can be increased by, e.g., increasing the molecular weight of the Protein S-binding peptide to avoid renal clearance and/or incorporating a ligand for the nFc receptor-mediated recycling pathway. In one embodiment, the peptide of the invention is fused to or chemically conjugated to an albumin polypeptide or a fragment thereof (e.g., human serum albumin (HSA) or bovine serum albumin (BSA)). The albumin fragment comprises 10%, 25%, 50%, or 75% of the full length albumin protein. An exemplary peptide-albumin conjugate is JBS3754 (SEQ ID NO: 999), which is JBS3216 (SEQ ID NO: 462) conjugated to albumin. JBS3761 also is an example of an albumin fusion (SEQ ID NO: 1005). Alternatively or in addition, the peptide of the invention is fused to or complexed with an albumin binding domain or fatty acid that binds albumin when administered in vivo. An example of an albumin binding domain is "albu-tag," a moiety derived from on 4-(p-iodophenyl)-butanoic acid (Dumelin et al., *Angew Chem Int Ed Engl* 47:3196-3201 (2008)). Other suitable fusion partners include, but are not limited to, a proline-alanine-serine multimer (PASylation) and an antibody or fragment thereof (e.g., an Fc portion of an antibody).

In one embodiment, two or more peptides of the invention are fused together, linked by a multimerization domain, or attached via chemical linkage to generate a peptide complex. The peptides of the multimer may be the same or different. Thus, the invention provides a homo-dimer (i.e., a dimer comprising two identical peptides), a homo-multimer (i.e., a complex comprising three or more identical peptides), a hetero-dimer (i.e., a dimer comprising two different peptides), and hetero-multimer (i.e., a complex comprising three or more peptides, wherein at least two of the peptides are different) comprising or consisting of any of the peptides described herein, optionally attached by one or more linkers. A representative multimer is JBS3179 (SEQ ID NO: 433), a tetramer of JBS2572 (SEQ ID NO: 62) monomers coupled via a 40 kD, four-arm PEG moiety.

In this regard, the invention provides a peptide complex comprising a first peptide and a second peptide. Any of the peptides described herein are suitable subunits (e.g., first peptide or second peptide) for the peptide complex. In some embodiments, the peptide complex comprises 25-100 amino acids, e.g., 30-80 amino acids, 30-60 amino acids, or 30-50 amino acids. The level of inhibition of at least one Protein S activity (e.g., Protein S binding to FVa, phospholipid binding, or APC cofactor activity) mediated by the peptide complex is optionally greater than the level of inhibition achieved by the first peptide or the second peptide (alone or, optionally, in combination) in various embodiments of the invention. The functional characteristics and therapeutic and diagnostic applications of monomeric Protein S-binding peptides described herein also are applicable to the peptide complexes described herein. Similarly, descriptions of modifications to monomeric Protein S-binding peptides also relate to peptide complexes.

In various aspects of the disclosure, the peptide subunits (e.g., first peptide and second peptide) of the peptide complex are fused together directly or are linked by a linker moiety. Any linker moiety is suitable for use in the context of the peptide complex. The linker moiety, in some aspects of the invention, bridges a distance of about 1 Å to about 100 Å, e.g., about 5 Å to about 80 Å (about 5 Å to about 50 Å), about 10 Å to about 70 Å (about 10 Å to about 60 Å, about 10 Å to about 50 Å, about 10 Å to about 40 Å, or about 10 Å to about 30 Å), in one of its conformations. Thus, the linker is optionally about 1 Å to about 100 Å in length, e.g., about 5 Å to about 50 Å or about 10 Å to about 30 Å in length in one of its conformations. Linkers of greater length (greater than about 100 Å) also are contemplated. For example, biocompatible polymers, optionally having a molecular weight of about 2 kDa to about 60 kDa, also are contemplated for use in the peptide complex. Examples of biocompatible polymers include, but are not limited to, PEG, PSA, proline-alanine-serine multimer, and hydroxyethyl starch. Additional description of linker moieties and reactive groups is provided in International Patent Publication No. WO 2011/143209, incorporated herein by reference in its entirety.

In one aspect, the linker moiety comprises the structure $Z_{1-20}$, wherein Z is an oligomer building block. Examples of oligomer building blocks include, but are not limited to, an amino acid, hydroxy acid, ethylene glycol, propylene glycol, or a combination of any of the foregoing. For example, the linker moiety is optionally an amino acid, a dipeptide, a tripeptide, or a polypeptide comprising 4-20 amino acids. In some embodiments, Z is G, s, S, a, A, Bal, Gaba, Ahx, Ttds, or a combination of any of the foregoing (such as peptide ten-mer comprising A, S, or a combination of A and S). If desired, the linking moiety comprises an amine, ether, thioether, maleimide, disulfide, amide, ester, alkene, cycloalkene, alkyne, trizoyl, carbamate, carbonate, or hydrazone.

The terms "first peptide" and "second peptide" are not meant to imply a particular physical order of the peptides, but merely to distinguish different subunits of the peptide complex. The subunits of the peptide complex may be linked in any of a number of configurations so long as the first peptide and second peptide interact with a target (e.g., Protein S). For example, the C-terminus of the first peptide is connected to the N-terminus of the second peptide, the N-terminus of the first peptide is connected to the C-terminus of the second peptide, the N- or C-terminus of the first (or second) peptide is connected to an internal attachment point in the second (or first) peptide, or the first and second peptides are connected via internal attachment points (i.e., attachment points located within the amino acid sequence of the peptide and not at the N- or C-terminus). More than one linker may be used, e.g., a first linking moiety is attached at the N-terminus of the first peptide and the C-terminus of the second peptide, and a second linking moiety (which may be the same type of moiety or a different type of moiety) is attached at the C-terminus of the first peptide and attached at the N-terminus of the second peptide. While the discussion of possible configurations refers to the first and second peptides, it will be appreciated that additional peptides may be linked to the first and/or second peptides as described herein.

Derivatives are included in the invention and include peptides that have been chemically modified in some manner distinct from addition, deletion, or substitution of amino acids. In this regard, a peptide provided herein is chemically bonded with polymers, lipids, other organic moieties, and/or inorganic moieties. Examples of peptide and protein modifications are given in Hermanson, *Bioconjugate Techniques*, Academic Press, (1996). The peptides described herein optionally comprise a functional group that facilitates conjugation to another moiety (e.g., a peptide moiety). Exemplary functional groups include, but are not limited to, isothiocyanate, isocyanate, acyl azide, NHS ester, sulfonyl chloride, aldehyde, epoxide, oxirane, carbonate, arylating agent, imidoester, carbodiimide, anhydride, alkyl halide derivatives (e.g., haloacetyl derivatives), maleimide, aziridine, acryloyl derivatives, arylating agents, thiol-disulfide exchange reagents (e.g., pyridyl disulfides or TNB thiol), diazoalkane, carboyldiimadazole, N,N'-Disuccinyl carbonate, N-Hydroxysuccinimidyl chloroformate, and hydrazine derivatives. Maleimide is useful, for example, for generating a Protein S-binding peptide that binds with albumin in vivo.

In one aspect, the invention includes peptides described herein covalently modified to include one or more water soluble polymer attachments. A water soluble polymer (or other chemical moiety) is attached to any amino acid residue, although attachment to the N- or C-terminus is preferred in some embodiments. Useful polymers include, but are not limited to, PEG (e.g., PEG approximately 40 kD, 30 kD, 20 kD, 10 kD, 5 kD, or 1 kD in size), polyoxyethylene glycol, polypropylene glycol, monomethoxy-polyethylene glycol, dextran, hydroxyethyl starch, cellulose, poly-(N-vinyl pyrrolidone)-polyethylene glycol, propylene glycol homopolymers, a polypropylene oxide/ethylene oxide co-polymer, polysialic acid (PSA), polyoxyethylated polyols (e.g., glycerol) and polyvinyl alcohol, as well as mixtures of any of the foregoing. In one aspect, the peptide of the invention is a PEGylated peptide. PEG moieties are available in different shapes, e.g., linear or branched. Exemplary PEGylated peptides include JBS3755 (SEQ ID NO: 1000), which comprises the amino acid sequence of JBS3216 (SEQ ID NO: 462) attached to 20 kD linear PEG moieties at the N-terminus via Ahx (6-aminohexanoic acid) and the C-terminal end via the ε amino group of Lys, and JBS3757 (SEQ ID NO: 1002), wherein the 20 kD PEG moieties are branched. For further discussion of water soluble polymer attachments, see U.S. Pat. Nos. 4,640,835; 4,496,689; 4,301,144; 4,670,417; 4,791,192; and 4,179,337. Other moieties useful for improving peptide half life or stability are described herein and include, for instance, albumin (optionally modified to allow conjugation to the inventive peptide), fatty acid chains (e.g., C12-C18 fatty acid, such as a C14 fatty acid, or dicarboxylic acids, such as octadecane dicarboxylic acid (oddc)), an antibody or fragment thereof (e.g., an Fc portion of an antibody), and proline-alanine-serine multimers.

In another aspect, a peptide derivative includes a targeting moiety specific for a particular cell type, tissue, and/or organ. Alternatively, the peptide is linked to one or more chemical moieties that facilitate purification, detection, multimerization, binding with an interaction partner, and characterization of peptide activity. An exemplary chemical moiety is biotin. Other moieties suitable for conjugation to the peptide of the invention include, but are not limited to, a photosensitizer, a dye, a fluorescence dye, a radionuclide, a radionuclide-containing complex, an enzyme, a toxin, and a cytotoxic agent. Photosensitizers include, e.g., Photofrin, Visudyne, Levulan, Foscan, Metvix, Hexvix®, Cysview™, Laserphyrin, Antrin, Photochlor, Photosens, Photrex, Lumacan, Cevira, Visonac, BF-200 ALA, and Amphinex. If desired, a His tag, a FLAG tag, a strep tag, or a myc tag is conjugated to the peptide.

In addition, in one aspect, the peptides of the invention are acylated at the N-terminal amino acid of the peptide. In another aspect, the peptides of the invention are amidated at the C-terminal amino acid of the peptide. In a still further aspect, the peptides of the invention are acylated at the N-terminal amino acid of the peptide and are amidated at the C-terminal amino acid of the peptide.

Derivatives also include peptides comprising modified or non-proteinogenic amino acids or a modified linker group (see, e.g., Grant, *Synthetic Peptides: A User's Guide*, Oxford University Press (1992)). Modified amino acids include, for example, amino acids wherein the amino and/or carboxyl group is replaced by another group. Non-limiting examples include modified amino acids incorporating thioamides, ureas, thioureas, acylhydrazides, esters, olefines, sulfonamides, phosphoric acid amides, ketones, alcohols, boronic acid amides, benzodiazepines and other aromatic or non-aromatic heterocycles (see Estiarte et al., *Burgers Medicinal Chemistry*, $6^{th}$ edition, Volume 1, Part 4, John Wiley & Sons, New York (2002)). Non-proteinogenic amino acids include, but are not limited, to β-alanine (Bal), norvaline (Nva), norleucine (Nle), 4-aminobutyric acid (γ-Abu), 2-aminoisobutyric acid (Aib), 6-aminohexanoic acid (ε-Ahx), ornithine (Orn), hydroxyproline (Hyp), taurine, sarcosine, citrulline (Cit), cysteic acid (Coh), cyclohexylalanine (Cha), methioninesulfoxide (Meo), methioninesulfone (Moo), homoserinemethylester (Hsm), propargylglycine (Eag), 5-fluorotryptophan (5Fw), 6-fluorotryptophan (6Fw), 3',4'-dimethoxyphenyl-alanine (Ear), 3',4'-difluorophenylalanine (Dff), 4'-fluorophenyl-alanine (Pff), 1-naphthyl-alanine (1Ni), 2-Naphthylalanine (2Ni), 1-methyltryptophan (1Mw), penicillamine (Pen), homoserine (Hse), t-butylglycine, t-butylalanine, phenylglycine (Phg), benzothienylalanine (Bta), L-homo-cysteine (Hcy), N-methyl-phenylalanine (Nmf), 2-thienylalanine (Thi), 3,3-diphenylalanine (Ebw), L-alpha-t-Butylglycine (Tle), Bpa, homophenylalanine (Hfe), and S-benzyl-L-cysteine (Ece). These and other non-proteinogenic amino acids may exist as D- or L-isomers. Examples of modified linkers include, but are not limited to, the flexible linker 4,7,10-trioxa-1,13-tridecanediamine (Ttds), glycine, 6-aminohexanoic acid, beta-alanine (Bal), pentynoic acid (Pyn), and combinations of Ttds, glycine, 6-aminohexanoic acid and Bal.

Homologs of the amino acids constituting the peptides of the invention may be as set forth in Table 1. In any embodiment, one or more amino acids of the peptide of the invention are substituted with an amino acid or building block set forth in Table 1.

TABLE 1

| Amino Acid | Exemplary homologs/substitutions |
|---|---|
| A | 2-Amino-isobutyric acid (Aib), β-Alanine (Bal), (S)-2-Propargylglycine (Eag), (S)-N-Methylalanine (Nma), 2-Aminobutyric acid (Abu), G, M, (S)-2-Aminopentanoic acid (Nva), (S)-Norleucine (Nle) |
| C | S, A, (S)-Homo-cysteine (Hcy), M, L, I, V, (R)-N-Methylcysteine (Nmc), β-Cysteine |
| D | E, Homoglutamic acid, γ-Hydroxy-glutamic acid, γ-Carboxy-glutamic acid, (S)-N-Methyl-Aspartic acid (Nmd), β-Aspartic acid, N, Q, Cysteic acid, β-Homoaspartic acid (Bhd) |

TABLE 1-continued

| Amino Acid | Exemplary homologs/substitutions |
|---|---|
| E | D, Glu, Homoglutamic acid, γ-Hydroxy-glutamic acid, γ-Carboxy-glutamic acid, α-Aminoadipic acid, (S)-N-Methyl-glutamic acid (Nme), β-glutamic acid, Q, N, Cysteic acid, β-Homoglutamatic acid (Bhe) |
| F | L-Homophenylalanine (Hfe), (S)-N-Methyl-phenylalanine (Nmf), β-Phenylalanine, L-Phenylglycin (Phg), β-Homophenylalanine (Bhf), Thienylalanine, Benzothienylalanine, Bromophenylalanine, Iodophenylalanione, Chlorophenylalanine, Methylphenylalanine, Nitrophenylalanine, Y, W, Naphtylalanine, 1,2,3,4-L-tetrahydroisoquinolinecarboxylic acid (Tic) |
| G | A, a, N-Methyl-glycine (Nmg) |
| H | (S)-N-Methyl-histidine (Nmh), 1-Methylhistidine, 3-Methylhistidine, Thienylalanine |
| I | L, V, (S)-2-Amino-5-methyl-hexanoic acid (Hle), (S)-2-Amino-pentanoic acid (Nva), Nle, β-Isoleucine, (S)-N-Methyl-leucine (Nml), M, N-Methyl-L-isoleucine (Nmi), β-Homoisoleucine (Bhi), (S)-Cyclohexylalanine (Cha), L-Cyclohexylglycine (Chg) |
| K | (S)-N-Methyl-lysine (Nmk), R, (S)-N-Methyl-arginine (Nmr), β-Lysine, (S)-2,4-Diaminobutyric acid (Dab), (S)-Diaminopropionic acid (Dap), β-(1-Piperazinyl)-alanine, 2,6-Diamino-4-hexynoic acid, δ-Hydroxy-lysine, (S)-Homo-arginine (Har), ω-Hydroxy-norarginine, ω-Amino-arginine, ω-Methyl-arginine, β-(2-Pyridyl)-alanine, β-(3-Pyridyl)-alanine, 3-Amino-tyrosine, 4-Amino-phenylalanine, (S)-Homo-citrulline (Hci), (S)-Citrullin (Cit), β-Homolysine (Bhk) |
| L | I, V, Hle, Nle, (S)-2-Amino-pentanoic acid (Nva), β-Isoleucine, (S)-N-Methyl-leucine (Nml), M, β-Homovaline(Bhv), β-Homoleucine (Bhl), (S)-Cyclohexylalanine (Cha) |
| M | I, V, Hle, Nva, R, (S)-Homo-arginine (Har), (S)-N-Methyl-methionine (Nmm), Methioninesulfone, Methionine-sulphoxid (Met(O)), Nle |
| N | (S)-N-Methyl-asparagine (Nmn), β-Asparagine, Q, (S)-N-Methyl-glutamine (Nmq), β-Glutamine, Cys(3-propionic acid amide)-OH, Cys(O2-3-propionic acid amide)-OH, β-Homoasparagine (Bhn), β-Homoglutamine (Bhq) |
| P | Azetidine-2-carboxylic acid, 4-Hydroxy-L-proline (Hyp), α-Methyl-methionine, 4-Hydroxy-piperidine-2-carboxylic acid, D-Pipecolic acid (Pip), α-Methyl-Pro, 3-Amino-Pro, 4-Amino-Pro |
| Q | N, Nmn, (S)-N-Methyl-glutamine (Nmq), β-Glutamine, Cys(3-propionic acid amide)-OH, Cys(O2-3-propionic acid amide)-OH, Bhn, Bhq |
| R | (S)-N-Methyl-lysine (Nmk), K, (S)-N-Methyl-arginine (Nmr), β-Lysine, Dab, Dap, (S)-Ornithine (Orn), β-(1-Piperazinyl)-alanine, 2,6-Diamino-4-hexynoic acid, δ-Hydroxy-lysine, Har, ω-Hydroxy-norarginine, ω-Amino-arginine, ω-Methyl-arginine, β-(2-Pyridyl)-alanine, β-(3-Pyridyl)-alanine, 3-Amino-tyrosine, 4-Amino-phenylalanine, (S)-Homo-citrulline (Hci), (S)-Citrullin (Cit), Hle, L, (S)-Norleucine (Nle), M, Bhk, (S)-N-Methyl-lysine (Nmk) |
| S | T, homoserine (Hse), β-Serine, C, β-Cyano-alanine, allo-Threonine, β-Homoserine (Bhs) |
| T | S, Homothreonine, β-Threonine, allo-Threonine |
| V | L, I, Hle, (S)-2-Amino-pentanoic acid (Nva), Nle, β-Valine, (S)-N-Methyl-valine (Nmv), M, Nmi, (S)-N-Methyl-leucine (Nml), (S)-Cyclohexylalanine (Cha), L-Cyclohexylglycine (Chg) |
| W | (S)-N-Methyl-tryptophane (Nmw), β-Tryptophan, F, L-Homophenylalanine (Hfe), (S)-N-Methyl-phenylalanine (Nmf), β-Phenylalanine, L-Phenylglycin (Phg), β-Homophenylalanine (Bhf), Thienylalanine, Benzothienylalanine, Bromophenylalanine, Iodophenylalanine, Chlorophenylalanine, Methylphenylalanine, Nitrophenylalanine, Y, Naphtylalanine, 1,2,3,4-L-tetrahydroisoquinolinecarboxylic acid (Tic), β-Homotyrosine (Bhy) |
| Y | (S)-N-Methyl-tyrosine (Nmy), β-Tyrosine, F, Hfe, Nmf, β-Phenylalanine, Phg, Bhf, Thienylalanine, Benzothienylalanine, Bromophenylalanine, Iodophenylalanine, Chlorophenylalanine, Methylphenylalanine, Nitrophenylalanine, W, Naphtylalanine, Tic, Bhy |

In some embodiments, the peptide (CO—NH) linkages joining amino acids within the peptide of the invention are reversed to create a "retro-modified" peptide, i.e., a peptide comprising amino acid residues assembled in the opposite direction (NH—CO bonds) compared to the reference peptide. The retro-modified peptide comprises the same amino acid chirality as the reference peptide. An "inverso-modified" peptide is a peptide of the invention comprising amino acid residues assembled in the same direction as a reference peptide, but the chirality of the amino acids is inverted. Thus, where the reference peptide comprises L-amino acids, the "inverso-modified" peptide comprises D-amino acids, and vice versa. Inverso-modified peptides comprise CO—NH peptide bonds. A "retro-inverso modified" peptide refers to a peptide comprising amino acid residues assembled in the opposite direction and which have inverted chirality. A retro-inverso analogue has reversed termini and reversed direction of peptide bonds (i.e., NH—CO), while approximately maintaining the side chain topology found in the reference peptide. Retro-inverso peptidomimetics are made using standard methods, including the methods described in Meziere et al, *J. Immunol.*, 159, 3230-3237 (1997), incorporated herein by reference. Partial retro-inverso peptides are peptides in which only part of the amino acid sequence is reversed and replaced with enantiomeric amino acid residues.

Peptides of the invention are made in a variety of ways. In one aspect, the peptides are synthesized by solid phase synthesis techniques including those described in Merrifield, *J. Am. Chem. Soc.*, 85, 2149 (1963); Davis et al., *Biochem. Intl.*, 10, 394-414 (1985); Larsen et al., *J. Am. Chem. Soc.*, 115, 6247 (1993); Smith et al., *J. Peptide Protein Res.*, 44, 183 (1994); O'Donnell et al., *J. Am. Chem. Soc.*, 118, 6070 (1996); Stewart and Young, *Solid Phase Peptide Synthesis*, Freeman (1969); Finn et al., *The Proteins*, 3$^{rd}$ ed., vol. 2, pp. 105-253 (1976); and Erickson et al., *The Proteins*, 3$^{rd}$ ed., vol. 2, pp. 257-527 (1976). The invention contemplates synthetic peptides. Alternatively, the peptide is expressed recombinantly by introducing a nucleic acid encoding a peptide of the invention into host cells, which are cultured to express the peptide. Such peptides are purified from the culture media or cell pellets.

The invention also encompasses a nucleic acid comprising a nucleic acid sequence encoding a peptide of the invention. Methods of preparing DNA and/or RNA molecules are well known in the art. If desired, a peptide coding sequence is incorporated into an expression vector. One of ordinary skill in the art will appreciate that any of a number of expression vectors known in the art are suitable in the context of the invention, such as, but not limited to, plasmids, plasmid-liposome complexes, and viral vectors. Any of these expression vectors are prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994). Optionally, the nucleic acid is operably linked to one or more regulatory sequences, such as a promoter, activator, enhancer, cap signal, polyadenylation signal, or other signal involved with the control of transcription or translation.

Any of the peptides (or peptide complexes) of the invention or nucleic acids encoding the peptides also is provided in a composition (e.g., a pharmaceutical composition). In this regard, the peptide (or peptide complex) is formulated with a physiologically-acceptable (i.e., pharmacologically-acceptable) carrier, buffer, excipient, or diluent, as described further herein. Optionally, the peptide is in the form of a physiologically acceptable salt, which is encompassed by the invention. "Physiologically acceptable salts" means any salts that are pharmaceutically acceptable. Some examples of appropriate salts include acetate, hydrochloride, hydrobromide, sulfate, citrate, tartrate, glycolate, and oxalate. If desired, the composition comprises one or more additional pharmaceutically-effective agents.

The peptide provided herein preferably binds Protein S and optionally inhibits at least one Protein S activity such as, but not limited to, an activity that downregulates the blood coagulation cascade. Without being bound by any specific mechanism of action, the peptide may inhibit binding (competitively or allosterically) of Protein S to activated Protein C (APC), Factor V, or lipid surfaces, thereby limiting the naturally occurring inhibition of coagulation by Protein S. With Protein S activity diminished, FVa and FVIIIa are not as readily degraded and less FXa is inhibited, resulting in enhanced conversion of prothrombin to thrombin.

In one aspect, the peptide of the invention exhibits Protein S antagonistic activity in model and/or plasmatic systems. An exemplary plasma-based assay examines Protein S/APC-dependent thrombin generation initiated via the extrinsic coagulation pathway (Nicolaes, *Blood Coagul. Fibrinolysis*, 8:28 (1997)). Protein S enhances the anticoagulation effect of APC in plasma. Thrombin formation is triggered in plasma substantially lacking FVIII or FIX activity (e.g., the residual coagulation factor activity is lower than 1%) in the presence of a candidate peptide. Thrombin formation is detected using, e.g., a fluorogenic or chromogenic substrate. A system for measuring thrombin activity is provided by Thrombinoscope BV (Maastricht, The Netherlands). Prothrombin conversion is measured using, e.g., a Thrombograph™ (Thermo Scientific, Waltham, Mass.), and the resulting data is compiled into a Calibrated Automated Thrombogram (CAT) generated by Thrombinoscope™ software available from Thrombinoscope BV. In various embodiments, the peptide demonstrates an EC50 of about 20 nM to about 100 µM (e.g., about 40 nM to about 50 µM) in the Protein S/APC-dependent thrombin generation assay.

In certain embodiments, the Protein S-inhibitory peptide increases the amount of peak thrombin generated during the assay and/or decreases the time required to achieve peak thrombin formation. For example, the peptide improves Protein S-regulated thrombin generation in the absence of FVIII (e.g., in FVIII-depleted plasma) to at least 1% of the level of Protein S-dependent thrombin generation in normal plasma. Generally, normal (unafflicted) plasma contains about 0.5 U/mL to about 2 U/mL Factor VIII. Accordingly, in some instances, a Protein S-binding peptide (e.g., Protein S-inhibitory peptide) will enhance thrombin formation in the absence of FVIII to at least about 1% of that observed in the presence of 0.5 U/mL to 2 U/mL FVIII.

In various aspects, the peptide is administered to an animal model of thrombin deficiency or hemophilia to characterize Protein S inhibitory activity in vivo. Such in vivo models are known in the art and include for example, mice administered anti-FVIII antibodies to induce hemophilia A (Tranholm et al., *Blood*, 102, 3615-3620 (2003)); coagulation factor knock-out models such as, but not limited to, FVIII knock-out mice (Bi et al., *Nat. Genet.*, 10(1), 119-121 (1995)) and FIX knock-out mice (Wang et al., *PNAS*, 94(21), 11563-66 (1997)); induced hemophilia-A in rabbits (Shen et al., *Blood*, 42(4), 509-521 (1973)); and Chapel Hill HA dogs (Lozier et al., *PNAS*, 99, 12991-12996 (2002)).

Various peptides bind Protein S from any source including, but not limited to, mouse, rat, rabbit, dog, cat, cow, horse, pig, guinea pig, and primate. In one embodiment, the peptide binds human Protein S. Optionally, the peptide of the invention binds Protein S from more than one species (i.e., the peptide is cross-reactive among multiple species). In certain aspects, the peptide binds Protein S with a dissociation constant ($K_D$) of less than or equal to $1 \times 10^{-4}$ M, less than or equal to $1 \times 10^{-5}$ M, less than or equal to $1 \times 10^{-6}$ M, or less than or equal to $1 \times 10^{-7}$ M, or less than or equal to $1 \times 10^{-8}$ M, or less than or equal to $1 \times 10^{-9}$ M, or less than or equal to $1 \times 10^{-10}$ M.

Affinity may be determined using, for example and without limitation, any one, two, or more of a variety of techniques, such as an affinity ELISA (EC50) assay, a competitive ELISA (IC50) assay, a competitive LANCE IC50 assay (e.g., a homogenous europium-based TR-FRET assay described herein) and/or a surface plasmon resonance (BIAcore™) assay. Optionally, when using an ELISA-based affinity (EC50) assay (e.g., the assay described in Example 1), the peptide demonstrates an EC50 of $1 \times 10^{-4}$ M, less than or equal to $1 \times 10^{-5}$ M, less than or equal to $1 \times 10^{-6}$ M, less than or equal to $1 \times 10^{-7}$ M, less than or equal to $1 \times 10^{-8}$ M, or less than or equal to $1 \times 10^{-9}$ M. When characterized using a competitive (IC50) ELISA assay or LANCE IC50 assay, the peptide of the invention optionally demonstrates an IC50 of less than or equal to about 10,000 nM. For example, the peptide demonstrates an IC50 of less than or equal to about 5,000 nM, less than or equal to about 1,000 nM, or less than or equal to about 500 nM. In one aspect, the peptide demonstrates an IC50 of less than or equal to about 250 nM, less than or equal to about 100 nM, less than or equal to about 50 nM, or less than or equal to about 10 nM (e.g., less than or equal to about 9 nM, less than or equal to about 8 nM, less than or equal to about 7 nM, less than or equal to about 6 nM, less than or equal to about 5 nM, less than or equal to about 4 nM, less than or equal to about 3 nM, or less than or equal to about 1 nM). Optionally, competitive assays utilize JBS0684 (SEQ ID NO: 1) as the "tracer" (i.e., competing peptide). Thus, in various embodiments, the peptide binds human Protein S with an IC50 of less than 25 nM, less than 10 nM, less than 5 nM, less than 3 nM, or less than 1 nM in a competitive LANCE assay using a peptide comprising (or consisting of) the amino acid sequence of SEQ ID NO: 1 (JBS0684) as a tracer. Exemplary peptides and their IC50 values are provided in FIG. 1.

Another suitable assay for characterizing the inventive peptides is a $k_{off}$ assay, which examines a peptide's release from Protein S. The $k_{off}$ assay result is not the dissociation rate constant, but a percentage of competitor peptide blocked from Protein S binding by a test peptide after an incubation period with Protein S. An exemplary $k_{off}$ assay includes the following steps: 1) incubation of a Protein S-coated microtiter plate with an amount of test peptide resulting in approximately 90% Protein S occupation; 2) removal of unbound test peptide; 3) addition of a biotinylated tracer (i.e., competitor) peptide (e.g., JBS0684) that competes with the test peptide for binding to Protein S; 4) incubation for a period of time during which binding sites released by the test peptide is occupied by the tracer; 5) removal of unbound tracer and test peptide; and 6) detection of bound tracer by a chromogenic reaction using streptavidin-horseradish peroxidase conjugate. The resulting signal is indicative of binding sites freed by the test peptide. A test peptide that does not dissociate from Protein S during the incubation period yields a weaker signal compared to an analyte that dissociates completely. Optionally, the peptide demonstrates a $k_{off}$ of less than or equal to $1\times10^{-3}$ $s^{-1}$, less than or equal to $1\times10^{-4}$ $s^{-1}$, less than or equal to $1\times10^{-5}$ $s^{-1}$, less than or equal to $1\times10^{-6}$ $s^{-1}$, or less than or equal to $1\times10^{-7}$ $s^{-1}$.

As with all binding agents and binding assays, one of skill in the art recognizes that the various moieties to which a binding agent should not detectably bind in order to be biologically (e.g., therapeutically) effective would be exhaustive and impractical to list. Therefore, the term "specifically binds" refers to the ability of a peptide to bind Protein S with greater affinity than it binds to an unrelated control protein that is not Protein S. For example, the peptide may bind to Protein S with an affinity that is at least, 5, 10, 15, 25, 50, 100, 250, 500, 1000, or 10,000 times greater than the affinity for a control protein. In some embodiments, the peptide binds Protein S with greater affinity than it binds to an "anti-target," a protein or other naturally occurring substance in humans to which binding of the peptide might lead to adverse effects. Because Protein S-inhibitory peptides exert their activity in the blood stream and/or at the endothelium, plasma proteins represent potential anti-targets. Protein S also is a multi-domain protein harboring domains highly homologous to other proteins of the coagulation system proteins containing Gla-domains (e.g., GAS6, Factor VII, Factor IX, Factor X, Protein C, Protein Z, and prothrombin), EGF-like domains (e.g., GAS6, Factor VII, Factor IX, Factor X, Protein C, Protein Z, and thrombomodulin), and laminin G-like domains (e.g., GAS6). Proteins having these domains also are potential anti-targets. In various embodiments, human GAS6 is the anti-target due to its homology to Protein S (42% identity, 57% consensus sequence). Thus, in one aspect, the peptide of the invention binds to Protein S with an affinity that is at least 5, 10, 15, 25, 50, or 100 times greater than the affinity for an anti-target, such as human GAS6 (tested using any suitable method, such as a surface plasmon resonance assay (e.g., BIAcore)).

Optionally, the peptide of the invention demonstrates one or more desired characteristics described herein, and the amino acid sequence of a peptide can be modified to optimize binding, stability, and/or activity, if desired. An exemplary peptide binds Protein S with a $K_D$ of less than or equal to 10 μM and/or exhibits a binding affinity for Protein S that is at least 10 times greater than the binding affinity for an anti-target. Alternatively or in addition, the peptide enhances thrombin generation in Protein S deficient plasma supplemented with Protein S and APC or FVIII inhibited/deficient plasma with an EC50 (as measured using any suitable assay, such as the assays described here) of less than or equal to 10 μM and/or improves Protein S-dependent thrombin generation in the absence of Factor VIII activity to at least about 20% (e.g., 40%) of the level of thrombin formation in plasma containing normal Factor VIII activity. Alternatively or in addition, the peptide achieves a desired level of plasma stability (e.g., 50% or more of a dose remains in human plasma after six hours or 12 hours, or 50% or more of a dose remains in mouse plasma after four or eight hours) and/or demonstrates a desired half life in vivo (e.g., at least two, three, four, five, six, seven, eight, nine, or ten hours) and/or demonstrates a desired level of solubility. Alternatively or in addition, the peptide of the invention exhibits a desired level of bioavailability, such as a desired level of bioavailability following intravenous or subcutaneous administration (e.g., greater than or equal to 5%, 10%, 15%, 20%, 25%, 30%, or 50%) and/or demonstrates a desired level of Protein S-inhibitory activity at a given dose in vivo.

The invention further includes a method of inhibiting Protein S. The method comprises contacting Protein S with a peptide described herein. Optionally, the method comprises inhibiting Protein S in a subject, and the method comprises administering to the subject the peptide in an amount effective to inhibit Protein S activity. Any degree of Protein S activity inhibition is contemplated. For example, a peptide of the invention reduces Protein S inhibition of the coagulation cascade at least about 5% (e.g., at least about 10%, at least about 25%, or at least about 30%). In some embodiments, the peptide reduces Protein S activity at least about 50%, at least about 75%, or at least about 90% compared to Protein S activity in the absence of the peptide.

In one aspect of the invention, peptides of the invention are used to detect and/or quantify Protein S in vivo or in vitro. An exemplary method of detecting and/or quantifying Protein S in a sample comprises (a) contacting a sample with a peptide of the invention, and (b) detecting binding of the peptide to Protein S. The method is useful for therapy and diagnosis of disease where Protein S is a suitable diagnostic marker. Peptide-Protein S complexes are directly or indirectly detected. Detection moieties are widely used in the art to identify biological substances and include, for example, dye (e.g., fluorescent dye), radionuclides and radionuclide-containing complexes, and enzymes. Moieties allowing detection are optionally attached or conjugated to the peptide. In some aspects, peptide-Protein S binding is detected indirectly. In this regard, the peptide is optionally contacted with an interaction partner that binds the peptide of invention without significantly interfering with peptide-Protein S binding, and the interaction partner is detected. Exemplary interaction partners include, but are not limited to, antibodies, antigen-binding antibody fragments, anticalins and antibody mimetics, aptamers, streptavidin, avidin, neutravidin, and spiegelmers. Optionally, the interaction partner comprises a detection moiety to facilitate detection of an interaction partner-peptide complex. The peptide is, in some embodiments, modified to facilitate binding of an interaction partner. For example, in one aspect, the peptide of the invention is conjugated to biotin, which is bound by an interaction partner comprising streptavidin. An exemplary interaction partner comprises strepavidin fused to horseradish peroxidase, which is detected in, e.g., an ELISA-like assay. Alternatively, the peptide of the invention is modified to include an antibody epitope, and binding of the corresponding antibody to the peptide-Protein S complex is detected.

Peptide-Protein S complexes and interaction partner-peptide complexes are identified using any of a number of methods, such as, but not limited to, biochemical assays (e.g., enzymatic assays), spectroscopy (e.g., detection based on optical density, fluorescence, FRET, BRET, TR-FRET, fluorescence polarization, electrochemoluminescence, or NMR), positron emission tomography (PET), and single Photon Emission Computed Tomography (SPECT). Detectable moieties that facilitate fluorescence detection of peptide-Protein S complexes or interaction partner-peptide complexes include, but are not limited to, fluorescein, Alexa Fluor® 350, Marina Blue™, Cascade Yellow™, Alexa Fluor® 405, Pacific Blue™, Pacific Orange™, Alexa Fluor® 430, Alexa Fluor® 488, Oregon Green® 488, Alexa Fluor® 500, Oregon Green® 514, Alexa Fluor® 514, Alexa Fluor® 532, Alexa Fluor® 555, Tetramethylrhodamine, Alexa Fluor® 546, Rhodamine B, Rhodamine Red™-X, Alexa Fluor® 568, Alexa Fluor® 594, Texas Red®, Texas Red®-X, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, B-Phycoerythrin, R-Phycoerythrin, Allophycocyanin, BODIPY®, Cy3, Cy5, TAMRA, and fluorescent proteins (GFP and derivatives thereof).

The invention also provides a method for diagnosing a subject suffering from a disease or disorder, or at risk of suffering from a disease or disorder, wherein the disease or disorder is associated with or caused by aberrant Protein S activity. The method comprises administering to the subject the peptide of the invention and detecting Protein S-peptide complex. Detection of complexes is described above. The presence of the complex indicates the presence of Protein S, thereby allowing diagnosis of a disease or disorder associated with Protein S (e.g., a disease or disorder which (i) can be treated by inhibiting Protein S or (ii) comprises symptoms which can be ameliorated or prevented by inhibiting Protein S). If administration of the peptide to the subject is not desired, a biological sample is obtained from the subject, contacted with the peptide as described herein, and Protein S-peptide complexes are detected. It will be appreciated that methods of using the peptides described herein also include use of any of the peptide complexes described herein.

Some diseases and disorders, such as thrombophilia, venous thrombosis, and pulmonary embolism, are linked to reduced Protein S levels. Protein S deficiency can be hereditary or result from, e.g., vitamin K deficiency, warfarin treatment, pregnancy, infection, and liver disease. To detect a deficiency, the method optionally entails quantifying Protein S. If Protein S in the biological sample is below a desired threshold, treatment for the disease or disorder is commenced. In some instances, the treatment comprises anticoagulation therapy (such as heparin or warfarin therapies).

The peptides described herein preferably bind Protein S and, therefore, are useful for purifying Protein S (e.g., recombinant Protein S) from a biological sample (e.g., a biological fluid, such as serum), fermentation extract, tissue preparations, culture medium, and the like. The peptides also are useful for purifying proteins that interact with Protein S, such as, but not limited to, C4BP. The invention includes methods of using the peptide of the invention in the commercial production of Protein S or in a method of characterizing Protein S. For example, the invention includes a method of purifying Protein S. The method comprises contacting a sample containing Protein S with a peptide as defined herein under conditions appropriate to form a complex between Protein S and the peptide; removing the complex from the sample; and, optionally, dissociating the complex to release Protein S. Exemplary conditions appropriate to form a complex between Protein S and the peptide are disclosed in the Examples. In some embodiments, the peptide is immobilized to a support, e.g., a solid support, to facilitate recovery of Protein S. For example, in one embodiment, the peptide is immobilized to chromatography stationary phase (e.g., silica, affinity chromatography beads, or chromatography resins), a sample comprising Protein S is applied to the stationary phase such that Protein S-peptide complexes are formed, the remainder of the sample is removed from the stationary phase, and Protein S is eluted from the stationary phase. In this regard, the peptides of the invention are, in one aspect, suitable for use in affinity chromatography techniques.

A method of enhancing thrombin formation in a subject also is provided. The method comprises administering to the subject a peptide provided herein under conditions effective to inhibit Protein S. In this regard, the peptide is administered in an amount and under conditions effective to enhance thrombin formation in the subject. In various aspects of the invention, the subject is "clotting factor-deficient" meaning that the subject suffers from a deficiency in one or more blood factors required for thrombin formation, such as FVIII, FIX, or FXI. Indeed, in one embodiment, the subject is deficient in FVIII. Clotting factor deficiencies are identified by examining the amount of factor in a clinical sample. Practitioners classify hemophilia according to the magnitude of clotting factor deficiency. Subjects suffering from mild hemophilia have approximately 5% to 30% of the normal amount (1 U/ml) of Factor VIII or Factor IX. Moderate hemophilia is characterized by approximately 1% to 5% of normal Factor VIII, Factor IX, or Factor XI levels, while subjects suffering from severe hemophilia have less than 1% of the normal amount of Factor VIII, Factor IX, or Factor XI. Deficiencies can be identified indirectly by activated partial thromboplastin time (APTT) testing. The invention further includes enhancing thrombin formation in a subject that does not suffer from a clotting factor deficiency. The method comprises administering to a subject (e.g., a subject comprising normal, physiological levels of clotting factor) a peptide provided herein under conditions effective to enhance thrombin formation.

In one aspect, the peptide is used for increasing blood clot formation in a subject. The method of increasing blood clot formation comprises administering to the subject a peptide described herein in an amount and under conditions effective to increase blood clot formation. It will be appreciated that the method need not completely restore the coagulation cascade to achieve a beneficial (e.g., therapeutic) effect. Any enhancement or increase in thrombin or blood clot formation that reduces the onset or severity of symptoms associated with clotting factor deficiencies is contemplated. Methods of determining the efficacy of the method in promoting thrombin formation and blood clotting are known in the art and described herein.

The invention further includes a method of treating a blood coagulation disorder in a subject, the method comprising administering to the subject one or more peptides (or peptide complex(es)) of the invention (i.e., any one or more of the peptides described herein), in an amount and under conditions effective to treat the blood coagulation disorder in the subject. "Coagulation disorders" include bleeding disorders (e.g., hypocoagulation) caused by deficient blood coagulation factor activity and deficient platelet activity. Blood coagulation factors include, but are not limited to, Factor V (FV), FVII, FVIII, FIX, FX, FXI, FXIII, FII (responsible for hypoprothrombinemia), and von Willebrand's factor. Factor deficiencies are caused by, for instance, a shortened in vivo half life of the factor, altered binding properties of the factor, genetic defects of the factor, and a reduced plasma concentration of the factor. Coagulation disorders can be congenital or acquired. Coagulation disorders also stem from development of inhibitors or autoimmunity (e.g., antibodies) against clotting factors. In one example, the coagulation disorder is hemophilia A. Alternatively, the coagulation disorder is hemophilia B or hemophilia C.

Platelet disorders are caused by deficient platelet function or abnormally low platelet number in circulation. Low platelet count may be due to, for instance, underproduction, platelet sequestration, or uncontrolled patent destruction. Thrombocytopenia (platelet deficiencies) may be present for various reasons, including chemotherapy and other drug therapy, radiation therapy, surgery, accidental blood loss, and other disease conditions. Exemplary disease conditions that involve thrombocytopenia are: aplastic anemia; idiopathic or immune thrombocytopenia (ITP), including idiopathic thrombocytopenic purpura associated with breast cancer; HIV-associated ITP and HIV-related thrombotic thrombocytopenic purpura; metastatic tumors which result in thrombocytopenia; systemic lupus erythematosus, including neonatal lupus syndrome splenomegaly; Fanconi's syndrome; vitamin B12 deficiency; folic acid deficiency; May-Hegglin anomaly; Wiskott-Aldrich syndrome; chronic liver disease; myelodysplastic syndrome associated with thrombocytopenia; paroxysmal nocturnal hemoglobinuria; acute profound thrombocytopenia following C7E3 Fab (Abciximab) therapy; alloimmune thrombocytopenia, including maternal alloimmune thrombocytopenia; thrombocytopenia associated with antiphospholipid antibodies and thrombosis; autoimmune thrombocytopenia; drug-induced immune thrombocytopenia, including carboplatin-induced thrombocytopenia and heparin-induced thrombocytopenia; fetal thrombocytopenia; gestational thrombocytopenia; Hughes' syndrome; lupoid thrombocytopenia; accidental and/or massive blood loss; myeloproliferative disorders; thrombocytopenia in patients with malignancies; thrombotic thrombocytopenia purpura, including thrombotic microangiopathy manifesting as thrombotic thrombocytopenic purpura/hemolytic uremic syndrome in cancer patients; post-transfusion purpura (PTP); autoimmune hemolytic anemia; occult jejunal diverticulum perforation; pure red cell aplasia; autoimmune thrombocytopenia; nephropathia epidemica; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes (e.g., uremic conditions in childhood); and hematologic manifestations related to viral infection including hepatitis A virus and CMV-associated thrombocytopenia. Platelet disorders also include, but are not limited to, Von Willebrand Disease, paraneoplastic platelet dysfunction, Glanzman's thrombasthenia, and Bernard-Soulier disease. Additional bleeding disorders include, but are not limited to, hemorrhagic conditions induced by trauma; a deficiency in one or more contact factors, such as FXI, FXII, prekallikrein, and high molecular weight kininogen (HMWK); vitamin K deficiency; a fibrinogen disorder, including afibrinogenemia, hypofibrinogenemia, and dysfibrinogenemia; and alpha2-antiplasmin deficiency. In one embodiment, the peptide of the invention is used to treat excessive bleeding, such as excessive bleeding caused by surgery, trauma, intracerebral hemorrhage, liver disease, renal disease, thrombocytopenia, platelet dysfunction, hematomas, internal hemorrhage, hemarthroses, hypothermia, menstruation, pregnancy, and Dengue hemorrhagic fever. All of the above are considered "blood coagulation disorders" in the context of the disclosure.

In one aspect, the peptide of the invention is used to reverse the effects (in whole or in part) of one or more anticoagulants in a subject. Numerous anticoagulants are known in the art and include, for instance, heparin; coumarin derivatives, such as warfarin or dicumarol; TFPI; AT III; lupus anticoagulant; nematode anticoagulant peptide (NAPc2); FVIIa inhibitors; active-site blocked FVIIa (FVIIai); active-site blocked FIXa (FIXai); FIXa inhibitors; FXa inhibitors, including fondaparinux, idraparinux, DX-9065a, and razaxaban (DPC906); active-site blocked FXa (FXai); inhibitors of FVa or FVIIIa, including activated protein C (APC) and soluble thrombomodulin; thrombin inhibitors, including hirudin, bivalirudin, argatroban, and ximelagatran; and antibodies or antibody fragments that bind a clotting factor (e.g., FV, FVII, FVIII, FIX, FX, FXIII, FII, FXI, FXII, von Willebrand factor, prekallikrein, or high molecular weight kininogen (HMWK)).

As used herein, "treating" and "treatment" refers to any reduction in the severity and/or onset of symptoms associated with disease or disorder (e.g., a blood coagulation disorder). One of ordinary skill in the art will appreciate that any degree of protection from, or amelioration of, a disorder or symptom associated therewith is beneficial to a subject, such as a human patient. The quality of life of a patient is improved by reducing to any degree the severity of symptoms in a subject and/or delaying the appearance of symptoms. Accordingly, the method in one aspect is performed as soon as possible after it has been determined that a subject is at risk for developing a blood coagulation disorder (e.g., a deficiency in a clotting factor (e.g., FVIII, FIX, or FXI) is detected or inhibitory antibodies are detected) or as soon as possible after a blood coagulation disorder (e.g., hemophilia A, hemophilia B, or hemophilia C) is detected. In an additional aspect, the peptide is administered to protect, in whole or in part, against excessive blood loss during injury or surgery.

In view of the above, the invention provides a peptide (or peptide complex) for use in medicine, i.e., for use in a method for the treatment of a subject, such as a method for the treatment of a disease where the inhibition of Protein S is beneficial. In one aspect, the disease or disorder is a blood coagulation disorder. The subject is suffering from a disease or disorder or is at risk from suffering from a disease or disorder (or adverse biological event, such as excessive blood loss). The method comprises administering to the subject the peptide (or peptide complex) in an amount and under conditions effective to treat or prevent, in whole or in part, the disease or disorder. The invention further provides a peptide (or peptide complex) for use in the manufacture of a medicament. For example, the peptide (or peptide complex) can be used in the manufacture of a medicament for the treatment of a blood coagulation disorder, as described in detail herein.

In some embodiments, it is advantageous to administer to a subject a nucleic acid comprising a nucleic acid sequence encoding a peptide complex or peptide of the invention. Such a nucleic acid, in one aspect, is provided instead of, or in addition to, a peptide complex or peptide. Expression vectors, nucleic acid regulatory sequences, administration methods, and the like, are further described herein and in U.S. Patent Publication No. 20030045498.

The amount of peptide administered to a subject (e.g., a mammal, such as a human) and the conditions of administration (e.g., timing of administration, route of administration, dosage regimen) are sufficient to affect the desired biological response over a reasonable time frame. Purely by way of illustration, in one aspect, the method comprises administering, e.g., from about 0.1 µg/kg to about 100 mg/kg or more. Given the chronic nature of many blood coagulation disorders, it is envisioned that a subject will receive the peptide of the invention over a treatment course lasting weeks, months, or years, and may require one or more doses daily or weekly. In other embodiments, the peptide of the invention is administered to treat an acute condition (e.g., bleeding caused by surgery or trauma, or factor inhibitor/autoimmune episodes in subjects receiving coagulation replacement therapy) for a relatively short treatment period, e.g., one to 14 days.

Suitable methods of administering a physiologically-acceptable composition, such as a pharmaceutical composition comprising a peptide described herein, are well known in the art. Depending on the circumstances, a pharmaceutical composition is applied or instilled into body cavities, absorbed through the skin or mucous membranes, ingested, inhaled, and/or introduced into circulation. In one aspect, a composition comprising a peptide of the invention is administered intravenously, intraarterially, or intraperitoneally to introduce the peptide of the invention into circulation. Non-intravenous administration also is appropriate, particularly with respect to low molecular weight therapeutics. In certain circumstances, it is desirable to deliver a pharmaceutical composition comprising the peptide of the invention orally, topically, sublingually, vaginally, rectally, pulmonary; through injection by intracerebral (intra-parenchymal), intracerebroventricular, intramuscular, intra-ocular, intraportal, intralesional, intramedullary, intrathecal, intraventricular, transdermal, subcutaneous, intranasal, urethral, or enteral means; by sustained release systems; or by implantation devices. If desired, the peptide is administered regionally via intraarterial or intravenous administration feeding a region of interest, e.g., via the femoral artery for delivery to the leg. In one embodiment, the peptide is incorporated into a microparticle as described in, for example, U.S. Pat. Nos. 5,439,686 and 5,498,421, and U.S. Patent Publications 2003/0059474, 2003/0064033, 2004/0043077, 2005/0048127, 2005/0170005, 2005/0142205, 2005/142201, 2005/0233945, 2005/0147689. 2005/0142206, 2006/0024379, 2006/0260777, 2007/0207210, 2007/0092452, 2007/0281031, and 2008/0026068. Alternatively, the composition is administered via implantation of a membrane, sponge, or another appropriate material on to which the desired molecule has been absorbed or encapsulated. Where an implantation device is used, the device in one aspect is implanted into any suitable tissue, and delivery of the desired molecule is in various aspects via diffusion, timed-release bolus, or continuous administration. In other aspects, the peptide is administered directly to exposed tissue during surgical procedures or treatment of injury, or is administered via transfusion of blood procedures. Therapeutic delivery approaches are well known to the skilled artisan, some of which are further described, for example, in U.S. Pat. No. 5,399,363.

To facilitate administration, the peptide or peptide complex in one embodiment is formulated into a physiologically-acceptable composition comprising a carrier (i.e., vehicle, adjuvant, buffer, or diluent). Sterile, physiologically-acceptable carriers are well known in the art. Illustrative pharmaceutical forms suitable for injectable use include without limitation sterile aqueous solutions or dispersions and sterile powders for the extemporaneous preparation of sterile injectable solutions or dispersions (for example, see U.S. Pat. No. 5,466,468). A pharmaceutical composition comprising a peptide provided herein is optionally placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents that may be necessary to reconstitute the pharmaceutical composition.

When appropriate, the peptide or peptide complex of the invention is administered in combination with other substances and/or other therapeutic modalities to achieve an additional or augmented biological effect. Co-treatments include, but are not limited to, plasma-derived or recombinant coagulation factors, hemophilia prophylaxis treatments, immunosuppressants, plasma factor-inhibiting antibody antagonists (i.e., anti-inhibitors), antifibrinolytics, antibiotics, hormone therapy, anti-inflammatory agents (e.g., Non-Steroidal Anti-Inflammatory Drugs (NSAIDs) or steroidal anti-inflammatory substances), procoagulants, and pain relievers. In one aspect, the method is an adjunct therapy to traditional replacement factor treatment regimens involving administration of, e.g., FXIII, FXII, FXI (e.g., HEMOLEVEN® (Laboratoire francais du Fractionnement et des Biotechnologies, Les Ulis, France) and FXI concentrate (BioProducts Laboratory, Elstree, Hertfordshire, UK)), FX, FIX (e.g., BENEFIX® Coagulation Factor IX (Wyeth, Madison, N.J.); ALPHANINE® SD (Grifols, Los Angeles, Calif.); MONONINE® (CSL Behring, King of Prussia, Pa.); BEBULIN-VH™ (Baxter, Deerfield, Ill.); PROFILNINE® SD (Grifols, Los Angeles, Calif.); or PROPLEX T™ (Baxter, Deerfield, Ill.)), FVIII (e.g., ADVATE™ (Baxter, Deerfield, Ill.); HELIXATE® FS (CSL Behring, King of Prussia, Pa.); REFACTO® (Wyeth, Madison, N.J.), XYNTHA™ (Wyeth, Madison, N.J.), KOGENATE® and KOGENATE® FS (Bayer, Pittsburgh, Pa.); ALPHANATE® (Grifols, Los Angeles, Calif.); HEMOPHIL M™ (Baxter, Deerfield, Ill.); KOATE®-DVI (Talecris Biotherapeutics-USA, Research Triangle Park, N.C.); or MONARC-M™ (Baxter, Deerfield, Ill.)), FVIIa (e.g., NOVOSEVEN® FVIIa (Novo Nordisk, Princeton, N.J.) and FVII concentrate (Baxter Bioscience, Vienna, Austria, or BioProducts Laboratory, Elstree, Hertfordshire, UK)), FV, FVa, FII, and/or FIII, to a subject. In some instances, the subject also receives FEIBA VH Immuno™ (Baxter BioScience, Vienna, Austria), which is a freeze-dried sterile human plasma fraction with Factor VIII inhibitor bypassing activity. FEIBA VH Immuno™ contains approximately equal units of Factor VIII inhibitor bypassing activity and Prothrombin Complex Factors (Factors II, VII, IX, and X and protein C). Other exemplary co-treatments include, but are not limited to, prekallikrein, high molecular weight kininogen (HMWK), Von Willebrand's factor, Tissue Factor, and thrombin. Alternatively or in addition, the peptide is co-formulated with one or more different Protein S-binding peptides, such as one or more different peptides of the inventions. In one aspect, administration of the peptide allows a reduction in the dose of co-therapeutic required to achieve a desired biological response. Also optionally, the peptide (or peptide complex) is part of a therapeutic regimen that includes administration of a Tissue Factor Pathway Inhibitor (TFPI)-binding peptide, such as the TFPI-binding peptides described in International Patent Publication No. WO 2013/141965.

The invention thus includes administering to a subject a peptide of the invention (or multiple peptides, or a peptide complex), in combination with one or more additionally suitable substances(s), each being administered according to a regimen suitable for that medicament. Administration strategies include concurrent administration (i.e., substantially simultaneous administration) and non-concurrent administration (i.e., administration at different times, in any order, whether overlapping or not) of the peptide (or peptide complex) and one or more additionally suitable agent(s). It will be appreciated that different components are optionally administered in the same or in separate compositions, and by the same or different routes of administration.

The invention further provides a method for identifying a Protein S-binding compound, such as a Protein S-binding peptide. In one aspect, the method comprises (a) contacting Protein S with a peptide described herein and a test compound (which may be a second peptide) under conditions that allow formation of Protein S-peptide complexes. The method further comprises (b) measuring Protein S-peptide complexes formed in step (a), and (c) comparing the number of Protein S-peptide complexes formed in the presence of the test compound with the number of Protein S-peptide complexes formed in the absence of the test compound. A reduction in the number of Protein S-peptide complexes formed in the presence of the test compound compared to the number of Protein S-peptide complexes formed in the absence of the test compound indicates that the test compound is a Protein S-binding compound. In one aspect, the method further comprises forming Protein S-peptide complexes in the absence of the test compound for comparison in step (c), although this is not required inasmuch as the information may be obtained separately (e.g., from previously prepared reference standards).

Protein S, the peptide, and the test compound are combined simultaneously or sequentially, optionally with washing steps before and/or after addition of the peptide and/or the test compound. In one embodiment, Protein S is contacted with a peptide described herein under conditions that allow formation of Protein S-peptide complexes, unbound peptide is removed, and the remaining Protein S-peptide complexes are contacted with a test compound. Displacement of the peptide from the Protein S-peptide complexes is detected, and indicates that the test compound is a Protein S-binding compound. Displacement is detected by, for example, measuring the number of Protein S-peptide complexes before and after exposure to the test compound.

Protein S-binding peptide complexes are detected and/or measured (quantified) using any suitable detection means, including detection means known in the art for detecting peptides in a sample. For example, in one embodiment of the invention, the peptide of the invention comprises a label that generates a signal. Exemplary labels are described herein and include, e.g., radionuclides, fluorescent dyes, isotopes, enzyme substrates, and enzymes. The method comprises measuring signal generated by Protein S-peptide complexes and comparing signal generated by Protein S-peptide complexes formed in the presence of the test compound with signal generated by Protein S-peptide complexes formed in the absence of the test compound. A reduction in signal from a sample comprising Protein S-peptide complexes exposed to test compound (compared to signal generated by a similar sample of Protein S-peptide complexes not exposed to the test compound) indicates that complex formation has been inhibited or disrupted, and that the test compound is a Protein S-binding compound.

The methods of the invention to identify Protein S-binding compounds are particularly amenable to the various high throughput screening techniques known in the art. Any "test compound" (e.g., small molecule, peptide, protein (such as an antibody or fragment thereof), peptidomimetic, or polynucleotide (DNA or RNA)) is suitable for screening using the methods described herein. If desired, a collection, population, or library of test compounds is screened for Protein S binding (and, optionally, anti-Protein S activity) using the methods described herein. High throughput screening methods embraced by the invention include automated procedures allowing screening of tens to hundreds of thousands of test compounds.

This entire document is intended to be related as a unified disclosure, and it should be understood that all combinations of features described herein are contemplated, even if the combination of features are not found together in the same sentence, or paragraph, or section of this document. For example, where protein therapy is described, embodiments involving polynucleotide therapy (using polynucleotides/vectors that encode the protein) are specifically contemplated, and the reverse also is true. Unless explicitly indicated to the contrary, the description provided herein with respect to one peptide of the invention or method of the invention applies to each and every peptide of the invention and method of the invention, respectively. Also, unless explicitly indicated to the contrary, the description provided herein with respect to a peptide of the invention or use thereof applies to peptide complexes of the invention.

The invention also includes, for instance, all embodiments of the invention narrower in scope in any way than the variations specifically mentioned above. With respect to aspects of the invention described as a genus, all individual species are considered separate aspects of the invention. With respect to aspects of the invention described or claimed with "a" or "an," it should be understood that these terms mean "one or more" unless context unambiguously requires a more restricted meaning. If aspects of the invention are described as "comprising" a feature, embodiments also are contemplated "consisting of" or "consisting essentially of" the feature.

All publications, patents and patent applications cited in this specification are herein incorporated by reference as if each individual publication or patent application were specifically and individually indicated to be incorporated by reference.

EXAMPLES

The invention will be understood more readily by reference to the following examples, which are provided by way of illustration and are not intended to limit the invention.

Example 1

The following example describes production and selection of peptides described herein and characterization Protein S binding.

Peptides were synthesized by Fmoc solid phase synthesis mostly with acetylated N-terminus and amidated C-terminus. Raw products were purified to >90% by HPLC and lyophilized as TFA salts. Lyophilized peptides were stored at <-15° C. Protein S-binding peptide sequences were identified using an mRNA display library and panel of selection assays. The mRNA display method is described in, e.g., International Patent Publication No. WO 2005/051985 and Liu et al., *Methods in Enzymology*, 318, 268-293 (2000). In brief, mRNA is directly linked to its encoded peptide through a puromycin molecule. The peptide-RNA complexes were exposed to full length Protein S in a series of selection rounds during which and Protein S-bound candidate peptide-RNA complexes were isolated and enriched. The RNA encoding peptides with desired properties was reverse transcribed to obtain coding DNA.

The selection rounds included moderate and high stringency selection steps, as well as competitive conditions based on inhibitory anti-Protein S antibodies. The selection process began with five selection rounds of progressive stringency. A library consisting of ~$10^{13}$ random 20-mer peptide-mRNA complexes was incubated for 1 hour with 100 nM biotinylated human Protein S immobilized on paramagnetic streptavidin beads. The binding of peptide/mRNA fusions to Protein S beads and non-coated streptavidin control beads was monitored by scintillation measurement of radioactive-labeled peptide-mRNA complexes. Unbound peptide-mRNA complexes were removed by four washing steps. Subsequently, peptide/mRNA fusions bound to the Protein S-coated beads were amplified and subjected to the next round of selection. A progressive enrichment of Protein S-binding peptide-mRNA complexes was observed over five selection rounds. For example, high stringency selection of peptides identified in round 2 eliminated ~99% of the population, leaving a subpopulation of high affinity binders.

Unique peptide sequences identified by mRNA display (296 peptides) were synthesized as N-terminally biotinylated variants in order to facilitate affinity testing. Peptides with detectable affinity for Protein S in the various screening assays described above were further characterized in an ELISA-based EC50 binding assay. Briefly, Nunc Polysorb MTP wells were coated with 50 µl Protein S (3 µg/ml) and blocked with 2% yeast extract and 0.1% Tween80. Biotinylated peptides were incubated in Protein S-coated wells and blocked control wells (without Protein S). After several washing steps, bound peptide was detected by Streptavidin-HRP using TMB as chromogenic substrate. EC50 values were obtained from peptide titration curves by non-linear regression of the background-corrected and normalized binding signals. The affinities of the peptides range from two-digit micromolar to sub-nanomolar (EC50). Exemplary peptides identified by the mRNA display and screening assays include JBS0684 (SEQ ID NO: 1) and JBS2512 (SEQ ID NO: 2).

Example 2

This example describes the generation of additional Protein S binding peptides and characterization of Protein S binding. This example further describes plasma-based hemophilia model and demonstrates the Protein S-inhibitory activity of the peptides described herein.

Peptides identified in Example 1 were subjected to substitution analysis to further investigate Protein S binding and to identify peptides with improved activity. For example, each amino acid position of parent peptide JBS2512 was separately replaced by a set of eight representative amino acids (Ala, Asp, Phe, Gly, Leu, Lys, Ser, Pro). Thus, approximately 160 new peptide candidates were created from one parent peptide. Each of these new peptide candidates carried a single amino acid exchange compared to the parent peptide.

The new peptide candidates were synthesized (purity>60%) and screened for affinity in a competitive binding assay (ELISA IC50) and activity in a thrombin generation assay (CAT). The competition (IC50) ELISA was performed using biotinylated tracer peptide JBS0684 to compete for Protein S-binding with candidate peptides. Peptides that compete with the tracer bind the same region of Protein S as the tracer (and each other). Ninety-six well PolySorp plates (Nunc) were coated with 3 µg/mL Protein S in coating buffer (15 mM $Na_2CO_3$, 35 mM $NaHCO_3$, pH 9.6) over night. Plates were washed three times with wash buffer (HNaT: 175 mM NaCl, 25 mM HEPES, 5 mM $CaCl_2$, 0.1% Tween 80, pH 7.35), and blocked with 100 µl 2% yeast extract in HNaT for at least 1 hour. Plates were then washed three times with HNaT. JBS0684 was applied at a concentration corresponding to the EC90 value determined in the binding ELISA. A competitor stock solution of peptide (10 mM) was diluted 1/33.3 in HNaT without HSA, and a serial 1/3 dilution was prepared with HNaT with 3% DMSO. The dilution was further diluted with the biotinylated tracer peptide in a ratio of 1:6 (20 µl competitor dilution and 100 µl tracer peptide). The mixture of competitor and tracer peptide was applied to the Protein S-coated microtiter plate and incubated for 1.5 hours. The plates were washed three times with HNaT. Peptide-Protein S binding was detected by applying HRP-conjugated streptavidin to the microtiter plate, incubating the mixture for one hour, washing the plate three times with HNaT, applying TMB (3,3'5,5'-Tetramethylbenzidin), and detecting the subsequent chromogenic conversion of TMB by HRP. IC50 measurements of peptides are provided herein (see, e.g., Table 3).

Peptides also were tested for improvement of Protein S/APC-dependent thrombin generation in hemophilic plasma using a CAT assay. Protein S enhances the anticoagulation of APC in plasma. The CAT assay quantifies the effect of Protein S on APC-mediated thrombin generation initiated via the extrinsic coagulation pathway (Nicolaes, *Blood Coagul. Fibrinolysis*, 8:28 (1997)). APC (35 nM) and Protein S (25 nM) was added to Protein S-depleted plasma, and plasma samples were incubated with high titer heat inactivated anti-human FVIII plasma raised in goat (4490 BU/ml; Baxter BioScience, Vienna, Austria; 50 BU/ml final plasma concentration). Thrombin formation in plasma was followed by calibrated automated thrombography (CAT) in a Fluoroskan Ascent® reader (Thermo Labsystems, Helsinki, Finland) and quantified via the thrombin peak-height. Thrombin generation was determined at high tissue factor (TF) concentration in the absence and in the presence of APC at a concentration that reduces the peak height to ~20%. The inhibitory effect of peptides described herein on the APC cofactor activity of Protein S (PS) in plasma was measured in FVIII-inhibited pooled normal plasma supplemented with APC. Complete (100%) Protein S/APC inhibition is the height of the thrombin peak without addition of APC. Lack of (0%) PS/APC inhibition correlates to the thrombin peak-height value with a certain amount of APC. Peptides were ranked by their normalized values in comparison to the mean of wild-type controls including SD at two defined peptide concentrations (EC50 and EC90).

Exemplary conditions for the CAT assay are as follows. Protein S-depleted plasma was supplemented with 35 nM APC and 35 nM Protein S. Stock APC was diluted with 10 pM TF and 15 µM PL. Lyophilized peptides were dissolved in 100% DMSO to a 5 mM stock concentration and further diluted with HNABSA5-buffer+0.1% Tween80. The final peptide plasma concentrations were 140 nM (EC90 wild-types) and 90 nM (EC50 wildtypes). In a 96 well Immulon 2HB (transparent), U-bottom (ThermoElectron) plate was mixed 80 µl plasma (+CTI+Z994-5), 10 µl peptide dilution, and 10 µl APC-TF-PL-MIX or Calibrator. Thrombin generation was initiated by dispensing 20 µL of FluCa reagent containing fluorogenic substrate and HEPES-buffered CaCl$_2$ (100 mM) into each well. Fluorescence intensity was recorded at 37° C. using the Fluoroskan Ascent® reader (filters 390 nm excitation and 460 nm emission). The parameters of the resulting thrombin generation curves were calculated using the Thrombinoscope™ software (Thrombinoscope) and thrombin calibrator to correct for inner filter and substrate consumption effects (Hemker, *Pathophysiol Haemost Thromb*, 33: 415 (2003)).

For both the competitive binding assay and the CAT assay, peptide candidates were characterized as having better, similar, or less activity than the parent. The analysis revealed enhancing substitutions at six different positions located within the three N-terminal positions and positions 13, 15 and 17. Tolerated substitutions (substitutions that did not negatively affect activity) were identified at several positions, including positions 1-3, 11, 13, 15, 17, 18, and 20. Selected peptides with enhancing substitutions were re-synthesized (purity>90%) and run in the ELISA IC50 assay, the results of which are provided in Table 2.

TABLE 2

| Peptide | Sequence | SEQ ID NO. | IC50 [nM] | CAT EC50 [nM] |
|---|---|---|---|---|
| JBS2512 | Ac-TGHVSAGWYDYNFDHYREFT-NH2 | 2 | 3.9 | 24 |
| JBS2516 | Ac-TAHVSAGWYDYNFDHYREFT-NH2 | 6 | 3.3 | 21 |
| JBS2526 | Ac-TGHVSAGWYDYNADHYREFT-NH2 | 16 | 3.6 | 19 |
| JBS2528 | Ac-TGHVSAGWYDYNFDAYREFT-NH2 | 18 | 5.2 | 23 |
| JBS2546 | Ac-TGHVSAGWYDYNFDDYREFT-NH2 | 36 | 6.8 | 30 |
| JBS2552 | Ac-GGHVSAGWYDYNFDHYREFT-NH2 | 42 | 5.5 | 24 |
| JBS2572 | Ac-TGLVSAGWYDYNFDHYREFT-NH2 | 62 | 2.5 | 14 |
| JBS2582 | Ac-TGHVSAGWYDYNLDHYREFT-NH2 | 72 | 2.3 | 15 |
| JBS2584 | Ac-TGHVSAGWYDYNFDLYREFT-NH2 | 74 | 2.7 | 9 |
| JBS2586 | Ac-TGHVSAGWYDYNFDHYLEFT-NH2 | 76 | 2.6 | 19 |
| JBS2591 | Ac-TKHVSAGWYDYNFDHYREFT-NH2 | 81 | 4.2 | n.d. |
| JBS2592 | Ac-TGKVSAGWYDYNFDHYREFT-NH2 | 82 | 5.6 | 68 |
| JBS2602 | Ac-TGHVSAGWYDYNKDHYREFT-NH2 | 92 | 3.4 | 30 |
| JBS2604 | Ac-TGHVSAGWYDYNFDKYREFT-NH2 | 94 | 4.1 | 19 |
| JBS2625 | Ac-TGHVSAGWYDYNFDHYFEFT-NH2 | 115 | 1.6 | 29 |
| JBS2629 | Ac-TPHVSAGWYDYNFDHYREFT-NH2 | 119 | 3.1 | 25 |
| JBS2661 | Ac-TGHVSAGWYDYNFDSYREFT-NH2 | 151 | 2.8 | 16 |

Many peptides from the mRNA display selections and the substitution analysis showed very good inhibition of Protein S/APC cofactor activity in the plasmatic system at low peptide concentration. JBS2512, for example, demonstrated very good binding affinity to Protein S and a low EC50 value in the CAT assay. JBS2572 has a non-homologous His to Leu substitution at position 3 which increases the affinity and the activity in the CAT-assay 1.6-fold compared to JBS2512. In the competition binding assay (ELISA IC50), JBS2572 demonstrated an IC50 of 2.5±0.3 nM. JBS2572 improved PS/APC-dependent thrombin generation in hemophilic plasma.

Peptides also were characterized in a competition, homogenous europium-based TR-FRET assay (LANCE IC50 assay) using JBS0684 as a tracer (i.e., competitor for Protein S binding). The following reagents were mixed together in a Perkin-Elmer ProxiPlate MTP well (indicated concentration is the final concentration): Eu-labeled Protein S (10 nM), Ulight™-labeled Streptavidin (100 nM), tracer (JBS0684 (300 nM)), and peptide (titrated in three-fold dilution steps). The final volume was 50 µl/well. The reaction mix was incubated for 1 hour at room temperature, then the fluorescence emission at 665 nm was recorded on a multi-mode reader (SpectraMax® M5, Molecular Devices) using the following instrument settings: Ex 340 nm, Em 665 nm, delay 50 µsec, integration 100 µsec, reads 100. Binding of tracer peptides to soluble europium-labeled Protein S was detected by Streptavidin labeled with an acceptor fluorophor (ULight™). Inhibition of tracer-binding to Protein S by a non-biotinylated peptide results in a decrease of TR-FRET between the Eu-labeled Protein S and ULight™-labeled Streptavidin. IC50 values were obtained from peptide titration curves at constant tracer concentration using non-linear regression of the fluorescence emission signals at 665 nm. JBS2572 demonstrated an IC50 of 49±6 nM using a Molecular Devices M5 reader. Additional measurements were taken using a Tecan F500 reader, which enables the use of lower Protein S (2 nM) and tracer concentrations (60 nM); the LANCE IC50 value for JBS2572 was in the range of 10 nM.

Protein S affinity also was determined via Biacore (Biacore 3000 or Biacore T200) using human full-length Protein S and human GAS6. Briefly, 1000 RU of Protein S or GAS6 were immobilized on a CMS chip. In order to probe the kinetics of Protein S binding peptides to Protein S, the peptides were injected at various concentrations in a HBS-buffer containing 3 mM CaCl$_2$ and 1% DMSO to the flow cell and allowed to interact with the immobilized proteins on the sensor chip. The chip could be regenerated with 4 M MgCl$_2$ in HBS-buffer. Sensorgrams were fitted to a Langmuir binding model for the determination of $k_{on}$ and $k_{off}$ and the calculation of $K_D$. Peptides were tested on their specificity to Protein S with peptide binding studies on the anti-target GAS6. JBS2572 demonstrated $K_D$ for binding to Protein S of 6 nM ($k_{on}$=2.48×10$^5$ 1/Ms, $k_{off}$=1.48×10$^{-3}$ 1/s) at 25° C. At 37° C., the $K_D$ was 3.8×10$^{-9}$ (4 nM) ($k_{on}$=1.14× 10$^6$ 1/Ms, $k_{off}$: 4.31×10$^{-3}$ 1/s).

Examples 1 and 2 provide exemplary methods of generating and characterizing Protein S-binding peptides (e.g., Protein S-inhibitory peptides). Hundreds of peptides were identified that bind to human Protein S. Substitution analysis of an exemplary peptide generated additional Protein S-binding peptides, and demonstrated that substitutions within the Protein S-binding peptide were tolerated (i.e., retained affinity for Protein S) and, in some instances, improved affinity. Many peptides bound human Protein S with a dissociation constant or IC50 of <10 µM. The Examples further demonstrates that peptides of the invention inhibit Protein S cofactor activity in a plasma assay system with an EC50 of <10 µM. In vitro activity was demonstrated in the presence of physiological Protein S concentrations.

Example 3

This example demonstrates that peptides of the invention exhibit reduced affinity for non-Protein S proteins ("anti-targets").

Protein S comprises domains highly homologous to regions of other coagulation system proteins containing Gla-domains (such as, e.g., GAS6 (the protein encoded by the Growth Arrest Specific-6 gene), Factor VII, Factor IX, Factor X, Protein C, Protein Z, and prothrombin), EGF-like domains (such as, e.g., GAS6, Factor VII, Factor IX, Factor X, Protein C, Protein Z, and thrombomodulin), and laminin G-like domains (such as GAS6). These other coagulation system proteins, therefore, are potential anti-targets. Human GAS6 was used to determine anti-target binding because it is the most similar to Protein S (42% identity, 57% consensus sequence).

Interactions with the anti-target GAS6 were measured via Biacore (surface plasmon resonance) (see Example 2). The maximum signal from the interaction of the peptides with human GAS6 was much lower than the signals obtained with Protein S as interaction partner. Kinetic analysis of the low GAS6 binding signals was error prone, and sensorgrams were reviewed visually to estimate anti-target binding. JBS2572 showed no specific binding to GAS6 at 1 μM concentration. The affinity of JBS2572 for the anti-target was at least 10 times less (indeed, at least 150 times less) than the affinity of the peptides for human Protein S. The data provided by this example confirm that peptides described herein specifically bind Protein S.

Example 4

Peptides with increased affinity for human Protein S were obtained from a partially randomized library based on the sequence of JBS2572 (SEQ ID NO: 62). Selection of high affinity binders was accomplished by mRNA display and screening assays using methods similar to those described in Examples 1 and 2. The selection conditions applied to the peptide pool resulted in increased binding signals to Protein S. Enriched peptide pools from three rounds of selection were sequenced, which yielded the amino acid sequences of e.g., JBS3216-3223 (SEQ ID NO: 462-469) and JBS3231-3314 (SEQ ID NO: 477-560). Several peptides from the affinity maturation pool were chemically modified. JBS3319 was conjugated to 40 kD PEG moiety to yield JBS3318 (SEQ ID NO: 564). A tetramer of JBS3319 monomers together with a four arm 10 kD PEG moiety yielded JBS3321 (SEQ ID NO: 567). JBS3179 (SEQ ID NO: 433) is a JBS3206 tetramer comprising a 40 kD PEG moiety. JBS3322 (SEQ ID NO: 568) is a JBS3206 monomer comprising a 40 kD PEG moiety.

Protein S binding affinity was evaluated for 18 representative peptides (JBS3216, JBS3218, JBS3221, JBS3223, JBS3232, JBS3235, JBS3236, JBS3258, JBS3260, JBS3263, JBS3274, JBS3281, JBS3283, JBS3284, JBS3296, JBS3297, JBS3306, and JBS3314) via Biacore and LANCE IC50 assays. The peptides' ability to inhibit Protein S activity was determined via CAT assay, and plasma stability was also examined.

Affinity and activity of all 18 peptides was improved compared to parent JBS2572. The results demonstrate that multiple substitutions within the amino acid sequence of the peptides described herein are tolerated (i.e., does not destroy the ability of the peptide to bind Protein S). For example, JBS3216, which comprises substitutions at seven amino acid positions in the sequence of JBS2572 (positions 1-3, 13, 15, 17, and 20) and JBS2512, demonstrated a higher affinity for Protein S ($K_D$=0.2 nM) than the parent peptide JBS2572 ($K_D$=4 nM). Indeed, the optimized peptides demonstrated pM-affinities (20-fold improvement) with a $k_{off}$ in the range of $1\times10^{-4}$ to $6\times10^{-4}$ $s^{-1}$. Activity and stability were improved up to 1.5-fold. Exemplary Biacore results using methods similar to those described above are provided in Table 4. Plasma stability was determined in pooled normal human plasma and mouse plasma at 37° C.; exemplary results also are provided in Table 3. Stability analysis also revealed that, after 24 hours of incubation in human plasma, greater than 80% binding activity of JBS3318, JBS3179, and JBS3322 and ~50% of binding activity of JBS3216 remained. JBS3179, JBS3318, and JBS3322 also were determined not to interact with GAS6, an anti-target (at 1 μM).

TABLE 3

| Peptide | $k_{on}$ (1/Ms) | $k_{off}$ (1/s) | $K_D$ (nM) | Stability in mouse plasma; 4 hours [%] | Stability in human plasma; 6 hours [%] |
|---|---|---|---|---|---|
| JBS3179 | 4.10E+05 | 1.79E−04 | 0.4 | 89 ± 13 | 105 ± 7 |
| JBS3318 | 1.52E+05 | 2.13E−04 | 1.4 | 102 ± 20 | 114 ± 8 |
| JBS3322 | 7.80E+04 | 2.78E−04 | 3.6 | 91 ± 26 | 131 ± 14 |
| JBS3216 | 1.14E+06 | 2.33E−04 | 0.2 | 66 ± 23 | 80 ± 2 |
| JBS3263 | 6.29E+05 | 2.64E−04 | 0.4 | 56 ± 6 | 74 ± 12 |
| JBS3283 | 7.35E+05 | 3.22E−04 | 0.4 | 94 ± 6 | 90 ± 9 |
| JBS3306 | 1.00E+06 | 4.02E−04 | 0.4 | 80 ± 14 | 84 ± 12 |
| JBS3321 | 1.58E+06 | 3.88E−05 | 0.02 | 94 ± 12 | 99 ± 6 |

The inhibitory activity of the peptides was analyzed in the CAT assay (i.e., thrombin-based, APC resistance test) in plasmas from three individuals with severe hemophilia A. JBS3179, JBS3318, and JBS3322, for example, improved Protein S/APC dependent thrombin generation in the plasmas with an EC50 lower than 100 nM. JBS3179 demonstrated an EC50 of 6 nM in the CAT assay, and JBS3216 also efficiently improved coagulation in a CAT assay in human hemophilia A patient plasma (EC50=85 nM). JBS3216 also improved thrombin generation in several non-human mammals: cynomolgous monkey, marmoset monkey, pig, sheep, dog, rabbit, rat, and mouse.

JBS3179 also demonstrated beneficial in vivo activity. The peptide dose-dependently reduced bleeding in a hemophilia mouse tail cut model when administered with 25 U/kg ADVATE, significantly reduced joint bleeding in a hemarthrosis hemophilia A mouse model when co-administered with sub-efficient FVIII doses, and improved ex vivo thrombin generation in a rabbit model of induced hemophilia.

Example 5

This example describes additional peptides that bind Protein S and demonstrates that variability within the amino acid sequences of the peptides described herein is tolerated with respect to Protein S binding and inhibition.

Several peptides having multiple substitutions in the JBS2572 amino acid sequence were synthesized and evaluated using LANCE IC50 and CAT assays described above. For the assays, pooled normal plasma was supplemented with 3 nM APC and triggered with 6 pM TF, and 15 μM phospholipids (DOPC/POPS 80/20). Stock APC was diluted with TF-PL-MIX to 24 nM (plasma concentration: 3 nM). Exemplary results are provided in Table 4. The analysis focused on positions 1, 4, 5, 13, 15 and 17, and demonstrated that multiple substitutions within the parent sequence are tolerated and, in many instances, increased binding affinity and inhibitory activity compared to peptides having single substitutions within the JBS2572 parent sequence.

TABLE 4

| Peptide | Sequence | SEQ ID NO | Substitutions in JBS2572 | LANCE IC50 [nM] | CAT EC50 [nM] |
|---|---|---|---|---|---|
| JBS2572 | Ac-TGLVSAGWYDYNFDHYREFT-NH2 | 62 | Parent | 9.7 | 151 |
| JBS3186 | Ac-TGLVSAGWYDYNFDTYMEFT-NH2 | 438 | H15T, R17M | 2.6 | 176 |
| JBS3188 | Ac-TGLVSAGWYDYNFDTYTEFT-NH2 | 440 | H15T, R17T | 2.9 | 155 |
| JBS3189 | Ac-TGLVSAGWYDYNFDVYTEFT-NH2 | 441 | H15V, R17T | 5.0 | 281 |
| JBS3190 | Ac-YGLVSAGWYDYNFDTYREFT-NH2 | 442 | H15T, T01Y | 1.6 | 130 |
| JBS3191 | Ac-YGLVSAGWYDYNFDVYREFT-NH2 | 443 | H15V, T01Y | 1.6 | 147 |
| JBS3192 | Ac-TGLVEAGWYDYNFDTYREFT-NH2 | 444 | H15T, S05E | 2.8 | 117 |
| JBS3193 | Ac-TGLVEAGWYDYNFDVYREFT-NH2 | 445 | H15V, S05E | 2.5 | 116 |
| JBS3194 | Ac-TGLVSAGWYDYNNDTYREFT-NH2 | 446 | H15T, F13N | 1.8 | 122 |
| JBS3195 | Ac-TGLVSAGWYDYNNDVYREFT-NH2 | 447 | H15V, F13N | 2.0 | 139 |
| JBS3196 | Ac-YGLVSAGWYDYNFDHYMEFT-NH2 | 448 | R17M, T01Y | 2.2 | 155 |
| JBS3197 | Ac-TGLVEAGWYDYNFDHYMEFT-NH2 | 449 | R17M, S05E | 6.1 | 146 |
| JBS3198 | Ac-TGLVSAGWYDYNNDHYMEFT-NH2 | 450 | R17M, F13N | 2.5 | 149 |
| JBS3201 | Ac-YGLVEAGWYDYNNDTYMEFT-NH2 | 453 | T01Y, S05E, F13N, 15T, R17M | 1.9 | 127 |
| JBS3202 | Ac-TGL-Tle-SAGWYDYNFDTYREFT-NH2 | 454 | V4Tle, H15T | 1.6 | 129 |
| JBS3203 | Ac-TGL-Tle-SAGWYDYNFDHYMEFT-NH2 | 455 | V4Tle, R17M | 1.8 | 127 |

Example 6

This example demonstrates the ability of peptides described herein to interrupt Protein S (PS) binding to C4BP. C4BP is an octopus-like molecule which contains seven identical α-chains (MW 70 kDa) and a smaller β-chain (45 kDa). Protein S binds to the β-chain, and Protein S complex formation with C4BP abolishes the APC cofactor activity of Protein S. The dissociation constant of Protein S and C4BP in presence of calcium ions is ~0.5 nM. Due to this high affinity, the level of free PS corresponds to its molar excess over β-chain-containing C4BP.

To investigate the effect of the peptides described herein on PS/C4BP complexes, a LANCE IC50 assay was established using methods similar to those described above. JBS2572 or JBS3216 was added to a preformed C4BP/PS complex. Changes in the complex concentration were followed by recording the TR-FRET signal. For both peptides, a time- and concentration-dependent dissociation of the C4BP/PS complex was observed. The IC50 of JBS3216 was 0.3 nM, and the IC50 of JBS2572 was 2 nM. The time-dependency of the complex reduction was similar for both peptides. After two hours of incubation in the presence of 100 nM JBS2572 or JBS3216, the C4BP/PS complex was reduced to 60% and 50%, respectively. In addition, binding of biotinylated JBS2572 to Protein S was inhibited by C4BP in the LANCE IC50 assay. Pull-down experiments where JBS2697 was coupled to streptavidin sepharose and incubated for one hour at room temperature with (a) Protein S (1.6 pmol) (b) C4BP (8.5 pmol) and (c) Protein S (1.6 pmol)+C4BP (8.5 pmol) supported the results from the modified LANCE IC50 assay. JBS2697 interacted with free Protein S only from experiment (a) with Protein S alone and from experiment (c) with the C4BP-Protein S mixture.

These findings demonstrate that the peptides described herein can reduce the fraction of preformed C4BP/PS complex at nM concentration in a time-dependent manner. Disruption of the C4BP/PS interaction by the peptides (and vice versa) may stem from competitive or allosteric inhibition of the C4BP/PS complex. The binding site of C4BP on Protein S was mapped to the Laminin G-domains of Protein S with a $K_D$ of 0.1-0.6 nM. Thus, Laminin G domains appear to be involved in the interaction between the peptides and Protein S. Binding site mapping experiments using limited proteolysis support the observation. N-terminal sequencing of proteolytic fragments identified a peptide-protected region within the LG1 domain of Protein S, strongly suggesting the LG1 domain as the peptides' target binding region.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09447147B2). An electronic copy of the "Sequence Listing" will also be available from the USPTO upon request and payment of the fee set forth in 37 CFR 1.19(b)(3).

What is claimed is:

1. A peptide comprising an amino acid sequence at least 50% identical to the amino acid sequence EYYVSAGWYDYNTDTYYEFE (SEQ ID NO: 2924) and having the structure:

X1001-X1002-X1003-X1004-X1005-X1006-X1007-X1008-X1009-X1010-X1011-X1012-X1013-X1014-X1015-X1016-X1017-X1018-X1019-X2020, wherein X1001 is A, Bpa, C, D, E, e, F, G, H, I, K, L, M, N, P, p, Q, R, S, T, V, W, or Y;
wherein X1002 is A, C, D, E, F, G, H, I, K, L, M, N, P, p, Q, R, S, T, V, W, Y, or y;
wherein X1003 is A, C, D, E, F, G, H, I, K, L, M, N, P, p, Q, R, S, T, Tle, V, W, Y, or y;
wherein X1004 is F, I, L, Tle, V, or W;
wherein X1005 is A, E, F, G, H, I, K, L, M, R, S, T, V, W, or Y;
wherein X1006 is A, F, G, I, L, Tle V, W, or Y;
wherein X1007 is G or a;
wherein X1008 is F, 1Ni, 2Ni, Bta, or W;
wherein X1009 is F or Y;
wherein X1010 is D, E, F, H, I, K, L, N, Q, V, W, or Y;
wherein X1011 is F, G, I, K, L, M, R, T, V, W, or Y;
wherein X1012 is A, D, E, F, G, H, I, K, L, N, Q, R, S, T, V, or Y;
wherein X1013 is D, E, F, G, H, I, K, L, Q, R, S, T, V, or W;
wherein X1014 is D, E, or H;
wherein X1015 is D, E, H, I, K, M, Q, R, S, T, V, or W;
wherein X1016 is F, H, W, or Y;
wherein X1017 is D, E, G, H, I, T, W, or Y;
wherein X1018 is A, D, E, G, H, I, K, L, M, P, Q, R, S, T, V, or W;
wherein X1019 is F or W; and
wherein X2020 is A, C, D, E, e, F, G, H, I, K, L, M, N, P, p, Q, R, S, T, V, W, or Y.

2. The peptide of claim 1, wherein X1004 is V, X1005 is S, X1006 is A, X1007 is G, X1008 is W, and X1009 is Y.

3. The peptide of claim 1 comprising an amino acid sequence at least about 80% identical to the amino acid sequence EYYVSAGWYDYNTDTYYEFE (SEQ ID NO: 2924).

4. The peptide of claim 3, wherein the amino acid sequence comprises the amino acid sequence EYYVSAGWYDYNTDTYYEFE (SEQ ID NO: 2924).

5. The peptide of claim 1,
wherein X1003 is A, E, F, G, H, I, K, L, N, P, R, T, V, W, y, or Y; and
wherein X1002 is A, D, E, F, G, H, I, K, L, N, P, R, T, V, W, y, or Y.

6. The peptide of claim 1 comprising an amino acid sequence at least about 90% identical to the amino acid sequence EYYVSAGWYDYNTDTYYEFE (SEQ ID NO: 2924).

7. A peptide consisting of an amino acid sequence at least about 80% identical to EYYVSAGWYDYNTDTYYEFE (SEQ ID NO: 2924).

8. The peptide of claim 1, wherein the peptide is conjugated to a polyethylene glycol (PEG) moiety, albumin, an antibody or fragment thereof, hydroxyethyl starch, a proline-alanine-serine multimer, a C12-C18 fatty acid, or polysialic acid.

9. The peptide of claim 1, wherein the peptide is conjugated or attached to a moiety selected from the group consisting of Bpa, Bpa-K(Bio)-C, C(Atf-Bio), C(Atf-LC-Bio), C(FeBABE), C(MalCy5), C(NEM), C(PEG), K, K(Ac), K(Ttds), K(Ttds-γGlu), T, Ttds, or Ttds-K(Bio).

* * * * *

UNITED STATES PATENT AND TRADEMARK OFFICE
CERTIFICATE OF CORRECTION

PATENT NO. : 9,447,147 B2
APPLICATION NO. : 14/634028
DATED : September 20, 2016
INVENTOR(S) : Michael Dockal et al.

It is certified that error appears in the above-identified patent and that said Letters Patent is hereby corrected as shown below:

On the Title Page

Item (71), replace:
"BAXTER INTERNATIONAL INC., Deerfiled, IL (US); BAXTER HEALTHCARE SA, Glattpark (Opfikon) (CH)"
With:
"BAXALTA GMBH, Glattpark (Opfikon) (CH); BAXALTA INCORPORATED, Bannockburn, IL (US)".

In the Claims

Column 35, Line 18, "Tle" should read "Tle,".

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*